US012622909B2

(12) United States Patent
Gray et al.

(10) Patent No.: US 12,622,909 B2
(45) Date of Patent: May 12, 2026

(54) ALLOSTERIC EGFR INHIBITORS AND METHODS OF USE THEREOF

(71) Applicant: Dana-Farber Cancer Institute, Inc., Brookline, MA (US)

(72) Inventors: Nathanael S. Gray, Jamaica Plain, MA (US); David A. Scott, Newton, MA (US); Thomas Gero, Stow, MA (US); Michael Eck, Brookline, MA (US); David Heppner, Brookline, MA (US); Tyler Beyett, Brookline, MA (US); Ciric To, Medford, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 353 days.

(21) Appl. No.: 17/596,639

(22) PCT Filed: Jun. 19, 2020

(86) PCT No.: PCT/US2020/038705

§ 371 (c)(1),
(2) Date: Dec. 15, 2021

(87) PCT Pub. No.: WO2020/257632

PCT Pub. Date: Dec. 24, 2020

(65) Prior Publication Data

US 2022/0233545 A1 Jul. 28, 2022

Related U.S. Application Data

(60) Provisional application No. 63/027,734, filed on May 20, 2020, provisional application No. 62/877,093, filed on Jul. 22, 2019, provisional application No. 62/864,914, filed on Jun. 21, 2019.

(51) Int. Cl.

| | |
|---|---|
| ***A61K 31/519*** | (2006.01) |
| ***A61K 31/4725*** | (2006.01) |
| ***A61K 31/496*** | (2006.01) |
| ***A61K 31/502*** | (2006.01) |
| ***A61K 31/506*** | (2006.01) |
| ***A61K 31/517*** | (2006.01) |
| ***A61K 31/5377*** | (2006.01) |
| ***A61K 39/395*** | (2006.01) |
| ***A61P 35/00*** | (2006.01) |
| ***C07D 401/10*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 417/12*** | (2006.01) |
| ***C07D 417/14*** | (2006.01) |
| ***C07D 471/04*** | (2006.01) |

(52) U.S. Cl.

CPC ........ *A61K 31/519* (2013.01); *A61K 31/4725* (2013.01); *A61K 31/496* (2013.01); *A61K 31/502* (2013.01); *A61K 31/506* (2013.01); *A61K 31/517* (2013.01); *A61K 31/5377* (2013.01); *A61K 39/3955* (2013.01); *A61P 35/00* (2018.01); *C07D 401/10* (2013.01); *C07D 401/12* (2013.01); *C07D 401/14* (2013.01); *C07D 403/12* (2013.01); *C07D 403/14* (2013.01); *C07D 417/12* (2013.01); *C07D 417/14* (2013.01); *C07D 471/04* (2013.01)

(58) Field of Classification Search

CPC .............. A61K 31/519; A61K 31/4725; A61K 31/496; A61K 31/502; A61K 31/506; A61K 31/517; A61K 31/5377; A61K 39/3955; A61P 35/00; C07D 401/10; C07D 401/12; C07D 401/14; C07D 403/12; C07D 403/14; C07D 417/12; C07D 417/14; C07D 471/04

See application file for complete search history.

(56) References Cited

U.S. PATENT DOCUMENTS

| | | | | |
|---|---|---|---|---|
| 8,034,822 B2 * | 10/2011 | Cheruvallath ............ | A61P 3/06 514/266.1 |
| 10,836,733 B2 * | 11/2020 | Kozikowski ......... | A61K 31/427 |
| 2007/0213349 A1 | 9/2007 | Cheruvallath et al. | |

FOREIGN PATENT DOCUMENTS

| | | |
|---|---|---|
| WO | WO 2017/004383 A1 | 1/2017 |
| WO | WO 2018/115218 A1 | 6/2018 |
| WO | WO 2018/220149 A1 | 12/2018 |
| WO | 2019007696 A1 | 1/2019 |

OTHER PUBLICATIONS

Xiang et al., Org Lett, 2004, 6:3155-3158 (Year: 2004).*
Ritchie et al., Eur J Med Chem, 2016, 124:1057-1068 (Year: 2016).*
Jia et al., "Overcoming EGFR(T790M) and EGFR(C797S) resistance with mutant-selective allosteric inhibitors", *Nature* 534:129-132 (2016).
Lee et al., "Allosteric Inhibitor TREA-0236 Containing Non-hydrolysable Quinazoline-4-one for EGFR T790M/C797S Mutants Inhibition", *Bulletin of the Korean Chemical Society* 39:895-898 (2018).
Ward et al., "Structure- and Reactivity-Based Development of Covalent Inhibitors of the Activating and Gatekeeper Mutant Forms of the Epidermal Growth Factor Receptor (EGFR)", *Journal of Medicinal Chemistry* 56:7025-7048 (2013).
Xiang et al., Concise Synthesis of Isoquinoline via the Ugi and Heck Reactions, Organic Letters, Aug. 4, 2004, vol. 6, pp. 3155-3158.

(Continued)

*Primary Examiner* — Andrew D Kosar
*Assistant Examiner* — Jonathan D Mahlum
(74) *Attorney, Agent, or Firm* — Nielsen IP Law LLC

(57) ABSTRACT

The disclosure relates to compounds that act as an allosteric inhibitors of epidermal growth factor receptor (EGFR); pharmaceutical compositions comprising the compounds; and methods of treating or preventing kinase-mediated disorders, including cancer and other proliferation diseases.

20 Claims, No Drawings

(56) References Cited

OTHER PUBLICATIONS

Pubmed Compound Record for CID 16611162, '3-(2-Anilino-2-oxo-1-phenylethyl)-4-oxophthalazine-1-carboxylic acide', U.S. National Library of Medicine, Jul. 31, 2007 (Jul. 31, 2007), pp. 1-8 (https://pubchem.ncbi.nlm.nih.gov/compound/67435267).
Pubmed Compound Record for CID 67435267, '(2S)-2-Cyclohexyl-2-(4-oxoquinazolin-3-yl)-N-pyridin-2-ylpropanamide', U.S. National Library of Medicine, Nov. 30, 2012 (Nov. 30, 2012), pp. 1-10 (https://pubchem.ncbi.nlm.nih.gov/compound/6743267).
Written Opinion of the International Searching Authority for International Application No. PCT/US2020/038705, dated Sep. 25, 2020, 4 pages.

* cited by examiner

ALLOSTERIC EGFR INHIBITORS AND METHODS OF USE THEREOF

RELATED APPLICATIONS

This application claims priority to U.S. Provisional Application No. 62/864,914, filed on Jun. 21, 2019, 62/877,093, filed on Jul. 22, 2019, and 63/027,734, filed on May 20, 2020, the contents of which are hereby incorporated by reference in their entirety.

FEDERALLY SPONSORED RESEARCH OR DEVELOPMENT

This invention was made with government support under Grant No. R01 CA201049 awarded by the National Institute of Health (NIH). The government has certain rights in the invention.

BACKGROUND

The epidermal growth factor receptor (EGFR, Erb-B1) belongs to a family of receptor tyrosine kinases that mediate the proliferation, differentiation, and survival of normal and malignant cells (Arteaga, C. L., *J. Clin. Oncol.* 19, 2001, 32-40). Deregulation of EGFR has been implicated in many types of human cancer, with overexpression of the receptor present in at least 70% of human cancers (Seymour, L. K., *Curr. Drug Targets* 2, 2001, 117-133), including non-small lung cell carcinomas, breast cancers, gliomas, squamous cell carcinomas of the head and neck, and prostate cancer (Raymond, E., et al., *Drugs* 60 (Suppl. 1), 2000, 15-23, discussion 41-2; Salomon, D. S., et al., *Crit. Rev. Oncol. Hematol.* 19, 1995, 183-232; Voldborg B. R., et al., *Ann. Oncol.* 8, 1997, 1197-1206). EGFR has, therefore, emerged as an attractive target for the design and development of diagnostic and therapeutic agents that can specifically bind and inhibit the receptor's tyrosine kinase activity and signal transduction pathway in cancer cells. For example, the EGFR tyrosine kinase (EGFR-TK) reversible inhibitor TARCEVA® is approved by the FDA for treatment of NSCLC and advanced pancreatic cancer. Other anti-EGFR targeted molecules have also been approved, including Lapatinib and IRESSA®.

Epidermal growth factor receptor (EGFR) tyrosine kinase inhibitors (TKIs) are effective clinical therapies for EGFR mutant advanced non-small cell lung cancer (NSCLC) patients (Mok, T. S., et al., *N. Engl. J. Med.* 361, 2009, 947-57; Paez, J. G., et al., *Science* 304, 2004, 1497-500; Lynch, T. J., et al., *N. Engl. J. Med.* 350, 2004, 2129-39; Rosell, R., et al., *Lancet Oncol.* 13, 2012, 239-46). Several randomized clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., *N. Engl. J. Med.* 361, 2009, 947-57: Rosell, R., et al., *Lancet Oncol.* 13, 2012, 239-46; Sequest, L. V. et al., *J. Clin. Oncol.* 31, 2013, 3327-34; Wu, Y. L, et al., *Lancet Oncol.* 15, 2014, 213-22; Maemondo, M., et al., *N. Engl. J. Med.* 362, 2010, 2380-8; Zhou, C., et al., *Lancet Oncol.* 12, 2011, 735-42; Mitsudomi, T., et al., *Lancet Oncol.* 11, 2010, 121-8). However, the vast majority of patients will develop disease progression following successful treatment with an EGFR TKI. The most common mechanism of acquired resistance, detected in 60% of patients, is a secondary mutation in EGFR at position T790 (T790M) (Yu, H. A., et al., *Clin. Cancer Res.* 19, 2013, 2240-7). This mutation leads to an increase in ATP affinity, thus making it more difficult for reversible EGFR TKIs gefitinib and erlotinib to bind the EGFR TKI domain (Yun C. H., et al., *Proc. Natl. Acad. Sci. USA* 105, 2008, 2070-5).

Covalent EGFR inhibitors have emerged for inhibiting EGFR T790M-containing cancers. However, in lung cancer patients, afatinib is only effective in EGFR TKI naïve EGFR mutant cancers and has a RR of less than 10% in patients with NSCLC that have developed resistance to gefitinib or erlotinib (Miller, V. A., et al., *Lancet Oncol.* 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors including the tool compound WZ4002 and clinical compounds CO-1686 and AZD9291, overcome many of the limitations of afatinib (Zhou, W., et al., *Nature* 462, 2009, 1070-4; Walter, A. O., et al., *Cancer Discov.* 3, 2013, 1404-15; Cross, D. A. E., et al., *Cancer Discov.* 4, 2014, 1046-61). They are not only more potent on EGFR T790M, but also selectively inhibit mutant over WT EGFR and hence should lead to increased clinical efficacy and less toxicity compared with afatinib (Zhou, W., et al; Walter A. O., et al, Cross, D. A. E., et al.).

However, all current EGFR TKIs target the ATP site, and while third generation irreversible inhibitors can overcome T790M, they are all rendered impotent by the C797S mutation, which is already arising in treated patients. Cetuximab, an anti-EGFR antibody that blocks receptor dimerization, is not effective in EGFR-mutant NSCLC because mutational activation of the kinase is effectively "downstream" of receptor dimerization. Hence, alternative strategies to inhibit EGFR are needed. At present, suitable compounds with alternative mechanisms of action targeting mutant EGFR are not available. Thus, there is a need for potent small molecule EGFR inhibitors with alternative mechanisms of action targeting mutant EGFR.

SUMMARY

Provided herein is a compound of Formula I:

(I)

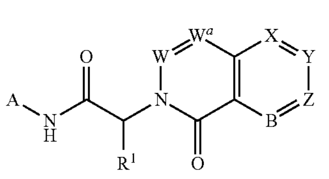

or a pharmaceutically acceptable salt thereof:

wherein:

A is a 6-10 membered aryl or a 5-10 membered heteroaryl;

W and $W^a$ are each, independently, CH, $CR^6$, or N;

X and B are each, independently, N, CH, CF, or C—($C_1$-$C_3$ alkyl);

Y and Z are each independently N, CH, or $CR^2$;

provided that at least one of X, Y, Z, or B is CH;

$R^1$ is phenyl or pyridinyl, wherein phenyl or pyridinyl is optionally substituted one or two times, independently, with $R^7$;

$R^2$ is independently, at each occurrence, selected from the group consisting of halo, 6-10 membered aryl, 5-6 membered heteroaryl, 3-6 membered cycloalkyl, 3-6 membered cycloalkenyl, 4-7 membered heterocycloalkyl, $OR^4$, $NR^4R^4$, $SO_2R^4$, $SO_2NHR^4$, $NHSO_2R^4$, C(O)$OR^4$, C(O)$NHR^4$, C(O)$R^4$, $C_1$-$C_6$ alkyl, $C_2$-$C_6$ alkenyl, and $C_2$—C alkynyl, wherein 6-10 membered aryl, 5-10 membered heteroaryl, 4-7 membered heterocycloalkyl, and 3-6 membered cycloalkyl are optionally substituted with $R^3$, and wherein $C_1$-$C_6$ alkyl, $C_2$-$C_6$ alkenyl, or $C_2$-$C_6$ alkynyl are each optionally substituted one, two, or three times with $R^4$;

$R^3$ is selected from the group consisting of halo, —OH, —SH, —CN, —$NO_2$, —$NH_2$, $OR^4$, $NR^4R^4$, $SO_2R^4$, $SO_2NHR^4$, $NHSO_2R^4$, C(O)$OR^4$, C(O)$NHR^4$, C(O)$R^4$, $C_1$-$C_6$ alkyl, $C_2$-$C_6$ alkenyl, $C_2$-$C_6$ alkynyl, 6-10 membered aryl, 5-6 membered heteroaryl, 3-6 membered cycloalkyl, 3-6 membered cycloalkenyl, and 4-7 membered heterocycle, wherein 4-7 membered heterocycle is optionally substituted with $C_1$-$C_4$ alkyl, $C_1$-$C_4$ alkyl-OH, halo, and =O;

$R^4$ is independently, at each occurrence, selected from the group consisting of hydrogen, $(CH_2)_{0-3}$-(3-7 membered cycloalkyl), $(CH_2)_{0-3}$-(4-7 membered cycloalkenyl), $(CH_2)_{0-3}$-(6-10 membered aryl), $(CH_2)_{0-3}$-(5- to 6-membered heteroaryl), or $(CH_2)_{0-3}$-(4- to 7-membered heterocycloalkyl), wherein 6-10 membered aryl, 5- to 6-membered heteroaryl, or 4- to 7-membered heterocycloalkyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$alkoxy, $C_1$-$C_6$ haloalkoxy, halo, COOH, C(O)O($C_1$-$C_6$ alkyl), $O(CH_2)_{1-3}OH$, $NH_2$, OH, CN, $(CH_2)_{0-3}$(6-10 membered aryl), $(CH_2)_{0-3}$(5- to 6-membered heteroaryl), and $(CH_2)_{0-3}$(4- to 7-membered heterocycloalkyl), wherein 6-10 membered aryl, 5- to 6-membered heteroaryl, and 4- to 7-membered heterocycloalkyl are optionally substituted with one or more substituents independently selected from $C_1$-$C_6$ alkyl, $C_1$-$C_6$ haloalkyl, $C_1$-$C_6$alkoxy, $C_1$-$C_6$ haloalkoxy, halo, $NH_2$, NH($C_1$-$C_6$ alkyl), N($C_1$-$C_6$ alkyl)$_2$, $SO_2NH_2$, $(CH_2)_{1-2}OH$, C(O)$(CH_2)_{1-2}OH$, and C(O)O($C_1$-$C_6$ alkyl);

$R^6$ is independently, at each occurrence, $C_1$-$C_6$ alkyl or halo; and $R^7$ is independently, at each occurrence, $C_1$-$C_3$ alkyl, $C_1$-$C_3$ haloalkyl, $C_1$-$C_3$ alkoxy, $C_1$-$C_3$ haloalkoxy, halo, OH, SH, $NO_2$, $NH_2$, $(CH_2)_{1-4}OH$, $S(O)_{0-2}H$, $S(O)_{0-2}NH_2$, or CN.

In an embodiment, the compound of Formula I is selected from the group consisting of:

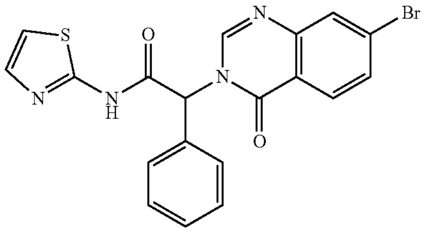

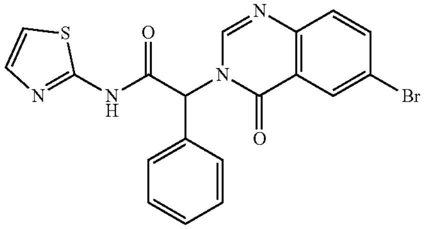

-continued

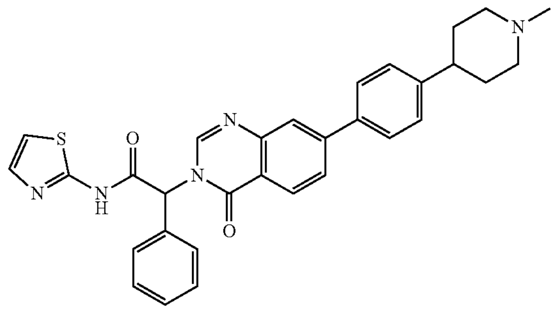

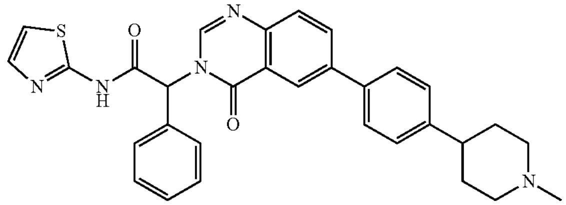

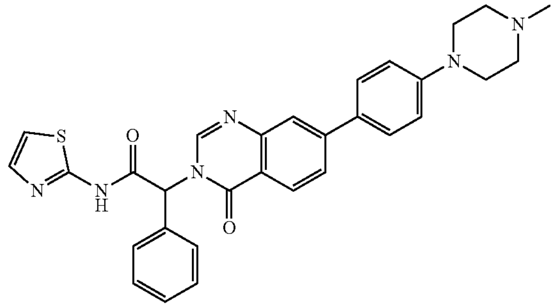

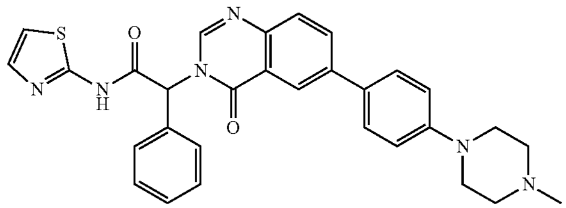

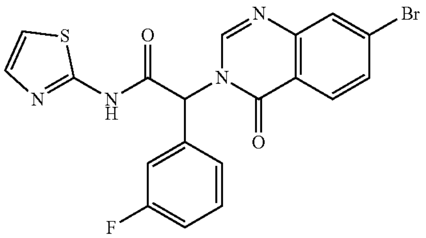

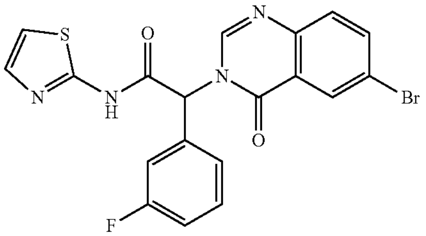

-continued
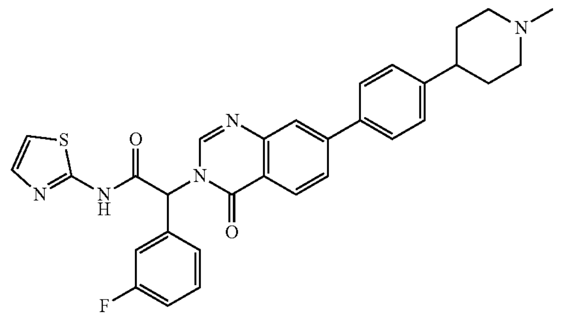
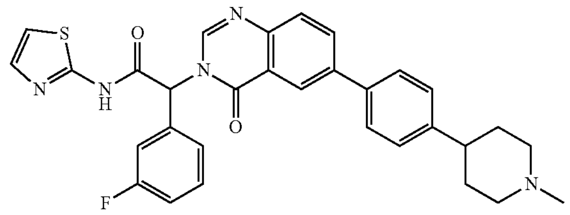
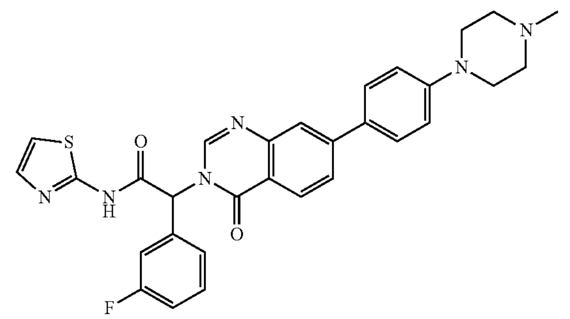
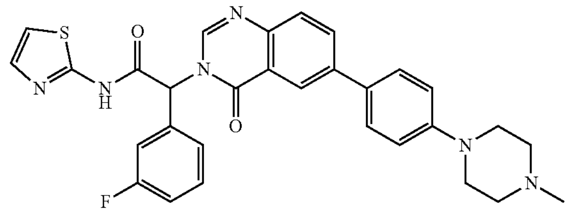
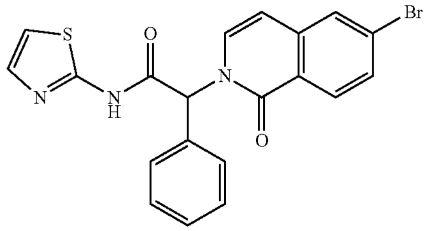
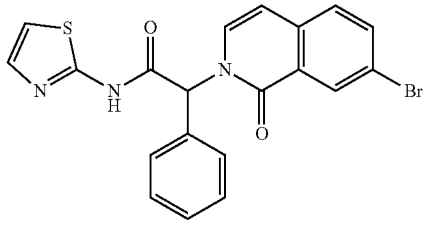
-continued
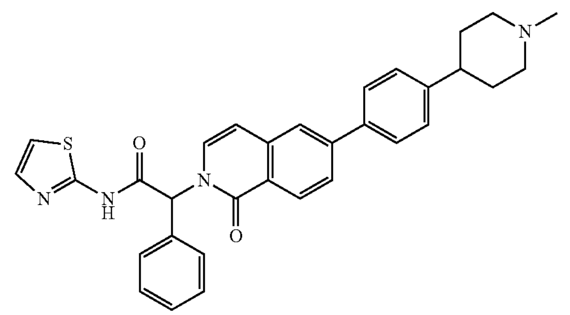
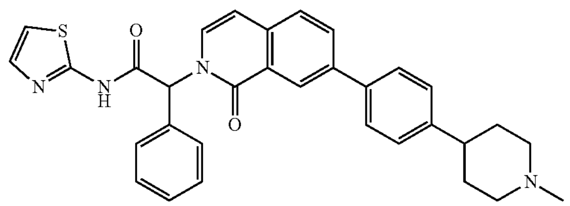
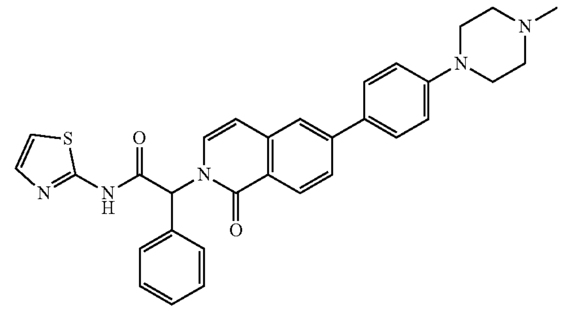
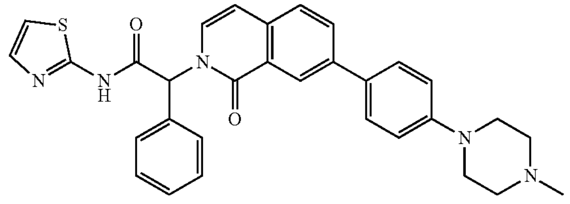
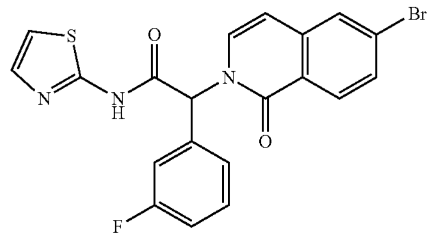
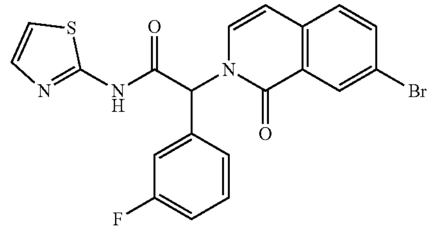

-continued
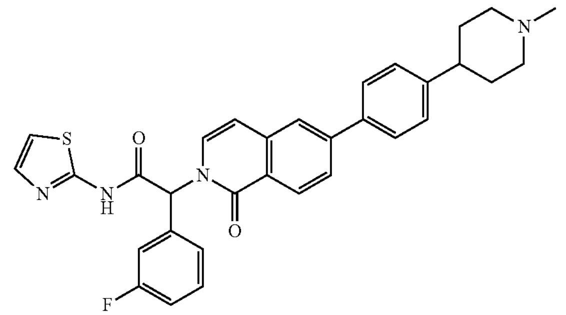
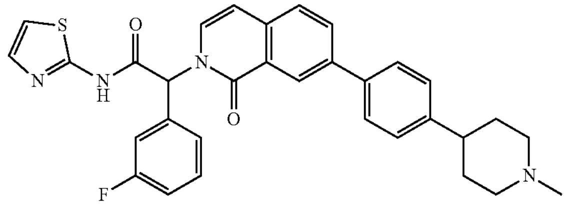
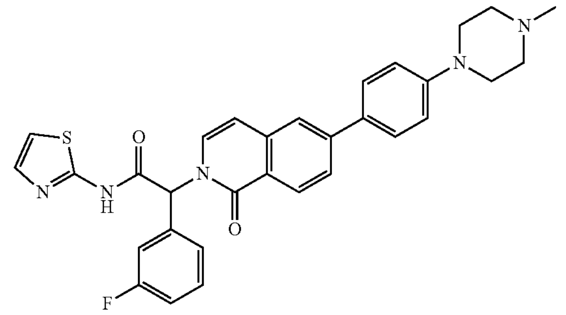
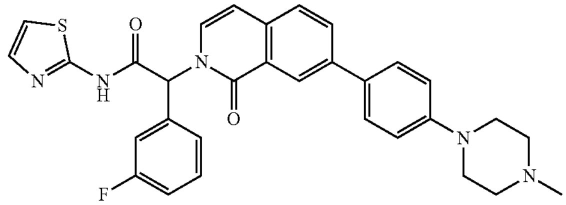
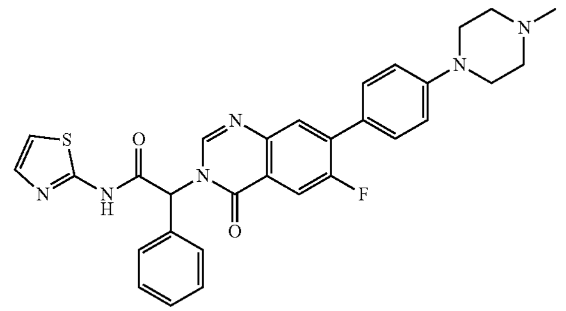
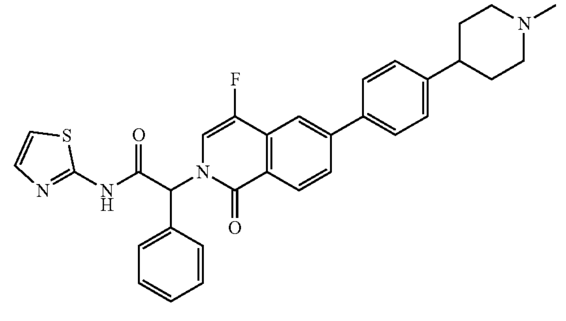
-continued
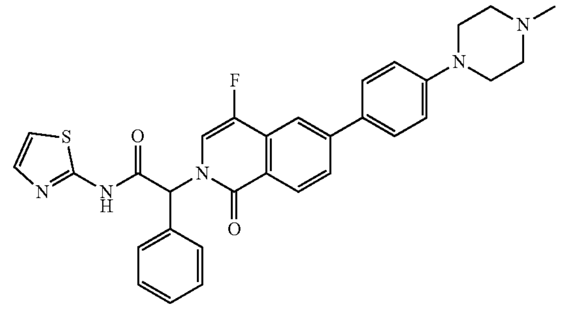
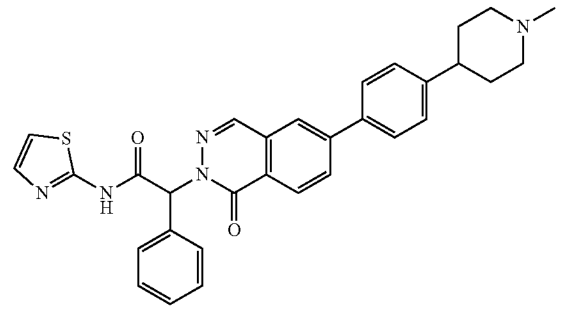
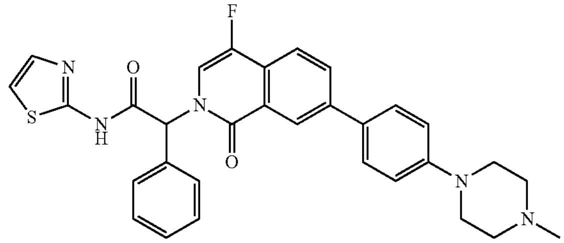
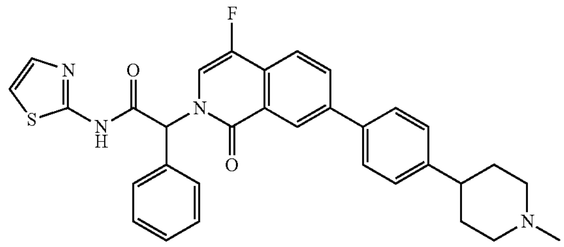
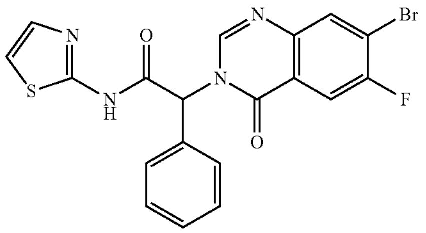
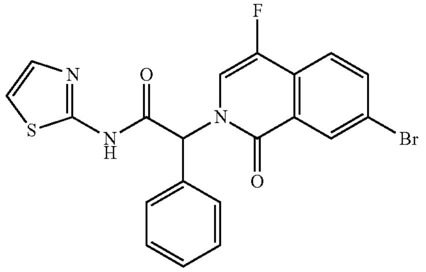

-continued
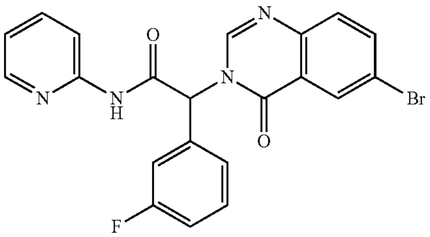
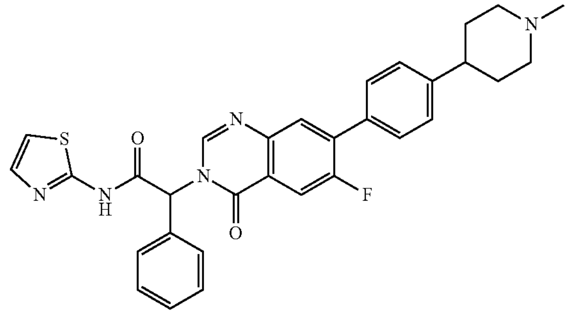
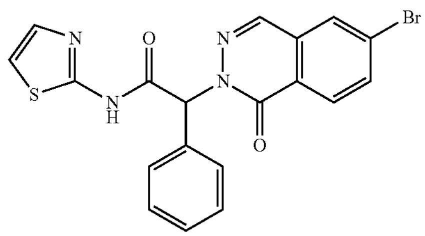
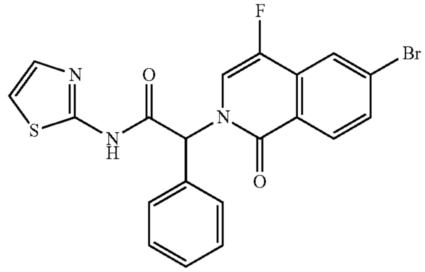
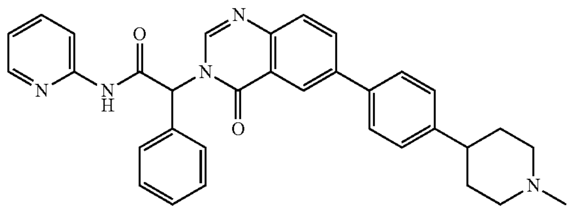
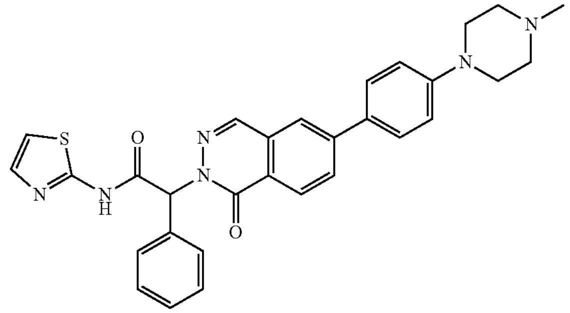
-continued
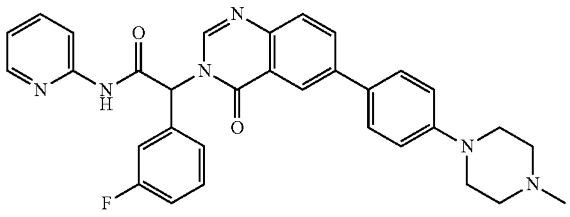
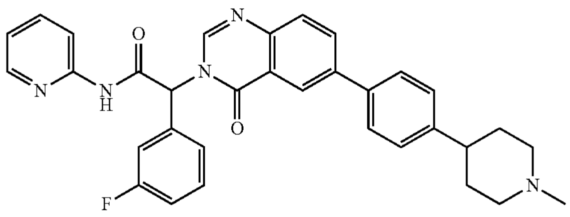
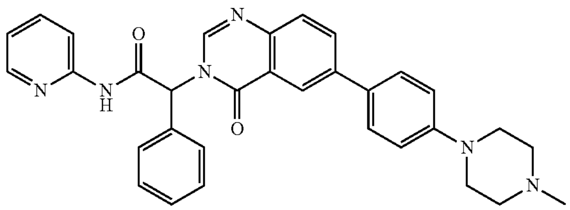
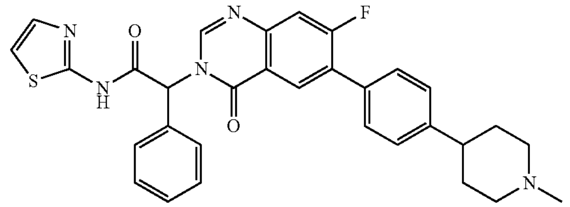
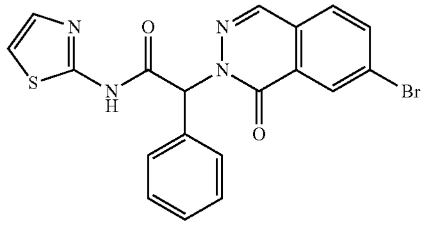
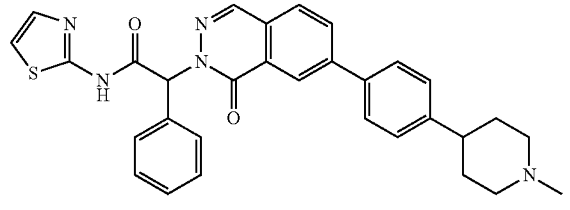
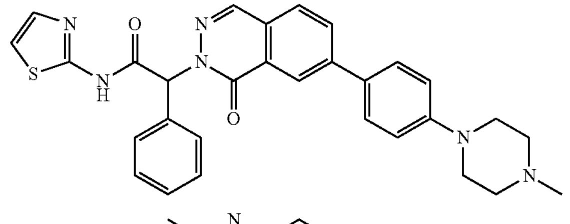
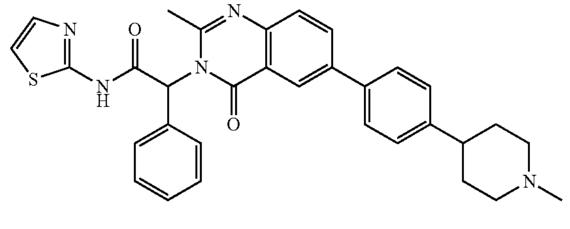

-continued
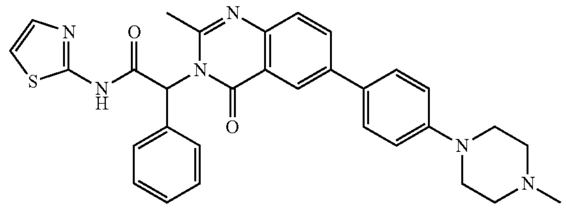
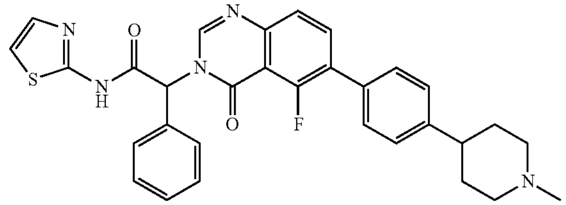
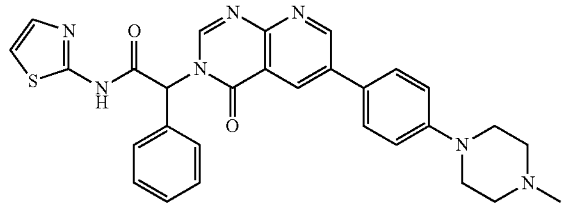
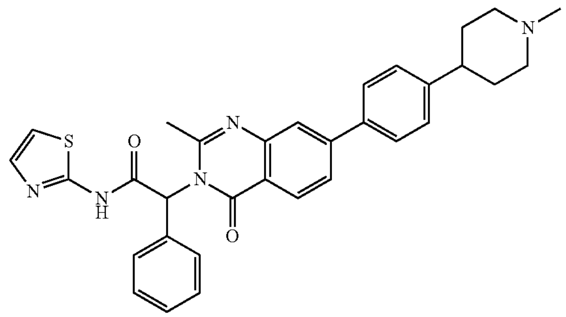
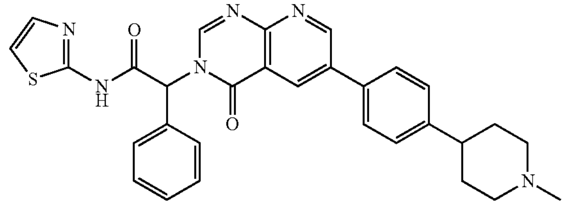
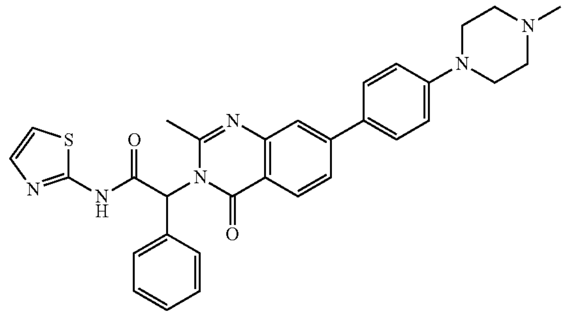
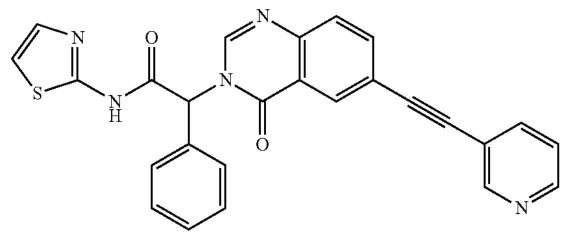
-continued
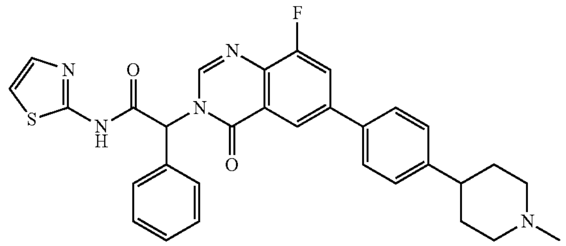
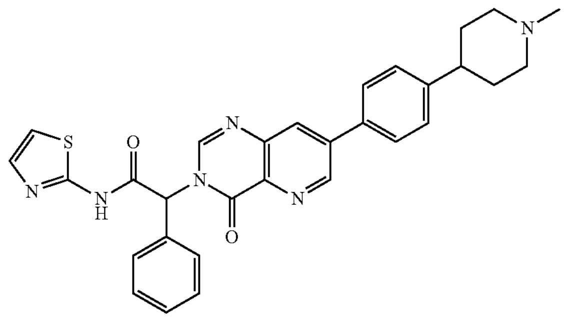
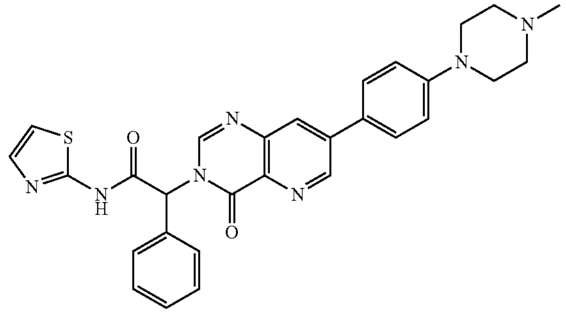
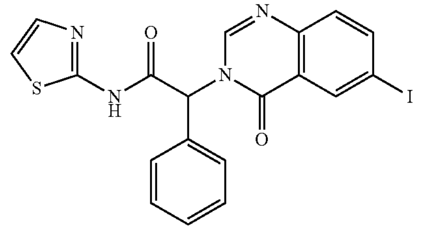
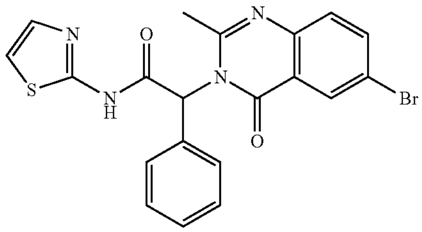
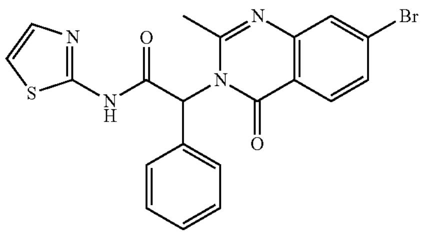

-continued
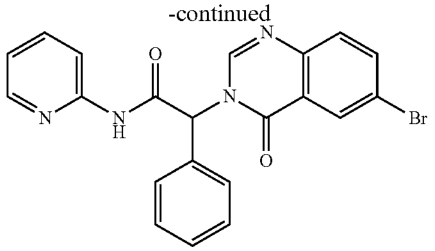
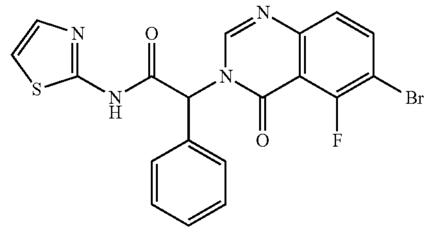
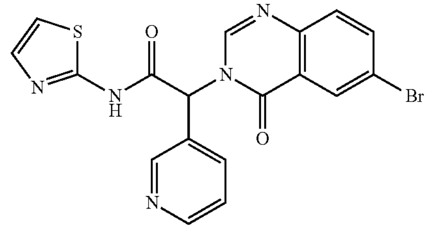
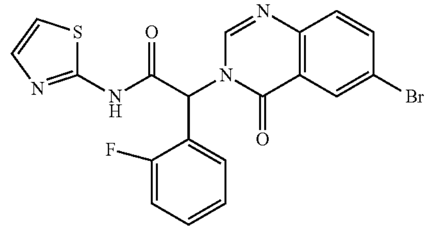
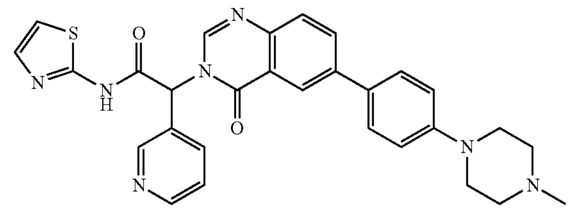
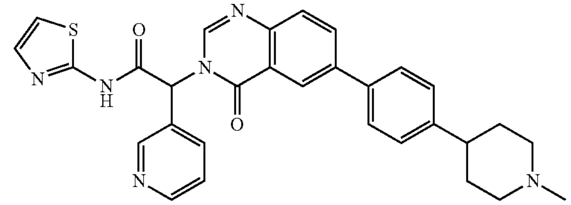
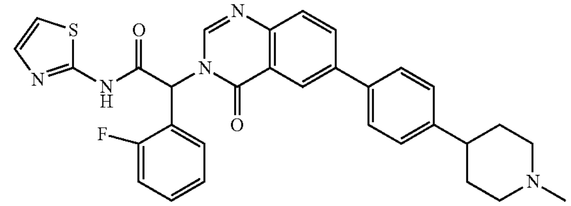
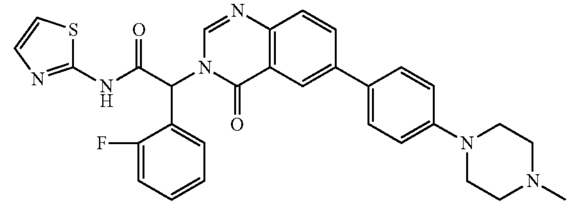
-continued
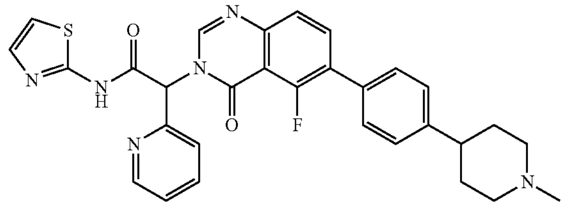
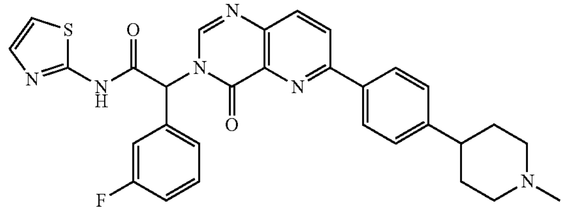
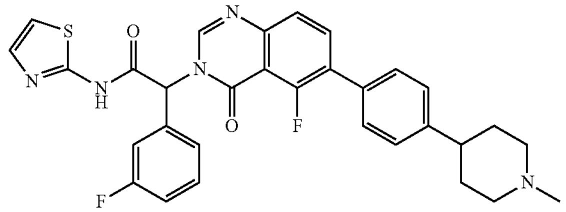
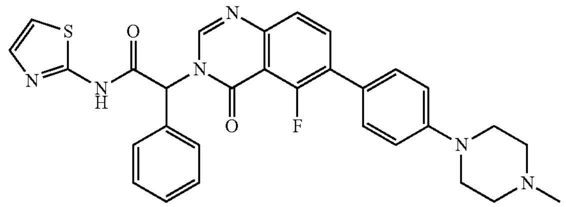
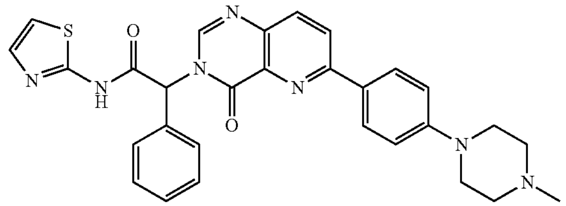
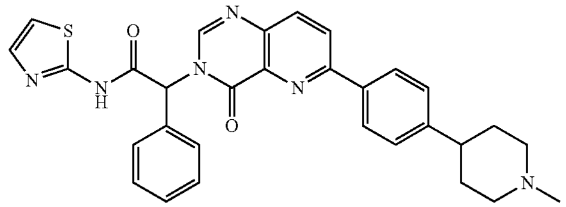
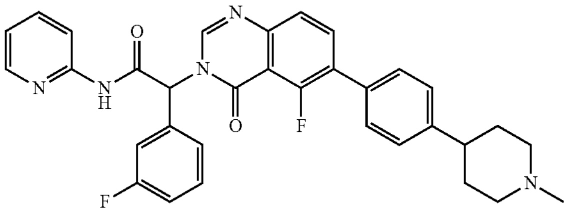
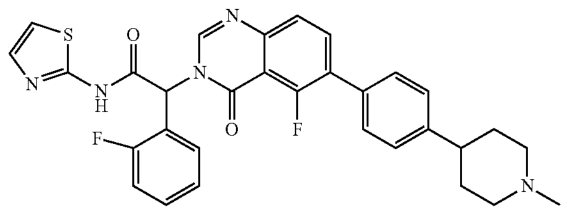

-continued

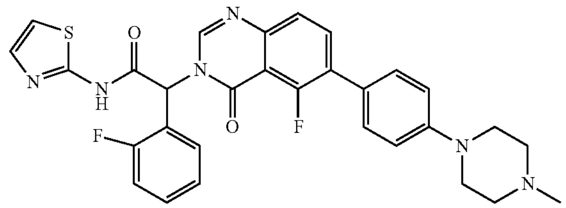

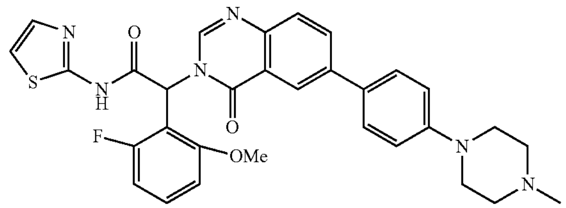

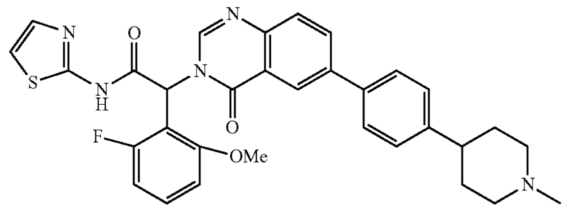

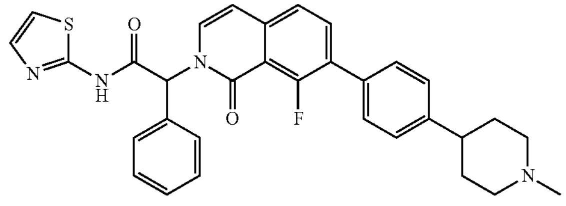

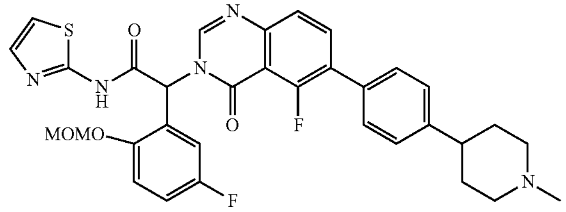

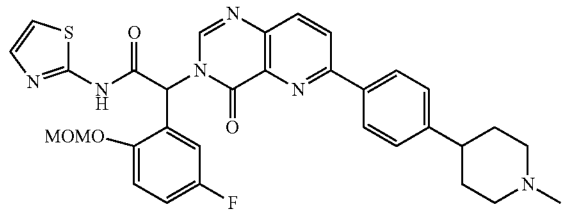

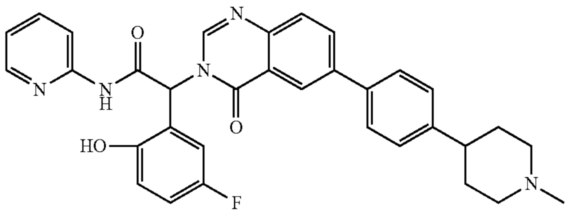

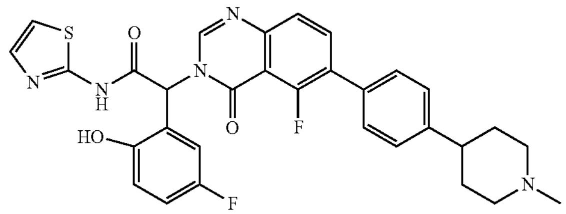

-continued

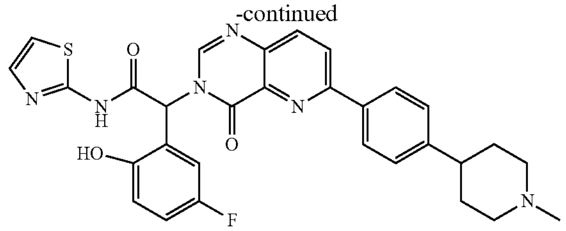

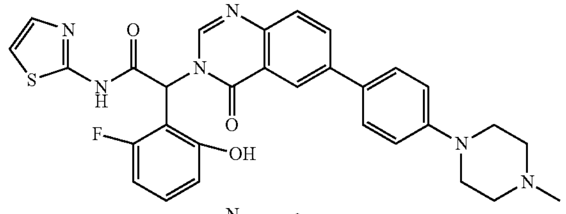

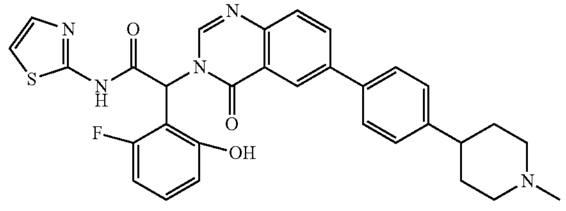

or a pharmaceutically acceptable salt thereof.

In another aspect, provided herein are pharmaceutical compositions comprising any of the compounds disclosed herein, or a pharmaceutically acceptable salt thereof, and at least one pharmaceutically acceptable carrier.

In yet another aspect, provided herein is a method of inhibiting a kinase comprising administering to a subject in need thereof an effective amount of a compound of Formula I or a pharmaceutical composition comprising a compound of Formula I and a pharmaceutically acceptable carrier. In one embodiment, the kinase to be inhibited is epidermal growth factor receptor (EGFR). In a further embodiment, the EGFR to be inhibited contains one or more mutations. In yet a further embodiment, the EGFR to be inhibited contains one or more mutations selected from the group consisting of T790M, L718Q, L844V, V948R, L858R, I941R, C797S, and Del. In another embodiment, the compound of Formula I exhibits at least 5-fold greater inhibition of EGFR containing one or more mutations relative to wild-type EGFR. In another embodiment, the method further comprises administering to the subject a second active agent, wherein said second active agent prevents EGFR dimer formation. In another embodiment, the subject is a human.

In still another aspect, provided herein is a method of treating or preventing a kinase-mediated disorder, comprising administering to a subject in need thereof an effective amount of a compound of Formula I or a pharmaceutical composition comprising a compound of Formula I and a pharmaceutically acceptable carrier. In one embodiment, the kinase-mediated disorder is resistant to an EGFR-targeted therapy. In a further embodiment, the EGFR-treated therapy is selected from the group consisting of gefitinib, erlotinib, osmertinib, CO-1686, and WZ4002. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osmertinib. In another embodiment, the subject is a human.

In an aspect, provided herein is a method of treating cancer or a proliferation disease, comprising administering to a subject in need thereof an effective amount of a compound of Formula I or a pharmaceutical composition comprising a compound of Formula I and a pharmaceutically acceptable carrier. In one embodiment, the cancer is lung cancer, breast cancer, glioma, squamous cell carcinoma, or prostate cancer. In another embodiment, the method further comprises administering to the subject a second active agent, wherein said second active agent prevents EGFR dimer formation. In another embodiment, the subject is a human.

The disclosure also provides a kit comprising a compound capable of inhibiting EGFR activity selected from a compound of Formula I, or a pharmaceutically acceptable salt thereof, and instructions for use in treating cancer. In one embodiment, the kit further comprises components for performing a test to determine whether a subject has an activating mutation in EGFR or a resistance mutation in EGFR. In another embodiment, the kit further comprises a second active agent, wherein said second active agent prevents EGFR dimer formation.

The disclosure also relates to a prodrug of a compound of Formula I.

DETAILED DESCRIPTION

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "treat," "treated," "treating," or "treatment" includes the diminishment or alleviation of at least one symptom associated or caused by the state, disorder or disease being treated. In certain embodiments, the treatment comprises bringing into contact with wild-type or mutant EGFR an effective amount of a compound disclosed herein for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "prodrug" refers to a precursor compound that will undergo metabolic activation in vivo to produce an active drug. Thus, for example, a prodrug of a compound of Formula I will, when administered to a subject, undergo metabolic activation to generate the compound of Formula I.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the disclosure and a co-agent, are both administered to a patient simultaneously in the form of a single entity or dosage. The term "non-fixed combination" means that the active ingredients, e.g. a compound of the disclosure and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes: oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide: surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

An "oral dosage form" includes a unit dosage form prescribed or intended for oral administration. In an embodiment of the pharmaceutical combinations provided herein, the EGFR inhibitors disclosed herein is administered as an oral dosage form.

As used herein, the term "EGFR" refers to epidermal growth factor receptor (alternately referred to as ErbB-1 or HER1) and may refer to the wild-type receptor or to a receptor containing one or more mutations.

As used herein, the term "HER" or Her" refers to members of the ErbB receptor tyrosine kinase family, including EGFR, ERBB2, HER3, and HER4.

As used herein, the term "allosteric site" refers to a site on EGFR other than the ATP binding site, such as that characterized in a crystal structure of EGFR. An "allosteric site" can be a site that is close to the ATP binding site, such as that characterized in a crystal structure of EGFR. For example. For example, one allosteric site includes one or more of the following amino acid residues of epidermal growth factor receptor (EGFR): Lys745, Leu788, Ala743, Cys755, Leu777, Phe856, Asp855, Met766, Ile759, Glu762, and/or Ala763.

As used herein, the term "agent that prevents EGFR dimer formation," or iterations thereof, refers to an agent that prevents dimer formation in which the C-lobe of the "activator" subunit impinges on the N-lobe of the "receiver" subunit. Examples of agents that prevent EGFR dimer formation include, but are not limited to, cetuximab, cobimetinib, trastuzumab, panitumumab, and Mig6.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

As used herein, the term "haloalkyl" refers to an alkyl group, as defined above, substituted with one or more halo substituents, wherein alkyl and halo are as defined herein.

Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "haloalkoxy" refers to the group —O-haloalkyl, wherein haloalkyl is as defined herein. Haloalkoxy includes, by way of example, chloromethoxy, trifluoromethoxy, bromoethoxy, chlorofluoroethoxy, and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term “alkynyl” refers to a monovalent group derived from a hydrocarbon moiety containing, in certain embodiments, from two to six, or two to eight carbon atoms having at least one carbon-carbon triple bond. The alkynyl group may or may not be the point of attachment to another group. The term “alkynyl” includes, but is not limited to, ethynyl, 1-propynyl, 1-butynyl, heptynyl, octynyl and the like.

As used herein, the term “halo” or “halogen” alone or as part of another substituent means, unless otherwise stated, a fluorine, chlorine, bromine, or iodine atom, preferably, fluorine, chlorine, or bromine, more preferably, fluorine or chlorine.

As used herein, the term “cycloalkyl” means a non-aromatic carbocyclic system that is fully saturated having 1, 2 or 3 rings wherein such rings may be fused. The term “fused” means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term “cycloalkyl” includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term “cycloalkenyl” means a non-aromatic carbocyclic system that is partially saturated having 1, 2 or 3 rings wherein such rings may be fused, and wherein at least one ring contains an $sp^2$ carbon-carbon bond. The term “cycloalkenyl” includes, but is not limited to, cyclopropenyl, cyclobutenyl, cyclopentenyl, cyclohexenyl, bicyclo[3.1.0]hexenyl, spiro[3.3]heptanenyl, and bicyclo[1.1.1]pentenyl.

As used herein, the term “heterocyclyl” or “heterocycloalkyl” means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term “heterocyclyl” includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo-[2.1.1]hexanyl, 5-azabicyclo[2.1.1]hexanyl, 6-azabicyclo[3.1.1]heptanyl, 2-azabicyclo[2.2.1]-heptanyl, 3-aza-bicyclo[3.1.1]heptanyl, 2-azabicyclo[3.1.1]heptanyl, 3-azabicyclo[3.1.0]-hexanyl, 2-azabicyclo-[3.1.0]hexanyl, 3-azabicyclo[3.2.1]octanyl, 8-azabicyclo[3.2.1]octanyl, 3-oxa-7-azabicyclo[3.3.1]-nonanyl, 3-oxa-9-azabicyclo[3.3.1]nonanyl, 2-oxa-5-azabicyclo-[2.2.1]heptanyl, 6-oxa-3-aza-bicyclo[3.1.1]heptanyl, 2-azaspiro[3.3]heptanyl, 2-oxa-6-azaspiro[3.3]heptanyl, 2-oxaspiro[3.3]-heptanyl, 2-oxaspiro[3.5]nonanyl, 3-oxaspiro[5.3]-nonanyl, and 8-oxabicyclo[3.2.1]octanyl.

As used herein, the term “aromatic” refers to a carbocycle or heterocycle with one or more polyunsaturated rings and having aromatic character, i.e., having (4n+2) delocalized π (pi) electrons, where n is an integer.

As used herein, the term “aryl” means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term “aryl” includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term “heteroaryl” means an aromatic carbocyclic system containing 1, 2, 3, or 4 heteroatoms selected independently from N, O, and S and having 1, 2, or 3 rings wherein such rings may be fused, wherein fused is defined above. The term “heteroaryl” includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term “pyridinyl” means 2-, 3- or 4-pyridinyl, the term “thienyl” means 2- or 3-thienyl, and so forth.

As used herein, the term “substituted” means that an atom or group of atoms has replaced hydrogen as the substituent attached to another group.

As used herein, the term “optionally substituted” means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

Provided herein are compounds that are allosteric inhibitors of epidermal growth factor receptor (EGFR) useful in the treatment of kinase-mediated disorders, including cancer and other proliferation diseases.

In an aspect, provided herein is a compound of Formula I:

(I)

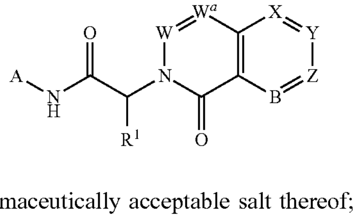

or a pharmaceutically acceptable salt thereof;

wherein:

A is a 6-10 membered aryl or a 5-10 membered heteroaryl;

W and $W^a$ are each, independently, CH, $CR^6$, or N;

X and B are each, independently, N, CH, CF, or C—($C_1$-$C_3$ alkyl);

Y and Z are each independently N, CH, or $CR^2$;

provided that at least one of X, Y, Z, or B is CH;

$R^1$ is phenyl or pyridinyl, wherein phenyl or pyridinyl is optionally substituted one or two times, independently, with $R^7$;

$R^2$ is independently, at each occurrence, selected from the group consisting of halo, 6-10 membered aryl, 5-6 membered heteroaryl, 3-6 membered cycloalkyl, 3-6 membered cycloalkenyl, 5-7 membered heterocycloalkyl, $OR^4$, $NR^4R^4$, $SO_2R^4$, $SO_2NHR^4$, $NHSO_2R^4$, C(O)$OR^4$, C(O)$NHR^4$, C(O)$R^4$, $C_1$-$C_6$ alkyl, $C_2$-$C_6$ alkenyl, $C_2$-$C_6$ alkynyl, wherein 6-10 membered aryl, 5-10 membered heteroaryl, and 3-6 membered cycloalkyl are optionally substituted with $R^3$, and wherein $C_1$-$C_6$ alkyl, $C_2$-$C_6$ alkenyl, or $C_2$-$C_6$ alkynyl are each optionally substituted one, two, or three times with $R^4$;

$R^3$ is selected from the group consisting of halo, —OH, —SH, —CN, —$NO_2$, —$NH_2$, and a 5-7 membered heterocycle, wherein the 5-7 membered heterocycle is optionally substituted with $C_1$-$C_4$ alkyl;

$R^4$ is independently, at each occurrence, selected from the group consisting of hydrogen, $(CH_2)_{0-3}$—($C_3$-$C_7$ cycloalkyl), $(CH_2)_{0-3}$—($C_4$-$C_7$ cycloalkenyl), $(CH_2)_{0-3}$—($C_6$-$C_{10}$ aryl), $(CH_2)_{0-3}$-(5- to 6-membered heteroaryl), or $(CH_2)_{0-3}$-(5- to 7-membered heterocycloalkyl), wherein the aryl, heteroaryl, or heterocycloalkyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, halo, COOH, C(O)O($C_1$-$C_6$ alkyl), $O(CH_2)_{1-3}OH$, $NH_2$, OH, CN, $(CH_2)_{0-3}$($C_6$-$C_{10}$ aryl), $(CH_2)_{0-3}$(5- to 6-membered heteroaryl), and $(CH_2)_{0-3}$(5- to 7-membered heterocycloalkyl), wherein $C_6$-$C_{10}$ aryl, 5- to 6-membered heteroaryl, and 5- to 7-membered heterocycloalkyl are optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halo, $NH_2$, NH($C_1$-$C_6$ alkyl), N($C_1$-$C_6$ alkyl)$_2$, $SO_2NH_2$, $(CH_2)_{1-2}OH$, C(O)$(CH_2)_{1-2}OH$, and C(O)O($C_1$-$C_6$ alkyl);

$R^6$ is independently, at each occurrence, $C_1$-$C_6$ alkyl or halo; and $R^7$ is independently, at each occurrence, $C_1$-$C_3$ alkyl, $C_1$-$C_3$ haloalkyl, $C_1$-$C_3$ alkoxy, $C_1$-$C_3$ haloalkoxy, halo, OH, SH, $NO_2$, $NH_2$, $(CH_2)_{1-4}OH$, $S(O)_{0-2}H$, $S(O)_{0-2}NH_2$, or CN.

In an embodiment, the compound of Formula I is a compound of Formula II:

(II)

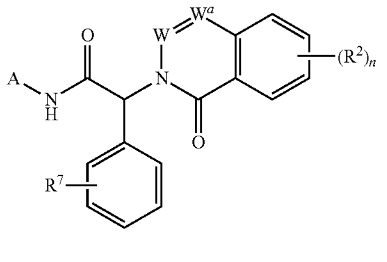

or a pharmaceutically acceptable salt thereof;

wherein:

A is a 6-10 membered aryl or a 5-10 membered heteroaryl;

Wand $W^a$ are each, independently, CH, $CR^6$, or N;

$R^2$ is selected from the group consisting of absent, halo, 6-10 membered aryl, 5-10 membered heteroaryl, and 3-6 membered cycloalkyl, wherein 6-10 membered aryl, 5-10 membered heteroaryl, and 3-6 membered cycloalkyl are optionally substituted with $R^3$;

$R^3$ is selected from the group consisting of halo, —OH, —SH, —CN, —$NO_2$, —$NH_2$, and a 5-7 membered heterocycle, wherein the 5-7 membered heterocycle is optionally substituted with $C_1$-$C_4$ alkyl;

$R^6$ is independently, at each occurrence, $C_1$-$C_6$ alkyl or halo;

$R^7$ is selected from the group consisting of absent, halo, —OH, —SH, —CN, —$NO_2$, and —$NH_2$; and n is 1 or 2.

In another embodiment, $R^7$ is absent. In yet another embodiment, $R^7$ is halo. In still another embodiment, $R^7$ is fluoro.

In an embodiment, A is 5-7 membered heteroaryl. In another embodiment, A is thiazole. In yet another embodiment, A is pyridine.

In still another embodiment, $R^2$ is selected from the group consisting of absent, halo, 6-10 membered aryl, 5-10 membered heteroaryl, and 3-6 membered cycloalkyl, wherein 6-10 membered aryl is optionally substituted with $R^4$. In an embodiment, $R^2$ is halo. In another embodiment, $R^2$ is bromo. In yet another embodiment, $R^2$ is fluoro. In still another embodiment, $R^2$ is phenyl further substituted with $R^3$. In an embodiment, $R^3$ is a 6-membered heterocycle optionally substituted with $C_1$-$C_4$ alkyl. In another embodiment, $R^3$ is piperidine further substituted with methyl. In still another embodiment, $R^3$ is piperazine further substituted with methyl. In an embodiment, $R^3$ is in the para position.

In another embodiment, the compound of Formula I is a compound of Formula III:

(III)

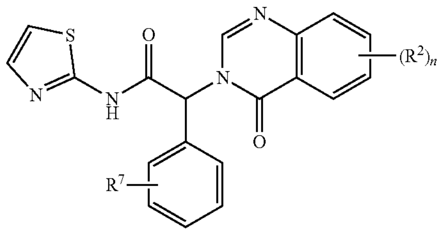

or a pharmaceutically acceptable salt thereof.

In yet another embodiment, the compound of Formula I is a compound of Formula V:

(V)

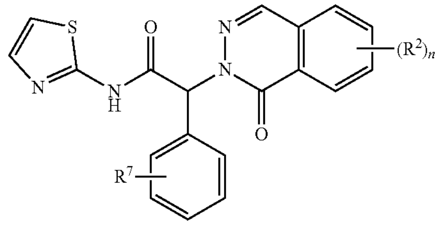

or a pharmaceutically acceptable salt thereof.

In still another embodiment, the compound of Formula I is a compound of Formula VI:

(VI)

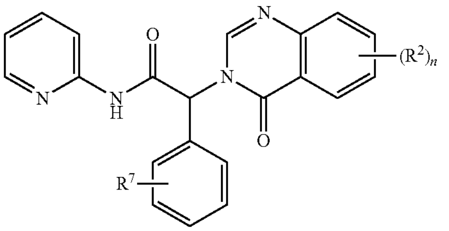

or a pharmaceutically acceptable salt thereof.

In an embodiment, the compound of Formula I is a compound of Formula VII:

(VII)

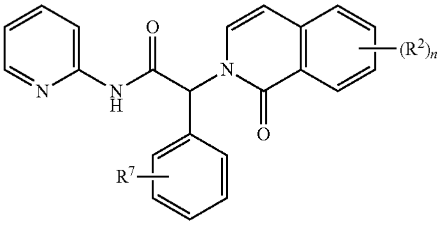

or a pharmaceutically acceptable salt thereof.

In another embodiment, the compound of Formula I is a compound of Formula VIII:

(VIII)

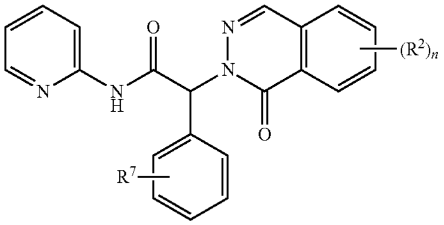

or a pharmaceutically acceptable salt thereof.

In yet another embodiment, the compound of Formula I is selected from a compound, or pharmaceutically acceptable salt thereof, in Table 1

TABLE 1

| Compound No. | Structure |
|---|---|
| 001 | 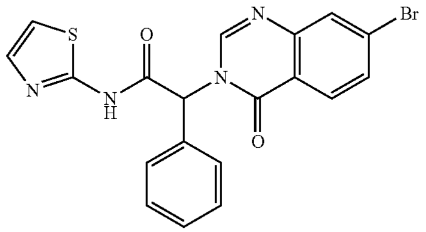 [SMILES: O=C(Nc1nccs1)C(c1ccccc1)n1cnc2cc(Br)ccc2c1=O] |
| 002 | 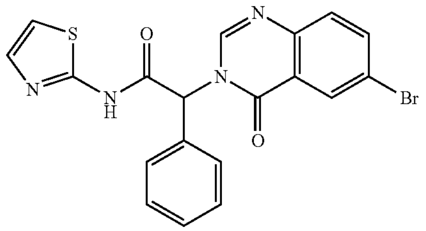 [SMILES: O=C(Nc1nccs1)C(c1ccccc1)n1cnc2ccc(Br)cc2c1=O] |
| 003 | 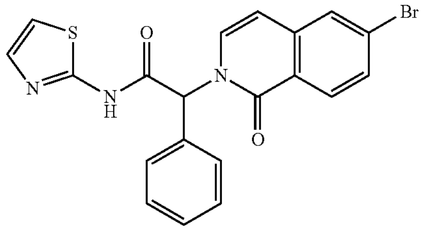 [SMILES: O=C(Nc1nccs1)C(c1ccccc1)n1ccc2cc(Br)ccc2c1=O] |

TABLE 1-continued
| Compound No. | Structure |
| --- | --- |
| 004 | 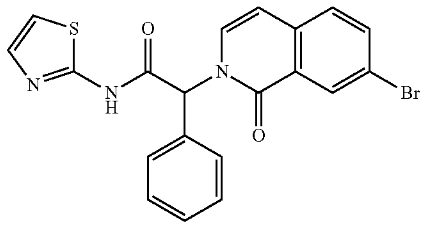 [SMILES: O=C(Nc1nccs1)C(c1ccccc1)n1ccc2ccc(Br)cc2c1=O] |
| 005 | 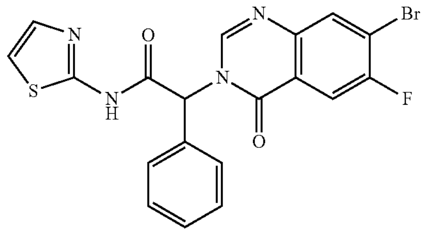 [SMILES: O=C(Nc1nccs1)C(c1ccccc1)n1cnc2cc(Br)c(F)cc2c1=O] |
| 006 | 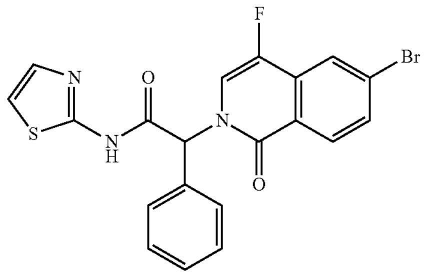 [SMILES: O=C(Nc1nccs1)C(c1ccccc1)n1cc(F)c2cc(Br)ccc2c1=O] |
| 007 | 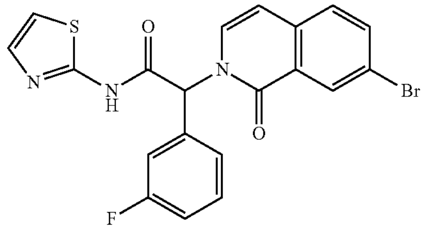 [SMILES: O=C(Nc1nccs1)C(c1cccc(F)c1)n1ccc2ccc(Br)cc2c1=O] |
| 008 | 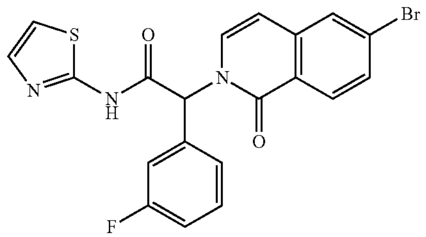 [SMILES: O=C(Nc1nccs1)C(c1cccc(F)c1)n1ccc2cc(Br)ccc2c1=O] |
| 009 | 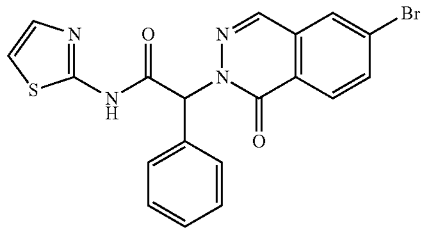 [SMILES: O=C(Nc1nccs1)C(c1ccccc1)n1ncc2cc(Br)ccc2c1=O] |

TABLE 1-continued
| Compound No. | Structure |
| --- | --- |
| 010 | 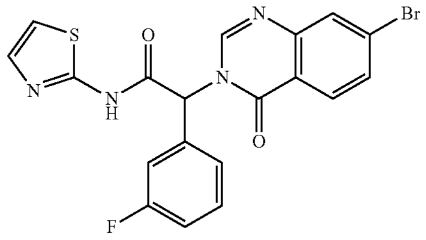 [SMILES: O=C(Nc1nccs1)C(c1cccc(F)c1)n1cnc2cc(Br)ccc2c1=O] |
| 011 | 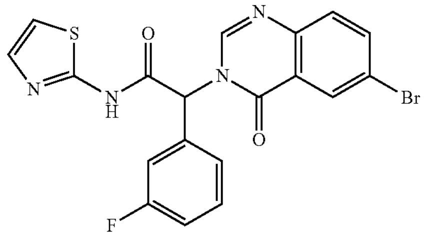 [SMILES: O=C(Nc1nccs1)C(c1cccc(F)c1)n1cnc2ccc(Br)cc2c1=O] |
| 012 | 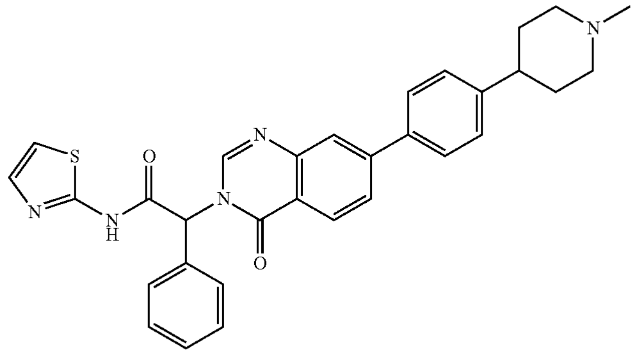 [SMILES: CN1CCC(c2ccc(-c3ccc4c(=O)n(C(C(=O)Nc5nccs5)c5ccccc5)cnc4c3)cc2)CC1] |
| 013 | 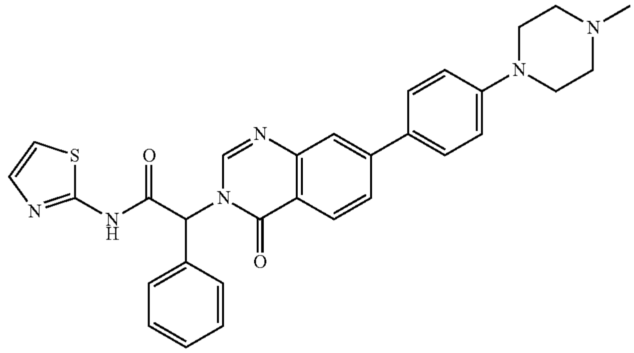 |
| 014 | 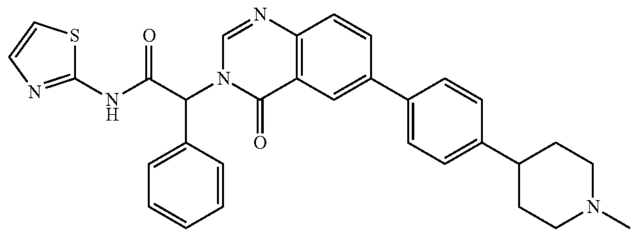 |

TABLE 1-continued
| Compound No. | Structure |
| --- | --- |
| 015 | 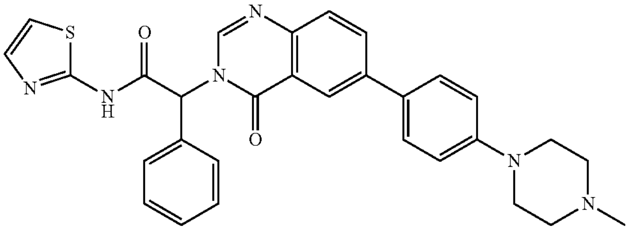 [SMILES: CN1CCN(c2ccc(-c3ccc4ncn(C(C(=O)Nc5nccs5)c5ccccc5)c(=O)c4c3)cc2)CC1] |
| 016 | 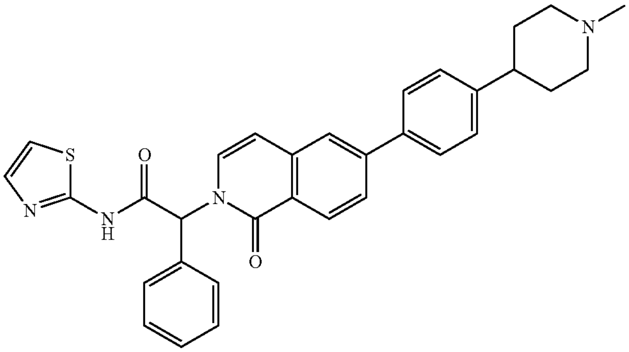 [SMILES: CN1CCC(c2ccc(-c3ccc4c(=O)n(C(C(=O)Nc5nccs5)c5ccccc5)ccc4c3)cc2)CC1] |
| 017 | 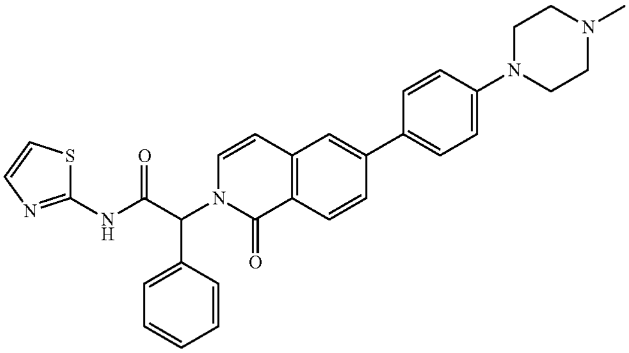 [SMILES: CN1CCN(c2ccc(-c3ccc4c(=O)n(C(C(=O)Nc5nccs5)c5ccccc5)ccc4c3)cc2)CC1] |
| 018 | 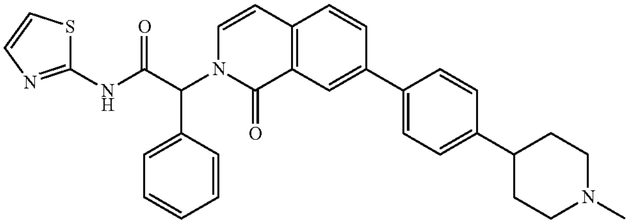 |
| 019 | 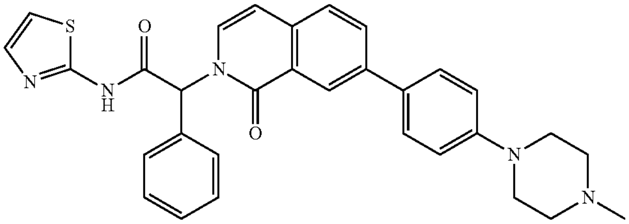 [SMILES: CN1CCN(c2ccc(-c3ccc4ccn(C(C(=O)Nc5nccs5)c5ccccc5)c(=O)c4c3)cc2)CC1] |

TABLE 1-continued
| Compound No. | Structure |
|---|---|
| 020 | 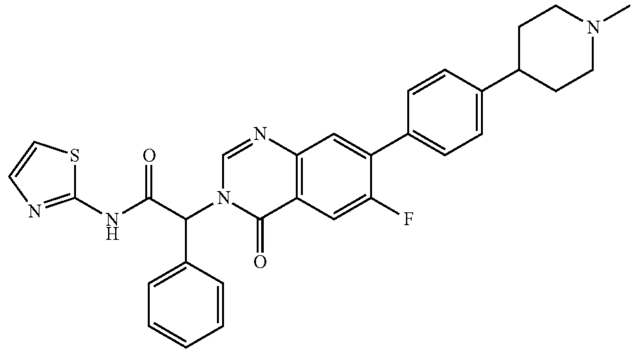 |
| 021 | 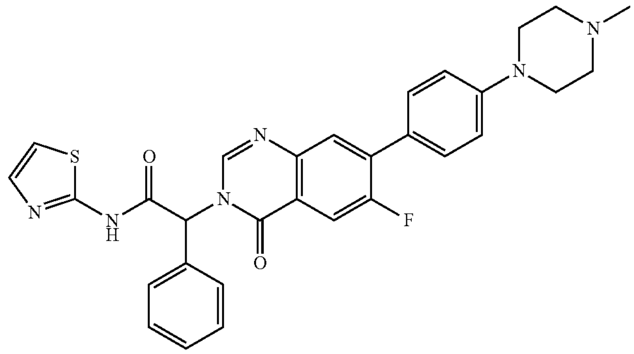 [SMILES: CN1CCN(c2ccc(-c3cc4ncn(C(C(=O)Nc5nccs5)c5ccccc5)c(=O)c4cc3F)cc2)CC1] |
| 022 | 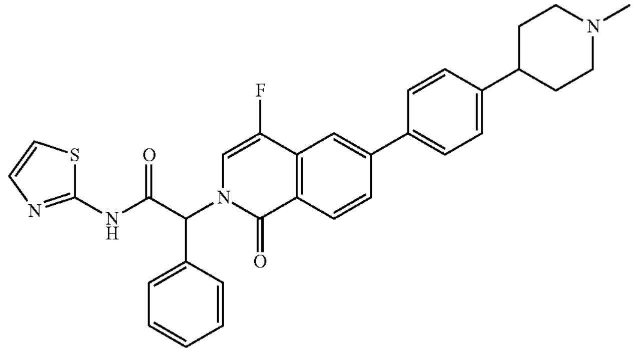 [SMILES: CN1CCC(c2ccc(-c3ccc4c(=O)n(C(C(=O)Nc5nccs5)c5ccccc5)cc(F)c4c3)cc2)CC1] |
| 023 | 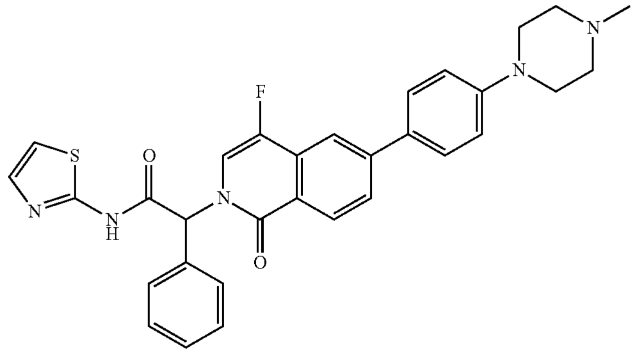 [SMILES: CN1CCN(c2ccc(-c3ccc4c(=O)n(C(C(=O)Nc5nccs5)c5ccccc5)cc(F)c4c3)cc2)CC1] |

TABLE 1-continued
| Compound No. | Structure |
|---|---|
| 024 | 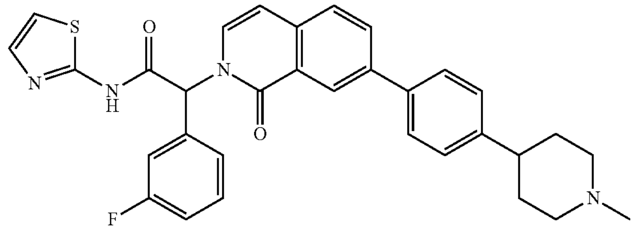 [SMILES: CN1CCC(c2ccc(-c3ccc4ccn(C(C(=O)Nc5nccs5)c5cccc(F)c5)c(=O)c4c3)cc2)CC1] |
| 025 | 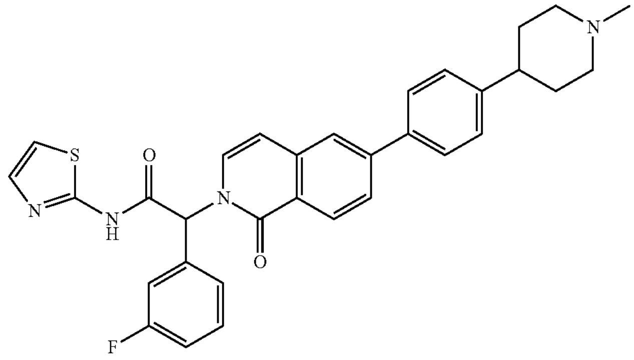 [SMILES: CN1CCC(c2ccc(-c3ccc4c(=O)n(C(C(=O)Nc5nccs5)c5cccc(F)c5)ccc4c3)cc2)CC1] |
| 026 | 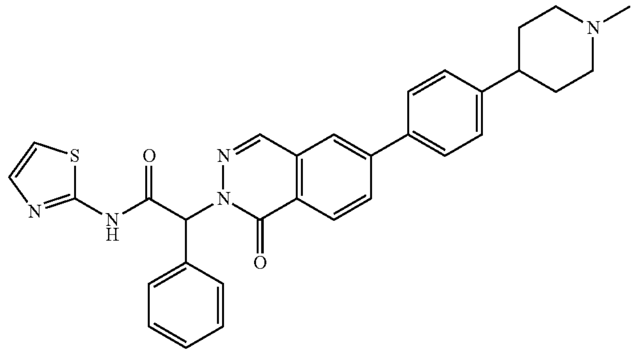 [SMILES: CN1CCC(c2ccc(-c3ccc4c(=O)n(C(C(=O)Nc5nccs5)c5ccccc5)ncc4c3)cc2)CC1] |
| 027 | 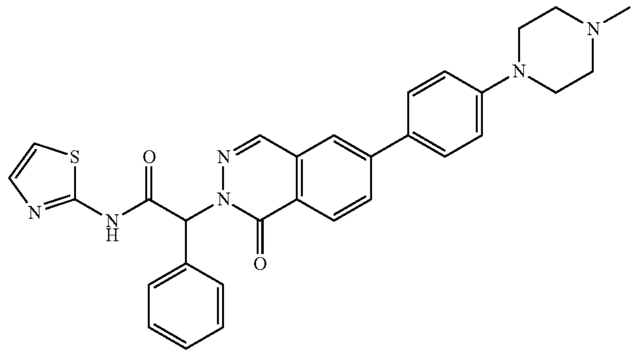 |

TABLE 1-continued
| Compound No. | Structure |
| --- | --- |
| 028 | 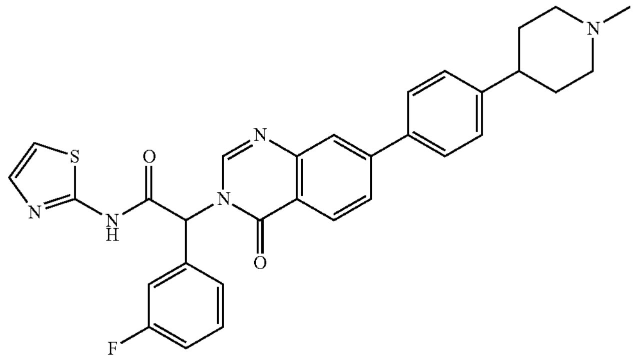 [SMILES: CN1CCN(c2ccc(-c3ccc4c(=O)n(C(C(=O)Nc5nccs5)c5cccc(F)c5)cnc4c3)cc2)CC1] |
| 029 | 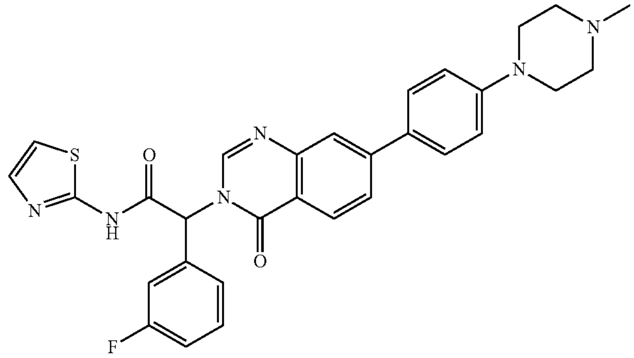 |
| 030 | 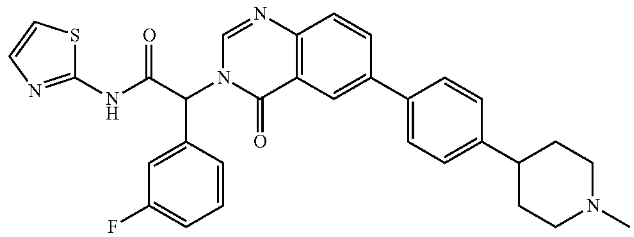 |
| 031 | 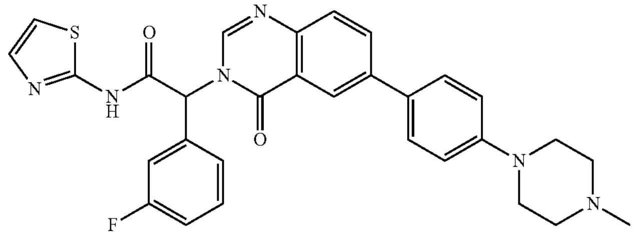 [SMILES: CN1CCN(c2ccc(-c3ccc4ncn(C(C(=O)Nc5nccs5)c5cccc(F)c5)c(=O)c4c3)cc2)CC1] |
| 032 | 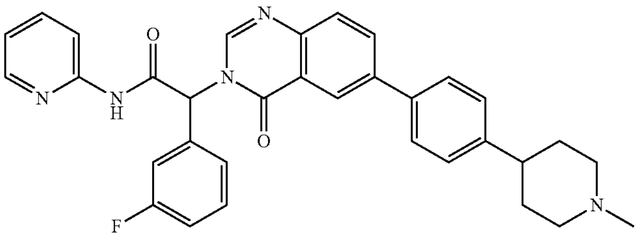 [SMILES: CN1CCC(c2ccc(-c3ccc4ncn(C(C(=O)Nc5ccccn5)c5cccc(F)c5)c(=O)c4c3)cc2)CC1] |

TABLE 1-continued
| Compound No. | Structure |
|---|---|
| 033 | 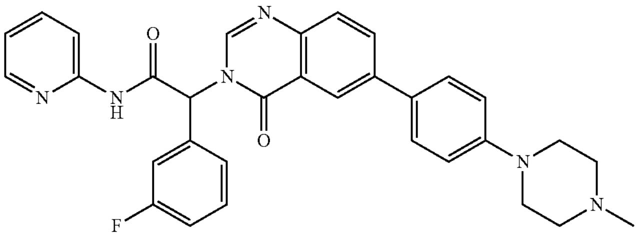 [SMILES: CN1CCN(c2ccc(-c3ccc4ncn(C(C(=O)Nc5ccccn5)c5cccc(F)c5)c(=O)c4c3)cc2)CC1] |
| 034 | 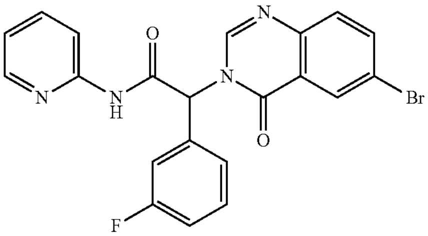 [SMILES: O=C(Nc1ccccn1)C(c1cccc(F)c1)n1cnc2ccc(Br)cc2c1=O] |
| 035 | 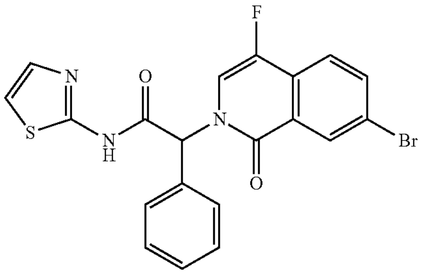 [SMILES: O=C(Nc1nccs1)C(c1ccccc1)n1cc(F)c2ccc(Br)cc2c1=O] |
| 036 | 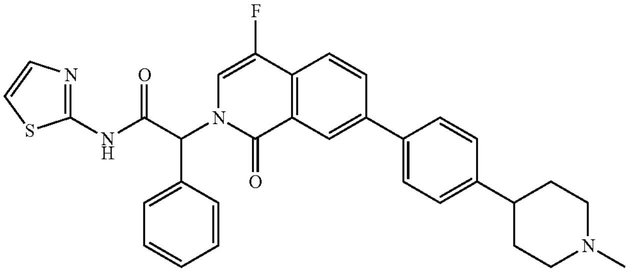 |
| 037 | 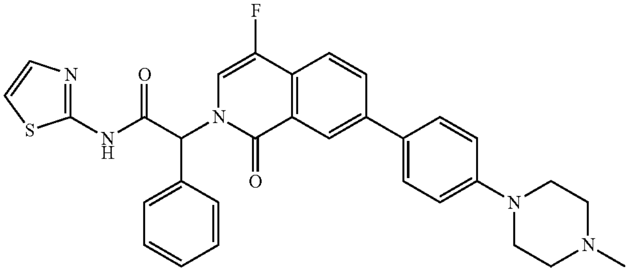 [SMILES: CN1CCN(c2ccc(-c3ccc4c(F)cn(C(C(=O)Nc5nccs5)c5ccccc5)c(=O)c4c3)cc2)CC1] |
| 038 | 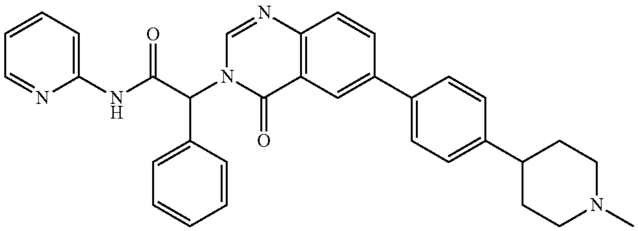 [SMILES: CN1CCC(c2ccc(-c3ccc4ncn(C(C(=O)Nc5ccccn5)c5ccccc5)c(=O)c4c3)cc2)CC1] |

TABLE 1-continued
| Compound No. | Structure |
|---|---|
| 039 | 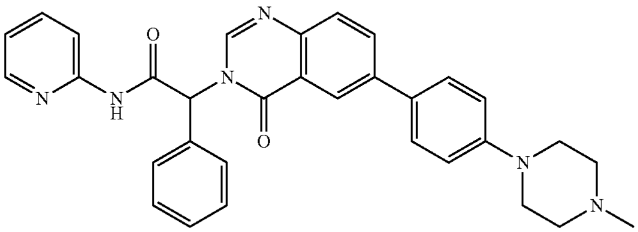 [SMILES: CN1CCN(c2ccc(-c3ccc4ncn(C(C(=O)Nc5ccccn5)c5ccccc5)c(=O)c4c3)cc2)CC1] |
| 040 | 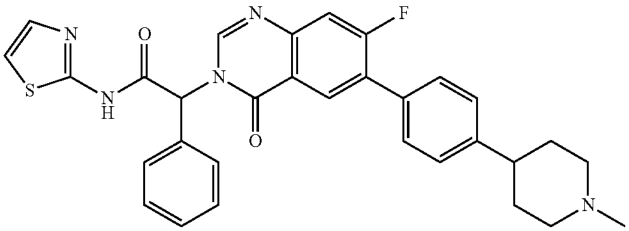 [SMILES: CN1CCC(c2ccc(-c3cc4c(=O)n(C(C(=O)Nc5nccs5)c5ccccc5)cnc4cc3F)cc2)CC1] |
| 041 | 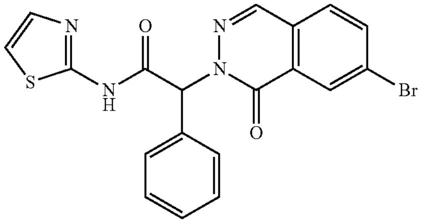 [SMILES: O=C(Nc1nccs1)C(c1ccccc1)n1ncc2ccc(Br)cc2c1=O] |
| 042 | 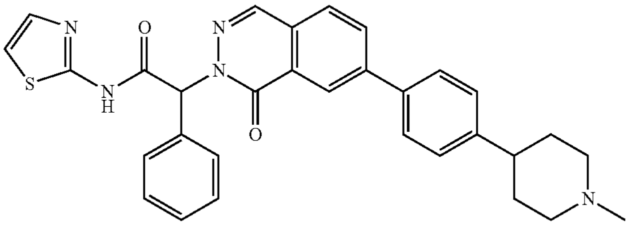 [SMILES: CN1CCC(c2ccc(-c3ccc4cnn(C(C(=O)Nc5nccs5)c5ccccc5)c(=O)c4c3)cc2)CC1] |
| 043 | 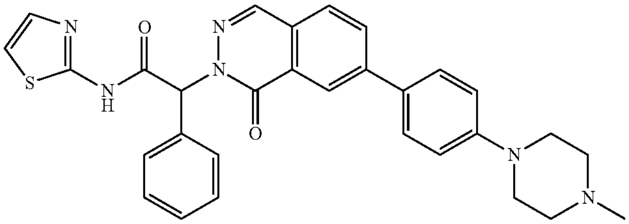 [SMILES: CN1CCN(c2ccc(-c3ccc4cnn(C(C(=O)Nc5nccs5)c5ccccc5)c(=O)c4c3)cc2)CC1] |
| 044 | 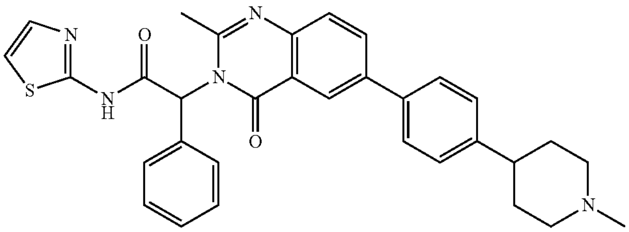 [SMILES: Cc1nc2ccc(-c3ccc(N4CCN(C)CC4)cc3)cc2c(=O)n1C(C(=O)Nc1nccs1)c1ccccc1] |

TABLE 1-continued
| Compound No. | Structure |
|---|---|
| 045 | 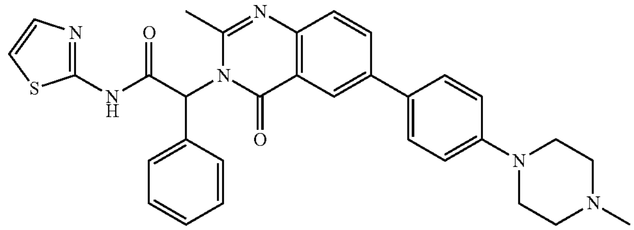 |
| 046 | 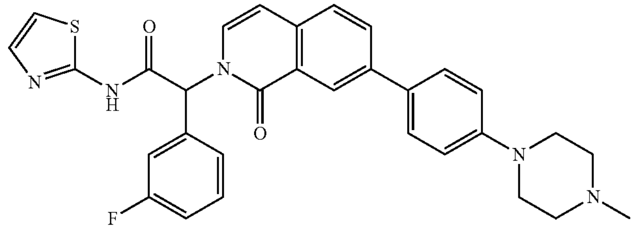 [SMILES: CN1CCN(c2ccc(-c3ccc4ccn(C(C(=O)Nc5nccs5)c5cccc(F)c5)c(=O)c4c3)cc2)CC1] |
| 047 | 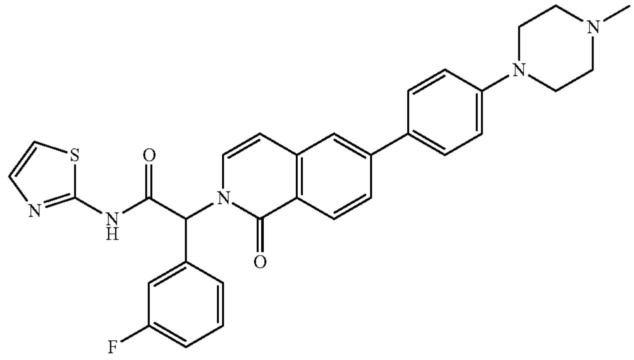 [SMILES: CN1CCN(c2ccc(-c3ccc4c(=O)n(C(C(=O)Nc5nccs5)c5cccc(F)c5)ccc4c3)cc2)CC1] |
| 048 | 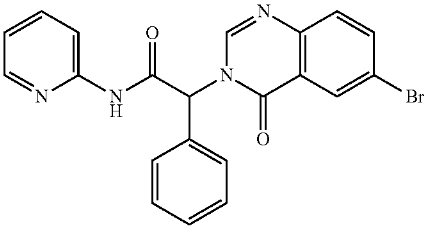 [SMILES: O=C(Nc1ccccn1)C(c1ccccc1)n1cnc2ccc(Br)cc2c1=O] |
| 049 | 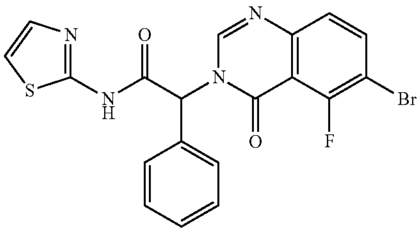 [SMILES: O=C(Nc1nccs1)C(c1ccccc1)n1cnc2ccc(Br)c(F)c2c1=O] |
| 050 | 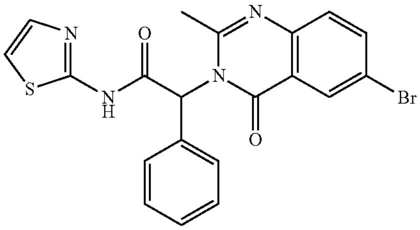 [SMILES: Cc1nc2ccc(Br)cc2c(=O)n1C(C(=O)Nc1nccs1)c1ccccc1] |

TABLE 1-continued
| Compound No. | Structure |
| --- | --- |
| 051 | 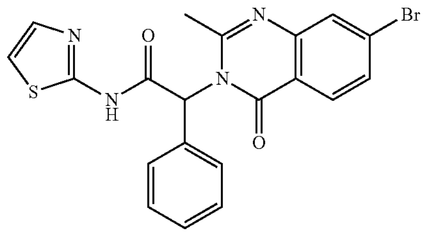 [SMILES: Cc1nc2cc(Br)ccc2c(=O)n1C(C(=O)Nc1nccs1)c1ccccc1] |
| 052 | 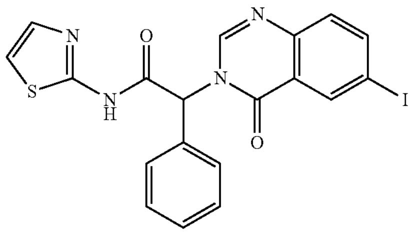 [SMILES: O=C(Nc1nccs1)C(c1ccccc1)n1cnc2ccc(I)cc2c1=O] |
| 053 | 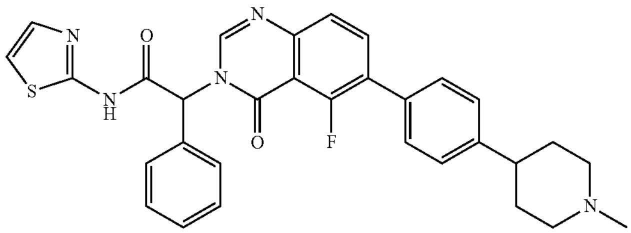 [SMILES: CN1CCC(c2ccc(-c3ccc4ncn(C(C(=O)Nc5nccs5)c5ccccc5)c(=O)c4c3F)cc2)CC1] |
| 054 | 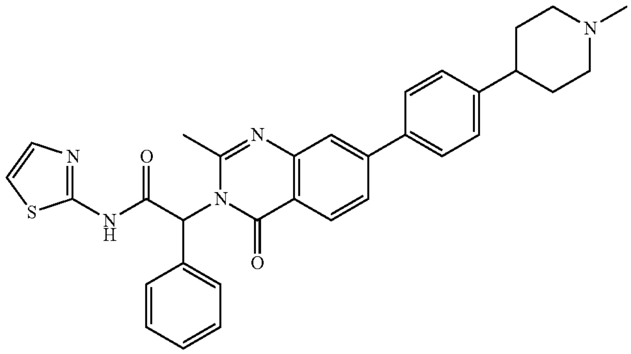 [SMILES: Cc1nc2cc(-c3ccc(C4CCN(C)CC4)cc3)ccc2c(=O)n1C(C(=O)Nc1nccs1)c1ccccc1] |
| 055 | 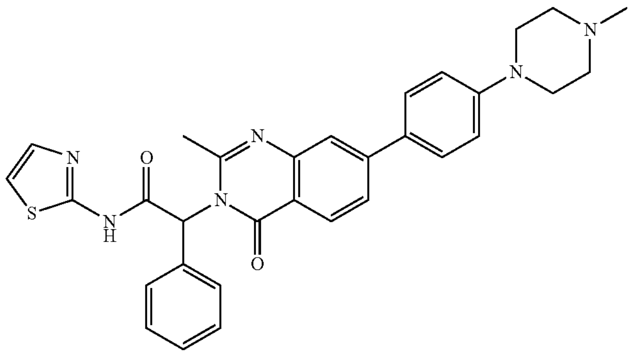 [SMILES: Cc1nc2cc(-c3ccc(N4CCN(C)CC4)cc3)ccc2c(=O)n1C(C(=O)Nc1nccs1)c1ccccc1] |

TABLE 1-continued
| Compound No. | Structure |
|---|---|
| 056 | 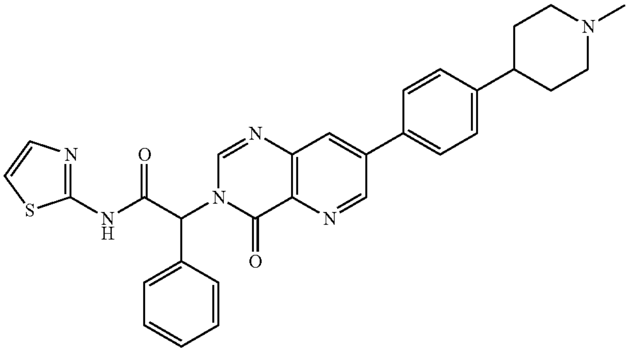 [SMILES: CN1CCC(c2ccc(-c3cnc4c(=O)n(C(C(=O)Nc5nccs5)c5ccccc5)cnc4c3)cc2)CC1] |
| 057 | 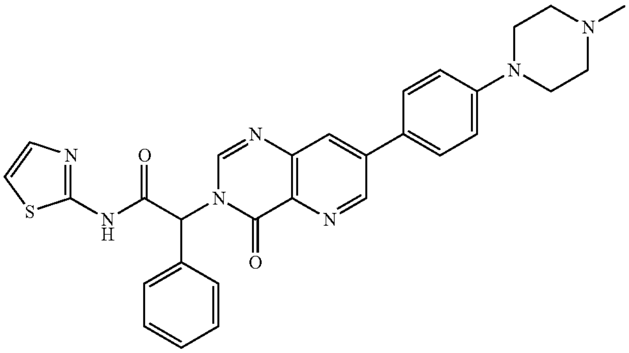 |
| 058 | 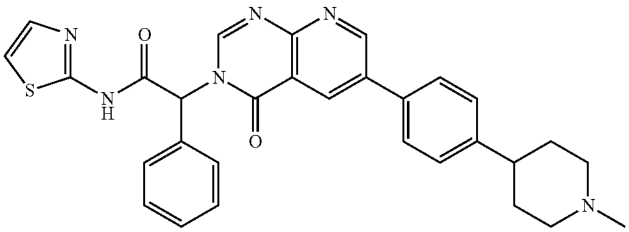 [SMILES: CN1CCC(c2ccc(-c3cnc4ncn(C(C(=O)Nc5nccs5)c5ccccc5)c(=O)c4c3)cc2)CC1] |
| 059 | 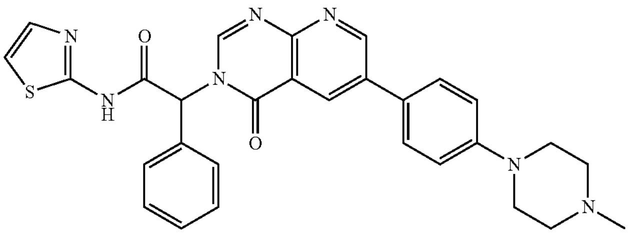 [SMILES: CN1CCN(c2ccc(-c3cnc4ncn(C(C(=O)Nc5nccs5)c5ccccc5)c(=O)c4c3)cc2)CC1] |
| 060 | 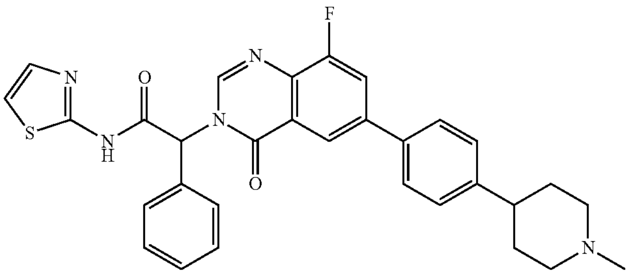 [SMILES: CN1CCC(c2ccc(-c3cc(F)c4ncn(C(C(=O)Nc5nccs5)c5ccccc5)c(=O)c4c3)cc2)CC1] |

TABLE 1-continued
| Compound No. | Structure |
| --- | --- |
| 061 | 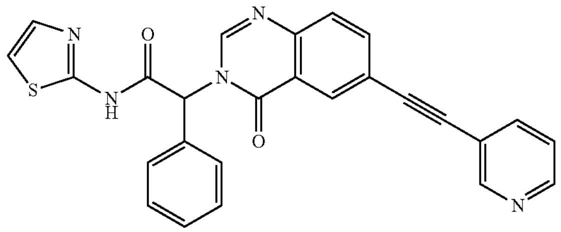 [SMILES: O=C(Nc1nccs1)C(c1ccccc1)n1cnc2ccc(C#Cc3cccnc3)cc2c1=O] |
| 062 | 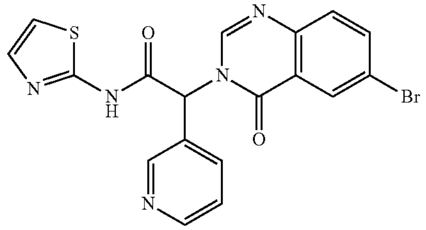 [SMILES: O=C(Nc1nccs1)C(c1cccnc1)n1cnc2ccc(Br)cc2c1=O] |
| 063 | 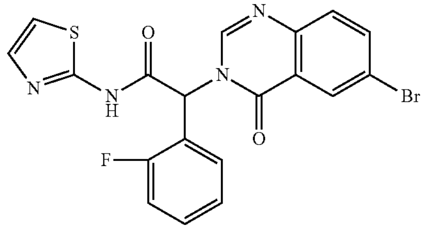 [SMILES: O=C(Nc1nccs1)C(c1ccccc1F)n1cnc2ccc(Br)cc2c1=O] |
| 064 | 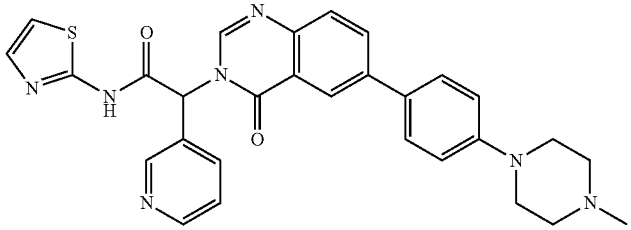 [SMILES: CN1CCN(c2ccc(-c3ccc4ncn(C(C(=O)Nc5nccs5)c5cccnc5)c(=O)c4c3)cc2)CC1] |
| 065 | 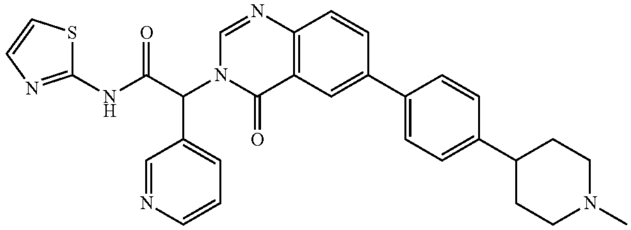 |
| 066 | 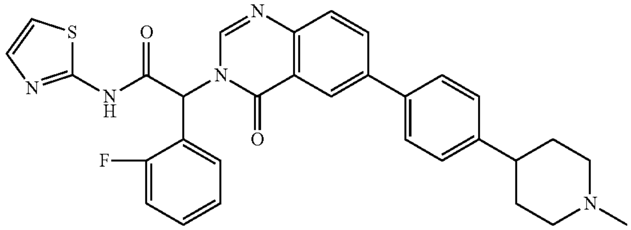 [SMILES: CN1CCC(c2ccc(-c3ccc4ncn(C(C(=O)Nc5nccs5)c5ccccc5F)c(=O)c4c3)cc2)CC1] |

TABLE 1-continued
| Compound No. | Structure |
|---|---|
| 067 | 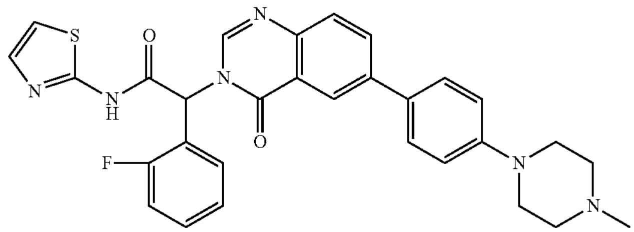 [SMILES: CN1CCN(c2ccc(-c3ccc4ncn(C(C(=O)Nc5nccs5)c5ccccc5F)c(=O)c4c3)cc2)CC1] |
| 068 | 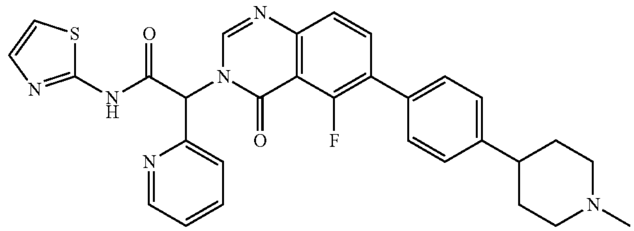 [SMILES: CN1CCC(c2ccc(-c3ccc4ncn(C(C(=O)Nc5nccs5)c5ccccn5)c(=O)c4c3F)cc2)CC1] |
| 069 | 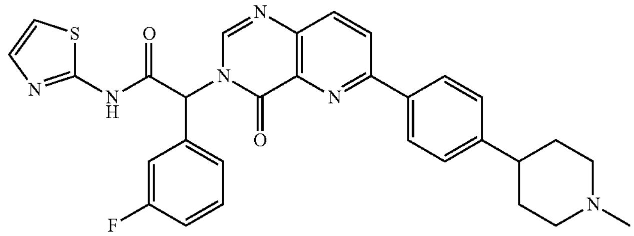 [SMILES: CN1CCC(c2ccc(-c3ccc4ncn(C(C(=O)Nc5nccs5)c5cccc(F)c5)c(=O)c4n3)cc2)CC1] |
| 070 | 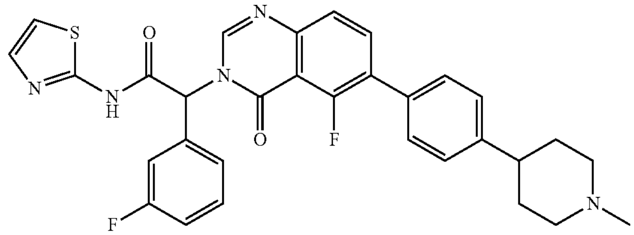 [SMILES: CN1CCC(c2ccc(-c3ccc4ncn(C(C(=O)Nc5nccs5)c5cccc(F)c5)c(=O)c4c3F)cc2)CC1] |
| 071 | 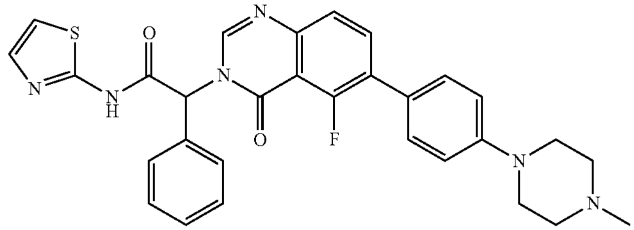 [SMILES: CN1CCN(c2ccc(-c3ccc4ncn(C(C(=O)Nc5nccs5)c5ccccc5)c(=O)c4c3F)cc2)CC1] |
| 072 | 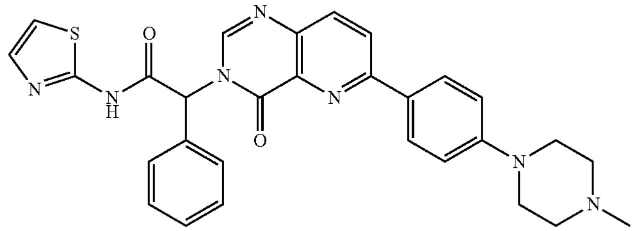 |

TABLE 1-continued
| Compound No. | Structure |
|---|---|
| 073 | 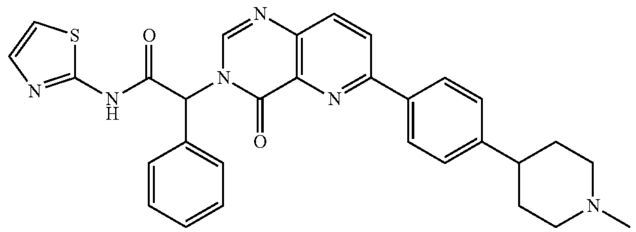 [SMILES: CN1CCC(c2ccc(-c3ccc4ncn(C(C(=O)Nc5nccs5)c5ccccc5)c(=O)c4n3)cc2)CC1] |
| 074 | 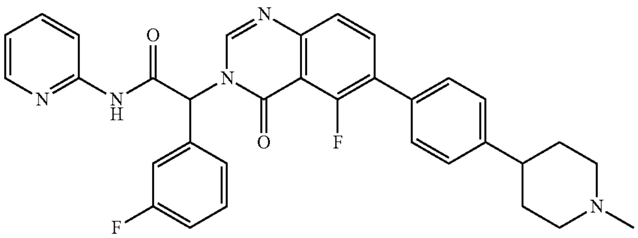 [SMILES: CN1CCC(c2ccc(-c3ccc4ncn(C(C(=O)Nc5ccccn5)c5cccc(F)c5)c(=O)c4c3F)cc2)CC1] |
| 075 | 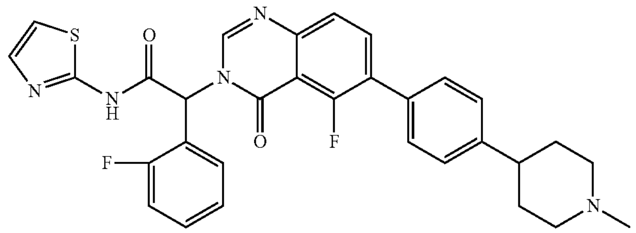 [SMILES: CN1CCC(c2ccc(-c3ccc4ncn(C(C(=O)Nc5nccs5)c5ccccc5F)c(=O)c4c3F)cc2)CC1] |
| 076 | 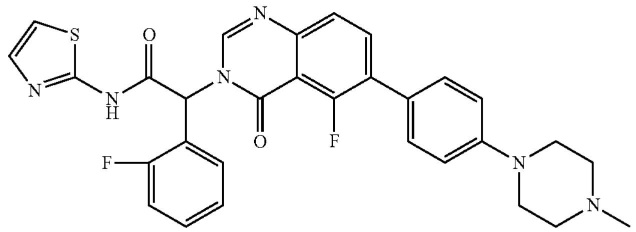 [SMILES: CN1CCN(c2ccc(-c3ccc4ncn(C(C(=O)Nc5nccs5)c5ccccc5F)c(=O)c4c3F)cc2)CC1] |
| 077 | 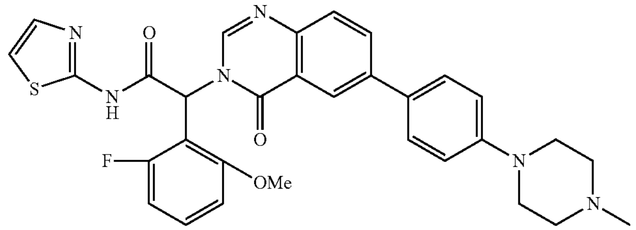 [SMILES: COc1cccc(F)c1C(C(=O)Nc1nccs1)n1cnc2ccc(-c3ccc(N4CCN(C)CC4)cc3)cc2c1=O] |
| 078 | 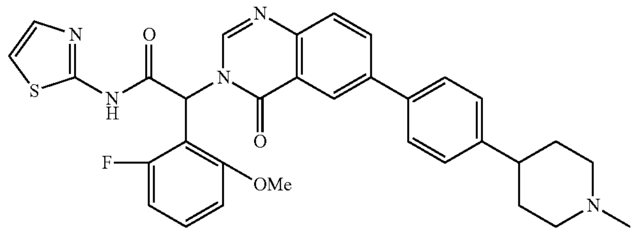 [SMILES: COc1cccc(F)c1C(C(=O)Nc1nccs1)n1cnc2ccc(-c3ccc(C4CCN(C)CC4)cc3)cc2c1=O] |

TABLE 1-continued
| Compound No. | Structure |
| --- | --- |
| 079 | 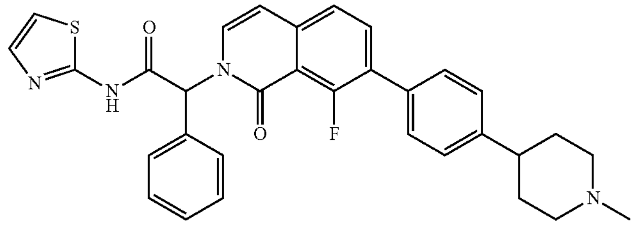 [SMILES: CN1CCC(c2ccc(-c3ccc4ccn(C(C(=O)Nc5nccs5)c5ccccc5)c(=O)c4c3F)cc2)CC1] |
| 080 | 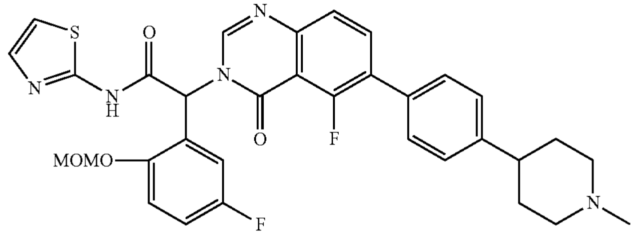 |
| 081 | 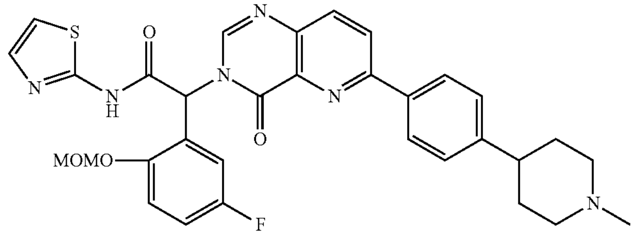 |
| 082 | 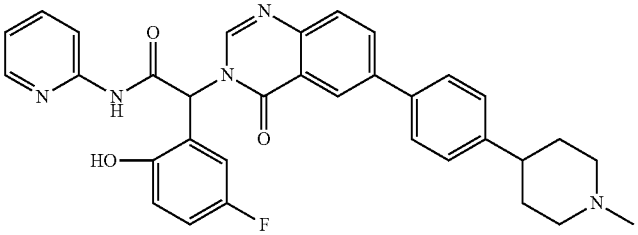 [SMILES: CN1CCC(c2ccc(-c3ccc4ncn(C(C(=O)Nc5ccccn5)c5cc(F)ccc5O)c(=O)c4c3)cc2)CC1] |
| 083 | 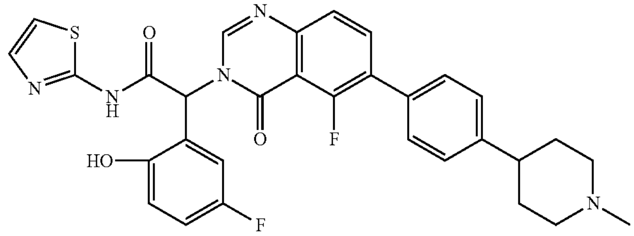 [SMILES: CN1CCC(c2ccc(-c3ccc4ncn(C(C(=O)Nc5nccs5)c5cc(F)ccc5O)c(=O)c4c3F)cc2)CC1] |
| 084 | 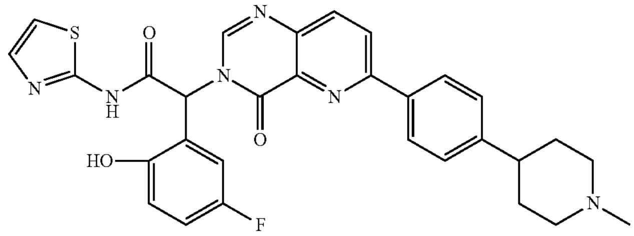 [SMILES: CN1CCC(c2ccc(-c3ccc4ncn(C(C(=O)Nc5nccs5)c5cc(F)ccc5O)c(=O)c4n3)cc2)CC1] |

TABLE 1-continued

| Compound No. | Structure |
|---|---|
| 085 | 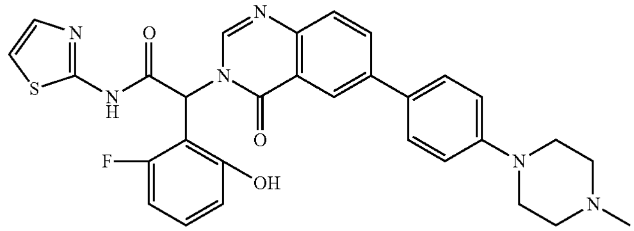 [SMILES: CN1CCN(c2ccc(-c3ccc4ncn(C(C(=O)Nc5nccs5)c5c(O)cccc5F)c(=O)c4c3)cc2)CC1] |
| 086 | 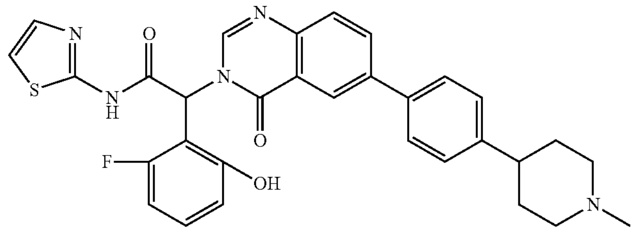 [SMILES: CN1CCC(c2ccc(-c3ccc4ncn(C(C(=O)Nc5nccs5)c5c(O)cccc5F)c(=O)c4c3)cc2)CC1] |

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound of Formulae I-VIII is a prodrug within the scope of the present disclosure.

Provided herein are compounds and compositions with improved pharmacokinetic profiles relative to known EGFR inhibitors, specifically with respect to lipophilicity.

In another aspect, provided herein are pharmaceutical compositions comprising a compound of the present disclosure, or a pharmaceutically acceptable salt thereof, and a pharmaceutically acceptable carrier. In another aspect, the pharmaceutical composition further comprises a second active agent, wherein said second active agent prevents EGFR dimer formation, and a pharmaceutically acceptable carrier. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

A compound that binds to an allosteric site in EGFR, such as the compounds of the present disclosure (e.g., the compounds of the formulae disclosed herein), optionally in combination with a second active agent, wherein said second active agent prevents EGFR dimer formation, are capable of modulating EGFR activity. In some embodiments, the compounds of the present disclosure are capable of inhibiting or decreasing EGFR activity without a second active agent (e.g., an antibody such as cetuximab, trastuzumab, or panitumumab). In other embodiments, the compounds of the present disclosure in combination with a second active agent. In an embodiment, the second active agent prevents EGFR dimer formation and/or are capable of inhibiting or decreasing EGFR activity. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

Methods of Treatment

In an aspect, provided herein is a method of treating cancer in an individual in need thereof, comprising administering to the individual a therapeutically effective amount of a compound of Formula I. In an embodiment, the cancer is selected from the group consisting of lung cancer, colon cancer, breast cancer, endometrial cancer, thyroid cancer, glioma, squamous cell carcinoma, and prostate cancer. In another embodiment, the cancer is non-small cell lung cancer (NSCLC).

In another aspect, provided herein is a method of inhibiting a kinase in an individual in need thereof, comprising administering to the individual a therapeutically effective amount of a compound of Formula I. In an embodiment, the kinase is EGFR.

In yet another aspect, provided herein is a method of treating or preventing a kinase-mediated disorder in an individual in need thereof, comprising administering to the individual a therapeutically effective amount of a compound of Formula I. In an embodiment, the kinase-mediated disorder is resistant to an EGFR-targeted therapy. In another embodiment, the EGFR-treated therapy is selected from the group consisting of gefitinib, erlotinib, osimertinib, CO-1686, and WZ4002.

In some embodiments, the compounds of the present disclosure are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/

T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M.

In some embodiments, the compounds of the present disclosure in combination with a second active agent, wherein said second active agent prevents EGFR dimer formation, are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, C797S, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/C797S, L858R/T790M/C797S, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/C797S, Del/T790M, Del/T790M/C797S, and L858R/T790M. In other embodiments, the mutant EGFR contains a combination of mutations, wherein the combination is selected from L858R/T790M, L858R/T790M/I941R, L858R/T790M/C797S, Del/T790M, Del/T790M/C797S, and L858R/T790M. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the compounds of the present disclosure are capable of modulating (e.g., inhibiting or decreasing) the activity of EGFR containing one or more mutations, but do not affect the activity of a wild-type EGFR.

In other embodiments, the compounds of the present disclosure in combination with a second active agent, wherein said second active agent prevents EGFR dimer formation, are capable of modulating (e.g., inhibiting or decreasing) the activity of EGFR containing one or more mutations, but do not affect the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

Modulation of EGFR containing one or more mutations, such as those described herein, but not a wild-type EGFR, provides an approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of EGFR containing one or more mutations as described herein relative to a wild-type EGFR. In certain embodiments, the compounds of the disclosure exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure exhibit up to 1000-fold greater inhibition of EGFR containing one or more mutations as described herein relative to a wild-type EGFR. In various embodiments, the compounds of the disclosure exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR.

In other embodiments, the compounds of the disclosure in combination with a second active agent, wherein said second active agent prevents EGFR dimer formation, exhibit greater inhibition of EGFR containing one or more mutations as described herein relative to a wild-type EGFR. In certain embodiments, the compounds of the disclosure in combination with a second active agent, wherein said second active agent prevents EGFR dimer formation, exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure in combination with a second active agent, wherein said second active agent prevents EGFR dimer formation, exhibit up to 1000-fold greater inhibition of EGFR containing one or more mutations as described herein relative to a wild-type EGFR. In various embodiments, the compounds of the disclosure in combination with a second active agent, wherein said second active agent prevents EGFR dimer formation, exhibit up to 10000-fold greater inhibition of EGFR having a combination of mutations described herein (e.g., L858R/T790M, L858R/T790M/I941R, L858R/T790M/C797S, Del/T790M, Del/T790M/C797S, and L858R/T790M) relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the compounds of the disclosure exhibit from about 2-fold to about 10-fold greater inhibition of EGFR containing one or more mutations as described herein relative to a wild-type EGFR. In various embodiments, the compounds of the disclosure exhibit from about 10-fold to about 100-fold greater inhibition of EGFR containing one or more mutations as described herein relative to a wild-type EGFR. In various embodiments, the compounds of the disclosure exhibit from about 100-fold to about 1000-fold greater inhibition of EGFR containing one or more mutations as described herein relative to a wild-type EGFR. In various embodiments, the compounds of the disclosure exhibit from about 1000-fold to about 10000-fold greater inhibition of EGFR containing one or more mutations as described herein relative to a wild-type EGFR.

In other embodiments, the compounds of the disclosure in combination with a second active agent, wherein said second active agent prevents EGFR dimer formation, exhibit from about 2-fold to about 10-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 10-fold to about 100-fold greater inhibition of EGFR containing one or more mutations as described herein relative to a wild-type EGFR. In other embodiments, the compounds of the disclosure in combination with a second active agent wherein said second active agent prevents EGFR dimer formation exhibit from about 100-fold to about 1000-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 1000-fold to about 10000-fold greater inhibition of EGFR containing one or more mutations as described herein relative to a wild-type EGFR. In other embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In certain embodiments, the compounds of the disclosure exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure exhibit at least 50-fold greater inhibition of EGFR having a combination of mutations selected from L L858R/T790M, L858R/T790M/I941R, L858R/T790/C797S, Del/T790M, Del/T790M/C797S, and L858R/T790M relative to a wild-type EGFR. In certain embodiments, the compounds of the disclosure exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR.

In certain embodiments, the compounds of the disclosure in combination with a second active agent, wherein said second active agent prevents EGFR dimer formation, exhibit at least 2-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 3-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 5-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 10-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 25-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 50-fold greater inhibition of EGFR having a combination of mutations selected from L L858R/T790M, L858R/T790M/I941R, L858R/T790M/C797S, Del/T790M, Del/T790M/C797S, and L858R/T790M relative to a wild-type EGFR. In certain embodiments, the compounds of the disclosure in combination with a second active agent, wherein said second active agent prevents EGFR dimer formation, exhibit at least 100-fold greater inhibition of EGFR having a combination of mutations selected from L858R/T790M, L858R/T790M/I941R, L858R/T790M/C797S, Del/T790M, Del/T790M/C797S, and L858R/T790M relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the inhibition of EGFR activity is measured by $IC_{50}$.

In some embodiments, the inhibition of EGFR activity is measured by $EC_{50}$.

In some embodiments, the inhibition of EGFR by a compound of the disclosure can be measured via a biochemical assay. By illustrative and non-limiting example, a homogenous time-resolved fluorescence (HTRF) assay may be used to determine inhibition of EGFR activity using conditions and experimental parameters disclosed herein. The HTRF assay may, for example, employ concentrations of substrate (e.g., biotin-Lck-peptide substrate) of about 1 μM; concentrations of EGFR (mutant or WAT) from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM. In certain embodiments, a compound of the disclosure screened under the above conditions for inhibition of EGFR having a mutation or combination of mutations selected from L858R/T790M, L858R, and T790M may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM.

In some embodiments, the compounds of the disclosure bind to an allosteric site in EGFR. In some embodiments, the compounds of the disclosure interact with at least one amino acid residue of epidermal growth factor receptor (EGFR) selected from Lys745, Leu788, and Ala 743. In other embodiments, the compounds of the disclosure interact with at least one amino acid residue of epidermal growth factor receptor (EGFR) selected from Cys755, Leu777, Phe856, and Asp855. In other embodiments, the compounds of the disclosure interact with at least one amino acid residue of epidermal growth factor receptor (EGFR) selected from Met766, Ile759, Glu762, and Ala763. In other embodiments, the compounds of the disclosure interact with at least one amino acid residue of epidermal growth factor receptor (EGFR) selected from Lys745, Leu788, and Ala 743; at least one amino acid residue of epidermal growth factor receptor (EGFR) selected from Cys755, Leu777, Phe856, and Asp855; and at least one amino acid residue of epidermal growth factor receptor (EGFR) selected from Met766, Ile759, Glu762, and Ala763. In other embodiments, the compounds of the disclosure do not interact with any of the amino acid residues of epidermal growth factor receptor (EGFR) selected from Met793, Gly796, and Cys797.

In some embodiments, the disclosure provides a compound comprising an allosteric kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib.

In some embodiments, the drug-resistant EGFR mutant comprises a sensitizing mutation, such as Del and L858R.

In some embodiments, the disclosure provides a compound comprising an allosteric kinase inhibitor in combination with a second active agent, wherein said second active agent prevents EGFR dimer formation, wherein the compound is a more potent inhibitor of a drug-resistant EGFR mutant relative to a wild type EGFR. For example, the compound in combination with a second active agent, wherein said second active agent prevents EGFR dimer formation, can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib. In some embodiments, the drug-resistant EGFR mutant comprises a sensitizing mutation, such as Del and L858R. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disclosure provides a compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T790M, L7180, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In other embodiments, the disclosure provides a compound comprising an allosteric kinase inhibitor in combination with a second active agent, wherein said second active agent prevents EGFR dimer formation, wherein the compound in combination with the second active agent inhibits kinase activity of a drug-resistant EGFR mutant harboring a sensitizing mutation (e.g., Del and L858R) and a drug-resistance mutation (e.g., T790M, L718Q, C797S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disclosure provides a compound comprising an allosteric kinase inhibitor, wherein the compound is more potent than one or more known EGFR inhibitors, including but not limited to gefitinib, erlotinib, lapatinib, WZ4002, HKI-272, CL-387785, and osimertinib, at inhibiting the activity of EGFR containing one or more mutations as described herein, such as T790M, L718Q, L844V, L858R, C797S, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein.

In other embodiments, the disclosure provides a compound comprising an allosteric kinase inhibitor in combination with a second active agent, wherein said second active agent prevents EGFR dimer formation, wherein the compound in combination with the second active agent is more potent than one or more known EGFR inhibitors, including but not limited to gefitinib, erlotinib, lapatinib, WZ4002, HKI-272, CL-387785, and osimertinib, at inhibiting the activity of EGFR containing one or more mutations as described herein, such as T790M, L718Q, L844V, L858R, C797S, and Del. For example, the compound in combination with a second active agent, wherein said second active agent prevents EGFR dimer formation, can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disclosure provides a compound comprising an allosteric kinase inhibitor, wherein the compound is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR.

In other embodiments, the disclosure provides a compound comprising an allosteric kinase inhibitor in combination with a second active agent, wherein said second active agent prevents EGFR dimer formation, wherein the compound in combination with the second active agent is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound in combination with a second active agent, wherein said second active agent prevents EGFR dimer formation can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q, C797S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGFR (such as VIII; containing a WT EGFR kinase domain), or Ba/F3 cells transfected with L858R/T790M, Del/T790M/L718Q, L858R/T790M/L718Q, L858R/T790M/C797S, Del/T790M/C797S, L858R/T790M/I941R, or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, I nM) and an $EC_{50}$ is calculated.

An alternative method to measure effects on EGFR activity is to assay EGFR phosphorylation. Wild type or mutant (L858R/T790M, Del/T790M, Del/T790M/L718Q, L858R/T790M/C797S, Del/T790M/C797S, L858R/T790M/I941R, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, the present disclosure relates to a compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, L858R/T790M/C797S, Del/T790M/C797S, L858R/T790M/I941R, or L858R/T790M/L718Q) relative to a wild-type EGFR.

In other embodiments, the disclosure provides a compound that binds to an allosteric site in EGFR in combination with a second active agent, wherein said second active agent prevents EGFR dimer formation, wherein the compound in combination with the second active agent greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, Del/T790M/C797S, L858R/T790M/C797S, L858R/T790M/I941R, or L858R/T790M/L718Q) relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In still another aspect, the disclosure provides a method of inhibiting epidermal growth factor receptor (EGFR), the method comprising administering to a subject in need thereof an effective amount of a compound of disclosed herein, or a pharmaceutically acceptable salt thereof. In some embodiments, the method further comprises administering a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In another aspect, provided herein is a method of treating or preventing a disease, the method comprising administering to a subject in need thereof an effective amount of a compound of disclosed herein, or a pharmaceutically acceptable salt thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Bilk, Bmx, Btk, HER2 (ErbB2), HER4 (ErbB4), Itk, Tec, and Txk. In some embodiments, the method further comprises administering a second active agent, wherein said second active agent prevents dimer formation of the kinase. In some embodiments, the second active agent that prevents kinase dimer formation is an antibody. In further embodiments, the second active agent prevents EGFR dimer formation. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disease is mediated by EGFR (e.g., EGFR plays a role in the initiation or development of the disease). In some embodiments, the disease is mediated by a Her-kinase. In further embodiments, the Her-kinase is HER1, HER2, or HER4.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In yet another aspect, provided herein is a method of treating a kinase-mediated disorder comprising administering to a subject in need thereof an effective amount of a compound disclosed herein, or a pharmaceutically acceptable salt thereof. In some embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, the disclosure provides a method of treating a kinase mediated disorder, the method comprising administering to a subject in need thereof an effective amount of a compound of disclosed herein, or a pharmaceutically acceptable salt thereof, and a second active agent, wherein said second active agent prevents EGFR dimer formation. In some embodiments, the compound is an inhibitor of HER1, HER2, or HER4. In other embodiments, the subject is administered an additional therapeutic agent. In other embodiments, the compound, the second active agent that prevents EGFR dimer formation, and the additional therapeutic agent are administered simultaneously or sequentially. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In certain embodiments, the EGFR activation is selected from mutation of EGFR, amplification of EGFR, expression of EGFR, and ligand mediated activation of EGFR.

In further embodiments, the mutation of EGFR is selected from G719S, G719C, G719A, L858R, L861Q, an exon 19 deletion mutation, and an exon 20 insertion mutation.

In still another aspect, provided herein is a method of treating cancer in a subject, wherein the subject is identified as being in need of EGFR inhibition for the treatment of cancer, comprising administering to the subject an effective amount of a compound disclosed herein, or a pharmaceutically acceptable salt thereof.

In certain embodiments, the subject identified as being in need of EGFR inhibition is resistant to a known EGFR inhibitor, including but not limited to, gefitinib, erlotinib, osimertinib, CO-1686, or WZ4002. In certain embodiments, a diagnostic test is performed to determine if the subject has an activating mutation in EGFR. In certain embodiments, a diagnostic test is performed to determine if the subject has an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, C797S, or D761Y. The diagnostic test can comprise sequencing, pyrosequencing, PCR, RT-PCR, or similar analysis techniques known to those of skill in the art that can detect nucleotide sequences.

In an aspect, provided herein is a method of preventing resistance to a known EGFR inhibitor (including but not limited to gefitinib, erlotinib, osimertinib, CO-1686, or WZ4002) in a subject, comprising administering to a subject in need thereof an effective amount of a compound disclosed herein, or a pharmaceutically acceptable salt thereof.

In another aspect, provided herein is a method of preventing resistance to a known EGFR inhibitor (including but not limited to gefitinib, erlotinib, osimertinib, CO-1686, or WZ4002) in a disease, comprising administering to a subject in need thereof an effective amount of a compound disclosed herein, or a pharmaceutically acceptable salt thereof, and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In an embodiment of the methods disclosed herein, the subject is a human.

In another aspect, the disclosure provides a compound disclosed herein, or a pharmaceutically acceptable salt thereof, for use in the manufacture of a medicament for treating or preventing a disease in which EGFR plays a role.

In an aspect, provided herein is a method of treating or preventing a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

The term "cancerous cell" as provided herein, includes a cell afflicted by any one of the above-identified conditions.

The disclosure further provides a method for the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes *dorsalis*, and toxic encephalopathy.

Another aspect of this disclosure provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof. In other embodiments, the method further comprises administering a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

The activity of the compounds and compositions of the present disclosure as EGFR kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second active agent, wherein said second active agent prevents EGFR dimer formation. For any of the above uses, the required dosage will vary depending on the mode of administration, the particular condition to be treated and the effect desired.

In other embodiments, the compound and the second active agent that prevents EGFR dimer formation are administered simultaneously or sequentially.

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

In certain embodiments, these compositions optionally further comprise one or more additional therapeutic agents. For example, an agent that prevents EGFR dimer formation, chemotherapeutic agents or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting kinase activity selected from one or more compounds of disclosed herein, or pharmaceutically acceptable salts thereof, and instructions for use in treating cancer. In certain embodiments, the kit further comprises components for performing a test to determine whether a subject has activating and/or drug resistance mutations in EGFR.

In another aspect, the disclosure provides a kit comprising a compound capable of inhibiting EGFR activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second active agent, wherein said second active agent prevents EGFR dimer formation; and instructions for use in treating cancer. In certain embodiments, the kit further comprises components for performing a test to determine whether a subject has activating and/or drug resistance mutations in EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In another aspect, the disclosure provides a kit comprising a compound capable of inhibiting EGFR activity selected from a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations

ACN acetonitrile
AcOH acetic acid
DBU 1,8-diazabicyclo[5.4.0]undec-7-ene
DCM dichloromethane
DIEA/DIPEA N,N-diisopropylethylamine
DMF N,N-dimethylformamide
DMSO dimethyl sulfoxide
EDC 1-ethyl-3-(3-dimethylaminopropyl)carbodiimide
$Et_2O$ diethyl ether
EtOAc ethyl acetate
HATU 1-[bis(dimethylamino)methylene]-1H-1,2,3-triazolo [4,5-b]pyridinium 3-oxid hexafluorophosphate
Hex hexanes
HOBt hydroxybenzotriazole
MeOH methanol
OAc acetate
TFA trifluoroacetic acid
THF tetrahydrofuran

Example 1: Preparation of Compounds of Formula I and Intermediates

Compound 001 was prepared following the reaction protocol in Scheme 1.

Scheme 1.

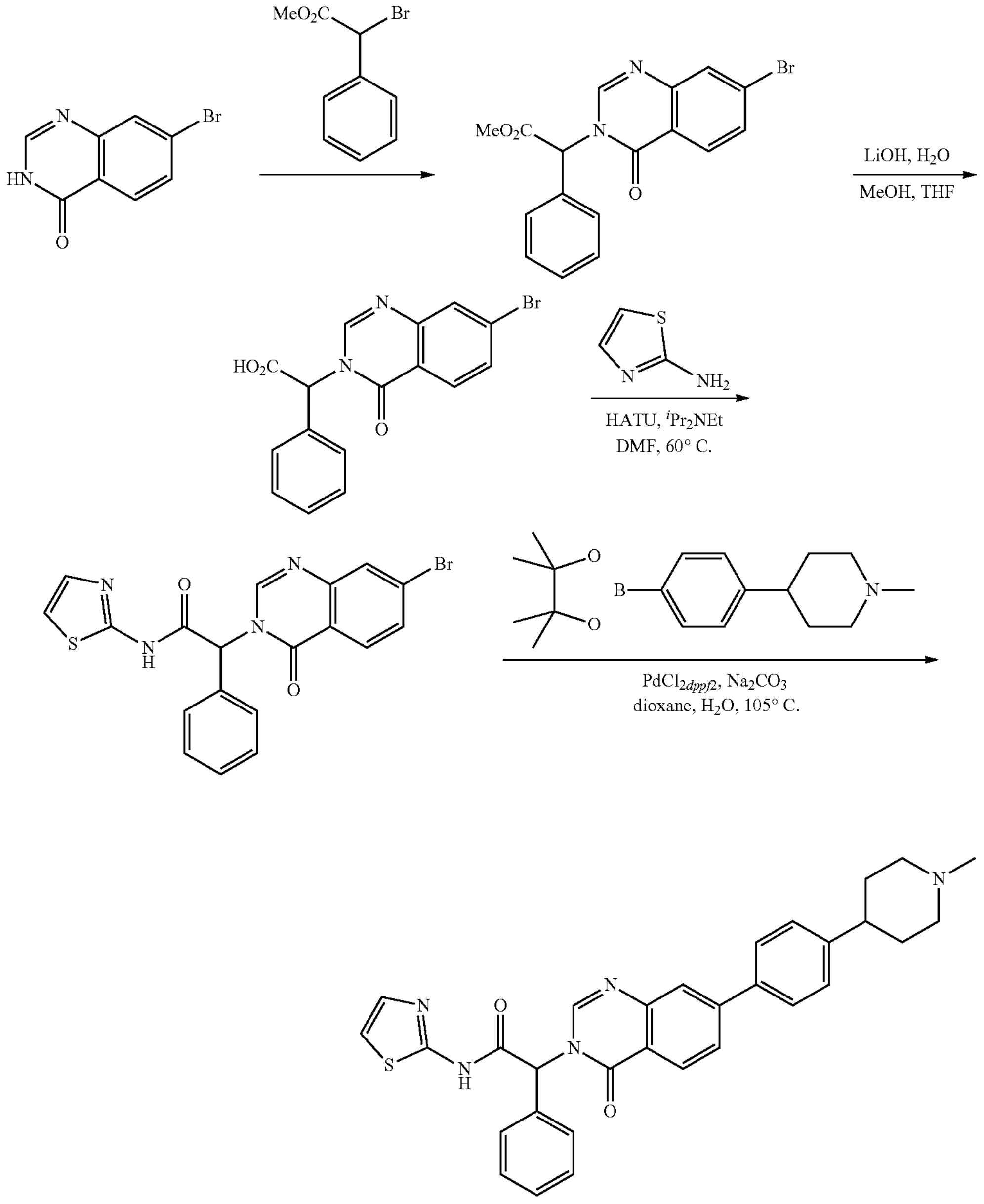

Methyl 2-(7-bromo-4-oxoquinazolin-3(4H)-yl)-2-phenylacetate (Ester 1)

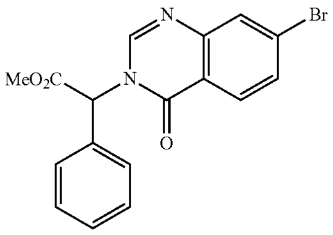 [SMILES: COC(=O)C(c1ccccc1)n1cnc2cc(Br)ccc2c1=O]

A mixture of 7-bromoquinazolin-4(3H)-one (1.0 g, 4.44 mmol), methyl 2-bromo-2-phenylacetate (0.92 mL, 4.67 mmol) and cesium carbonate (2.9 g, 8.89 mmol) in DMF (3 mL) was heated to 50° C. After 2 hours, and a further 1 hour, additional portions of methyl 2-bromo-2-phenylacetate (0.10 mL, 0.51 mmol) were added, and the mixture was stirred for a further 30 minutes. The reaction mixture was added to water and extracted with EtOAc. The organic layer was washed with brine, dried ($MgSO_4$), filtered and the residue purified by silica chromatography (0-35% EtOAc in Hex) to give the title compound (1.09 g, 66%) as a white solid. $^1$H NMR (500 MHz, $CDCl_3$-d) δ 8.19 (d, 1H) 7.89 (s, 1H) 7.88 (d, 1H) 7.63 (dd, 1H) 7.47 (m, 3H) 7.38 (m, 2H) 6.74 (s, 1H) 3.88 (s, 3H); MS (m/z): 375.0 $[M+1]^+$.

2-(7-Bromo-4-oxoquinazolin-3(4H)-yl)-2-phenylacetic acid (Acid 1)

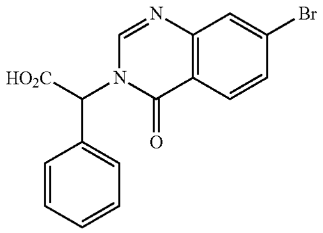 [SMILES: O=C(O)C(c1ccccc1)n1cnc2cc(Br)ccc2c1=O]

A mixture of methyl 2-(7-bromo-4-oxoquinazolin-3(4H)-yl)-2-phenylacetate (1.09 g, 2.9 mmol) and lithium hydroxide (1.2 g, 29 mmol) was in THF (4 mL), MeOH (4 mL) and water (4 mL) was stirred for 20 minutes. The organic solvents were removed under reduced pressure, water was added and the solution acidified with 6N HCl. The resulting precipitate was filtered and dried in a vacuum over to give the title compound (0.28 g, 27%) as a white solid. $^1$H NMR (500 MHz, $d_6$-DMSO) δ 8.19 (s, 1H) 8.09 (d, 1H) 7.84 (d, 1H) 7.68 (dd, 1H) 7.38 (m, 2H) 7.33 (m, 2H) 7.27 (m, 1H) 6.30 (s, 1H); MS (n/z): 358.9 $[M+1]^+$.

Compound 001: 2-(7-Bromo-4-oxoquinazolin-3(4H)-yl)-2-phenyl-N-(thiazol-2-yl)acetamide

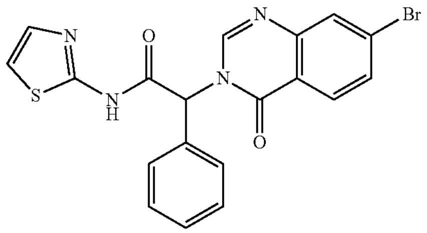 [SMILES: O=C(Nc1nccs1)C(c1ccccc1)n1cnc2cc(Br)ccc2c1=O]

Diisopropylethylamine (0.68 mL, 3.9 mmol) was added to a mixture of 2-(7-bromo-4-oxoquinazolin-3(4H)-yl)-2-phenylacetic acid (0.28 g, 0.78 mmol) and HATU (0.59 g, 1.6 mmol) in DMF (3 mL). The reaction mixture was stirred at 60° C. for 2 hours, then poured into water. The mixture was extracted with EtOAc, and the organic layer was washed with brine, dried ($MgSO_4$), filtered and the residue purified by silica chromatography (0-50% EtOAc in Hex) to give the title compound (198 mg, 58%) as a white solid. $^1$H NMR (500 MHz, $d_6$-DMSO) δ 8.11 (d, 1H) 7.94 (d, 1H) 7.87 (s, 1H) 7.77 (dd, 1H) 7.51 (m, 4H) 7.44 (m, 2H) 7.32 (d, 1H) 6.84 (s, 1H); MS (m/z): 442.9 $[M+1]^+$.

The following compounds in Table 2 were prepared by a similar method to Compound 001 from the corresponding carboxylic acid and 2-aminothiazole or 2-aminopyridine.

TABLE 2

| No. | Structure/Name | m/z $[M+1]^+$ | $^1$H NMR (500 MHz, $d_6$-DMSO) δ | Starting material |
|---|---|---|---|---|
| 002 | 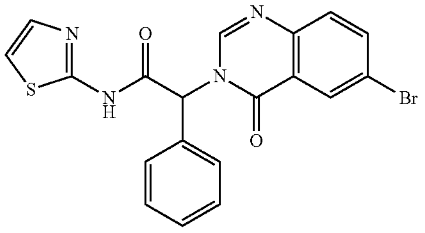 [SMILES: O=C(Nc1nccs1)C(c1ccccc1)n1cnc2ccc(Br)cc2c1=O] 2-(6-Bromo-4-oxoquinazolin-3(4H)-yl)-2-phenyl-N-(thiazol-2-yl)-acetamide | 443.0 | 8.29 (d, 1H) 8.03 (dd, 1H) 7.88 (s, 1H) 7.66 (d, 1H) 7.51 (m, 4H) 7.45 (m, 2H) 7.32 (d, 1H) 6.85 (s, 1H) | 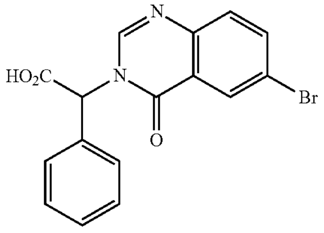 |

TABLE 2-continued

| No. | Structure/Name | m/z [M + 1]+ | $^1$H NMR (500 MHz, $d_6$-DMSO) δ | Starting material |
|---|---|---|---|---|
| 003 | 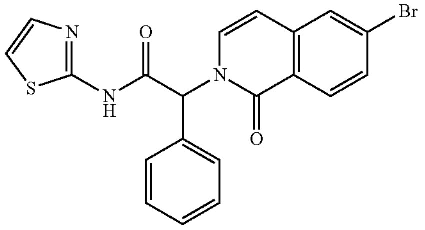 [SMILES: O=C(Nc1nccs1)C(c1ccccc1)n1ccc2cc(Br)ccc2c1=O] 2-(6-Bromo-1-oxoisoquinolin-2(1H)-yl)-2-phenyl-N-(thiazol-2-yl)-acetamide | 441.9 | 8.16 (d, 1H) 7.96 (d, 1H) 7.69 (dd, 1H) 7.50 (m, 4H) 7.37 (m, 2H) 7.29 (d, 1H) 6.97 (d, 1H) 6.90 (s, 1H) 6.58 (d, 1H) | 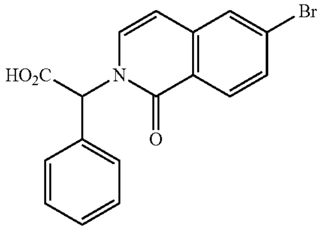 [SMILES: O=C(O)C(c1ccccc1)n1ccc2cc(Br)ccc2c1=O] |
| 004 | 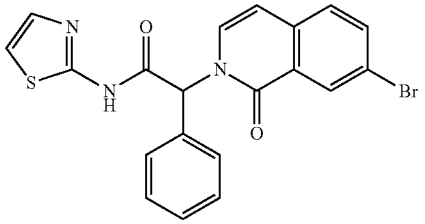 [SMILES: O=C(Nc1nccs1)C(c1ccccc1)n1ccc2ccc(Br)cc2c1=O] 2-(7-Bromo-1-oxoisoquinolin-2(1H)-yl)-2-phenyl-N-(thiazol-2-yl)-acetamide | 442.0 | 8.35 (d, 1H) 7.90 (dd, 1H) 7.66 (d, 1H) 7.51 (m, 4H) 7.37 (d, 2H) 7.30 (d, 1H) 6.97 (d, 1H) 6.91 (s, 1H) 6.63 (d, 1H) | 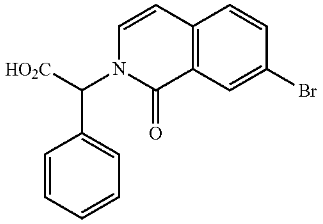 [SMILES: O=C(O)C(c1ccccc1)n1ccc2ccc(Br)cc2c1=O] |
| 005 | 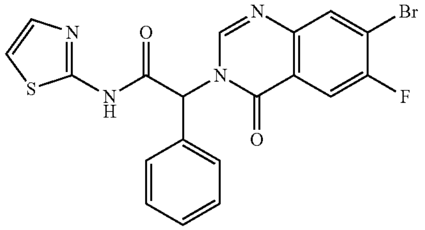 [SMILES: O=C(Nc1nccs1)C(c1ccccc1)n1cnc2cc(Br)c(F)cc2c1=O] 2-(7-Bromo-6-fluoro-4-oxoquinazolin-3(4H)-yl)-2-phenyl-N-(thiazol-2-yl)acetamide | 459.0 | $CDCl_3$-d 8.04 (s, 1H) 8.03 (d, 1H) 8.00 (d, 1H) 7.45 (m, 6H) 7.10 (s, 1H) 7.07 (d, 1H) | 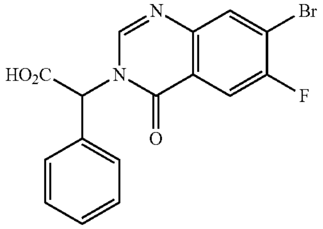 [SMILES: O=C(O)C(c1ccccc1)n1cnc2cc(Br)c(F)cc2c1=O] |
| 006 | 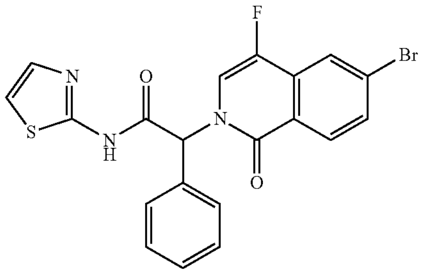 [SMILES: O=C(Nc1nccs1)C(c1ccccc1)n1cc(F)c2cc(Br)ccc2c1=O] 2-(6-Bromo-4-fluoro-1-oxo-isoquinolin-2(1H)-yl)-2-phenyl-N-(thiazol-2-yl)acetamide | 458.0 | $CDCl_3$-d 8.35 (dd, 1H) 7.92 (d, 1H) 7.69 (dd, 1H) 7.53 (d, 1H) 7.45 (m, 3H) 7.40 (m, 2H) 7.25 (s, 1H) 7.16 (d, 1H) 7.04 (d, 1H) | 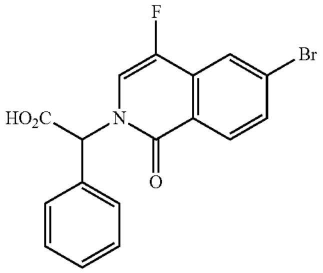 [SMILES: O=C(O)C(c1ccccc1)n1cc(F)c2cc(Br)ccc2c1=O] |
| 007 | 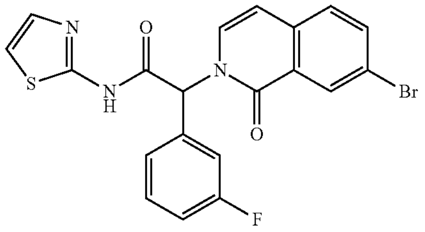 [SMILES: O=C(Nc1nccs1)C(c1cccc(F)c1)n1ccc2ccc(Br)cc2c1=O] 2-(7-Bromo-1-oxoisoquinolin-2(1H)-yl)-2-(3-fluorophenyl)-N-(thiazol-2-yl)acetamide | 457.9 | $CDCl_3$-d 8.73 (d, 1H) 7.76 (dd, 1H) 7.62 (d, 1H) 7.40 (m, 2H) 7.34 (s, 1H) 7.22 (d, 1H) 7.20 (d, 1H) 7.12 (m, 2H) 7.06 (d, 1H) 6.51 (d, 1H) | 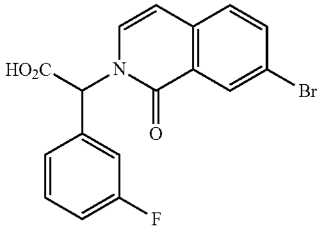 [SMILES: O=C(O)C(c1cccc(F)c1)n1ccc2ccc(Br)cc2c1=O] |

TABLE 2-continued

| No. | Structure/Name | m/z [M + 1]$^+$ | $^1$H NMR (500 MHz, $d_6$-DMSO) δ | Starting material |
|---|---|---|---|---|
| 008 | 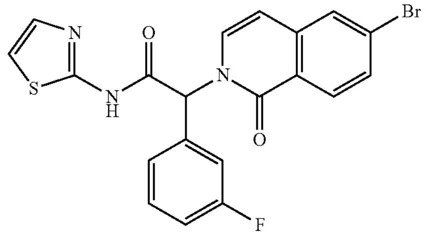 [SMILES: O=C(Nc1nccs1)C(c1cccc(F)c1)n1ccc2cc(Br)ccc2c1=O] 2-(6-Bromo-1-oxoisoquinolin-2(1H)-yl)-2-(3-fluorophenyl)-N-(thiazol-2-yl)acetamide | 457.9 | $CDCl_3$-d 8.31 (d, 1H) 7.69 (d, 1H) 7.60 (dd, 1H) 7.57 (d, 1H) 7.40 (m, 1H) 7.21 (d, 1H) 7.16 (m, 4H) 7.06 (d, 1H) 6.44 (d, 1H) | 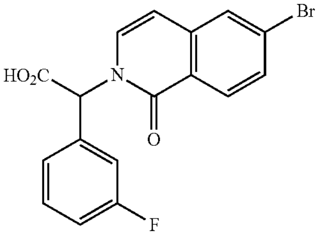 [SMILES: O=C(O)C(c1cccc(F)c1)n1ccc2cc(Br)ccc2c1=O] |
| 009 | 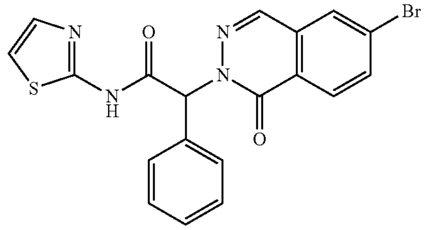 [SMILES: O=C(Nc1nccs1)C(c1ccccc1)n1ncc2cc(Br)ccc2c1=O] 2-(6-Bromo-1-oxophthalazin-2(1H)-yl)-2-phenyl-N-(thiazol-2-yl)-acetamide | 443.0 | $CDCl_3$-d 10.36 (br s, 1H) 8.29 (d, 1H) 8.16 (s, 1H) 7.89 (dd, 1H) 7.85 (d, 1H) 7.57 (m, 2H) 7.42 (m, 3H) 7.38 (d, 1H) 7.13 (s, 1H) 6.97 (d, 1H) | 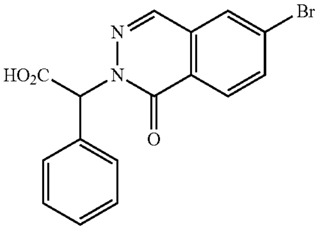 [SMILES: O=C(O)C(c1ccccc1)n1ncc2cc(Br)ccc2c1=O] |
| 010 | 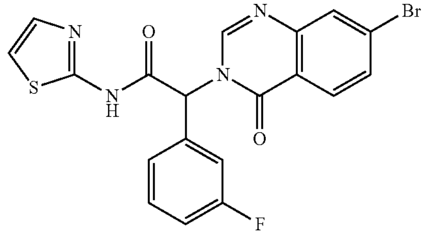 [SMILES: O=C(Nc1nccs1)C(c1cccc(F)c1)n1cnc2cc(Br)ccc2c1=O] 2-(7-Bromo-4-oxoquinazolin-3(4H)-yl)-2-(3-fluorophenyl)-N-(thiazol-2-yl)acetamide | 460.99 | 8.11 (d, 1H) 8.00 (s, 1H) 7.95 (d, 1H) 7.78 (dd, 1H) 7.55 (m, 1H) 7.52 (d, 1H) 7.33 (m, 3H) 7.28 (d, 1H) 6.81 (s, 1H) | 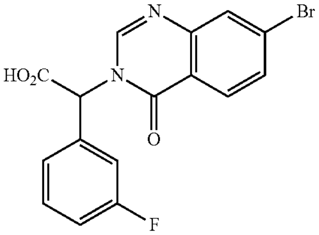 [SMILES: O=C(O)C(c1cccc(F)c1)n1cnc2cc(Br)ccc2c1=O] |
| 011 | 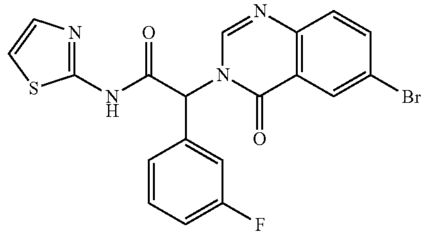 [SMILES: O=C(Nc1nccs1)C(c1cccc(F)c1)n1cnc2ccc(Br)cc2c1=O] 2-(6-Bromo-4-oxoquinazolin-3(4H)-yl)-2-(3-fluorophenyl)-N-(thiazol-2-yl)acetamide | 460.93 | 8.28 (d, 1H) 8.04 (dd, 1H) 8.01 (s, 1H) 7.67 (d, 1H) 7.54 (m, 1H) 7.51 (d, 1H) 7.32 (m, 3H) 7.28 (m, 1H) 6.82 (s, 1H) | 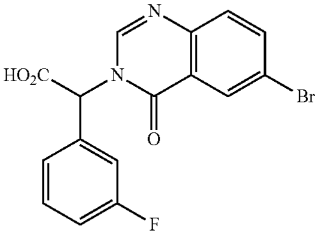 [SMILES: O=C(O)C(c1cccc(F)c1)n1cnc2ccc(Br)cc2c1=O] |
| 034 | 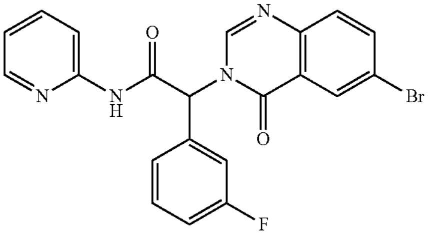 [SMILES: O=C(Nc1ccccn1)C(c1cccc(F)c1)n1cnc2ccc(Br)cc2c1=O] 2-(6-Bromo-4-oxoquinazolin-3(4H)-yl)-2-(3-fluorophenyl)-N-(pyridin-2-yl)acetamide | 453.03 | 11.36 (br s, 1H) 8.35 (d, 1H) 8.29 (d, 1H) 8.10 (d, 1H) 8.02 (dd, 1H) 7.91 (s, 1H) 7.83 (m, 1H) 7.66 (d, 1H) 7.55 (m, 1H) 7.32 (m, 3H) 7.17 (m, 1H) 6.94 (s, 1H) | 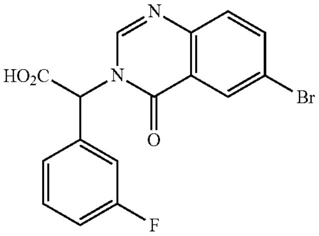 [SMILES: O=C(O)C(c1cccc(F)c1)n1cnc2ccc(Br)cc2c1=O] |

TABLE 2-continued

| No. | Structure/Name | m/z $[M + 1]^+$ | $^1H$ NMR (500 MHz, $d_6$-DMSO) δ | Starting material |
|---|---|---|---|---|
| 035 | 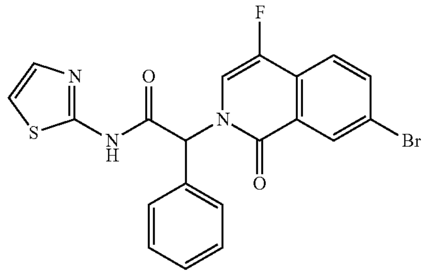 [SMILES: O=C(Nc1nccs1)C(c1ccccc1)n1cc(F)c2ccc(Br)cc2c1=O] 2-(7-Bromo-4-fluoro-1-oxo-isoquinolin-2(1H)-yl)-2-phenyl-N-(thiazol-2-yl)acetamide | 458.0 | 8.42 (m, 1H)<br>8.08 (dd, 1H)<br>7.76 (d, 1H)<br>7.51 (m, 5H)<br>7.41 (m, 2H)<br>7.31 (d, 1H)<br>7.08 (d, 1H)<br>6.90 (s, 1H) | 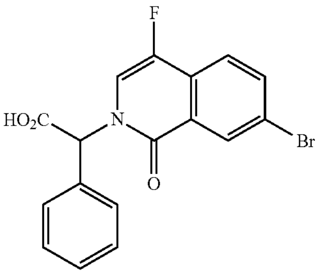 [SMILES: O=C(O)C(c1ccccc1)n1cc(F)c2ccc(Br)cc2c1=O] |
| 041 | 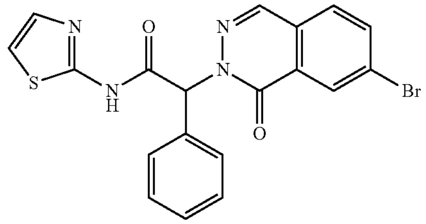 [SMILES: O=C(Nc1nccs1)C(c1ccccc1)n1ncc2ccc(Br)cc2c1=O] 2-(7-Bromo-1-oxophthalazin-2(1H)-yl)-2-phenyl-N-(thiazol-2-yl)-acetamide | 443.0 | — | 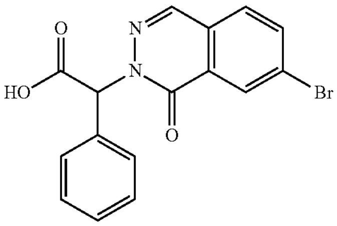 [SMILES: O=C(O)C(c1ccccc1)n1ncc2ccc(Br)cc2c1=O] |
| 062 | 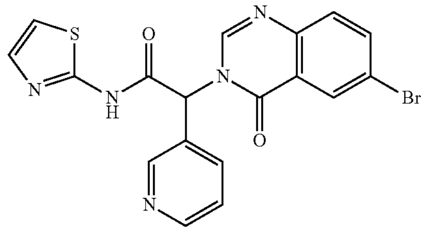 [SMILES: O=C(Nc1nccs1)C(c1cccnc1)n1cnc2ccc(Br)cc2c1=O] 2-(6-Bromo-4-oxoquinazolin-3(4H)-yl)-2-(pyridin-3-yl)-N-(thiazol-2-yl)-acetamide | 443.95 | 8.68 (d, 1H)<br>8.65 (dd, 1H)<br>8.28 (d, 1H)<br>8.18 (s, 1H)<br>8.04 (dd, 1H)<br>7.90 (m, 1H)<br>7.68 (d, 2H)<br>7.51 (m, 2H)<br>7.31 (br s, 1H)<br>6.83 (s, 1H) | 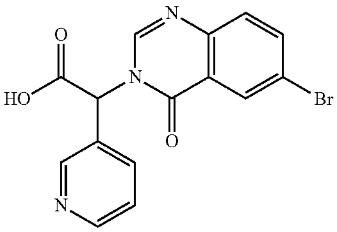 |
| 063 | 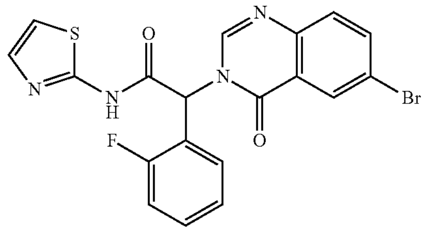 [SMILES: O=C(Nc1nccs1)C(c1ccccc1F)n1cnc2ccc(Br)cc2c1=O] 2-(8-Bromo-4-oxoquinazolin-3(4H)-yl)-2-(2-fluorophenyl)-N-(thiazol-2-yl)acetamide | 460.99 | 8.30 (d, 1H)<br>8.05 (dd, 1H)<br>8.00 (s, 1H)<br>7.68 (d, 1H)<br>7.58 (dd, 1H)<br>7.52 (d, 1H)<br>7.39 (m, 2H)<br>7.34 (m, 2H)<br>7.11 (s, 1H) | 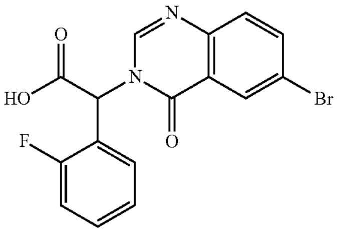 [SMILES: O=C(O)C(c1ccccc1F)n1cnc2ccc(Br)cc2c1=O] |

The following compounds in Table 3 were prepared by a similar method to Compound 001 from the corresponding carboxylic acid and 2-aminothiazole or 2-aminopyridine.

TABLE 3

| Number | Structure/Name | m/z $[M+1]^+$ | $^1H$ NMR (500 MHz, $d_6$-DMSO) δ | Starting material |
|---|---|---|---|---|
| 048 | 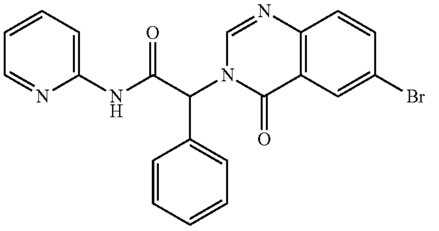 [SMILES: O=C(Nc1ccccn1)C(c1ccccc1)n1cnc2ccc(Br)cc2c1=O] 2-(6-Bromo-4-oxoquinazolin-3-(4H)-yl)-2-phenyl-N-(pyridin-2-yl)-acetamide | 435.0 | $CDCl_3$-d 8.43 (d, 1H) 8.21 (m, 1H) 8.15 (d, 1H) 7.95 (s, 1H) 7.77 (m, 1H) 7.65 (m, 1H) 7.51 (d, 1H) 7.38 (m, 5H) 7.01 (m, 1H) 6.83 (s, 1H) | 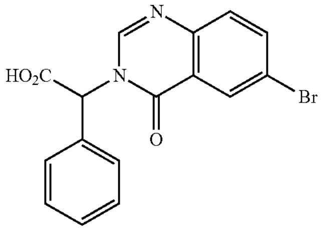 [SMILES: O=C(O)C(c1ccccc1)n1cnc2ccc(Br)cc2c1=O] |
| 049 | 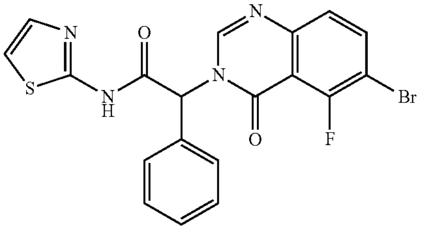 [SMILES: O=C(Nc1nccs1)C(c1ccccc1)n1cnc2ccc(Br)c(F)c2c1=O] 2-(6-Bromo-5-fluoro-4-oxo-quinazolin-3(4H)-yl)-2-phenyl-N-(thiazol-2-yl)acetamide | 461.0 | 8.14 (m, 1H) 7.85 (s, 1H) 7.52 (m, 5H) 7.43 (m, 2H) 7.33 (s, 1H) 6.81 (s, 1H) | 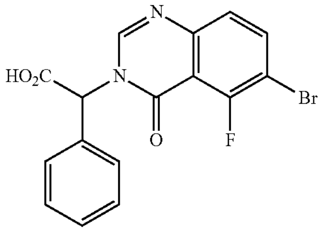 |
| 050 | 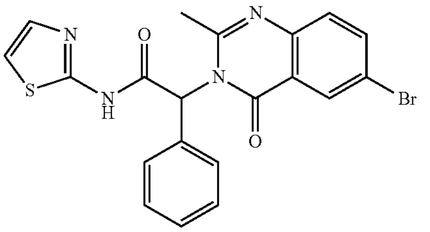 [SMILES: Cc1nc2ccc(Br)cc2c(=O)n1C(C(=O)Nc1nccs1)c1ccccc1] 2-(6-Bromo-2-methyl-4-oxo-quinazolin-3(4H)-yl)-2-phenyl-N-(thiazol-2-yl)acetamide | 454.9 | 8.21 (d, 1H) 8.01 (m, 1H) 7.63 (d, 1H) 7.43 (d, 1H) 7.38 (m, 5H) 7.22 (d, 1H) 6.59 (s, 1H) 2.53 (s, 3H) | 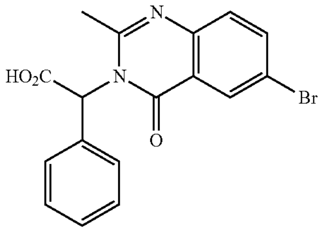 [SMILES: Cc1nc2ccc(Br)cc2c(=O)n1C(C(=O)O)c1ccccc1] |
| 051 | 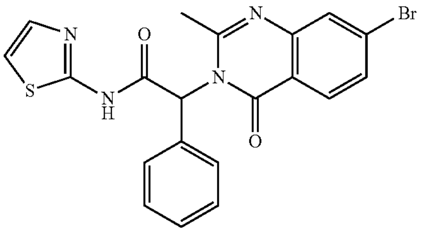 [SMILES: Cc1nc2cc(Br)ccc2c(=O)n1C(C(=O)Nc1nccs1)c1ccccc1] 2-(7-Bromo-2-methyl-4-oxo-quinazolin-3(4H)-yl)-2-phenyl-N-(thiazol-2-yl)acetamide | 455.0 | — | 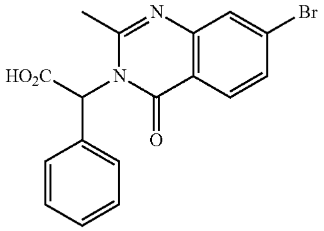 |
| 052 | 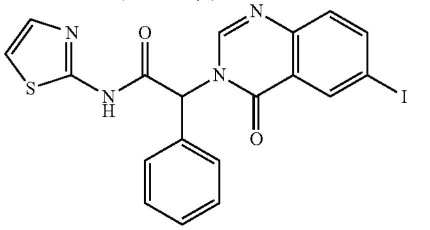 2-(6-Iodo-4-oxoquinazolin-3(4H)-yl)-2-phenyl-N-(thiazol-2-yl)-acetamide | 488.5 | $CDCl_3$-d 8.71 (d, 1H) 8.07 (s, 1H) 8.04 (dd, 1H) 7.57 (d, 1H) 7.45 (m, 5H) 7.06 (s, 1H) 7.05 (d, 1H) | 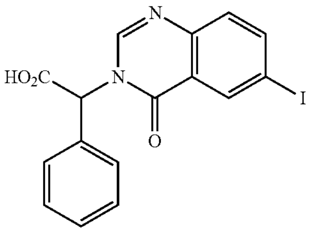 [SMILES: O=C(O)C(c1ccccc1)n1cnc2ccc(I)cc2c1=O] |

Esters in Table 4 below were prepared by a similar method to ester 1, from the corresponding starting material and methyl 2-bromo-2-phenylacetate or methyl 2-amino-2-(3-fluorophenyl)acetate.

TABLE 4

| Ester | Structure/Name | m/z $[M+1]^+$ | $^1H$ NMR (500 MHz, $CDCl_3$-d) δ | Starting material |
|---|---|---|---|---|
| 2 | 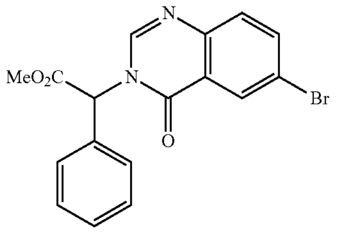 [SMILES: COC(=O)C(c1ccccc1)n1cnc2ccc(Br)cc2c1=O] Methyl 2-(6-bromo-4-oxo-quinazolin-3(4H)-yl)-2-phenylacetate | 375.0 | 8.49 (d, 1H) 7.90 (s, 1H) 7.86 (dd, 1H) 7.59 (d, 1H) 7.48 (m, 3H) 7.39 (m, 2H) 6.76 (s, 1H) 3.90 (s, 3H) | 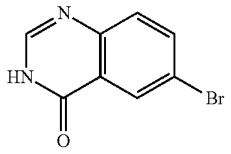 |
| 3 | 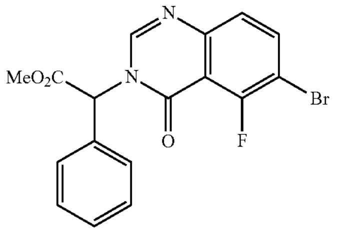 [SMILES: COC(=O)C(c1ccccc1)n1cnc2ccc(Br)c(F)c2c1=O] Methyl 2-(6-bromo-5-fluoro-4-oxoquinazolin-3(4H)-yl)-2-phenylacetate | 390.9 | 7.88 (dd, 1H) 7.85 (s, 1H) 7.47 (m, 3H) 7.40 (dd, 1H) 7.37 (m, 2H) 6.71 (s, 1H) 3.88 (s, 3H) | 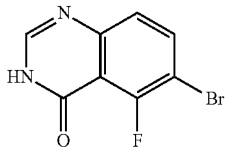 |
| 4 | 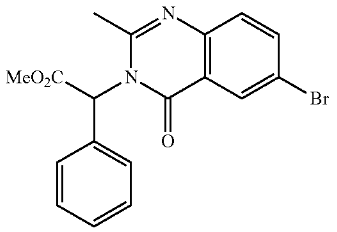 [SMILES: COC(=O)C(c1ccccc1)n1c(C)nc2ccc(Br)cc2c1=O] Methyl 2-(6-bromo-2-methyl-4-oxoquinazolin-3(4H)-yl)-2-phenylacetate | 387.0 | 8.15 (d, 1H) 7.86 (d, 1H) 7.61 (m, 1H) 7.40 (m, 5H) 6.38 (s, 1H) 3.75 (s, 3H) 2.55 (s, 3H) | 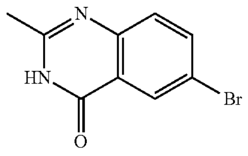 |
| 5 | 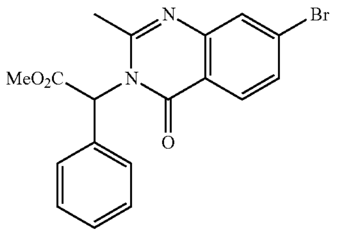 [SMILES: COC(=O)C(c1ccccc1)n1c(C)nc2cc(Br)ccc2c1=O] Methyl 2-(7-bromo-2-methyl-4-oxoquinazolin-3(4H)-yl)-2-phenylacetate | 387.0 | 8.15 (s, 1H) 7.86 (s, 1H) 7.59 (m, 1H) 7.38 (m, 5H) 6.38 (s, 1H) 3.84 (s, 3H) 2.55 (s, 3H) | 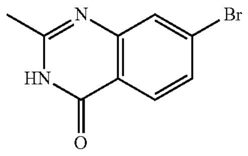 |

TABLE 4-continued

| Ester | Structure/Name | m/z $[M + 1]^+$ | $^1H$ NMR (500 MHz, $CDCl_3$-d) δ | Starting material |
|---|---|---|---|---|
| 6 | 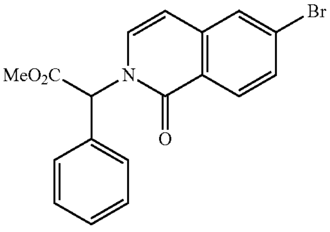 [SMILES: COC(=O)C(c1ccccc1)n1ccc2cc(Br)ccc2c1=O] Methyl 2-(6-bromo-1-oxo-isoquinolin-2(1H)-yl)-2-phenylacetate | 374.0 | DMSO 8.15 (d, 1H) 7.97 (d, 1H) 7.70 (dd, 1H) 7.45 (m, 5H) 7.16 (d, 1H) 6.61 (d, 1H) 6.55 (s, 1H) 3.74 (s, 3H) | 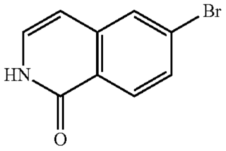 |
| 7 | 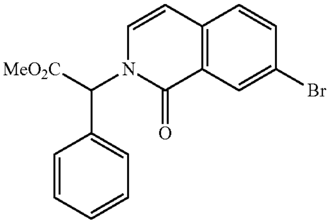 [SMILES: COC(=O)C(c1ccccc1)n1ccc2ccc(Br)cc2c1=O] Methyl 2-(7-bromo-1-oxo-isoquinolin-2(1H)-yl)-2-phenylacetate | 373.9 | DMSO 8.33 (d, 1H) 7.92 (dd, 1H) 7.66 (d, 1H) 7.45 (m, 5H) 7.15 (d, 1H) 6.66 (d, 1H) 6.55 (s, 1H) 3.74 (s, 3H) | 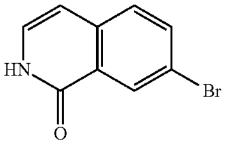 [SMILES: O=c1[nH]ccc2ccc(Br)cc12] |
| 8 | 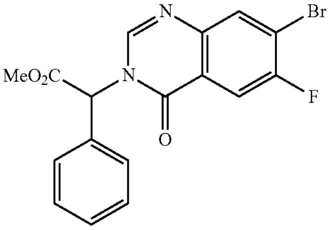 [SMILES: COC(=O)C(c1ccccc1)n1cnc2cc(Br)c(F)cc2c1=O] Methyl 2-(7-bromo-6-fluoro-4-oxoquinazolin-3(4H)-yl)-2-phenylacetate | 391.0 | 8.00 (d, 1H) 7.97 (d, 1H) 7.85 (s, 1H) 7.47 (m, 3H) 7.36 (m, 2H) 6.72 (s, 1H) 3.88 (s, 3H) | 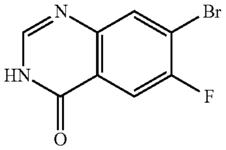 |
| 9 | 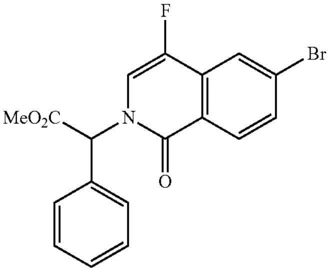 [SMILES: COC(=O)C(c1ccccc1)n1cc(F)c2cc(Br)ccc2c1=O] Methyl 2-(6-bromo-4-fluoro-1-oxoisoquinolin-2(1H)-yl)-2-phenylacetate | 390.0 | 8.31 (dd, 1H) 7.89 (d, 1H) 7.69 (dd, 1H) 7.47 (m, 3H) 7.35 (m, 2H) 6.91 (d, 1H) 6.80 (s, 1H) 3.86 (s, 3H) | 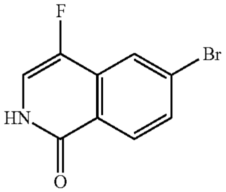 [SMILES: O=c1[nH]cc(F)c2cc(Br)ccc12] |
| 10 | 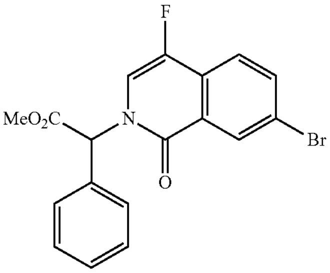 [SMILES: COC(=O)C(c1ccccc1)n1cc(F)c2ccc(Br)cc2c1=O] Methyl 2-(7-bromo-4-fluoro-1-oxoisoquinolin-2(1H)-yl)-2-phenylacetate | 390.0 | DMSO-$d_6$) 8.40 (m, 1H) 8.08 (m, 1H) 7.74 (d, 1H) 7.49 (m, 5H) 7.40 (d, 1H) 6.55 (s, 1H) 3.76 (s, 3H) | 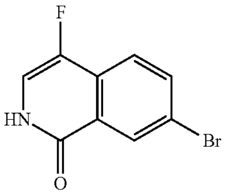 [SMILES: O=c1[nH]cc(F)c2ccc(Br)cc12] |

TABLE 4-continued

| Ester | Structure/Name | m/z $[M + 1]^+$ | $^1H$ NMR (500 MHz, $CDCl_3$-d) δ | Starting material |
|---|---|---|---|---|
| 11 | 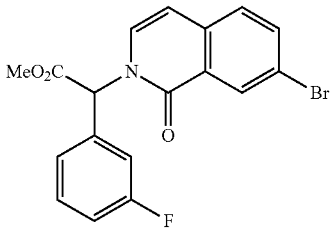 [SMILES: COC(=O)C(c1cccc(F)c1)n1ccc2ccc(Br)cc2c1=O] Methyl 2-(7-bromo-1-oxo-isoquinolin-2(1H)yl)-2-(3-fluorophenyl)acetate | 390.0 | 8.59 (d, 1H) 7.74 (dd, 1H) 7.42 (m, 1H) 7.38 (d, 1H) 7.14 (m, 2H) 7.08 (m, 1H) 6.94 (d, 1H) 6.87 (s, 1H) 6.42 (d, 1H) 3.87 (s, 3H) | 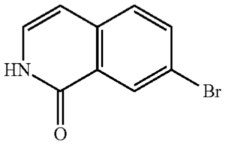 |
| 12 | 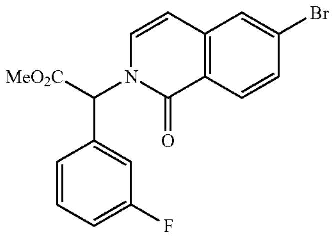 [SMILES: COC(=O)C(c1cccc(F)c1)n1ccc2cc(Br)ccc2c1=O] Methyl 2-(6-bromo-1-oxo-isoquinolin-2(1H)-yl)-2-(3-fluorophenyl)acetate | 390.0 | 8.30 (d, 1H) 7.67 (d, 1H) 7.60 (dd, 1H) 7.42 (m, 1H) 7.14 (m, 2H) 7.08 (m, 1H) 6.95 (d, 1H) 6.86 (s, 1H) 6.37 (d, 1H) 3.86 (s, 3H) | 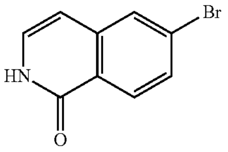 |
| 13 | 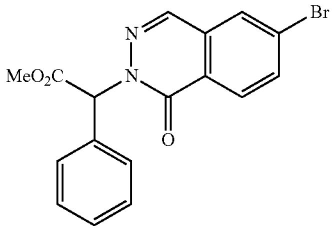 [SMILES: COC(=O)C(c1ccccc1)n1ncc2cc(Br)ccc2c1=O] Methyl 2-(6-bromo-1-oxo-phthalazin-2(1H)-yl)-2-phenyacetate | 375.0 | DMSO 8.42 (s, 1H) 8.25 (d, 1H) 8.19 (d, 1H) 8.07 (dd, 1H) 7.43 (m, 2H) 7.37 (m, 3H) 6.74 (s, 1H) 3.70 (s, 3H) | 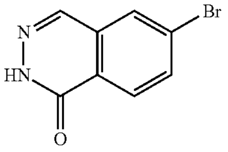 |
| 14 | 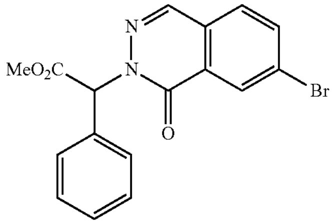 [SMILES: COC(=O)C(c1ccccc1)n1ncc2ccc(Br)cc2c1=O] Methyl 2-(7-bromo-1-oxo-phthalazin-2(1H)-yl)-2-phenylacetate | 372.95 | DMSO-$d_6$ 8.50 (s, 1H) 8.39 (d, 1H) 8.19 (m, 1H) 7.94 (d, 1H) 7.45 (m, 2H) 7.36 (m, 3H) 6.76 (s, 1H) 3.71 (s, 3H) | 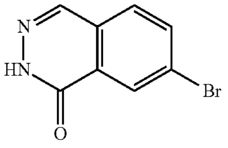 |
| 15 | 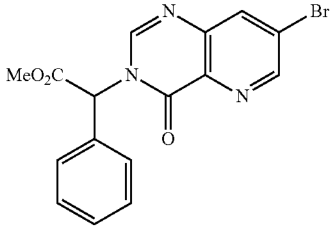 [SMILES: COC(=O)C(c1ccccc1)n1cnc2cc(Br)cnc2c1=O] Methyl 2-(7-bromo-4-oxo-pyrido[3,2-d]pyrimidin-3(4H)-yl)-2-phenylacetate | 373.8 | N/A | 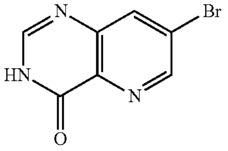 [SMILES: O=c1[nH]cnc2cc(Br)cnc12] |

TABLE 4-continued

| Ester | Structure/Name | m/z $[M + 1]^+$ | $^1H$ NMR (500 MHz, $CDCl_3$-d) δ | Starting material |
| --- | --- | --- | --- | --- |
| 16 | 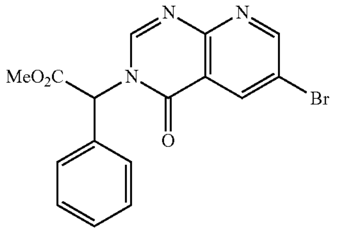 [SMILES: COC(=O)C(c1ccccc1)n1cnc2ncc(Br)cc2c1=O] Methyl 2-(6-bromo-4-oxo-pyrido[2,3-d]pyrimidin-3(4H)-yl)-2-phenylacetate | 374.0 | N/A | 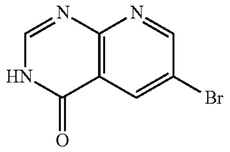 |
| 17 | 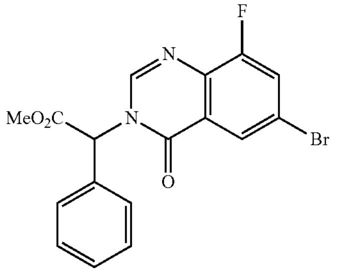 [SMILES: COC(=O)C(c1ccccc1)n1cnc2c(F)cc(Br)cc2c1=O] Methyl 2-(6-bromo-8-fluoro-4-oxoquinazolin-3(4H)-yl)-2-phenylacetate | 392.6 | 8.27 (m, 1H) 7.92 (s, 1H) 7.64 (m, 1H) 7.47 (m, 3H) 7.35 (m, 2H) 6.71 (s, 1H) 3.88 (s, 3H) | 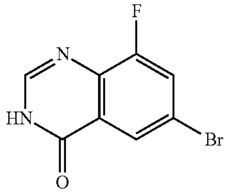 [SMILES: O=c1[nH]cnc2c(F)cc(Br)cc12] |
| 18 | 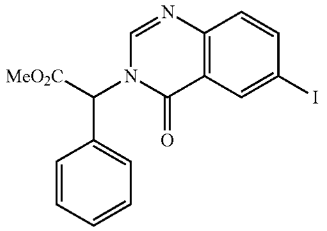 [SMILES: COC(=O)C(c1ccccc1)n1cnc2ccc(I)cc2c1=O] Methyl 2-(6-iodo-4-oxo-quinazolin-3(4H)-yl)-2-phenylacetate | 421.1 | 8.69 (d, 1H) 8.05 (dd, 1H) 7.90 (s, 1H) 7.48 (m, 3H) 7.44 (d, 1H) 7.39 (m, 2H) 6.75 (s, 1H) 3.89 (s, 3H) | 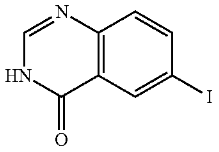 [SMILES: O=c1[nH]cnc2ccc(I)cc12] |
| A | 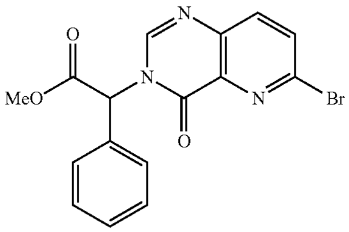 [SMILES: COC(=O)C(c1ccccc1)n1cnc2ccc(Br)nc2c1=O] Methyl 2-(6-bromo-4-oxo-pyrido[3,2-d]pyrimidin-3(4H)-yl)-2-phenylacetate | 373.96 | — | 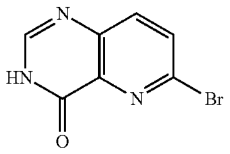 |
| B | 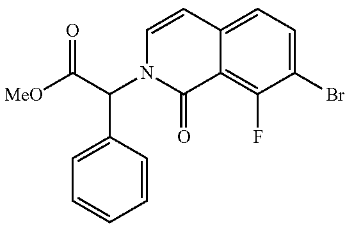 [SMILES: COC(=O)C(c1ccccc1)n1ccc2ccc(Br)c(F)c2c1=O] Methyl 2-(7-bromo-8-fluoro-1-oxoisoquinolin-2(1H)-yl)-2-phenylacetate | | 8.00 (dd, 1H) 7.46 (m, 6H) 7.15 (d, 1H) 6.64 (dd, 1H) 6.50 (s, 1H) 3.76 (s, 3H) | 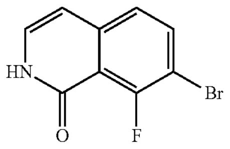 |

Scheme 2

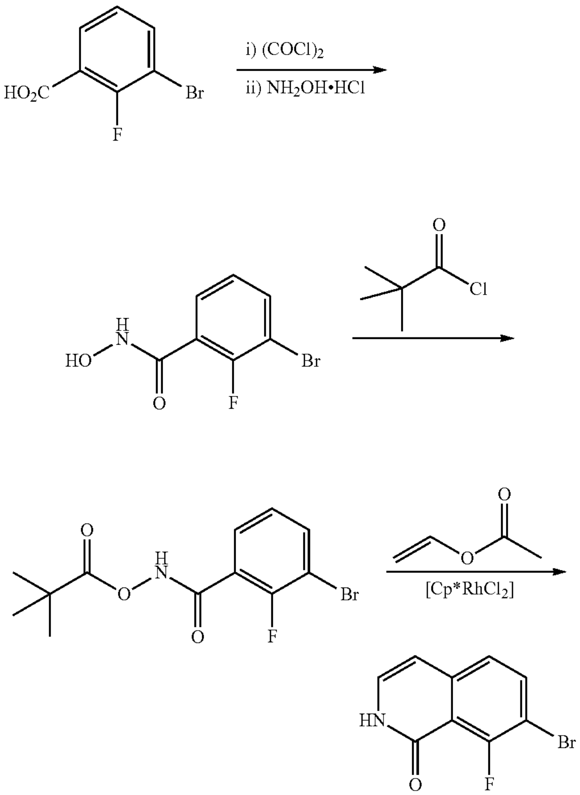

3-Bromo-2-fluoro-N-hydroxybenzamide

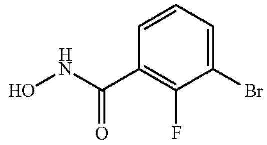 [SMILES: O=C(NO)c1cccc(Br)c1F]

A suspension of 3-bromo-2-fluorobenzoic acid (1 g, 4.6 mmol) in DCM (15 mL) at 0° C. was treated with oxalyl chloride (474 μL, 5.5 mmol) dropwise over 2 minutes. DMF (2 drops) was added and the reaction mixture was stirred at room temperature for 4 h. Solvent was removed under reduced pressure to give crude 3-bromo-2-fluorobenzoyl chloride, which was used immediately without further purification.

A solution of the crude 3-bromo-2-fluorobenzoyl chloride in EtOAc (10 mL) was added dropwise to a vigorously stirred suspension of EtOAc (36 mL), water (18 mL), and $K_2CO_3$ (1.27 g, 9.2 mmol) at 0° C. The reaction mixture was stirred overnight at room temperature. The layers were separated and the aqueous layer was extracted with EtOAc (2×30 mL). The combined organic extracts were washed with water, dried over $Na_2SO_4$, filtered, and concentrated under reduced pressure to give the title compound (700 mg, 65%). $^1H$ NMR (500 MHz, $d_6$-DMSO) δ 11.10 (s, 1H) 9.33 (s, 1H) 7.83 (m, 1H) 7.53 (m, 1H) 7.24 (m, 1H).

3-Bromo-2-fluoro-N-(pivaloyloxy)benzamide

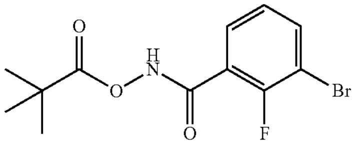 [SMILES: CC(C)(C)C(=O)ONC(=O)c1cccc(Br)c1F]

Pivaloyl chloride (407 μL, 3.3 mmol) was added dropwise to a solution of 3-bromo-2-fluoro-N-hydroxybenzamide (700 mg, 3.0 mmol) and DIEA (572 μL, 3.3 mmol) in anhydrous THF (9 mL). The reaction mixture was stirred for 1 h and then concentrated under reduced pressure. The residue was dissolved in EtOAc (15 mL), washed with 1 N HCl (15 mL) and saturated brine (15 mL), dried over $Na_2SO_4$; filtered and purified by silica chromatography (0-65% EtOAc/hexane) to give the title compound (850 mg, 89%). $^1H$ NMR (500 MHz, $d_6$-DMSO) δ 7.93 (m, 1H) 7.64 (m, 1H) 7.30 (m, 1H) 1.29 (s, 9H).

7-Bromo-8-fluoroisoquinolin-1(2H)-one

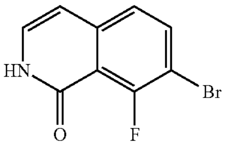

A mixture of 3-bromo-2-fluoro-N-(pivaloyloxy)benzamide (318 mg, 1.0 mmol), penta-methylcyclopentadienyl rhodium dichloride (6 mg, 0.01 mmol), Cs(OAc) (58 mg 0.3 mmol), vinyl acetate (131 μL, 1.5 mmol), and methanol (8 mL) was stirred under $N_2$ overnight at 45° C. Additional aliquots of pentamethylcyclopentadienyl rhodium dichloride (6 mg, 0.01 mmol) and vinyl acetate (131 μL, 1.5 mmol) were added and the reaction was stirred at 45° C. for a further 48 h. The solvent was removed under reduced pressure and the residue was triturated with 10 mL of 10% MeOH in $Et_2O$. The solid was collected and purified by reverse phase HPLC eluting with 0-80% ACN/$H_2O$ (0.038% TFA modifier) to give the title compound (116 mg, 48%). $^1H$ NMR (500 MHz, $d_6$-DMSO) δ 11.41 (br s, 1H) 7.93 (dd, 1H) 7.45 (d, 1H) 7.24 (d, 1H) 6.56 (dd, 1H).

Methyl 2-amino-2-(3-fluorophenyl)acetate

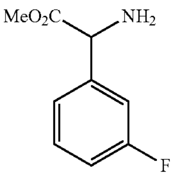 [SMILES: COC(=O)C(N)c1cccc(F)c1]

Thionyl chloride (7.72 ml, 0.106 mol) was added dropwise to a mixture of 2-amino-2-(3-fluorophenyl)acetic acid (6.0 g, 0.035 mol) in methanol (100 mL) at 0° C. The reaction was stirred at room temperature for 30 minutes, then at 60° C. for 16 hours. The solvents were removed under reduced pressure, and the residue was dissolved in EtOAc (150 mL). The organic layer was washed with saturated brine and saturated $NaHCO_3$, dried ($Na_2SO_4$) and concentrated to give the title compound, used without further purification (6.49 g). $^1H$ NMR (500 MHz, $d_6$-DMSO) δ 7.35 (m, 1H) 7.20 (d, 1H) 7.15 (d, 1H) 7.03 (m, 1H) 3.74 (s, 3H).

Ester 19: Methyl 2-(7-bromo-4-oxoquinazolin-3(4H)-yl)-2-(3-fluorophenyl)acetate

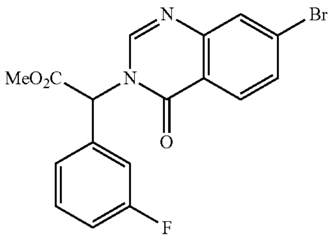 [SMILES: COC(=O)C(c1cccc(F)c1)n1cnc2cc(Br)ccc2c1=O]

DBU (1.00 mL, 6.66 mmol) and HATU (2.53 g, 6.66 mmol) were added to a mixture of 7-bromoquinazolin-4(3H)-one (1.00 g, 4.44 mmol) and methyl 2-amino-2-(3-fluorophenyl)acetate (977 mg, 5.33 mmol) in $CH_3CN$ (20 mL) and the reaction was stirred at 60° C. for 16 hours. The reaction mixture was diluted with EtOAc (100 mL) and washed with sat. $NH_4Cl$ solution. The organic layer was dried ($Na_2SO_4$) and the residue purified by silica chromatography (0-5% MeOH in DCM) to give the title compound (517 mg, 30%). $^1H$ NMR (500 MHz, $d_6$-DMSO) δ 8.37 (s, 1H) 8.10 (d, 1H) 7.95 (d, 1H) 7.77 (dd, 1H) 7.47 (m, 1H) 7.43 (m, 1H) 7.36 (d, 1H) 7.28 (m, 1H) 6.59 (s, 1H); MS (n/z): 392.97 $[M+1]^+$.

Esters 20, C, and D in Table 5 were prepared by a similar method to ester 19, from 6-bromoquinazolin-4(3H)-one and methyl 2-amino-2-(3-fluorophenyl)acetate.

TABLE 5

| Ester | Structure/Name | m/z $[M+1]^+$ | NMR $^1H$ NMR (500 MHz, $CDCl_3$-d) δ | Starting materials |
|---|---|---|---|---|
| 20 | 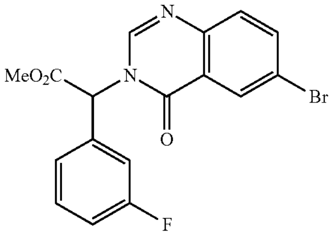 [SMILES: COC(=O)C(c1cccc(F)c1)n1cnc2ccc(Br)cc2c1=O] Methyl 2-(6-bromo-4-oxo-quinazolin-3(4H)-yl)-2-(3-fluoro-phenyl)acetate | 390.99 | 8.38 (d, 1H) 7.87 (s, 1H) 7.79 (dd, 1H) 7.56 (d, 1H) 7.38 (m, 1H) 7.09 (m, 2H) 7.02 (m, 1H) 6.88 (s, 1H) 3.82 (s, 3H) | 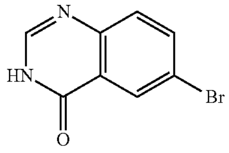 and 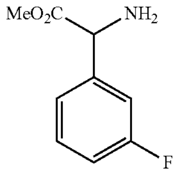 |
| C | 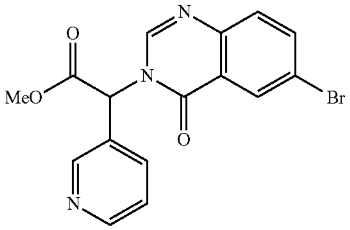 [SMILES: COC(=O)C(c1cccnc1)n1cnc2ccc(Br)cc2c1=O] Methyl 2-(6-bromo-4-oxo-quinazolin-3(4H)-yl)-2-(pyridin-3-yl)acetate | 375.93 | $CDCl_3$ 8.71 (m, 2H) 8.45 (d, 1H) 8.01 (s, 1H) 8.18 (s, 1H) 7.87 (dd, 1H) 7.85 (d, 1H) 7.60 (d, 1H) 7.46 (dd, 1H) 6.73 (s, 1H) 3.90 (s, 3H) | 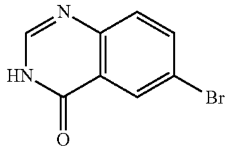 and 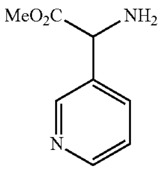 |

TABLE 5-continued

| Ester | Structure/Name | m/z [M + 1]+ | NMR $^1$H NMR (500 MHz, $CDCl_3$-d) δ | Starting materials |
|---|---|---|---|---|
| D | 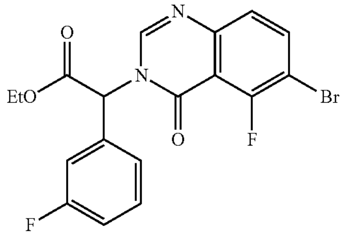 [SMILES: CCOC(=O)C(c1cccc(F)c1)n1cnc2ccc(Br)c(F)c2c1=O] Ethyl 2-(6-bromo-5-fluoro-4-oxo-quinazolin-3(4H)-yl)-2-(3-fluoro-phenyl)acetate | 425.00 | 8.32 (s, 1H) 8.15 (dd, 1H) 7.50 (m 2H) 7.41 (m, 1H) 7.36 (d, 1H) 7.29 (m, 1H) 6.54 (s, 1H) 4.26 (q, 2H) 1.19 (t, 3H) | 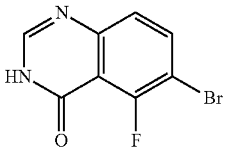 and 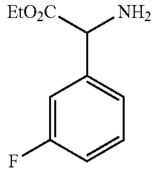 |

7-Bromo-2-methyl-4H-benzo[d][1,3]oxazin-4-one

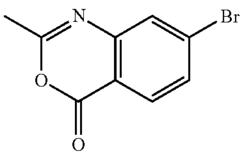

A mixture of 2-amino-4-bromobenzoic acid (1.50 g, 6.94 mmol) and acetic anhydride (10 mL, 106 mmol) was heated to reflux for 3 hours. The reaction mixture was cooled and the resulting solid was filtered, washed with 2 mL of acetic anhydride and dried to give the title compound (750 mg, 45%).

7-Bromo-2-methylquinazolin-4(3H)-one

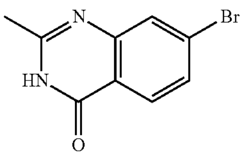

A mixture of 7-bromo-2-methyl-4H-benzo[d][1,3]oxazin-4-one (500 mg, 2.09 mmol) and 30% aqueous ammonia (6 mL) was heated to 80° C. for 2 hours in a sealed pressure tube. After cooling to room temperature, the solid was filtered, washed with water, and dried to give the title compound (240 mg, 47%). $^1$H NMR (500 MHz, DMSO-$d_F$) δ ppm 7.98 (d, 1H) 7.78 (d, 1H) 7.62 (m, 1H) 2.36 (s, 3H); MS (m/z): 238.9 [M+1]$^+$.

Scheme 3.

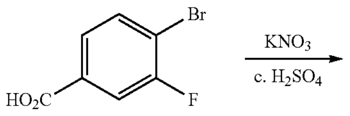

-continued

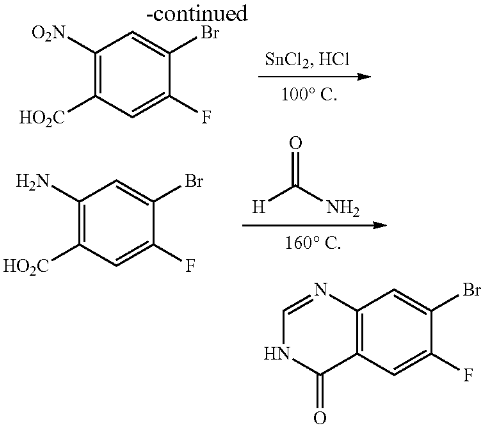

4-Bromo-5-fluoro-2-nitrobenzoic acid

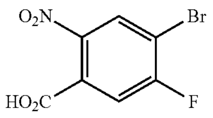

Potassium nitrate (9.69 g, 96 mmol) was added in portions to a solution of 4-bromo-3-fluorobenzoic acid (20.0 g, 91 mmol) in concentrated sulfuric acid (70 mL). The reaction solution was stirred for 3 hours, then poured carefully onto 250 mL of crushed ice. The mixture was stirred for 10 minutes, filtered, washed with water and dried to give the title compound (21 g, 87%). $^1$H NMR (500 MHz, DMSO-$d_6$) δ ppm 851 (d, 1H) 7.90 (m, 1H).

2-Amino-4-bromo-5-fluorobenzoic acid

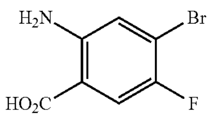

Stannous chloride dihydrate (24 g, 107 mmol) was added to a suspension of 4-bromo-5-fluoro-2-nitrobenzoic acid (9.4 g, 35.6 mmol) in 6N HCl (140 mL). The mixture was stirred at 100° C. for 3 hours then cooled. The resulting solid was filtered, washed with water and dried to give the title compound (7.68 g, 92%). $^{1}H$ NMR (500 MHz, DMSO-$d_6$) δ ppm 7.50 (d, 1H) 7.09 (d, 1H); MS (m/z): 233.9 $[M+1]^+$.

7-Bromo-6-fluoroquinazolin-4(3H)-one

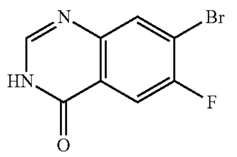

A mixture of 2-amino-4-bromo-5-fluorobenzoic acid (4.6 g, 20 mmol) and formamide (23 mL) was heated at 160° C. for 6 hours under nitrogen. The mixture was cooled and poured into ~200 mL of ice water. The solid was filtered, washed with water and dried to give the title compound (3.44 g, 71%). $^{1}H$ NMR (500 MHz, DMSO-$d_6$) δ ppm 8.12 (d, 1H) 806 (d, 1H) 7.91 (d, 1H); MS (m/z): 242.9 $[M+1]^+$.

6-Bromo-5-fluoroquinazolin-4(3H)-one

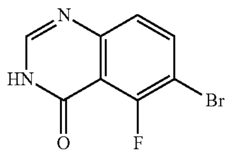

A mixture of 6-amino-3-bromo-2-fluorobenzoic acid (500 mg, 2.1 mmol) and formamide (10 mL) was heated at 160° C. for 8 hours. After cooling, the reaction mixture was added to 100 mL of water. The solid was filtered, washed with water and dried to give the title compound (250 mg, 48%). $^{1}H$ NMR (500 MHz, $CDCl_3$-d) δ ppm 8.05 (s, 1H) 7.93 (dd, 1H) 7.49 (dd, 1H). MS (m/z): 242.9 $[M+1]^+$.

6-Bromo-4-fluoroisoquinolin-1(2H)-one

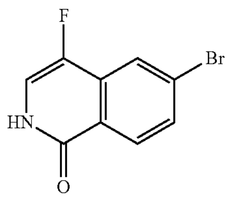

A mixture of 6-bromoisoquinolin-1(2H)-one (365 mg, 1.63 mmol), 1-chloromethyl-4-fluoro-1,4-diazoniabicyclo [2.2.2]octane bis(tetrafluoroborate) [Selectfluor] (576 mg, 1.63 mmol), and dimethylacetamide (3.5 mL) was heated in a microwave for 15 minutes at 150° C. This was repeated three more times. The four runs were combined and partitioned between EtOAc (100 mL) and water (100 mL). The aqueous layer was extracted with EtOAc (2×100 mL), and the combined organic extracts were washed with brine, dried ($Na_2SO_4$) and concentrated, and the residue was purified by silica chromatography (0-50% EtOAc in Hex) to give the title compound (230 mg, 25%). $^{1}H$ NMR (500 MHz, DMSO-$d_6$) δ ppm 11.30 (br s, 1H) 8.12 (dd, 1H) 7.91 (d, 1H) 7.78 (dd, 1H) 7.47 (m, 1H); MS (m/z): 241.9 $[M+1]^+$.

7-Bromo-4-fluoroisoquinolin-1(2H)-one

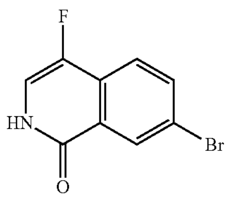

7-Bromo-4-fluoroisoquinolin-1(2H)-one was prepared according to a similar procedure to 6-bromo-4-fluoroisoquinolin-1(2H)-one from 7-bromoisoquinolin-1(2H)-one. $^{1}H$ NMR (500 MHz, DMSO-de) 6 ppm 8.30 (m, 1H) 8.01 (m, 1H) 7.71 (d, 1H) 7.46 (d, 1H).

36-Dibromoisobenzofuran-1(3H)-one

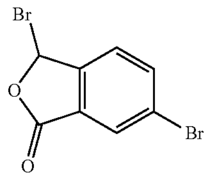 [SMILES: O=C1OC(Br)c2ccc(Br)cc21]

A mixture of 6-bromoisobenzofuran-1(3H)-one (1.0 g, 4.69 mmol), N-bromosuccinimide (958 mg, 5.38 mmol), and chloroform (25 mL) was heated at reflux for 2.5 hours. After cooling, the reaction was quenched with saturated aqueous $NaHCO_3$ (25 mL). The organic phase was washed with water and brine, dried ($Na_2SO_4$) and concentrated, and the residue was purified by silica chromatography (5-10% EtOAc in Hex) to give the title compound (350 mg, 26%). $^{1}H$ NMR (500 MHz, CDC13-d) δ ppm 7.99 (d, 1H) 7.83 (m, 1H) 7.44 (d, 1H) 7.29 (s, 1H).

7-Bromophthalazin-1(2H)-one

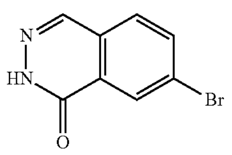

A mixture of 3,6-dibromoisobenzofuran-1(3H)-one (350 mg, 1.2 mmol) and hydroxylamine hydrate (300 μL, 6 mmol) in ethanol (15 ml) was heated to reflux for 1.5 hours. After cooling to room temperature, 20 mL of ice water was added. The resulting precipitate was filtered, washed with water, and dried to give the title compound (250 mg, 93%). $^{1}H$ NMR (500 MHz, DMSO-de) δ ppm 8.40 (s, 1H) 8.32 (d, 1H) 8.13 (m, 1H) 7.92 (d, 1H); MS (m/z): 224.9 $[M+1]^+$.

Acids 2-17, A, and B in Table 6 were prepared by a similar method to Acid 1, from the corresponding methyl ester.

TABLE 6

| Acid | Structure/Name | m/z [M + 1]$^+$ | $^1$H NMR (500 MHz, $d_6$-DMSO) δ |
|---|---|---|---|
| 2 | 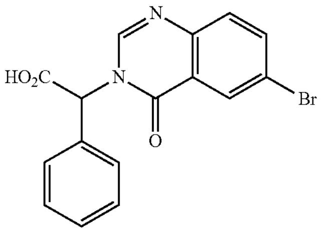 [SMILES: O=C(O)C(c1ccccc1)n1cnc2ccc(Br)cc2c1=O] 2-(6-Bromo-4-oxoquinazolin-4H)-yl)-2-phenyl-acetic acid | 360.9 | 8.28 (d, 1H) 8.15 (s, 1H) 8.02 dd, 1H) 7.65 (d, 1H) 7.51 (m, 2H) 7.45 (m, 3H) 6.50 (s, 1H) |
| 3 | 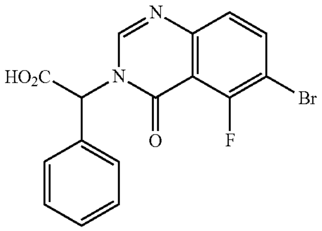 [SMILES: O=C(O)C(c1ccccc1)n1cnc2ccc(Br)c(F)c2c1=O] 2-(6-Bromo-5-fluoro-4-oxo-quinazolin-3(4H)-yl)-2-phenylacetic acid | 376.9 | 8.13 (m, 2H) 7.52 (m, 2H) 7.47 (m, 4H) 6.47 (s, 1H) |
| 4 | 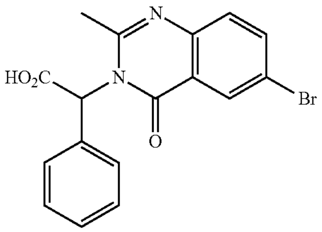 [SMILES: Cc1nc2ccc(Br)cc2c(=O)n1C(C(=O)O)c1ccccc1] 2-(6-Bromo-2-methyl-4-oxo-quinazolin-3(4H)-yl)-2-phenylacetic acid | 372.95 | 8.22 (d, 1H) 8.00 (m, 1H) 7.61 (d, 1H) 7.43 (m, 2H) 7.34 (m, 3H) 6.42 (s, 1H) 2.56 (s, 3H) |
| 5 | 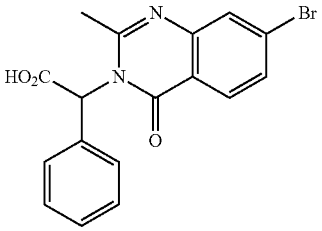 [SMILES: Cc1nc2cc(Br)ccc2c(=O)n1C(C(=O)O)c1ccccc1] 2-(7-Bromo-2-methyl-4-oxo-quinazolin-3(4H)-yl)-2-phenylacetic acid | 373.0 | — |

TABLE 6-continued
| Acid | Structure/Name | m/z [M + 1]$^+$ | $^1$H NMR (500 MHz, $d_6$-DMSO) δ |
|---|---|---|---|
| 6 | 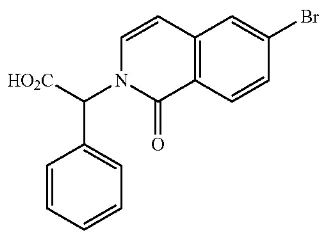 [SMILES: O=C(O)C(c1ccccc1)n1ccc2cc(Br)ccc2c1=O] 2-(6-Bromo-1-oxoisoquinolin-2-(1H)-yl)-2-phenyl-acetic acid | 359.9 | 8.16 (d, 1H) 7.95 (d, 1H) 7.69 (dd, 1H) 7.44 (m, 5H) 7.14 (d, 1H) 6.58 (d, 1H) 6.53 (s, 1H) |
| 7 | 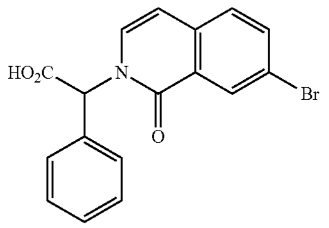 [SMILES: O=C(O)C(c1ccccc1)n1ccc2ccc(Br)cc2c1=O] 2-(7-Bromo-1-oxoisoquinolin-2-(1H)-yl)-2-phenyl-acetic acid | 359.9 | 8.34 (d, 1H) 7.89 (dd, 1H) 7.64 (d, 1H) 7.44 (m, 5H) 7.12 (d, 1H) 6.62 (d, 1H) 6.53 (s, 1H) |
| 8 | 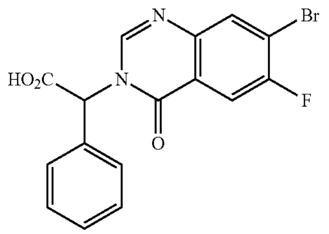 [SMILES: O=C(O)C(c1ccccc1)n1cnc2cc(Br)c(F)cc2c1=O] 2-(7-Bromo-6-fluoro-4-oxo-quinazolin-3(4H)-yl)-2-phenylacetic acid | 377.0 | — |
| 9 | 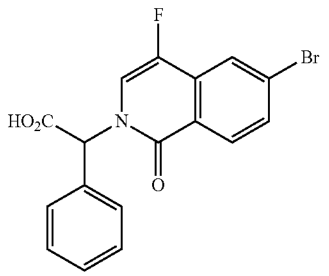 [SMILES: O=C(O)C(c1ccccc1)n1cc(F)c2cc(Br)ccc2c1=O] 2-(6-Bromo-4-fluoro-1-oxo-isoquinolin-2(1H)-yl)-2-phenyl-acetic acid | 376.0 | 8.22 (dd, 1H) 7.95 (d, 1H) 7.85 (dd, 1H) 7.47 (m, 5H) 7.32 (d, 1H) 6.52 (s, 1H) |

TABLE 6-continued

| Acid | Structure/Name | m/z [M + 1]+ | $^{1}H$ NMR (500 MHz, $d_6$-DMSO) δ |
|---|---|---|---|
| 10 | 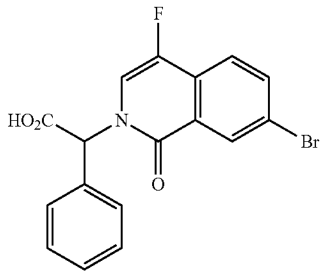 [SMILES: O=C(O)C(c1ccccc1)n1cc(F)c2ccc(Br)cc2c1=O] 2-(7-Bromo-4-fluoro-1-oxo-isoquinolin-2(1H)-yl)-2-phenyl-acetic acid | 375.9 | 8.41 (m, 1H) 8.07 (m, 1H) 7.74 (d, 1H) 7.48 (m, 5H) 7.32 (d, 1H) 6.53 (s, 1H) |
| 11 | 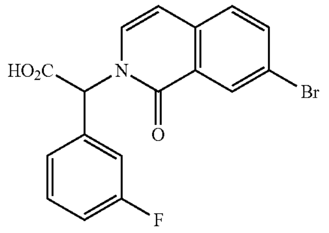 [SMILES: O=C(O)C(c1cccc(F)c1)n1ccc2ccc(Br)cc2c1=O] 2-(7-Bromo-1-oxoisoquinolin-2(1H)-yl)-2-(3-fluorophenyl)acetic acid | 376.0 | 8.33 (d, 1H) 7.90 (dd, 1H) 7.66 (d, 1H), 7.48 (m, 1H) 7.33 (m, 1H) 7.28 (d, 2H) 7.25 (m, 1H) 6.66 (d, 1H) 6.50 (s, 1H) |
| 12 | 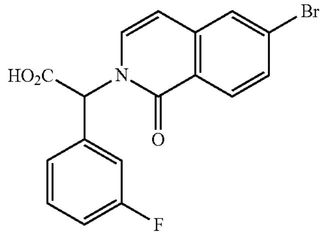 [SMILES: O=C(O)C(c1cccc(F)c1)n1ccc2cc(Br)ccc2c1=O] 2-(6-Bromo-1-oxoisoquinolin-2(1H)-yl)-2-(3-fluorophenyl)acetic acid | 376.0 | 8.14 (d, 1H) 7.96 (d, 1H) 7.68 dd, 1H) 7.48 (m, 1H) 7.33 (m, 1H) 7.26 (m, 3H) 6.61 (d, 1H) 6.50 (s, 1H) |
| 13 | 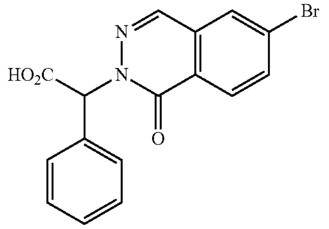 [SMILES: O=C(O)C(c1ccccc1)n1ncc2cc(Br)ccc2c1=O] 2-(6-Bromo-1-oxophthalazin-2(1H)-yl)-2-phenyl-acetic acid | 360.9 | 8.40 (s, 1H) 8.24 (d, 1H) 8.19 (d, 1H) 8.06 (dd, 1H) 7.44 (m, 2H) 7.36 (m, 3H) 6.64 (s, 1H) |
| 14 | 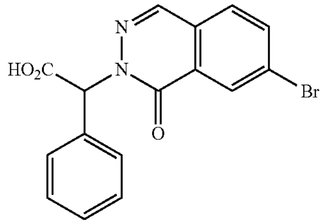 [SMILES: O=C(O)C(c1ccccc1)n1ncc2ccc(Br)cc2c1=O] 2-(7-Bromo-1-oxophthalazin-2(1H)-yl)-2-phenyl-acetic acid | 360.9 | 8.47 (s, 1H) 8.39 (d, 1H) 8.17 (m, 1H) 7.92 (d, 1H) 7.45 (m, 2H) 7.36 (m, 3H) 6.66 (s, 1H) |

TABLE 6-continued
| Acid | Structure/Name | m/z $[M + 1]^+$ | $^1H$ NMR (500 MHz, $d_6$-DMSO) δ |
|---|---|---|---|
| 15 | 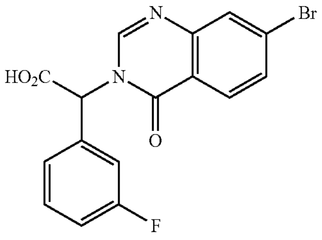 [SMILES: O=C(O)C(c1cccc(F)c1)n1cnc2cc(Br)ccc2c1=O] 2-(7-Bromo-4-oxoquinazolin-3(4H)-yl)-2-(3-fluoro-phenyl)acetic acid | 378.92 | — |
| 16 | 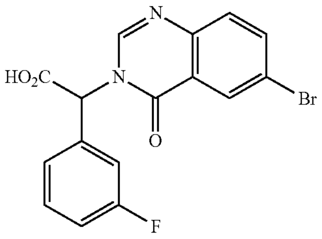 [SMILES: O=C(O)C(c1cccc(F)c1)n1cnc2ccc(Br)cc2c1=O] 2-(6-Bromo-4-oxoquinazolin-3(4H)-yl)-2-(3-fluoro-phenyl)acetic acid | 378.92 | — |
| 17 | 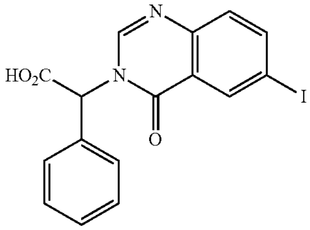 [SMILES: O=C(O)C(c1ccccc1)n1cnc2ccc(I)cc2c1=O] 2-(6-Iodo-4-oxoquinazolin-3-4H)-yl)-2-phenylacetic acid | 407.0 | 8.47 (d, 1H) 8.16 (dd, 1H) 8.14 (s, 1H) 7.52 (m, 2H) 7.49 (d, 1H) 7.45 (m, 3H) 6.50 (s, 1H) |
| A | 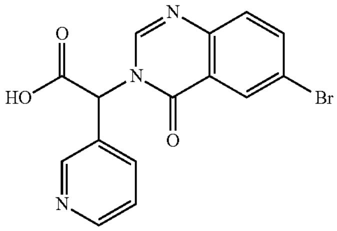 [SMILES: O=C(O)C(c1cccnc1)n1cnc2ccc(Br)cc2c1=O] 2-(6-Bromo-4-oxoquinazolin-3(4H)-yl)-2-(pyridin-3-yl)acetic acid | 359.92 | — |
| B | 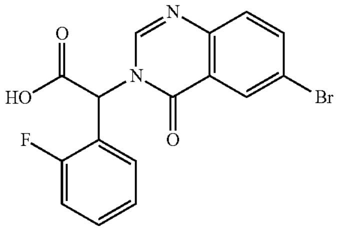 [SMILES: O=C(O)C(c1ccccc1F)n1cnc2ccc(Br)cc2c1=O] 2-(6-Bromo-4-exoquinazolin-3(4H)-yl)-2-(2-fluorophenyl)acetic acid | 376.89 | — |

Compound 012: 2-(7-(4-(1-Methylpiperidin-4-yl)phenyl)-4-oxoquinazolin-3(4H)-yl)-2-phenyl-N-(thiazol-2-yl)acetamide

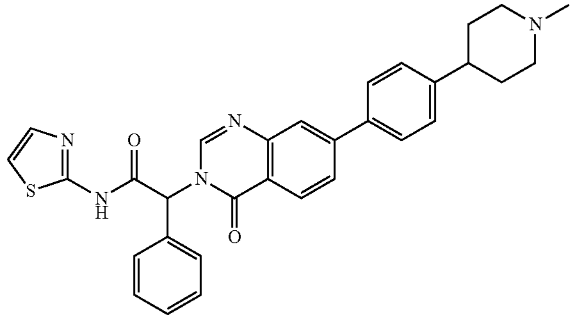 [SMILES: CN1CCC(c2ccc(-c3ccc4c(=O)n(C(C(=O)Nc5nccs5)c5ccccc5)cnc4c3)cc2)CC1]

A mixture of 2-(7-bromo-4-oxoquinazolin-3(4H)-yl)-2-phenyl-N-(thiazol-2-yl)acetamide (70 mg, 0.16 mmol), 1-methyl-4-(4-(4,4,5,5-tetramethyl-1,3,2-dioxaborolan-2-yl)phenyl)-piperidine (72 mg, 0.24 mmol), Pd(dppf)$Cl_2$. DCM (26 mg, 0.03 mmol) and sodium carbonate (50 mg, 0.48 mmol) was stirred in dioxane:water (4:1, 3.5 mL) at 100° C. for 3 hours. The reaction mixture was filtered and purified by reverse phase HPLC, eluting with 0-80% ACN/water, to give the title compound (21 mg, 25%). $^1H$ NMR (500 MHz, dDMSO) δ 9.39 (br s, 1H) 8.26 (d, 1H) 7.95 (d, 1H) 7.92 (dd, 1H) 7.87 (s, 1H) 7.83 (d, 2H) 7.52 (m, 4H) 7.45 (m, 2H) 7.40 (d, 2H) 7.32 (d, 1H) 6.89 (s, 1H) 3.54 (d, 2H) 3.10 (m, 2H) 2.88 (m, 1H) 2.83 (d, 3H) 2.07 (d, 2H) 1.86 (m, 2H); MS (m/z): 539.2 $[M+1]^+$.

The following compounds were prepared by a similar method to Compound 012 from the corresponding starting materials.

TABLE 7

| No. | Structure/Name | m/z $[M + 1]^+$ | $^1H$ NMR (500 MHz, $d_6$-DMSO) δ | Starting materials |
|---|---|---|---|---|
| 013 | 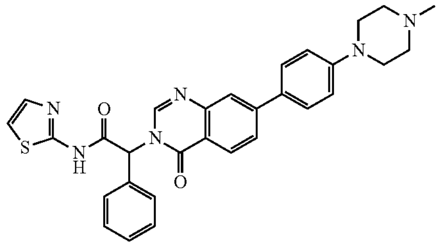 2-(7-(4-(4-Methylpiperazin-1-yl)-phenyl)-4-oxoquinazolin-3(4H)-yl)-2-phenyl-N-(thiazol-2-yl)acetamide | 537.2 | 8.20 (d, 1H) 7.88 (m, 2H) 7.84 (s, 1H) 7.74 (d, 2H) 7.52 (m, 4H) 7.45 (m, 2H) 7.32 (d, 1H) 7.08 (d, 2H) 6.88 (s, 1H) 2.66 (m, 4H) 2.37 (br s, 3H) 4 protons masked by water peak | Compound 001 and 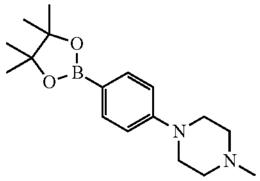 |
| 014 | 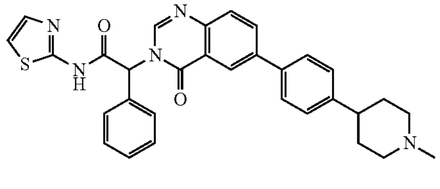 [SMILES: CN1CCC(c2ccc(-c3ccc4ncn(C(C(=O)Nc5nccs5)c5ccccc5)c(=O)c4c3)cc2)CC1] 2-(6-(4-(1-Methylpiperidin-4-yl)-phenyl)-4-oxoquinazolin-3(4H)-yl)-2-phenyl-N-(thiazol-2-yl)acetamide | 536.2 | 9.31 (br s, 1H) 8.40 (d, 1H) 8.19 (dd, 1H) 7.85 (s, 1H) 7.79 (d, 1H) 7.78 (d, 2H) 7.51 (m, 4H) 7.46 (m, 2H) 7.40 (d, 2H), 7.32 (d, 1H) 6.89 (s, 1H) 3.54 (d, 2H) 3.10 (m, 2H) 2.87 (m, 1H) 2.83 (d, 3H) 2.08 (d, 2H) 1.86 (m, 2H) | Compound 002 and 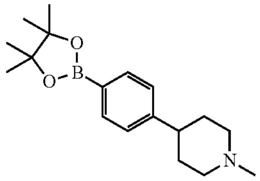 |
| 015 | 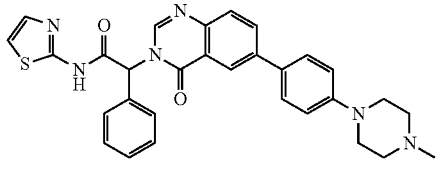 2-(6-(4-(4-Methylpiperazin-1-yl)-phenyl)-4-oxoquinazolin-3(4H)-yl)-2-phenyl-N-(thiazol-2-yl)acetamide | 537.2 | 9.60 (br s, 1H) 8.35 (d, 1H) 8.17 (dd, 1H) 7.82 (s, 1H) 7.75 (d, 1H) 7.73 (d, 2H) 7.51 (m, 4H) 7.46 (m, 2H) 7.32 (d, 1H) 7.15 (d, 2H) 6.88 (s, 1H) 3.97 (d, 2H) 3.53 (d, 2H) 3.18 (m, 2H) 3.03 (m, 2H) 2.88 (d, 3H) | Compound 002 and 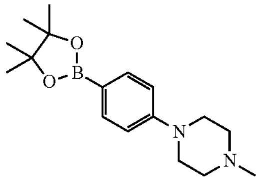 |

TABLE 7-continued

| No. | Structure/Name | m/z $[M + 1]^+$ | $^1$H NMR (500 MHz, $d_6$-DMSO) δ | Starting materials |
|---|---|---|---|---|
| 038 | 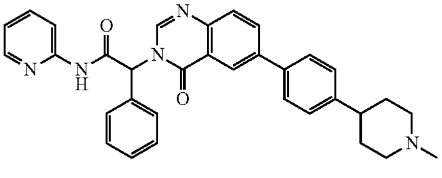 [SMILES: CN1CCC(c2ccc(-c3ccc4ncn(C(C(=O)Nc5ccccn5)c5ccccc5)c(=O)c4c3)cc2)CC1] 2-(6-(4-(1-Methylpiperidin-4-yl)-phenyl)-4-oxaquinazolin-3(4H)-yl)-2-phenyl-N-(pyridin-2-yl)acetamide | 530.3 | 11.37 (s, 1H) 9.33 (br s, 1H) 8.41 (d, 1H) 8.35 (dd, 1H) 8.19 (dd, 1H) 8.13 (d, 1H) 7.84 (m, 1H) 7.80 (m, 4H) 7.50 (m, 5H) 7.40 (d, 2H) 7.17 (m, 1H) 7.01 (s, 1H) 3.55 (d, 2H) 3.11 (m, 2H) 2.88 (m, 1H) 2.85 (d, 3H) 2.08 (d, 2H) 1.87 (m, 2H) | Compound 048 and 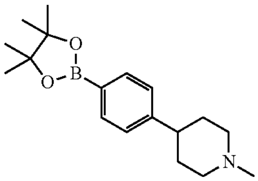 |
| 039 | 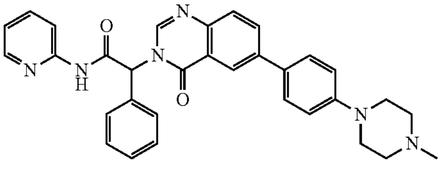 [SMILES: CN1CCN(c2ccc(-c3ccc4ncn(C(C(=O)Nc5ccccn5)c5ccccc5)c(=O)c4c3)cc2)CC1] 2-(6-(4-(4-Methylpiperazin-1-yl)-phenyl)-4-oxoquinazolin-3(4H)-yl)-2-phenyl-N-(pyridin-2-yl)acetamide | 531.3 | 11.36 (s, 1H) 9.65 (br s, 1H) 8.37 (d, 1H) 8.35 (dd, 1H) 8.16 (dd, 1H) 8.13 (d, 1H) 7.84 (m, 1H) 7.78 (s, 1H) 7.74 (d, 1H) 7.73 (d, 2H) 7.50 (m, 5H) 7.17 (m, 1H) 7.16 (d, 2H) 7.00 (s, 1H) 3.98 (d, 2H) 3.55 (d, 2H) 3.19 (m, 2H) 3.04 (m, 2H) 2.88 (d, 3H) | Compound 048 and 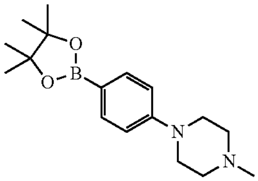 |
| 044 | 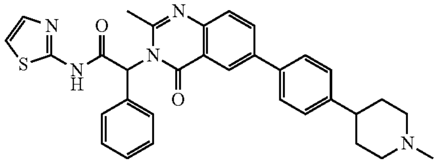 2-(2-Methyl-6-(4-(1-methylpiperidin-4-yl)phenyl)-4-oxoquinazolin-3(4H)-yl)-2-phenyl-N-(thiazol-2-yl)acetamide | 550.2 | 9.23 (br s, 1H) 8.25 (d, 1H) 8.10 (dd, 1H) 7.70 (d, 2H) 7.68 (d, 1H) 7.36 (d, 1H) 7.31 (m, 5H) 7.14 (d, 1H) 6.53 (s, 1H) 3.46 (d, 2H) 3.02 (m, 2H) 2.79 (m, 1H) 2.76 (d, 3H) 2.48 (s, 3H) 1.99 (d, 2H) 1.77 (m, 2H) | Compound 050 and 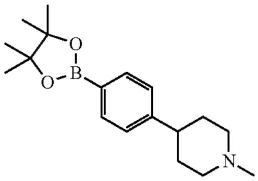 |
| 045 | 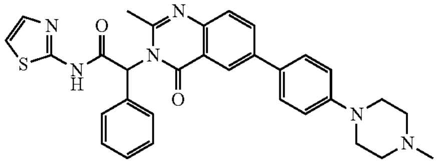 [SMILES: Cc1nc2ccc(-c3ccc(N4CCN(C)CC4)cc3)cc2c(=O)n1C(C(=O)Nc1nccs1)c1ccccc1] 2-(2-Methyl-6-(4-(4-methylpiperazin-1-yl)phenyl)-4-oxoquinazolin-3(4H)-yl)-2-phenyl-N-(thiazol-2-yl)-acetamide | 551.2 | 9.64 (br s, 1H) 8.20 (d, 1H) 8.09 (dd, 1H) 7.65 (d, 2H) 7.64 (d, 1H) 7.35 (d, 1H) 7.31 (m, 5H) 7.14 (d, 1H) 7.04 (d, 2H) 6.52 (s, 1H) 3.88 (d, 2H) 3.46 (d, 2H) 3.10 (m, 2H) 2.94 (m, 2H) 2.80 (d, 3H) 2.48 (s, 3H) | Compound 050 and 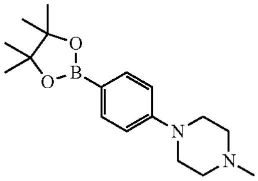 |
| 016 | 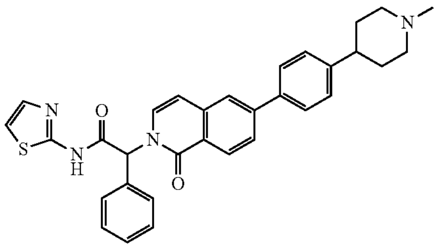 [SMILES: CN1CCC(c2ccc(-c3ccc4c(=O)n(C(C(=O)Nc5nccs5)c5ccccc5)ccc4c3)cc2)CC1] 2-(6-(4-(1-Methylpiperidin-4-yl)-phenyl)-1-oxoisoquinolin-2(1H)-yl)-2-phenyl-N-(thiazol-2-yl)acetamide | 535.2 | 9.33 (br s, 1H) 8.32 (d, 1H) 7.95 (d, 1H) 7.85 (dd, 1H) 7.80 (d, 2H) 4H) 7.30 (d, 1H) 6.95 (d, 1H) 6.94 (s, 1H) 6.66 (d, 1H) 3.54 (d, 2H) 3.10 (m, 2H) 2.88 (m, 1H) 2.83 (d, 3H) 2.08 (d, 2H) 1.86 (m, 2H) | Compound 003 and 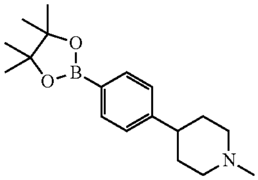 |

TABLE 7-continued

| No. | Structure/Name | m/z [M + 1]+ | $^1$H NMR (500 MHz, $d_6$-DMSO) δ | Starting materials |
|---|---|---|---|---|
| 017 | 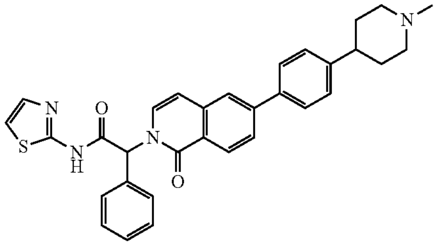 [SMILES: CN1CCC(c2ccc(-c3ccc4c(=O)n(C(C(=O)Nc5nccs5)c5ccccc5)ccc4c3)cc2)CC1] 2-(6-(4-(4-Methylpiperazin-1-yl)-phenyl)-1-oxoisoquinolin-2(1H)-yl)-2-phenyl-N-(thiazol-2-yl)acetamide | 536.2 | 9.72 (br s, 1H) 8.27 (d, 1H) 7.92 (d, 1H) 7.84 (dd, 1H) 7.76 (d, 2H) 7.51 (m, 4H) 7.38 (d, 2H) 7.30 (d, 1H) 7.14 (d, 2H) 6.93 (s, 1H) 6.92 (d, 1H) 6.64 (d, 1H) 3.98 (d, 2H) 3.52 (d, 2H) 3.18 (m, 2H) 3.03 (m, 2H) 2.88 (d, 3H) | Compound 003 and 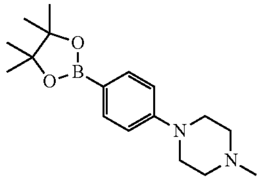 |
| 018 | 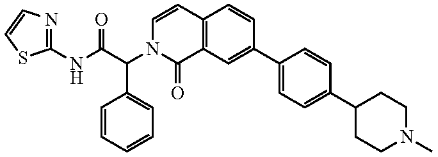 [SMILES: CN1CCC(c2ccc(-c3ccc4ccn(C(C(=O)Nc5nccs5)c5ccccc5)c(=O)c4c3)cc2)CC1] 2-(7-(4-(1-Methylpiperidin-4-yl)-phenyl)-1-oxoisoquinolin-2(1H)-yl)-2-phenyl-N-(thiazol-2-yl)acetamide | 535.4 | 9.30 (br s, 1H) 8.48 (d, 1H) 8.06 (dd, 1H) 7.76 (d, 3H) 7.51 (m, 4H) 7.38 (m, 4H) 7.30 (d, 1H) 6.94 (s, 1H) 6.93 (d, 1H) 6.65 (d, 1H) 3.54 (d, 2H) 3.10 (m, 2H) 2.87 (m, 1H) 2.83 (d, 3H) 2.08 (d, 2H) 1.86 (m, 2H) | Compound 004 and 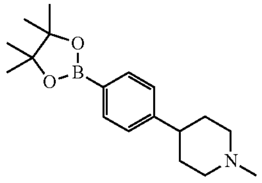 |
| 019 | 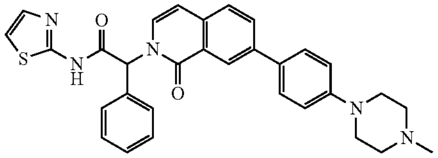 [SMILES: CN1CCN(c2ccc(-c3ccc4ccn(C(C(=O)Nc5nccs5)c5ccccc5)c(=O)c4c3)cc2)CC1] 2-(7-(4-(4-Methylpiperazin-1-yl)-phenyl)-1-oxoisoquinolin-2(1H)-yl)-2-phenyl-N-(thiazol-2-yl)acetamide | 536.4 | 9.66 (br s, 1H) 8.44 (d, 1H) 8.04 (dd, 1H) 7.72 (d, 1H) 7.71 (d, 2H) 7.51 (m, 4H) 7.39 (m, 2H) 7.29 (d, 1H) 7.15 (d, 2H) 6.92 (s, 1H) 6.91 (d, 1H) 6.63 (d, 1H) 3.96 (d, 2H) 3.54 (d, 2H) 3.18 (m, 2H) 3.03 (m, 2H) 2.88 (d, 3H) | Compound 004 and 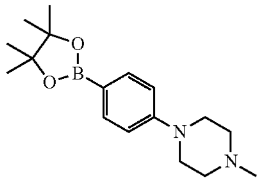 |
| 020 | 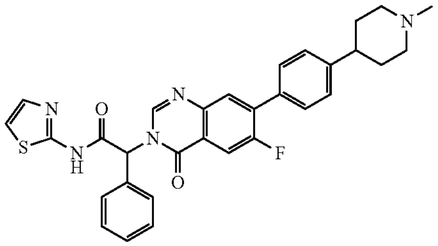 2-(6-Fluoro-7-(4-(1-methylpiperidin-4-yl)phenyl)-4-oxoquinazolin-3(4H)-yl)-2-phenyl-N-(thiazol-2-yl)acetamide | 554.2 | 9.45 (br s, 1H) 7.92 (d, 1H) 7.79 (s, 1H) 7.78 (d, 1H) 7.59 (d, 2H) 7.46 (m, 4H) 7.38 (d, 2H) 7.35 (d, 2H) 7.26 (d, 1H) 6.82 (s, 1H) 3.48 (d, 2H) 3.04 (m, 2H) 2.82 (m, 1H) 2.77 (d, 3H) 2.00 (d, 2H) 1.82 (m, 2H) | Compound 005 and 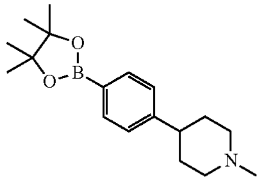 |
| 021 | 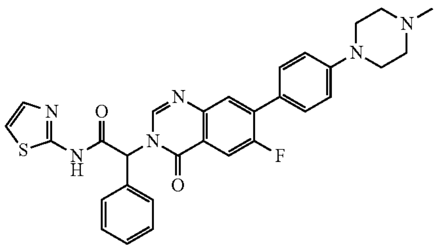 [SMILES: CN1CCN(c2ccc(-c3cc4ncn(C(C(=O)Nc5nccs5)c5ccccc5)c(=O)c4cc3F)cc2)CC1] 2-(6-Fluoro-7-(4-(4-methylpiperazin-1-yl)phenyl)-4-oxoquinazolin-3(4H)-yl)-2-phenyl-N-(thiazol-2-yl)acetamide | 555.2 | 9.81 (br s, 1H) 7.95 (d, 1H) 7.85 (s, 1H) 7.83 (d, 1H) 7.62 (d, 2H) 7.52 (m, 4H) 7.45 (m, 2H) 7.33 (d, 1H) 7.16 (d, 2H) 6.89 (s, 1H) 4.01 (d, 2H) 3.54 (d, 2H) 3.18 (m, 2H) 3.07 (m, 2H) 2.88 (s, 3H) | Compound 005 and 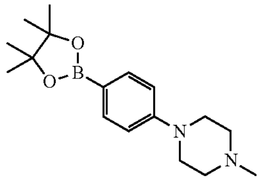 |

TABLE 7-continued

| No. | Structure/Name | m/z [M + 1]+ | $^1$H NMR (500 MHz, $d_6$-DMSO) δ | Starting materials |
|---|---|---|---|---|
| 022 | 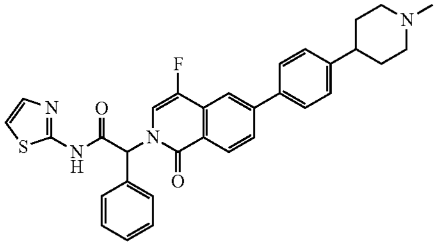 [SMILES: CN1CCC(c2ccc(-c3ccc4c(=O)n(C(C(=O)Nc5nccs5)c5ccccc5)cc(F)c4c3)cc2)CC1] 2-(4-Fluoro-6-(4-(1-methylpiperidin-4-yl)phenyl)-1-oxoisoquinolin-2(1H)-yl)-2-phenyl-N-(thiazol-2-yl)acetamide | 553.4 | 9.46 (br s, 1H) 8.39 (dd, 1H) 8.01 (d, 1H) 7.98 (d, 1H) 7.85 (d, 2H) 7.52 (m, 4H) 7.41 (m, 4H) 7.31 (d, 1H) 7.04 (d, 1H) 6.94 (s, 1H) 3.55 (d, 2H) 3.10 (m, 2H) 2.89 (m, 1H) 2.85 (d, 3H) 2.07 (d, 2H) 1.89 (m, 2H) | Compound 006 and 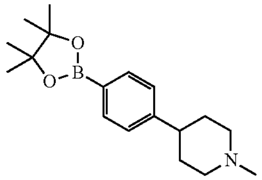 |
| 023 | 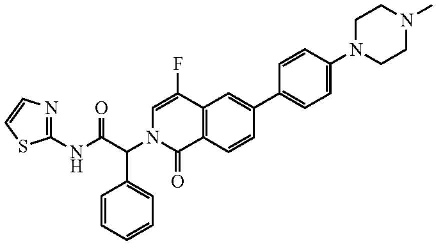 [SMILES: CN1CCN(c2ccc(-c3ccc4c(=O)n(C(C(=O)Nc5nccs5)c5ccccc5)cc(F)c4c3)cc2)CC1] 2-(4-Fluoro-6-(4-(4-methylpiperazin-1-yl)phenyl)-1-oxoisoquinolin-2(1H)-yl)-2-phenyl-N-(thiazol-2-yl)-acetamide | 554.2 | 9.90 (br s, 1H) 8.34 (dd, 1H) 7.99 (dd, 1H) 7.93 (d, 1H) 7.81 (d, 1H) 7.52 (m, 4H) 7.40 (m, 2H) 7.31 (d, 1H) 7.16 (d, 1H) 7.01 (d, 1H) 6.93 (s, 1H) 4.00 (d, 2H) 3.55 (d, 2H) 3.19 (m, 2H) 3.06 (m, 2H) 2.88 (s, 3H) | Compound 006 and 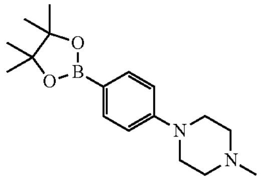 |
| 036 | 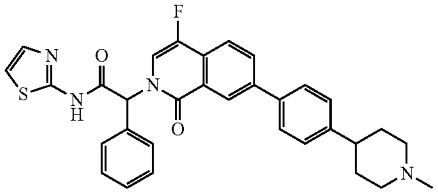 2-(4-Fluoro-7-(4-(1-methylpiperidin-4-yl)phenyl)-1-oxoisoquinolin-2(1H)-yl)-2-phenyl-N-(thiazol-2-yl)acetamide | 553.3 | 9.43 (br s, 1H) 8.53 (s, 1H) 8.22 (d, 1H) 7.88 (d, 1H) 7.79 (d, 2H) 7.52 (m, 4H) 7.42 (m, 4H) 7.31 (d, 1H) 7.02 (d, 1H) 6.93 (s, 1H) 3.55 (d, 2H) 3.10 (m, 2H) 2.88 (m, 1H) 2.83 (d, 3H) 2.07 (d, 2H) 1.88 (m, 2H) | Compound 035 and 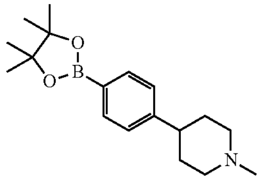 |
| 037 | 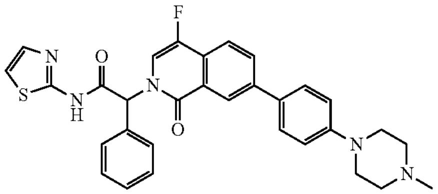 [SMILES: CN1CCN(c2ccc(-c3ccc4c(F)cn(C(C(=O)Nc5nccs5)c5ccccc5)c(=O)c4c3)cc2)CC1] 2-(4-Fluoro-7-(4-(4-methylpiperazin-1-yl)phenyl)-1-oxoisoquinolin-2(1H)-yl)-2-phenyl-N-(thiazol-2-yl)-acetamide | 554.3 | 9.69 (br s, 1H) 8.50 (m, 1H) 8.20 (dd, 1H) 7.84 (d, 1H) 7.75 (d, 2H) 7.53 (m, 4H) 7.42 (m, 2H) 7.31 (d, 1H) 7.17 (d, 2H) 6.98 (d, 1H) 6.92 (s, 1H) 3.99 (d, 2H) 3.19 (m, 2H) 3.05 (m, 2H) 2.88 (s, 3H) two protons masked by water peak | Compound 035 and 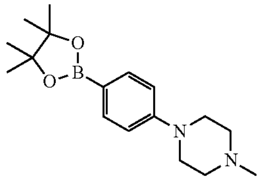 |
| 024 | 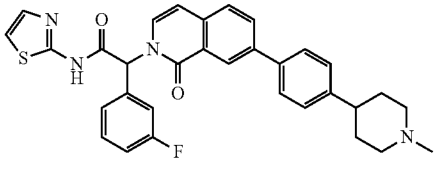 [SMILES: CN1CCC(c2ccc(-c3ccc4ccn(C(C(=O)Nc5nccs5)c5cccc(F)c5)c(=O)c4c3)cc2)CC1] 2-(3-Fluorophenyl)-2-(7-(4-(1-methylpiperidin-4-yl)phenyl)-1-oxo isoquinolin-2(1H)-yl)-N-(thiazol-2-yl)-acetamide | 553.3 | 9.43 (br s, 1H) 8.07 (dd, 1H) 7.78 (d, 1H) 7.76 (d, 2H) 7.57 (m, 1H) 7.53 (d, 1H) 7.39 (d, 2H) 7.35 (m, 1H) 7.31 (d, 1H) 7.2 (m, 2H) 7.01 (d, 1H) 6.93 (s, 1H) 6.68 (d, 1H) 3.55 (d, 2H) 3.10 (m, 2H) 2.87 (m, 1H) 2.85 (d, 3H) 2.07 (d, 2H) 1.86 (m, 2H) | Compound 007 and 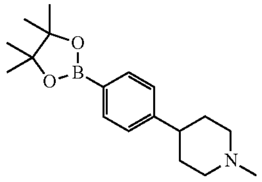 |

TABLE 7-continued

| No. | Structure/Name | m/z $[M + 1]^+$ | $^1H$ NMR (500 MHz, $d_6$-DMSO) δ | Starting materials |
|---|---|---|---|---|
| 025 | 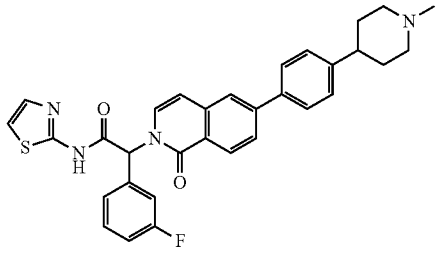 [SMILES: CN1CCC(c2ccc(-c3ccc4c(=O)n(C(C(=O)Nc5nccs5)c5cccc(F)c5)ccc4c3)cc2)CC1] 2-(3-Fluorophenyl)-2-(6-(4-(1-methyl-piperidin-4-yl)phenyl)-1-oxo-isoquinolin-2(1H)-yl)-N-(thiazol-2-yl)-acetamide | 553.2 | 9.35 (br s, 1H) 8.31 (d, 1H) 7.98 (d, 1H) 7.86 (dd, 1H) 7.81 (d, 2H) 7.57 (m, 1H) 7.52 (d, 1H) 7.40 (d, 2H) 7.35 (m, 1H) 7.31 (d, 1H) 7.24 (m, 2H) 7.03 (d, 1H) 6.93 (s, 1H) 6.69 (d, 1H) 3.55 (d, 2H) 3.10 (m, 2H) 2.88 (m, 1H) 2.85 (d, 3H) 2.07 (d, 2H) 1.87 (m, 2H) | Compound 008 and 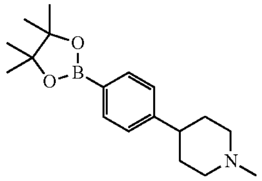 |
| 026 | 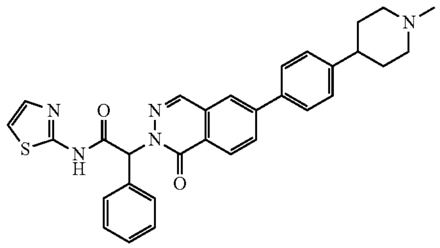 [SMILES: CN1CCC(c2ccc(-c3ccc4c(=O)n(C(C(=O)Nc5nccs5)c5ccccc5)ncc4c3)cc2)CC1] 2-(6-(4-(1-Methylpiperidin-4-yl)-phenyl)-1-oxophthalazin-2(1H)-yl)-2-phenyl-N-(thiazol-2-yl)acetamide | 536.2 | $CDCl_3$-d 8.50 (d, 1H) 8.30 (s, 1H) 7.99 (dd, 1H) 7.85 (d, 1H) 7.65 (d, 1H) 7.63 (m, 3H) 7.43 (m, 4H) 7.39 (d, 2H) 7.14 (s, 1H) 7.04 (d, 1H) 3.75 (d. 2H) 2.87 (s, 3H) 2.83 (m. 3H) 2.37 (m, 2H) 2.10 (d, 2H) | Compound 009 and 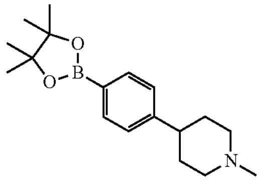 |
| 027 | 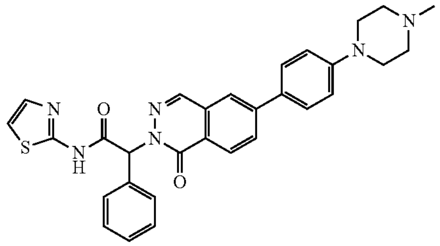 [SMILES: CN1CCN(c2ccc(-c3ccc4c(=O)n(C(C(=O)Nc5nccs5)c5ccccc5)ncc4c3)cc2)CC1] 2-(6-(4-(4-Methylpiperazin-1-yl)-phenyl)-1-oxophthalazin-2(1H)-yl)-2-phenyl-N-(thiazol-2-yl)acetamide | 537.2 | $CDCl_3$-d 8.46 (d, 1H) 8.27 (s, 1H) 7.97 (dd, 1H) 7.81 (d, 1H) 7.62 (m, 4H) 7.42 (m, 4H) 3H) 3.76 (m, 2H) 3.70 (m, 2H) 3.45 (m, 2H) 3.03 (m, 2H) 2.89 (s, 3H) | Compound 009 and 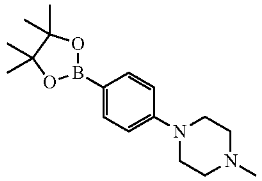 |
| 042 | 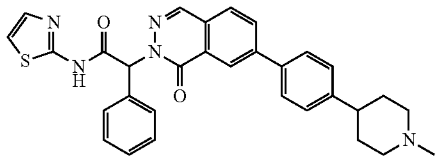 [SMILES: CN1CCC(c2ccc(-c3ccc4cnn(C(C(=O)Nc5nccs5)c5ccccc5)c(=O)c4c3)cc2)CC1] 2-(7-(4-(1-Methylpiperidin-4-yl)-phenyl)-1-oxophtharazin-2(1H)-yl)-2-phenyl-N-(thiazol-2-yl)acetamide | 536.2 | 9.38 (br s, 1H) 8.39 (m, 2H) 8.22 (dd, 1H) 7.97 (d, 1H) 7.76 (d, 2H) 7.40 (d, 1H) 7.34 (m, 7H) 7.18 (d, 1H) 6.80 (s, 1H) 3.03 (m, 2H) 2.82 (m, 1H) 2.76 (d, 3H) 2.00 (d, 2H) 1.80 (m, 2H) two protons masked by water peak | Compound 041 and 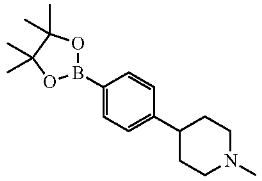 |
| 043 | 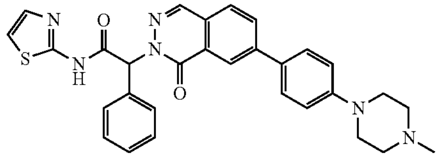 [SMILES: CN1CCN(c2ccc(-c3ccc4cnn(C(C(=O)Nc5nccs5)c5ccccc5)c(=O)c4c3)cc2)CC1] 2-(7-(4-(4-Methylpiperazin-1-yl)-phenyl)-1-oxophthalazin-2(1H)-yl)-2-phenyl-N-(thiazol-2-yl)acetamide | 537.2 | 9.76 (br s, 1H) 8.35 (s, 2H) 8.19 (dd, 1H) 7.92 (d, 1H) 7.71 (d, 2H) 7.41 (d, 1H) 7.34 (m, 5H) 7.17 (d, 1H) 7.10 (d, 2H) 6.78 (s, 1H) 3.93 (d, 2H) 3.47 (d, 2H) 3.11 (m, 2H) 2.98 (m, 2H) 2.81 (s, 3H) | Compound 041 and 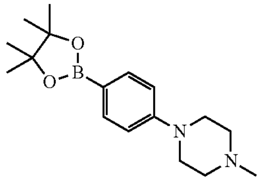 |

TABLE 7-continued

| No. | Structure/Name | m/z $[M + 1]^+$ | $^1H$ NMR (500 MHz, $d_6$-DMSO) δ | Starting materials |
|---|---|---|---|---|
| 028 | 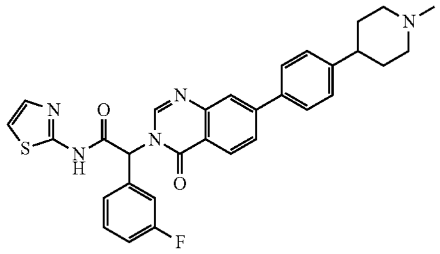 [SMILES: CN1CCC(c2ccc(-c3ccc4c(=O)n(C(C(=O)Nc5nccs5)c5cccc(F)c5)cnc4c3)cc2)CC1] 2-(3-Fluorophenyl)-2-(7-(4-(1-methyl-piperidin-4-yl)phenyl)-4-oxo-quinazolin-3(4H)-yl)-N-(thiazol-2-yl)-acetamide | 554.16 | 9.45 (br s, 1H) 8.25 (d, 1H) 7.99 (s, 1H) 7.96 (d, 1H) 7.92 (dd, 1H) 7.83 (d, 2H) 7.56 (m, 1H) 7.52 (d, 1H) 7.40 (d, 2H) 7.33 (m, 3H) 7.29 (d, 1H) 6.86 (s, 1H) 3.54 (d, 2H) 3.10 (m, 2H) 2.88 (m, 1H) 2.84 (d, 3H) 2.07 (d, 2H) 1.87 (m, 2H) | Compound 010 and 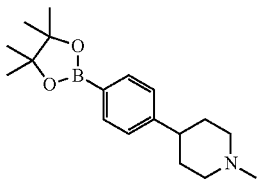 |
| 029 | 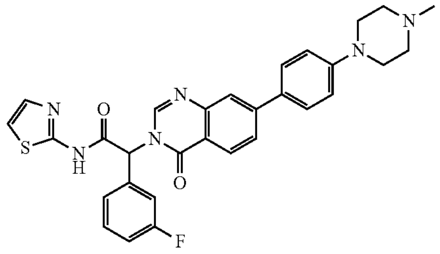 [SMILES: CN1CCN(c2ccc(-c3ccc4c(=O)n(C(C(=O)Nc5nccs5)c5cccc(F)c5)cnc4c3)cc2)CC1] 2-(3-Fluorophenyl)-2-(7-(4-(4-methyl-piperazin-1-yl)phenyl)-4-oxo-quinazolin-3(4H)-yl)-N-(thiazol-2-yl)-acetamide | 555.23 | 9.82 (br s, 1H) 8.21 (d, 1H) 7.96 (s, 1H) 7.92 (s, 1H) 7.91 (dd, 1H) 7.79 (d, 2H) 7.56 (m, 1H) 7.52 (d, 1H) 7.33 (m, 3H) 7.29 (d, 1H) 7.15 (d, 2H) 6.85 (s, 1H) 3.99 (d, 2H) 3.17 (m, 2H) 3.05 (m, 2H) 2.88 (s, 3H) two protons masked by water peak | Compound 010 and 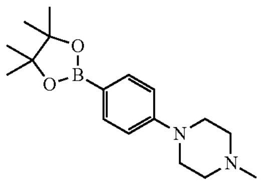 |
| 030 | 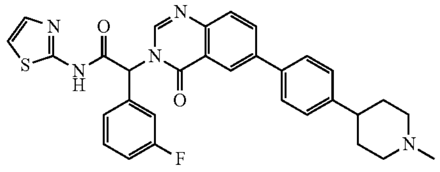 [SMILES: CN1CCC(c2ccc(-c3ccc4ncn(C(C(=O)Nc5nccs5)c5cccc(F)c5)c(=O)c4c3)cc2)CC1] 2-(3-Fluorophenyl)-2-(6-(4-(1-methyl-piperidin-4-yl)phenyl)-4-oxo-quinazolin-3(4H)-yl)-N-(thiazol-2-yl)-acetamide | 554.27 | 9.49 (br s, 1H) 8.39 (d, 1H) 8.19 (dd, 1H) 7.98 (s, 1H) 7.80 (d, 1H) 7.78 (d, 2H) 7.56 (m, 1H) 7.52 (d, 1H) 7.39 (d, 2H) 7.35 (d, 2H) 7.32 (m, 2H) 6.86 (s, 1H) 3.54 (d, 2H) 3.10 (m, 2H) 2.87 (m, 1H) 2.83 (d, 3H) 2.06 (d, 2H) 1.87 (m, 2H) | Compound 011 and 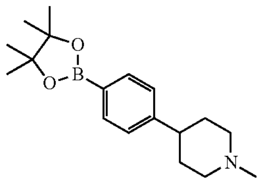 |
| 031 | 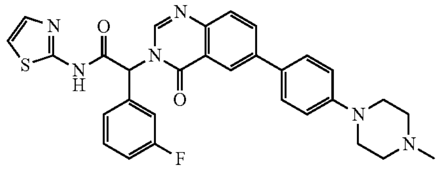 [SMILES: CN1CCN(c2ccc(-c3ccc4ncn(C(C(=O)Nc5nccs5)c5cccc(F)c5)c(=O)c4c3)cc2)CC1] 2-(3-Fluorophenyl)-2-(6-(4-(4-methyl-piperazin-1-yl)phenyl)-4-oxo-quinazolin-3(4H)-yl)-N-(thiazol-2-yl)-acetamide | 555.23 | 9.83 (br s, 1H) 8.34 (d, 1H) 8.17 (dd, 1H) 7.95 (s, 1H) 7.76 (d, 1H) 7.73 (d, 2H) 7.56 (m, 1H) 7.52 (d, 1H) 7.35 (d, 1H) 7.31 (m, 3H) 7.15 (d, 2H) 6.85 (s, 1H) 3.97 (d, 2H) 3.54 (d, 2H), 3.18 (m, 2H) 3.04 (m, 2H) 2.88 (s, 3H) | Compound 011 and 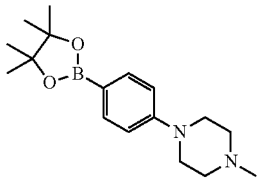 |
| 032 | 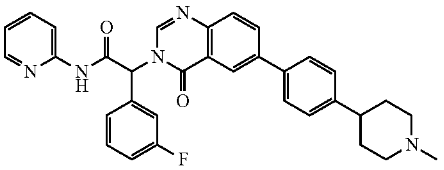 [SMILES: CN1CCC(c2ccc(-c3ccc4ncn(C(C(=O)Nc5ccccn5)c5cccc(F)c5)c(=O)c4c3)cc2)CC1] 2-(3-Fluorophenyl)-2-(6-(4-(1-methyl-piperidin-4-yl)phenyl)-4-oxo-quinazolin-3(4H)-yl)-N-(pyridin-2-yl)-acetamide | 548.24 | 11.38 (s, 1H) 9.45 (br s, 1H) 8.40 (d, 1H) 8.35 8.11 (d, 1H) 7.89 (s, 1H) 7.84 (m, 1H) 7.79 (d, 1H) 7.78 (d, 2H) 7.58 (m, 1H) 7.40 (d, 2H) 7.33 (m, 3H) 7.17 (m, 1H) 6.94 (s, 1H) 3.10 (m, 2H) 2.88 (m, 1H) 2.83 (d, 3H) 2.06 (d, 2H) 1.87 (m, 2H) two protons masked by water peak | Compound 034 and 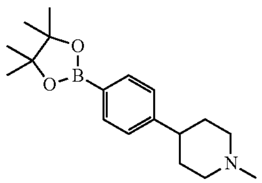 |

TABLE 7-continued

| No. | Structure/Name | m/z [M + 1]$^+$ | $^1$H NMR (500 MHz, $d_6$-DMSO) δ | Starting materials |
|---|---|---|---|---|
| 033 | 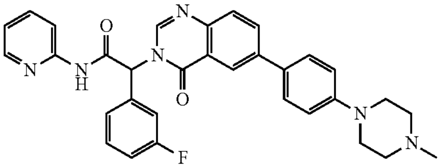 [SMILES: CN1CCN(c2ccc(-c3ccc4ncn(C(C(=O)Nc5ccccn5)c5cccc(F)c5)c(=O)c4c3)cc2)CC1] 2-(3-Fluorophenyl)-2-(6-(4-(4-methyl-piperazin-1-yl)phenyl)-4-oxo-quinazolin-3(4H)-yl)-N-(pyridin-2-yl)-acetamide | 549.24 | 11.37 (s, 1H) 9.83 (br s, 1H) 8.35 (m, 2H) 8.16 (dd, 1H) 8.11 (d, 1H) 7.86 (s, 1H) 7.83 (m, 1H) 7.75 (d, 1H) 7.72 (d, 2H) 7.57 (m, 1H) 7.33 (m, 3H) 7.17 (m, 1H) 7.15 (d, 2H) 6.97 (s, 1H) 3.96 (d, 2H) 3.54 (m, 2H) 3.18 (m, 1H) 3.0 (m, 2H) 2.88 (s, 3H) | Compound 034 and 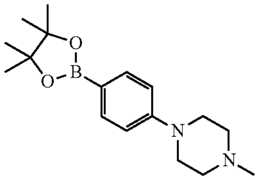 |
| 053 | 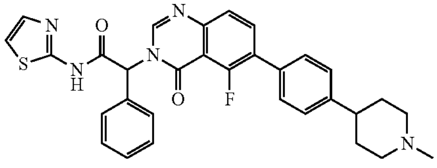 [SMILES: CN1CCC(c2ccc(-c3ccc4ncn(C(C(=O)Nc5nccs5)c5ccccc5)c(=O)c4c3F)cc2)CC1] 2-(5-Fluoro-6-(4-(1-methylpiperidin-4-yl)phenyl)-4-oxoquinazolin-3(4H)-yl)-2-phenyl-N-(thiazol-2-yl)acetamide | 554.4 | 9.38 (br s, 1H) 7.97 (t, 1H) 7.82 (s, 1H) 7.60 (d, 3H) 7.52 (m, 4H) 7.46 (m, 2H) 7.41 (d, 2H) 7.33 (d, 1H) 6.82 (s, 1H) 3.55 (d, 2H) 3.10 (m, 2H) 2.89 (m, 1H) 2.84 (d, 3H) 2.09 (d, 2H) 1.87 (m, 2H) | Compound 049 and 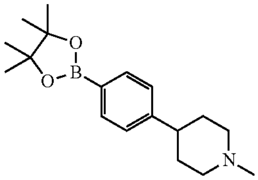 |
| 054 | 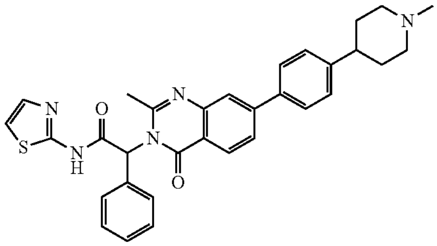 [SMILES: Cc1nc2cc(-c3ccc(N4CCN(C)CC4)cc3)ccc2c(=O)n1C(C(=O)Nc1nccs1)c1ccccc1] 2-(2-Methyl-7-(4-(1-methylpiperidin-4-yl)phenyl)-4-oxoquinazolin-3(4H)-yl)-2-phenyl-N-(thiazol-2-yl)acetamide | 550.2 | 9.30 (br s, 1H) 8.18 (d, 1H) 7.93 (s, 1H) 7.83 (m, 3H) 7.38 (m, 8H) 7.22 (s, 1H) 6.60 (s, 1H) 3.55 (d, 2H) 3.11 (m, 2H) 2.89 (m, 1H) 2.85 (s, 3H) 2.55 (s, 3H) 2.08 (d, 2H) 1.86 (m, 2H) | Compound 051 and 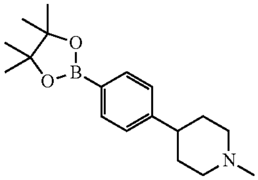 |
| 055 | 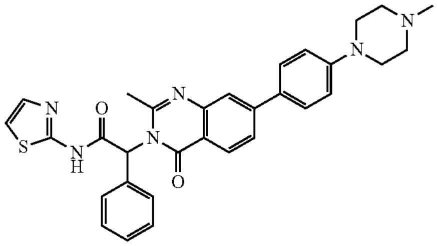 2-(2-Methyl-7-(4-(4-methylpiperazin-1-yl)phenyl)-4-oxoquinazolin-3(4H)-yl)-2-phenyl-N-(thiazol-2-yl)-acetamide | 551.4 | 9.72 (br s, 1H) 8.12 (d, 1H) 7.88 (d, 1H) 7.81 (dd, 1H) 7.79 (d, 2H) 7.42 (d, 1H) 7.37 (m, 5H) 7.21 (d, 1H) 7.15 2H) 6.57 (s, 1H) 3.99 (d, 2H) 3.54 (d, 2H) 3.18 (m, 2H) 3.04 (m, 2H) 2.87 (d, 3H) 2.53 (s, 3H) | Compound 051 and 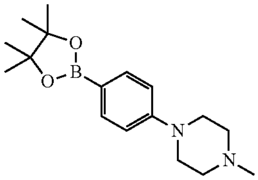 |
| 064 | 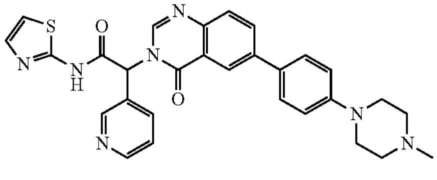 [SMILES: CN1CCN(c2ccc(-c3ccc4ncn(C(C(=O)Nc5nccs5)c5cccnc5)c(=O)c4c3)cc2)CC1] 2-(6-(4-(4-Methylpiperazin-1-yl)-phenyl)-4-oxoquinazolin-3(4H)-yl)-2-(pyridin-3-yl)-N-(thiazol-2-yl)-acetamide | 538.27 | 9.91 (br s, 1H) 8.75 (d, 1H) 8.69 (dd, 1H) 8.34 (d, 1H) 8.18 (dd, 1H) 8.15 (s, 1H) 8.00 (dd, 1H) 7.78 (d, 1H) 7.73 (d, 2H) 7.58 (dd, 1H) 7.51 (d, 1H) 7.31 (d, 1H) 7.14 (d, 2H) 6.86 (s, 1H) 3.96 (d, 2H) 3.54 (m, 2H) 3.17 (m, 2H) 3.04 (m, 2H) 2.88 (s, 3H) | Compound 062 and 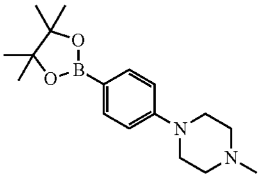 |

TABLE 7-continued

| No. | Structure/Name | m/z [M + 1]$^+$ | $^1$H NMR (500 MHz, $d_6$-DMSO) δ | Starting materials |
|---|---|---|---|---|
| 065 | 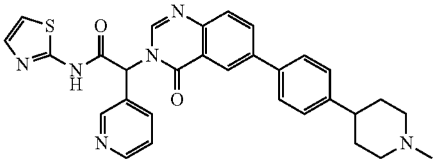 [SMILES: CN1CCC(c2ccc(-c3ccc4ncn(C(C(=O)Nc5nccs5)c5cccnc5)c(=O)c4c3)cc2)CC1] 2-(6-(4-(1-Methylpiperidin-4-yl)-phenyl)-4-oxoquinazolin-3(4H)-yl)-2-(pyridin-3-yl)-N-(thiazol-2-yl)-acetamide | 537.24 | 9.42 (br s, 1H) 8.74 (d, 1H) 8.69 (dd, 1H) 8.39 (d, 1H) 8.20 (dd, 1H) 8.17 (s, 1H) 7.99 (dd, 1H) 7.81 (d, 1H) 7.78 (d, 2H) 7.57 (dd, 1H) 7.51 (d, 1H) 7.39 (d, 2H) 7.31 (d, 1H) 6.86 (s, 1H) 3.55 (d, 2H) 3.10 (m, 2H) 2.87 (m, 1H) 2.84 (d, 3H) 2.06 (m, 2H) 1.87 (m, 2H) | Compound 062 and 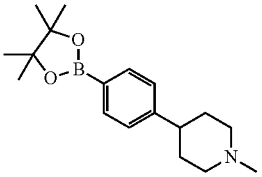 |
| 066 | 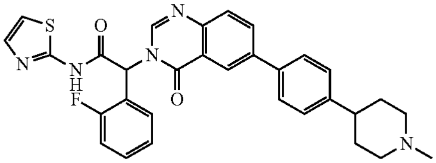 2-(2-Fluorophenyl)-2-(6-(4-(1-methylpiperidin-4-yl)phenyl)-4-oxo-quinazolin-3(4H)-yl)-N-(thiazol-2-yl)-acetamide | 554.27 | 9.43 (br s, 1H) 6.41 (d, 1H) 8.20 (dd, 1H) 7.96 (s, 1H) 7.81 (d, 1H) 7.79 (d, 2H) 7.59 (m, 1H) 7.52 (d, 2H) 7.40 (m, 4H) 7.37 (d, 1H) 7.33 (m, 1H) 7.15 (s, 1H) 3.54 (d, 2H) 3.16 (m, 2H) 2.88 (m, 1H) 2.84 (d, 3H) 2.07 (m, 2H) 1.87 (m, 2H) | Compound 063 and 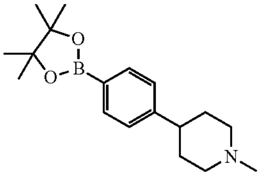 |
| 067 | 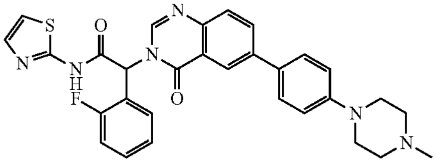 [SMILES: CN1CCN(c2ccc(-c3ccc4ncn(C(C(=O)Nc5nccs5)c5ccccc5F)c(=O)c4c3)cc2)CC1] 2-(2-fluorophenyl)-2-(6-(4-(4-methylpiperazin-1-yl)phenyl)-4-oxo-quinazolin-3(4H)-yl)-N-(thiazol-2-yl)-acetamide | 555.23 | 9.80 (br s, 1H) 8.36 (d, 1H) 8.18 (dd, 1H) 7.92 (s, 1H) 7.77 (d, 1H) 7.73 (d, 2H) 7.59 (m, 1H) 7.52 (d, 1H) 7.38 (m, 3H) 7.33 (d, 1H) 7.15 (d, 2H) 7.14 (s, 1H) 3.97 (d, 2H) 3.54 (m, 2H) 3.18 (m, 2H) 3.03 (m, 2H) 2.88 (s, 3H) | Compound 063 and 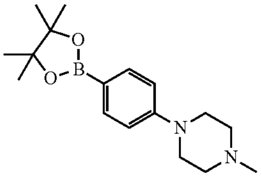 |
| 068 | 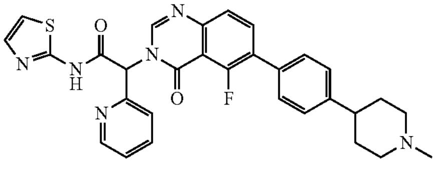 [SMILES: CN1CCC(c2ccc(-c3ccc4ncn(C(C(=O)Nc5nccs5)c5ccccn5)c(=O)c4c3F)cc2)CC1] 2-(5-Fluoro-6-(4-(1-methylpiperidin-4-yl)phenyl)-4-oxoquinazolin-3(4H)-yl)-2-(pyridin-2-yl)-N-(thiazol-2-yl)-acetamide | 555.35 | 9.29 (br s, 1H) 8.65 (d, 1H) 8.14 (s, 1H) 7.97 (m, 2H) 7.65 (d, 1H) 7.61 (m, 3H) 7.50 (m, 2H) 7.40 (d, 2H) 7.32 (d, 1H) 7.10 (s, 1H) 3.55 (d, 2H) 3.11 (m, 2H) 2.89 (m, 1H) 2.84 (d, 3H) 2.08 (d, 2H) 1.87 (m, 2H) | 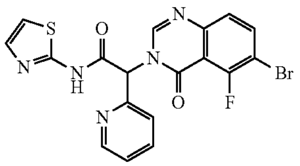 [SMILES: O=C(Nc1nccs1)C(c1ccccn1)n1cnc2ccc(Br)c(F)c2c1=O] and 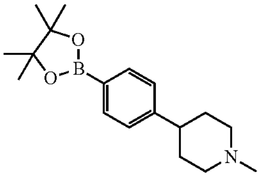 |

2-(6-Bromo-5-fluoro-4-oxoquinazolin-3(4H)-yl)-2-(pyridin-2-yl)-N-(thiazol-2-yl)acetamide

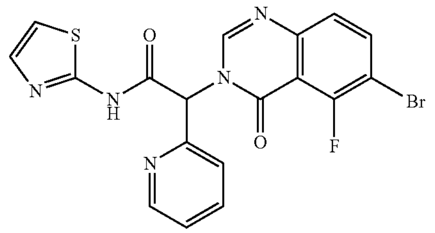 [SMILES: O=C(Nc1nccs1)C(c1ccccn1)n1cnc2ccc(Br)c(F)c2c1=O]

Step 1: A mixture of ethyl 2-(6-bromo-5-fluoro-4-oxoquinazolin-3(4H)-yl)-2-(pyridin-2-yl)-acetate (83 mg, 0.2 mmol), LiOH—$H_2O$ (17 mg, 0.4 mmol), MeOH (2 mL), and water (0.5 mL) was stirred at ambient temperature for 30 min. Solvent was removed under reduced pressure and the residue was dried under vacuum overnight at 60° C. This material was used without further purification in the subsequent step.

Step 2: A mixture of the material from step 1, HOBt-$H_2O$ (46 mg, 0.3 mmol), EDC (57 mg, 0.3 mmol), DIEA (52 μL, 0.3 mmol), 2-aminothiazole (20 mg, 0.2 mmol), and degassed DMF (3 mL) was stirred at room temperature for 1 h. HATU (116 mg, 0.3 mmol) was added and the reaction was continued for an additional 1.5 h. The reaction mixture was purified by reverse phase HPLC eluting with 0-80% ACN/$H_2O$ (0.038% TFA modifier) to give the title compound (15 mg, 16%, two steps). $^1H$ NMR (500 MHz, dc-DMSO) δ 8.32 (dd, 1H) 8.19 (s, 1H) 8.14 (dd, 1H) 7.95 (m, 1H) 7.64 (d, 1H) 7.49 (m, 3H) 7.30 (d, 1H) 7.08 (s, 1H).

Compound 040: 2-(6-(3-Fluoro-4-(1-methylpiperidin-4-yl)phenyl)-4-oxoquinazolin-3(4H)-yl)-2-phenyl-N-(thiazol-2-yl)acetamide Compound 040 was prepared following the procedure on Scheme 4.

Scheme 4.

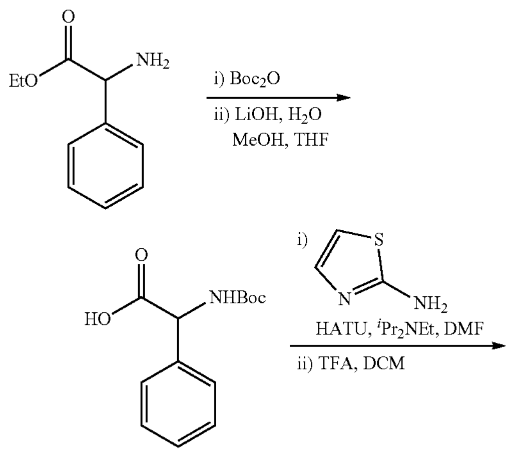

-continued

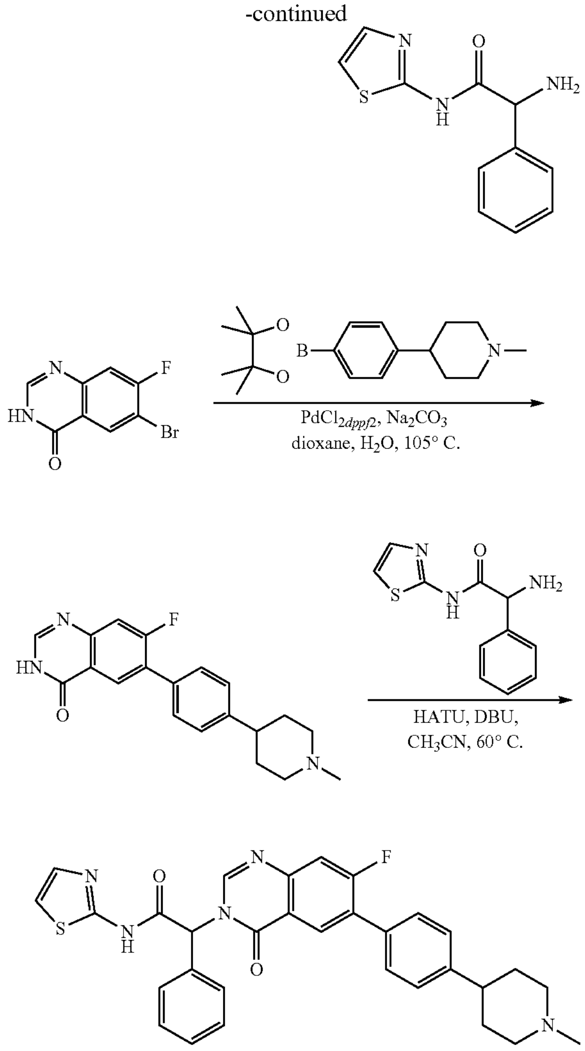

Ethyl 2-((tert-butoxycarbonyl)amino)-2-phenylacetate

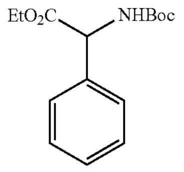

A mixture of ethyl 2-amino-2-phenylacetate (1.0 g, 4.6 mmol), di-tert-butyl dicarbonate (1.2 g, 5.5 mmol), DCM (20 mL), and DIEA (0.8 mL, 4.6 mmol) was stirred at room temperature for 1 hour. The reaction mixture was poured into ethyl acetate (100 mL) and washed with ice cold 0.1N HCl (40 mL), saturated $Na_2CO_3$ (40 mL), water (40 mL), and brine (40 mL). The organic phase was dried ($MgSO_4$) and concentrated under reduced pressure to give the title compound (1.3 g, 100%). $^1H$ NMR (500 MHz, $CDCl_3$-d) δ ppm 9.04 (d, 1H) 8.79 (d, 1H) 8.16 (s, 1H) 7.48 (m, 1H) 7.19 (s, 2H) 7.11 (m, 1H) 4.39 (m, 2H) 1.57 (s, 9H) 1.35 (t, 3H).

2-((tert-Butoxycarbonyl)amino)-2-phenylacetic acid

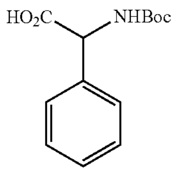 [SMILES: CC(C)(C)OC(=O)NC(C(=O)O)c1ccccc1]

2-((tert-Butoxycarbonyl)amino)-2-phenylacetic acid was prepared in a similar manner to acid 1, from ethyl 2-((tert-butoxycarbonyl)amino)-2-phenylacetate (1.3 g, 4.7 mmol), to give 550 mg, 47%.

tert-Butyl (2-oxo-1-phenyl-2-(thiazol-2-ylamino) ethyl)carbamate

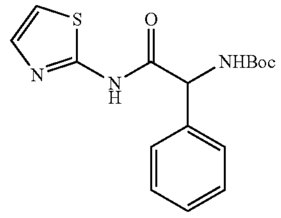 [SMILES: CC(C)(C)OC(=O)NC(C(=O)Nc1nccs1)c1ccccc1]

tert-Butyl (2-oxo-1-phenyl-2-(thiazol-2-ylamino)ethyl) carbamate was prepared in a similar manner to Example 1, from 2-((tert-butoxycarbonyl)amino)-2-phenylacetic acid (550 mg, 2.2 mmol), to give 670 mg, 92%. $^{1}$H NMR (500 MHz, $CDCl_3$-d) δ ppm 7.48 (d, 1H) 7.39 (m, 5H) 7.02 (d, 1H) 5.70 (br s, 1H) 5.48 (br s, 1H) 1.46 (s, 9H).

2-Amino-2-phenyl-N-(thiazol-2-yl)acetamide hydrochloride

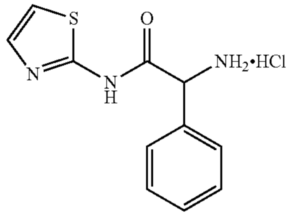

A solution of tert-butyl (2-oxo-1-phenyl-2-(thiazol-2-ylamino)ethyl)carbamate (670 mg, 2 mmol) in DCM (2.5 mL) and trifluoroacetic acid (2.5 mL) was stirred for 15 min at room temperature and then concentrated under reduced pressure. The residue was dissolved in DCM (25 mL) and treated with 4 N HCl in dioxane (5 mL). The resulting precipitate was collected by filtration, washed with DCM and dried to give the title compound, used without further purification. $^{1}$H NMR (500 MHz, DMSO-$d_6$) δ ppm 9.03 (br s, 3H) 7.59 (dd, 2H) 7.46 (m, 4H) 7.31 (d, 1H) 5.25 (m, 1H).

7-Fluoro-6-(4-(1-methylpiperidin-4-yl)phenyl)quinazolin-4(3H)-one

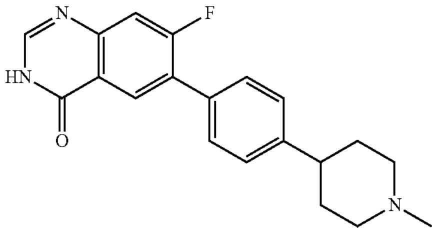 [SMILES: CN1CCC(c2ccc(-c3cc4c(=O)[nH]cnc4cc3F)cc2)CC1]

A mixture of 6-bromo-7-fluoroquinazolin-4(3H)-one (100 mg, 0.4 mmol), 1-methyl-4-(4-(4,4,5,5-tetramethyl-1,3,2-dioxaborolan-2-yl)phenyl)piperidine (187 mg, 0.6 mmol), Pd(dppf)$Cl_2$·DCM (67 mg, 0.08 mmol) and sodium carbonate (131 mg, 1.2 mmol) in dioxane:water (4:1, 4 mL) was degassed and re-suffused with nitrogen three times. The mixture was heated at 100° C. for 3 hours. After cooling, the reaction mixture was filtered and concentrated, and the residue was purified by reverse phase HPLC, eluting with 0-80% ACN/water (0.035% TFA modifier). The product was dissolved in ethyl acetate and washed with saturated $Na_2CO_3$ and saturated brine, dried ($MgSO_4$), filtered, and concentrated under reduced pressure to give the title compound (24 mg, 17%). $^{1}$H NMR (500 MHz, DMSO-$d_6$) δ ppm 8.17 (d, 1H) 8.15 (s, 1H) 7.55 (m, 3H) 7.40 (d, 2H) 2.88 (d, 2H) 2.21 (s, 3H) 1.98 (m, 2H) 1.78 (m, 2H) 1.70 (m, 2H) one proton masked by solvent peak.

Compound 040: 2-(6-(3-Fluoro-4-(1-methylpiperidin-4-yl)phenyl)-4-oxoquinazolin-3(4H)-yl)-2-phenyl-N-(thiazol-2-yl)acetamide

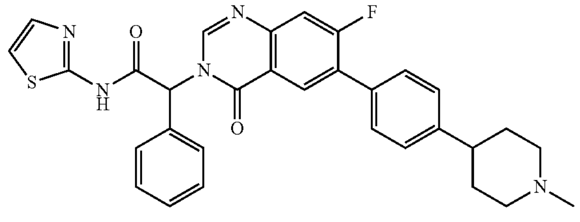 [SMILES: CN1CCC(c2ccc(-c3cc4c(=O)n(C(C(=O)Nc5nccs5)c5ccccc5)cnc4cc3F)cc2)CC1]

Compound 040 was prepared in a similar manner to ester 19, from 2-amino-2-phenyl-N-(thiazol-2-yl)acetamide hydrochloride and 7-fluoro-6-(4-(1-methylpiperidin-4-yl) phenyl)-quinazolin-4(3H)-one. $^{1}$H NMR (500 MHz, $d_6$-DMSO) δ 9.37 (br s, 1H) 8.26 (d, 1H) 7.91 (s, 1H) 7.67 (d, 1H) 7.64 (d, 2H) 7.52 (m, 4H) 7.46 (m, 2H) 7.42 (d, 2H), 7.32 (d, 1H) 6.88 (s, 1H) 3.56 (d, 2H) 3.11 (m, 2H) 2.89 (m, 1H) 2.84 (d, 3H) 2.08 (d, 2H) 1.87 (m, 2H); MS (m/z): 554.2 $[M+1]^+$.

Preparation of Compound 056: 2-(7-(4-(1-Methylpiperidin-4-yl)phenyl)-4-oxopyrido-[3,2-d]pyrimidin-3(4H)-yl)-2-phenyl-N-(thiazol-2-yl)acetamide
Compounds 056-060 were prepared with the following method. Scheme 5 below exemplifies the synthesis of Compound 056.
Scheme 5.
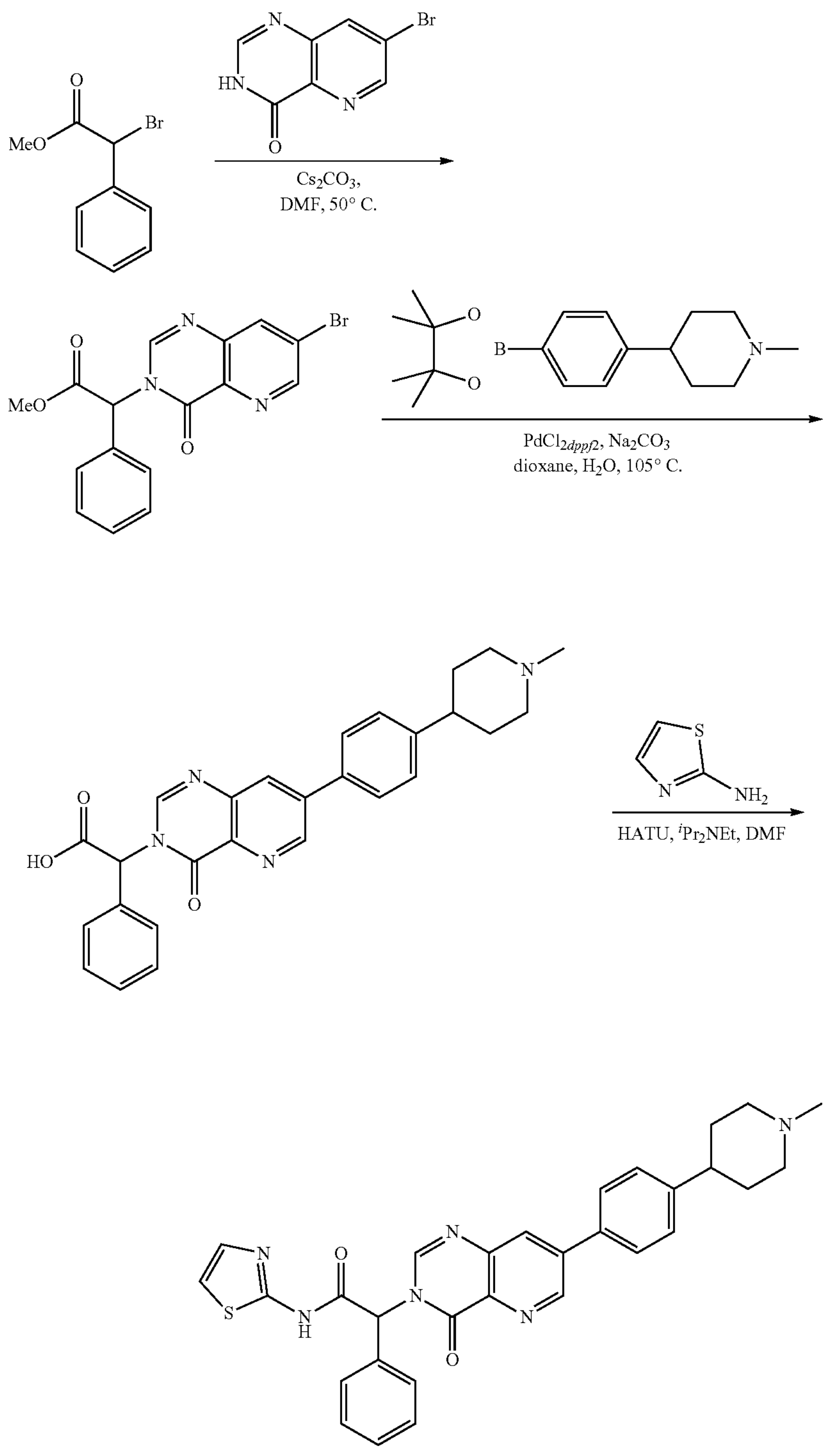

Acid X: 2-(7-(4-(1-Methylpiperidin-4-yl)phenyl)-4-oxopyrido[3,2-d]pyrimidin-3(4H)-yl)-2-phenylacetic acid

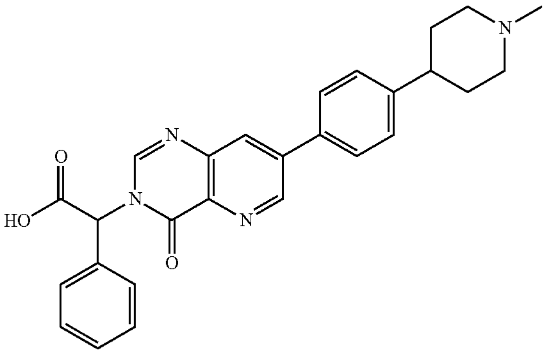 [SMILES: CN1CCC(c2ccc(-c3cnc4c(=O)n(C(C(=O)O)c5ccccc5)cnc4c3)cc2)CC1]

A mixture of methyl 2-(7-bromo-4-oxopyrido[3,2-d]pyrimidin-3(4H)-yl)-2-phenylacetate (100 mg, 0.27 mmol), 1-methyl-4-(4-(4,4,5,5-tetramethyl-1,3,2-dioxaborolan-2-yl)phenyl)-piperidine (88 mg, 0.29 mmol), $Pd(dppf)Cl_2$. DCM (44 mg, 0.054 mmol) and sodium carbonate (85 mg, 0.81 mmol) in dioxane:water (4:1, 2 mL) was degassed and re-suffused with nitrogen three times. The mixture was heated at 100° C. for 4 hours under nitrogen. After cooling, the reaction mixture was filtered and purified by reverse phase HPLC, eluting with 0-80% ACN/water (0.035% TFA modifier) to give the title compound (70 mg, 57%). MS (m/z): 454.9 $[M+1]^+$.

Compound 056: 2-(7-(4-(1-Methylpiperidin-4-yl)phenyl)-4-oxopyrido[3,2-d]pyrimidin-3(4H)-yl)-2-phenyl-N-(thiazol-2-yl)acetamide

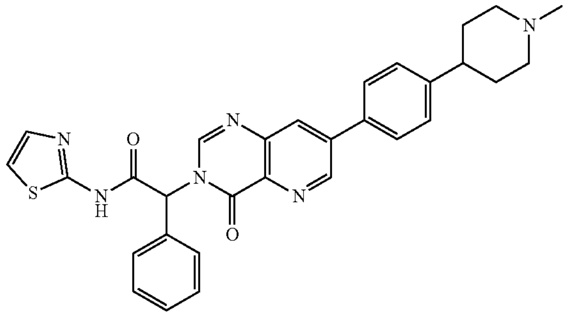 [SMILES: CN1CCC(c2ccc(-c3cnc4c(=O)n(C(C(=O)Nc5nccs5)c5ccccc5)cnc4c3)cc2)CC1]

A mixture of 2-(7-(4-(1-methylpiperidin-4-yl)phenyl)-4-oxopyrido[3,2-d]pyrimidin-3(4H)-yl)-2-phenylacetic acid (70 mg, 0.15 mmol), thiazol-2-amine (23 mg, 0.23 mmol), HATU (117 mg, 0.31 mmol), DIEA (80 μL, 0.46 mmol) and degassed DMF (2 mL) was heated to 60° C. for 2.5 hours. The reaction mixture was purified by reverse phase HPLC, eluting with 0-80% ACN/water (0.035% TFA modifier) to give the title compound (44 mg, 53%). $^1$H NMR (500 MHz, $d_6$-DMSO) δ 9.55 (br s, 1H) 9.22 (d, 1H) 8.39 (d, 1H) 7.95 (s, 1H) 7.93 (d, 2H) 7.53 (m, 4H) 7.48 (m, 2H) 7.44 (d, 2H) 7.33 (d, 1H) 6.92 (s, 1H) 3.56 (d, 2H) 3.11 (m, 2H) 2.91 (m, 1H) 2.85 (d, 3H) 2.07 (d, 2H) 1.89 (m, 2H); MS (m/z): 537.4 $[M+1]^+$.

The following compounds in Table 8 were prepared by a similar method to Compound 056 from the corresponding carboxylic acid and 2-aminothiazole.

TABLE 8

| No. | Structure/Name | m/z $[M+1]^+$ | $^1$H NMR (500 MHz, $d_6$-DMSO) δ | Starting material |
|---|---|---|---|---|
| 057 | 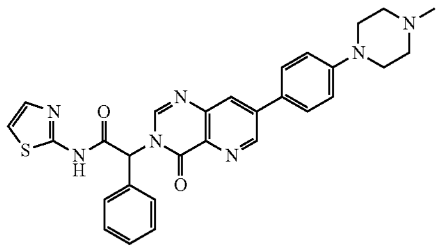 [SMILES: CN1CCN(c2ccc(-c3cnc4c(=O)n(C(C(=O)Nc5nccs5)c5ccccc5)cnc4c3)cc2)CC1] 2-(7-(4-(4-Methylpiperazin-1-yl)-phenyl)-4-oxopyrido[3,2-d]-pyrimidin-3(4H)-yl)-2-phenyl-N-(thiazol-2-yl)acetamide | 538.2 | 9.88 (br s, 1H) 9.22 (d, 1H) 8.33 (d, 1H) 7.92 (s, 1H) 7.90 (d, 2H) 7.53 (m, 4H) 7.48 (m, 2H) 7.33 (d, 1H) 7.18 (d, 2H) 6.91 (s, 1H) 4.04 (d, 2H) 3.55 (d, 2H) 3.18 (m, 2H) 3.07 (m, 2H) 2.88 (s, 3H) | 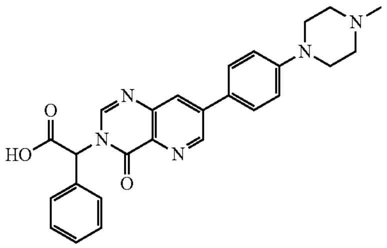 [SMILES: CN1CCN(c2ccc(-c3cnc4c(=O)n(C(C(=O)O)c5ccccc5)cnc4c3)cc2)CC1] |
| 058 | 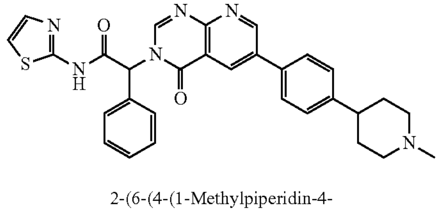 2-(6-(4-(1-Methylpiperidin-4-yl)phenyl)-4-oxopyrido[2,3-d]-pyrimidin-3(4H)-yl)-2-phenyl-N-(thiazol-2-yl)acetamide | 537.3 | 9.37 (br s, 1H) 9.36 (d, 1H) 8.75 (d, 1H) 2H) 7.53 (m, 4H) 7.49 (m, 2H) 7.43 (d, 2H) 7.33 (d, 1H) 6.87 (s, 1H) 3.56 (d, 2H) 3.11 (m, 2H) 2.90 (m, 1H) 2.84 (d, 3H) 2.08 (d, 2H) 1.87 (m, 2H) | 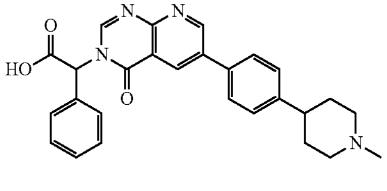 [SMILES: CN1CCC(c2ccc(-c3cnc4ncn(C(C(=O)O)c5ccccc5)c(=O)c4c3)cc2)CC1] |

TABLE 8-continued

| No. | Structure/Name | m/z $[M + 1]^+$ | $^1H$ NMR (500 MHz, $d_6$-DMSO) δ | Starting material |
|---|---|---|---|---|
| 059 | 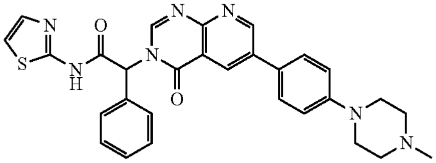 [SMILES: CN1CCN(c2ccc(-c3cnc4ncn(C(C(=O)Nc5nccs5)c5ccccc5)c(=O)c4c3)cc2)CC1] 2-(6-(4-(4-Methylpiperazin-1-yl)-phenyl)-4-oxopyrido[2,3-d]-pyrimidin-3(4H)-yl)-2-phenyl-N-(thiazol-2-yl)acetamide | 538.4 | 9.60 (br s, 1H) 9.26 (d, 1H) 8.62 (d, 1H) 7.97 (s, 1H) 7.75 (d, 2H) 7.45 (m, 4H) 7.40 (m, 2H) 7.25 (d, 1H) 7.10 (d, 2H) 6.78 (s, 1H) 3.93 (d, 2H) 3.47 (d, 2H) 3.11 (m, 2H) 2.97 (m, 2H) 2.80 (d, 3H) | 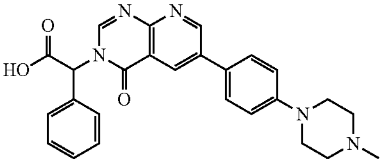 |
| 060 | 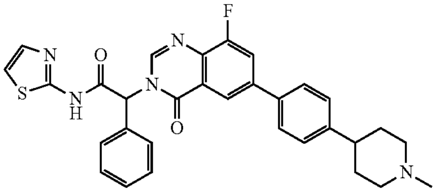 [SMILES: CN1CCC(c2ccc(-c3cc(F)c4ncn(C(C(=O)Nc5nccs5)c5ccccc5)c(=O)c4c3)cc2)CC1] 2-(8-Fluoro-6-(4-(1-methylpiperidin-4-yl)phenyl)-4-oxoquinazolin-3-(4H)-yl)-2-phenyl-N-(thiazol-2-yl)-acetamide | 554.4 | 8.24 (d, 1H) 8.14 (dd, 1H) 7.91 (s, 1H) 7.82 (d, 2H) 7.52 (m, 7.40 (d, 2H) 7.33 (d, 1H) 6.88 (s, 1H) 3.55 (d, 2H) 3.10 (m, 2H) 2.88 (m, 1H) 2.84 (d, 3H) 2.07 (d, 2H) 1.86 (m, 2H) | 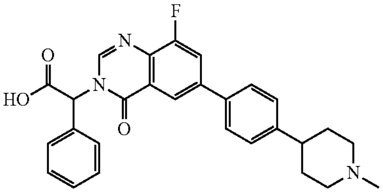 [SMILES: CN1CCC(c2ccc(-c3cc(F)c4ncn(C(C(=O)O)c5ccccc5)c(=O)c4c3)cc2)CC1] |
| 069 | 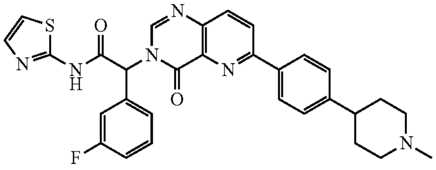 [SMILES: CN1CCC(c2ccc(-c3ccc4ncn(C(C(=O)Nc5nccs5)c5cccc(F)c5)c(=O)c4n3)cc2)CC1] 2-(3-Fluorophenyl)-2-(6-(4-(1-methylpiperidin-4-yl)phenyl)-4-oxo-pyrido[3,2-d]pyrimidin-3(4H)-yl)-N-(thiazol-2-yl)acetamide | — | 9.38 (br s, 1H) 8.46 (d, 1H) 8.22 (d, 3H) 7.44 (d, 2H) 7.38 (m, 6.87 (s, 1H) 3.55 (d, 2H) 3.11 (m, 2H) 2.90 (m, 1H) 2.84 (d, 3H) 2.08 (d, 2H) 1.88 (m, 2H) | 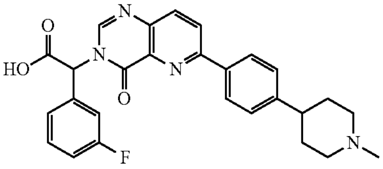 [SMILES: CN1CCC(c2ccc(-c3ccc4ncn(C(C(=O)O)c5cccc(F)c5)c(=O)c4n3)cc2)CC1] |
| 070 | 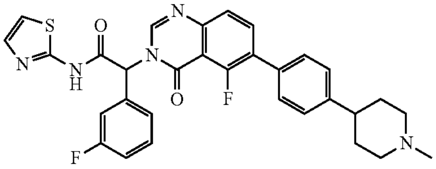 [SMILES: CN1CCC(c2ccc(-c3ccc4ncn(C(C(=O)Nc5nccs5)c5cccc(F)c5)c(=O)c4c3F)cc2)CC1] 2-(5-Fluoro-6-(4-(1-methylpiperidin-4-yl)phenyl)-4-oxoquinazolin-3-(4H)-yl)-2-(3-fluorophenyl)-N-(thiazol-2-yl)acetamide | 572.21 | 9.29 (br s, 1H) 7.97 (m, 2H) 7.60 (m, 4H) 2H) 7.34 (m, 3H) 7.28 (d, 1H) 6.80 (s, 1H) 3.54 (d, 2H) 3.10 (m, 2H) 2.88 (m, 1H) 2.84 (d, 3H) 2.08 (d, 2H) 1.86 (m, 2H) | 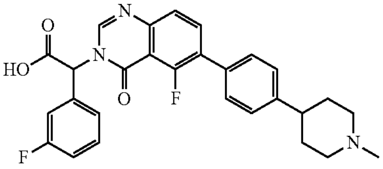 [SMILES: CN1CCC(c2ccc(-c3ccc4ncn(C(C(=O)O)c5cccc(F)c5)c(=O)c4c3F)cc2)CC1] |
| 071 | 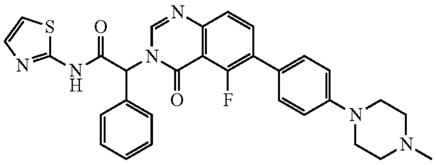 [SMILES: CN1CCN(c2ccc(-c3ccc4ncn(C(C(=O)Nc5nccs5)c5ccccc5)c(=O)c4c3F)cc2)CC1] 2-(5-Fluoro-6-(4-(4-methyl-piperazin-1-yl)phenyl)-4-oxo-quinazolin-3(4H)-yl)-2-phenyl-N-(thiazol-2-yl)acetamide | 555.23 | | 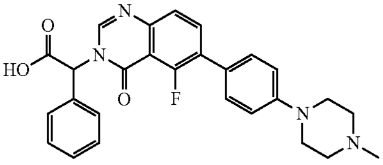 [SMILES: CN1CCN(c2ccc(-c3ccc4ncn(C(C(=O)O)c5ccccc5)c(=O)c4c3F)cc2)CC1] |

TABLE 8-continued

| No. | Structure/Name | m/z $[M + 1]^+$ | $^1$H NMR (500 MHz, $d_6$-DMSO) δ | Starting material |
|---|---|---|---|---|
| 072 | 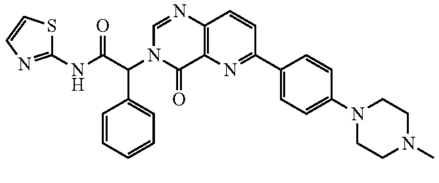 2-(6-(4-(4-Methylpiperazin-1-yl)-phenyl)-4-oxopyrido[3,2-d]-pyrimidin-3(4H)-yl)-2-phenyl-N-(thiazol-2-yl)acetamide | 538.2 | 9.76 (br s, 1H) 8.40 (d, 1H) 8.18 (d, 2H) 8.13 (d, 1H) 7.86 (s, 1H) 7.52 (m, 4H) 7.48 (m, 2H) 7.32 (d, 1H) 7.17 (d, 2H) 6.87 (s, 1H) 4.05 (d, 3.17 (m, 2H) 3.08 (m, 2H) 2.88 (s, 3H) | 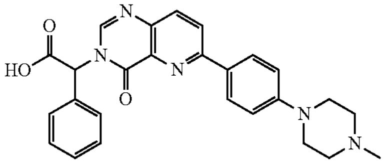 [SMILES: CN1CCN(c2ccc(-c3ccc4ncn(C(C(=O)O)c5ccccc5)c(=O)c4n3)cc2)CC1] |
| 073 | 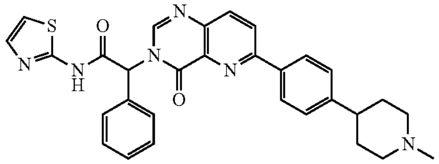 [SMILES: CN1CCC(c2ccc(-c3ccc4ncn(C(C(=O)Nc5nccs5)c5ccccc5)c(=O)c4n3)cc2)CC1] 2-(6-(4-(1-Methylpiperidin-4-yl)-phenyl)-4-oxopyrido[3,2-d]-pyrimidin-3(4H)-yl)-2-phenyl-N-(thiazol-2-yl)acetamide | 537.24 | 9.37 (br s, 1H) 8.45 7.90 (s, 1H) 7.52 (m, 4H) 7.48 (m, 2H) 7.44 (d, 2H) 7.33 (d, 1H) 6.89 (s, 1H) 3.54 (d, 2H) 3.10 (m, 2H) 2.91 (m, 1H) 2.84 (d, 3H) 2.08 (d, 2H) 1.88 (m, 2H) | 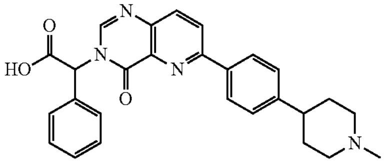 [SMILES: CN1CCC(c2ccc(-c3ccc4ncn(C(C(=O)O)c5ccccc5)c(=O)c4n3)cc2)CC1] |
| 074 | 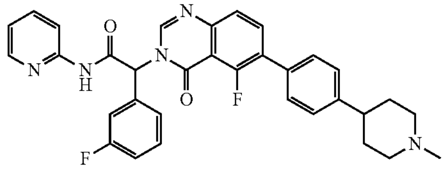 [SMILES: CN1CCC(c2ccc(-c3ccc4ncn(C(C(=O)Nc5ccccn5)c5cccc(F)c5)c(=O)c4c3F)cc2)CC1] 2-(5-Fluoro-6-(4-(1-methylpiperidin-4-yl)phenyl)-4-oxoquinazolin-3-(4H)-yl)-2-(3-fluorophenyl)-N-(pyridin-2-yl)acetamide | 566.29 | 11.30 (s, 1H) 9.27 7.90 (m, 1H) 7.79 (s, 1H) 7.77 (m, 1H) 7.53 (m, 3H) 7.50 (m, 1H) 7.33 (d, 2H) 7.27 (m, 3H) 7.11 (dd, 1H) 6.84 (s, 1H) 3.48 (d, 2H) 3.04 (m, 2H) 2.81 (m, 1H) 2.77 (d, 3H) 2.02 (m, 2H) 1.80 (m, 2H) | 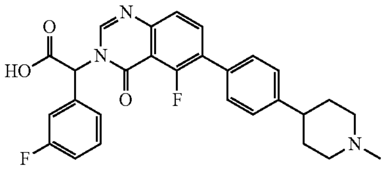 [SMILES: CN1CCC(c2ccc(-c3ccc4ncn(C(C(=O)O)c5cccc(F)c5)c(=O)c4c3F)cc2)CC1] |
| 075 | 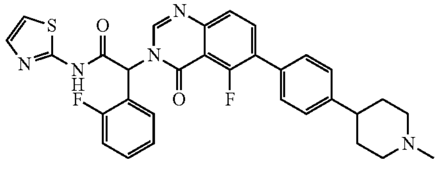 2-(5-Fluoro-6-(4-(1-methylpiperidin-4-yl)phenyl)-4-oxoquinazolin-3-(4H)-yl)-2-(2-fluorophenyl)-N-(thiazol-2-yl)acetamide | 572.32 | 9.45 (br s, 1H) 7.99 (m, 1H) 7.96 (s, 1H) 7.60 (m, 4H) 7.53 (d, 1H) 7.40 (m, 4H) 7.37 (d, 1H) 7.35 (d, 1H) 7.09 (s, 1H) 3.54 (d, 2H) 3.11 (m, 2H) 2.89 (m, 1H) 2.83 (d, 3H) 2.08 (m, 2H) 1.88 (m, 2H) | 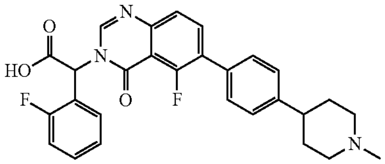 [SMILES: CN1CCC(c2ccc(-c3ccc4ncn(C(C(=O)O)c5ccccc5F)c(=O)c4c3F)cc2)CC1] |
| 076 | 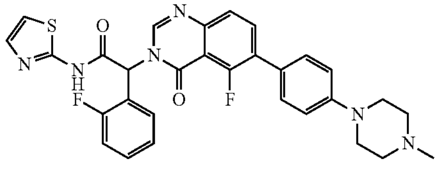 [SMILES: CN1CCN(c2ccc(-c3ccc4ncn(C(C(=O)Nc5nccs5)c5ccccc5F)c(=O)c4c3F)cc2)CC1] 2-(5-Fluoro-6-(4-(4-methyl-piperazin-1-yl)phenyl)-4-oxo-quinazolin-3(4H)-yl)-2-(2-fluoro-phenyl)-N-(thiazol-2-yl)acetamide | 573.27 | 9.78 (br s, 1H) 7.98 (m, 1H) 7.93 (s, 1H) 7.59 (m, 2H) 7.55 (d, 2H) 7.53 (d, 1H) 7.40 (m, 2H) 7.37 (d, 1H) 7.35 (d, 1H) 7.15 (d, 2H) 7.08 (s, 1H) 3.98 (d, 2H) 3.54 (d, 2H) 3.18 (m, 2H) 3.05 (m, 2H) 2.88 (s, 3H) | 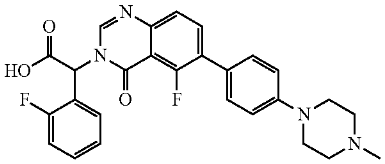 [SMILES: CN1CCN(c2ccc(-c3ccc4ncn(C(C(=O)O)c5ccccc5F)c(=O)c4c3F)cc2)CC1] |

TABLE 8-continued

| No. | Structure/Name | m/z [M + 1]$^+$ | $^1$H NMR (500 MHz, d$_6$-DMSO) δ | Starting material |
|---|---|---|---|---|
| 077 | 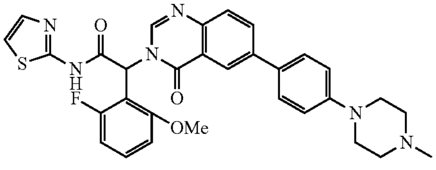 [SMILES: COc1cccc(F)c1C(C(=O)Nc1nccs1)n1cnc2ccc(-c3ccc(N4CCN(C)CC4)cc3)cc2c1=O] 2-(2-Fluoro-6-methoxyphenyl)-2-(6-(4-(4-methylpiperazin-1-yl)phenyl)-4-exoquinazolin-3(4H)-yl)-N-(thiazol-2-yl)acetamide | 585.33 | 9.77 (br s, 1H) 8.36 (d, 1H) 8.18 (dd, 1H) 7.88 (s, 1H) 7.75 (m, 3H) 7.56 (m, 1H) 7.48 (d, 1H) 7.28 (d, 1H) 7.16 (d, 2H) 7.08 (s, 1H) 7.06 (d, 1H) 6.97 (m, 1H) 3.98 (d, 2H) 3.76 (s, 3H) 3.54 (m, 2H) 3.19 (m, 2H) 3.05 (m, 2H) 2.88 (s, 3H) | 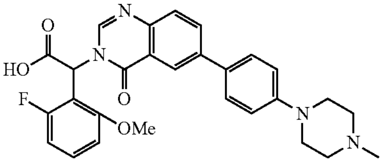 |
| 078 | 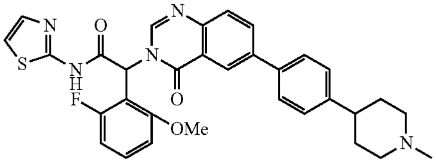 [SMILES: COc1cccc(F)c1C(C(=O)Nc1nccs1)n1cnc2ccc(-c3ccc(C4CCN(C)CC4)cc3)cc2c1=O] | 584.43 | 9.45 (br s, 1H) 8.42 7.91 (s, 1H) 7.80 (m, 3H) 7.57 (m, 1H) 7.48 (s, 1H) 7.40 (d, 2H) 7.27 (d, 1H) 7.08 (s, 1H) 7.06 (d, 1H) 6.98 (m, 1H) 3.77 (s, 3H) 3.54 (d, 2H) 3.11 (m, 2H) 2.88 (m, 1H) 2.84 (d, 3H) 2.07 (m, 2H) 1.88 (m, 2H) | 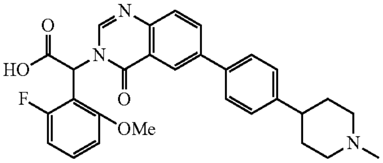 [SMILES: COc1cccc(F)c1C(C(=O)O)n1cnc2ccc(-c3ccc(C4CCN(C)CC4)cc3)cc2c1=O] |
| 079 | 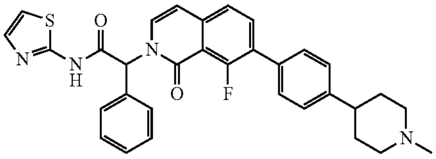 [SMILES: CN1CCC(c2ccc(-c3ccc4ccn(C(C(=O)Nc5nccs5)c5ccccc5)c(=O)c4c3F)cc2)CC1] 2-(8-Fluoro-7-(4-(1-methylpiperidin-4-yl)phenyl)-1-oxoisoquinolin-2-(1H)-yl)-2-phenyl-N-(thiazol-2-yl)-acetamide | | 9.33 (br s, 1H) 7.83 (dd, 1H) 7.59 (d, 2H) 7.53 (m, 5H) 7.39 (m, 4H) 7.30 (d, 1H) 6.93 (d, 1H) 6.84 (s, 1H) 6.63 (dd, 1H) 3.55 (d, 2H) 3.11 (m, 2H) 2.88 (m, 1H) 2.84 (d, 3H) 2.08 (d, 2H) 1.87 (m, 2H) | 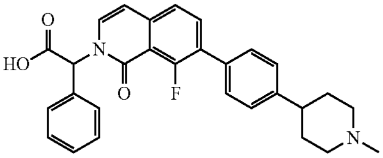 [SMILES: CN1CCC(c2ccc(-c3ccc4ccn(C(C(=O)O)c5ccccc5)c(=O)c4c3F)cc2)CC1] |
| 080 | 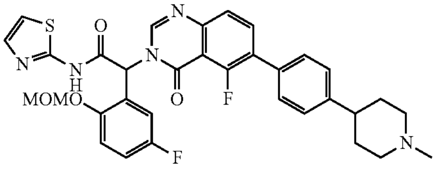 2-(5-Fluoro-2-(methoxymethoxy)-phenyl)-2-(5-fluoro-6-(4-(1-methyl-piperidin-4-yl)phenyl)-4-oxo-quinazolin-3(4H)-yl)-N-(thiazol-2-yl)acetamide | | | 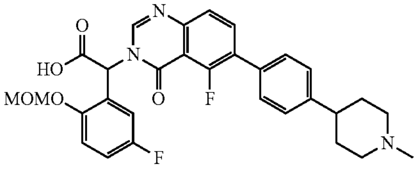 |
| 081 | 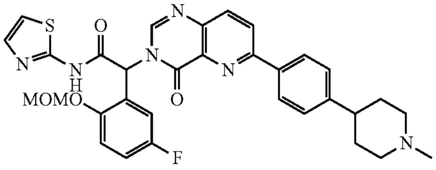 2-(5-fluoro-2-(methoxymethoxy)-phenyl)-2-(6-(4-(1-methylpiperidin-4-yl)phenyl)-4-oxopyrido[3,2-d]-pyrimidin-3(4H)-yl)-N-(thiazol-2-yl)-acetamide | | | 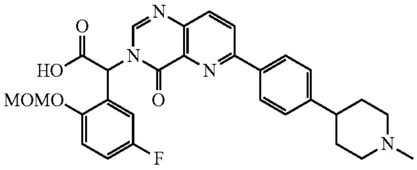 |

Acids 18-21 and C—O in Table 9 were prepared by a similar method to Acid X from the corresponding starting materials.

TABLE 9

| Acid | Structure/Name | m/z [M + 1]+ | $^1$H NMR (500 MHz, $d_6$-DMSO) δ | Starting materials |
|---|---|---|---|---|
| 18 | 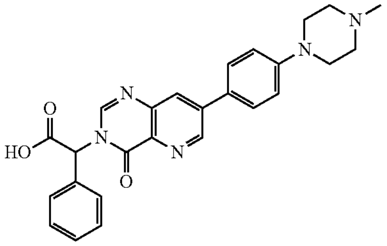 [SMILES: CN1CCN(c2ccc(-c3cnc4c(=O)n(C(C(=O)O)c5ccccc5)cnc4c3)cc2)CC1] 2-(7-(4-(4-Methylpiperazin-1-yl)-phenyl)-4-oxopyrido[3,2-d]-pyrimidin-3(4H)-yl)-2-phenylacetic acid | 455.9 | — | 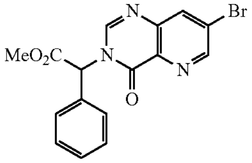 [SMILES: COC(=O)C(c1ccccc1)n1cnc2cc(Br)cnc2c1=O] and 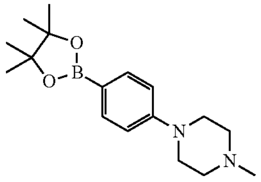 |
| 19 | 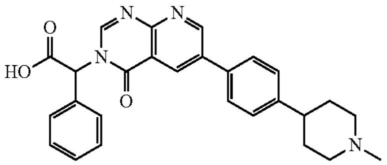 [SMILES: CN1CCC(c2ccc(-c3cnc4ncn(C(C(=O)O)c5ccccc5)c(=O)c4c3)cc2)CC1] 2-(6-(4-(1-Methylpiperidin-4-yl)-phenyl)-4-oxopyrido[2,3-d]-pyrimidin-3(4H)-yl)-2-phenylacetic acid | 455.2 | — | 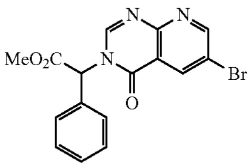 [SMILES: COC(=O)C(c1ccccc1)n1cnc2ncc(Br)cc2c1=O] and 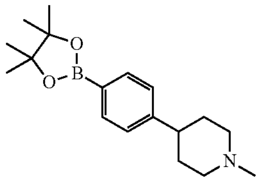 |
| 20 | 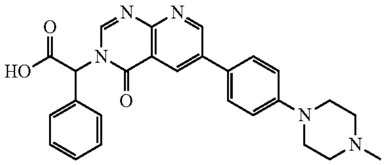 [SMILES: CN1CCN(c2ccc(-c3cnc4ncn(C(C(=O)O)c5ccccc5)c(=O)c4c3)cc2)CC1] 2-(6-(4-(4-Methylpiperazin-1-yl)-phenyl)-4-oxopyrido[2,3-d]-pyrimidin-3(4H)-yl)-2-phenyl-acetic acid | 456.2 | — | 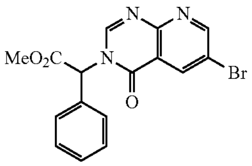 [SMILES: COC(=O)C(c1ccccc1)n1cnc2ncc(Br)cc2c1=O] and 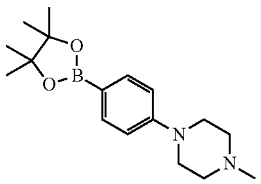 |
| 21 | 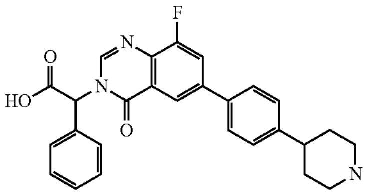 [SMILES: O=C(O)C(c1ccccc1)n1cnc2c(F)cc(-c3ccc(C4CCNCC4)cc3)cc2c1=O] | 472.4 | 8.23 (d, 1H) 8.19 (s, 1H) 8.12 (d, 1H) 7.80 (d, 2H) 7.54 (d, 2H) 7.43-7.50 (m, 3 H) 7.47 2H) 6.54 (s, 1H) 3.54 (d, 2H) 3.09 (m, 2H), 2.87 (m, 1H) 2.83 (s, 3H) 2.06 (d, 2H) 1.88 (m, 2H) | 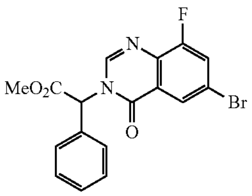 [SMILES: COC(=O)C(c1ccccc1)n1cnc2c(F)cc(Br)cc2c1=O] and |

TABLE 9-continued

| Acid | Structure/Name | m/z [M + 1]+ | $^{1}H$ NMR (500 MHz, $d_6$-DMSO) δ | Starting materials |
|---|---|---|---|---|
| | | | | 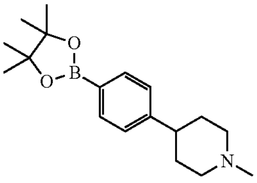 |
| C | 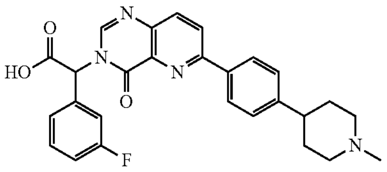 [SMILES: CN1CCC(c2ccc(-c3ccc4ncn(C(C(=O)O)c5cccc(F)c5)c(=O)c4n3)cc2)CC1] 2-(3-Fluorophenyl)-2-(6-(4-(1-methyl-piperidin-4-yl)phenyl)-4-oxo-pyrido[3,2-d]pyrimidin-3(4H)-yl)acetic acid | | — | 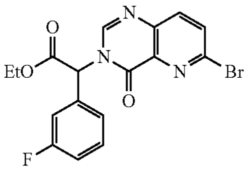 [SMILES: CCOC(=O)C(c1cccc(F)c1)n1cnc2ccc(Br)nc2c1=O] and 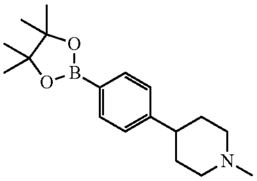 |
| D | 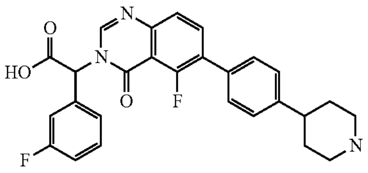 [SMILES: O=C(O)C(c1cccc(F)c1)n1cnc2ccc(-c3ccc(C4CCNCC4)cc3)c(F)c2c1=O] 2-(5-Fluoro-6-(4-(1-methyl-piperidin-4-yl)phenyl)-4-oxo-quinazolin-3(4H)-yl)-2-(3-fluorophenyl)acetic acid | | — | 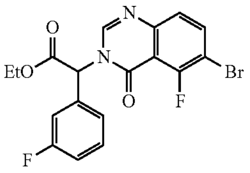 [SMILES: CCOC(=O)C(c1cccc(F)c1)n1cnc2ccc(Br)c(F)c2c1=O] and 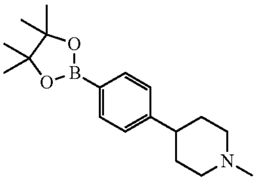 |
| E | 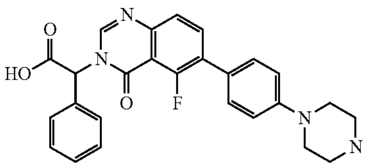 [SMILES: O=C(O)C(c1ccccc1)n1cnc2ccc(-c3ccc(N4CCNCC4)cc3)c(F)c2c1=O] 2-(5-Fluoro-6-(4-(4-methyl-piperazin-1-yl)phenyl)-4-oxoquinazolin-3(4H)-yl)-2-phenylacetic acid | 473.17 | 8.08 (s, 1H) 7.93 (m, 1H) 7.54 (d, 1H) 7.52 (m, 4H) 7.45 (m, 3H) 7.12 (d, 2H) 6.46 (s, 1H) 3.40 (m, 4H) 3.02 (m, 4H) 2.64 (br s, 3H) | 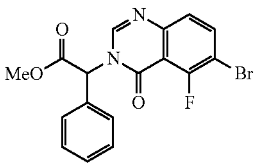 [SMILES: COC(=O)C(c1ccccc1)n1cnc2ccc(Br)c(F)c2c1=O] and 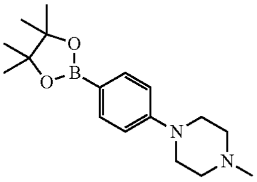 |

TABLE 9-continued

| Acid | Structure/Name | m/z [M + 1]$^+$ | $^1$H NMR (500 MHz, $d_6$-DMSO) δ | Starting materials |
|---|---|---|---|---|
| F | 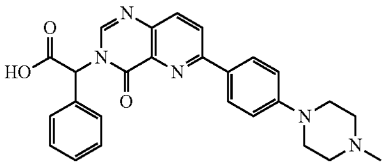 [SMILES: CN1CCN(c2ccc(-c3ccc4ncn(C(C(=O)O)c5ccccc5)c(=O)c4n3)cc2)CC1]<br>2-(6-(4-(4-Methylpiperazin-1-yl)-phenyl)-4-oxopyrido[3,2-d]pyrimidin-3(4H)-yl)-2-phenylacetic acid | | — | 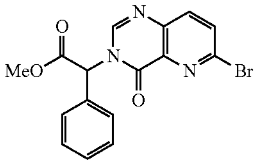 [SMILES: COC(=O)C(c1ccccc1)n1cnc2ccc(Br)nc2c1=O]<br>and<br>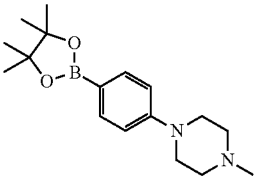 |
| G | 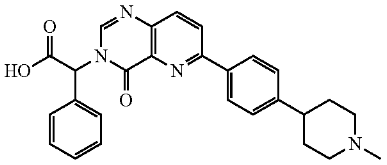 [SMILES: CN1CCC(c2ccc(-c3ccc4ncn(C(C(=O)O)c5ccccc5)c(=O)c4n3)cc2)CC1]<br>2-(6-(4-(1-Methylpiperidin-4-yl)-phenyl)-4-oxopyrido[3,2-d]pyrimidin-3(4H)-yl)-2-phenyl-acetic acid | | — | 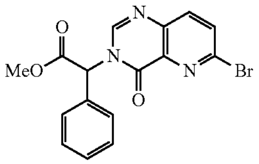 [SMILES: COC(=O)C(c1ccccc1)n1cnc2ccc(Br)nc2c1=O]<br>and<br>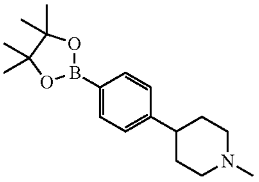 |
| H | 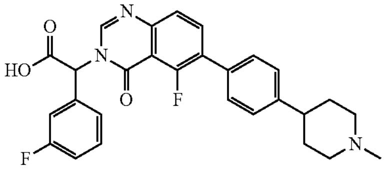 [SMILES: CN1CCC(c2ccc(-c3ccc4ncn(C(C(=O)O)c5cccc(F)c5)c(=O)c4c3F)cc2)CC1]<br>2-(5-Fluoro-6-(4-(1-methyl-piperidin-4-yl)phenyl)-4-oxoquinazolin-3(4H)-yl)-2-(3-fluorophenyl)acetic acid | 490.15 | — | 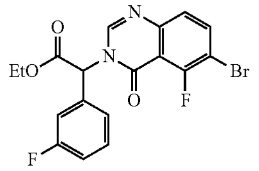 [SMILES: CCOC(=O)C(c1cccc(F)c1)n1cnc2ccc(Br)c(F)c2c1=O]<br>and<br>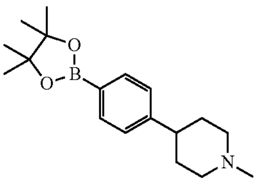 |
| I | 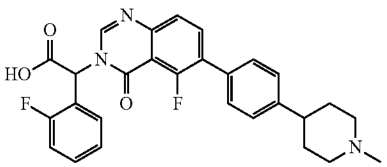 [SMILES: CN1CCC(c2ccc(-c3ccc4ncn(C(C(=O)O)c5ccccc5F)c(=O)c4c3F)cc2)CC1] | 490.15 | — | 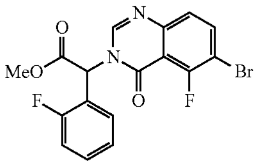 [SMILES: COC(=O)C(c1ccccc1F)n1cnc2ccc(Br)c(F)c2c1=O] |

TABLE 9-continued

| Acid | Structure/Name | m/z [M + 1]$^+$ | $^1$H NMR (500 MHz, $d_6$-DMSO) δ | Starting materials |
|---|---|---|---|---|
| | 2-(5-Fluoro-6-(4-(1-methyl-piperidin-4-yl)phenyl)-4-oxoquinazolin-3(4H)-yl)-2-(2-fluorophenyl)acetic acid | | | and 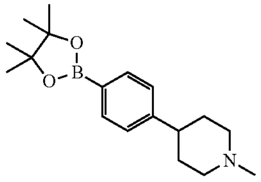 |
| J | 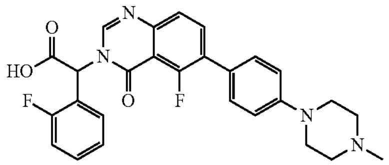 [SMILES: CN1CCN(c2ccc(-c3ccc4ncn(C(C(=O)O)c5ccccc5F)c(=O)c4c3F)cc2)CC1] 2-(5-Fluoro-6-(4-(4-methyl-piperazin-1-yl)phenyl)-4-oxoquinazolin-3(4H)-yl)-2-(2-fluorophenyl)acetic acid | 491.16 | — | 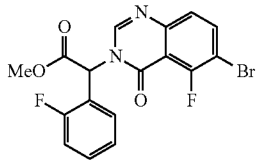 [SMILES: COC(=O)C(c1ccccc1F)n1cnc2ccc(Br)c(F)c2c1=O] and 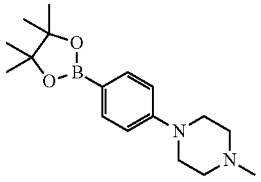 |
| K | 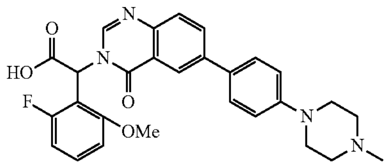 2-(2-Fluoro-6-methoxyphenyl)-2-(6-(4-(4-methylpiperazin-1-yl)phenyl)-4-oxoquinazolin-3(4H)-yl)acetic acid | 503.18 | — | 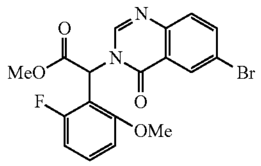 [SMILES: COC(=O)C(c1c(F)cccc1OC)n1cnc2ccc(Br)cc2c1=O] and 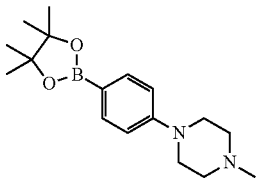 |
| L | 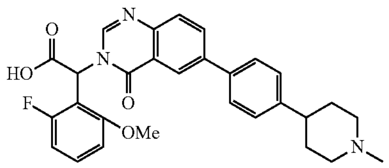 [SMILES: COc1cccc(F)c1C(C(=O)O)n1cnc2ccc(-c3ccc(C4CCN(C)CC4)cc3)cc2c1=O] 2-(2-Fluoro-6-methoxyphenyl)-2-(6-(4-(1-methylpiperidin-4-yl)phenyl)-4-oxoquinazolin-3(4H)-yl)acetic acid | 502.27 | — | 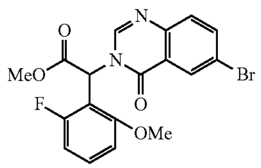 [SMILES: COC(=O)C(c1c(F)cccc1OC)n1cnc2ccc(Br)cc2c1=O] and 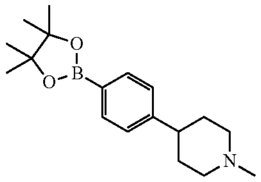 |

TABLE 9-continued

| Acid | Structure/Name | m/z [M + 1]+ | $^1$H NMR (500 MHz, $d_6$-DMSO) δ | Starting materials |
|---|---|---|---|---|
| M | 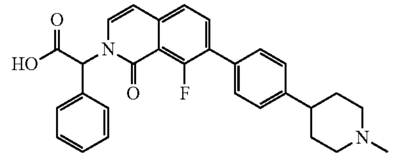 [SMILES: CN1CCC(c2ccc(-c3ccc4ccn(C(C(=O)O)c5ccccc5)c(=O)c4c3F)cc2)CC1] 2-(8-Fluoro-7-(4-(1-methylpiperidin-4-yl)phenyl)-1-oxoisoquinolin-2(1H)-yl)-2-phenylacetic acid | | | 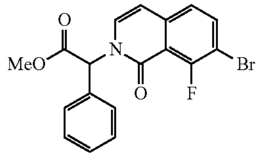 [SMILES: COC(=O)C(c1ccccc1)n1ccc2ccc(Br)c(F)c2c1=O] and 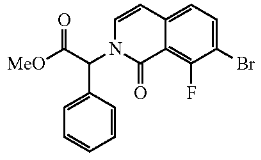 [SMILES: COC(=O)C(c1ccccc1)n1ccc2ccc(Br)c(F)c2c1=O] |
| N | 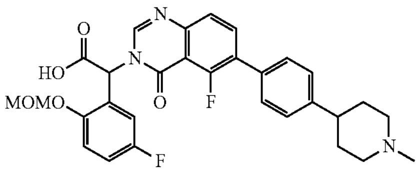 2-(5-Fluoro-2-(methoxymethoxy)-phenyl)-2-(5-fluoro-6-(4-(1-methyl-piperidin-4-yl)phenyl)-4-oxo-quinazolin-3(4H)-yl)acetic acid | | | 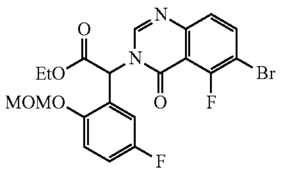 and 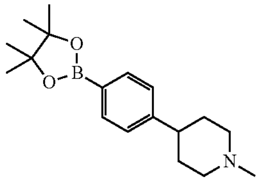 |
| O | 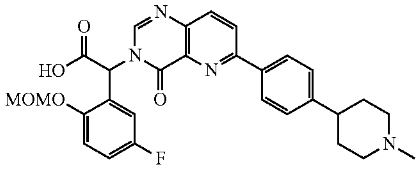 2-(5-Fluoro-2-(methoxymethoxy)-phenyl)-2-(6-(4-(1-methylpiperidin-4-yl)phenyl)-4-oxopyrido[3,2-d]-pyrimidin-3(4H)-yl)acetic acid | | | 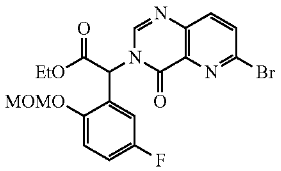 and 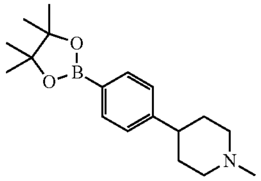 |

Scheme 6

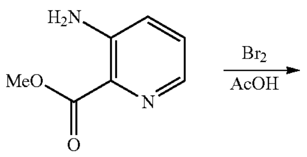

-continued

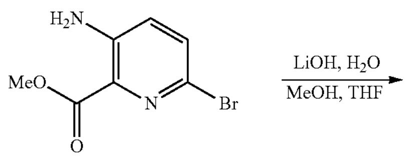

-continued

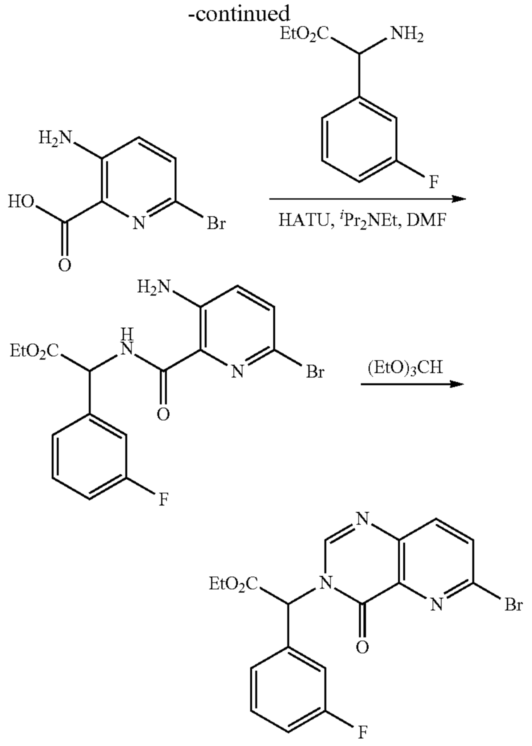

Methyl 3-amino-6-bromopicolinate

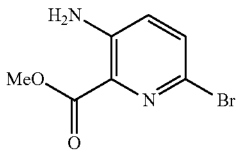 [SMILES: COC(=O)c1nc(Br)ccc1N]

A solution of bromine (220 μL, 4.27 mmol) in AcOH (800 μL) was added dropwise over one minute to a suspension of methyl 3-aminopicolinate (652 mg, 4.27 mmol) in 13 mL of water containing c. $H_2SO_4$ (207 μL, 4.0 mmol). The reaction mixture was stirred for 15 min then basified with 10 N NaOH to pH 6. The reaction mixture was extracted with EtOAc (3×30 mL). The combined organic extracts were washed with saturated brine, dried over $Na_2SO_4$, filtered, concentrated under reduced pressure, and purified by normal phase flash chromatography (0-60% EtOAc/hexane) to give the title compound (600 mg, 61%). $^1H$ NMR (500 MHz, $d_6$-DMSO) δ 7.45 (d, 1H) 7.22 (d, 1H) 6.89 (s, 2H) 3.82 (s, 3H).

3-Amino-6-bromopicolinic acid

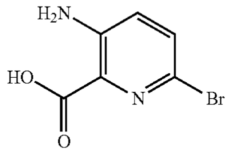 [SMILES: Nc1ccc(Br)nc1C(=O)O]

A mixture of methyl 3-amino-6-bromopicolinate (600 mg, 2.6 mmol), LiOH—$H_2O$ (600 mg, 5.5 mmol), THF (6 mL), MeOH (1.5 mL), and water (1.5 mL) was stirred for 45 min. Solvent was removed under reduced pressure and the residue was dissolved in water (20 mL). The pH of the solution was adjusted to pH 6 (pH paper) with 2N HCl. The resulting solid was filtered, washed with cold water (~10 mL) and dried to give 302 mg of the title compound. The mother liquor was acidified as above to give an additional 98 mg of the title compound to bring the total yield to 400 mg, 71%. $^1H$ NMR (500 MHz, $d_6$-DMSO) δ 7.43 (d, 1H) 7.20 (d, 1H).

Ethyl 2-(3-amino-6-bromopicolinamido)-2-(3-fluorophenyl)acetate (Amide A)

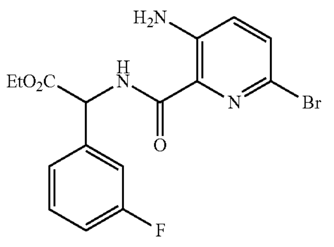 [SMILES: CCOC(=O)C(NC(=O)c1nc(Br)ccc1N)c1cccc(F)c1]

A solution of 3-amino-6-bromopicolinic acid (217 mg, 1.0 mmol), ethyl 2-amino-2-(3-fluorophenyl)acetate hydrochloride (280 mg, 1.2 mmol), HATU (760 mg, 2.0 mmol), DIEA (1 mL, 5.75 mmol) and degassed DMF (2 mL) was stirred at 60° C. for 1 h. After cooling, the reaction mixture was poured into saturated brine (~20 mL), and extracted with EtOAc (2×30 mL). The combined organic extracts were washed with saturated brine, dried over $Na_2SO_4$, filtered, concentrated under reduced pressure, and purified by normal phase flash chromatography (0-55% EtOAc/hexane) to give the title compound (340 mg, 86%).

Ethyl 2-(6-bromo-4-oxopyrido[3,2-d]pyrimidin-3(4H)-yl)-2-(3-fluorophenyl)acetate (Ester E)

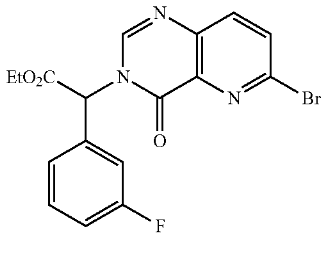 [SMILES: CCOC(=O)C(c1cccc(F)c1)n1cnc2ccc(Br)nc2c1=O]

A mixture of ethyl 2-(3-amino-6-bromopicolinamido)-2-(3-fluorophenyl)acetate (320 mg, 0.8 mmol) and triethylorthoformate (4 mL) in a sealed tube was subjected to MW irradiation at 210° C. for 70 min. The excess triethylorthoformate was removed under reduced pressure. The residue was purified by normal phase flash chromatography (0-65% EtOAc/hexane) to give the title compound (340 mg, quant). $^1H$ NMR (500 MHz, $d_6$-DMSO) δ 8.44 (s, 1H) 8.08 (m, 2H) 7.50 (m, 1H) 7.43 (m, 1H) 7.37 (d, 1H) 7.29 (m, 1H) 6.60 (s, 1H) 4.26 (m, 2H) 1.19 (t, 3H).

Esters F-K in Table 10 were prepared by a similar method to Ester E from the corresponding starting material.

TABLE 10

| Ester | Structure/Name | m/z $[M + 1]^+$ | $^1H$ NMR (500 MHz, $d_6$-DMSO) δ | Starting materials |
|---|---|---|---|---|
| F | 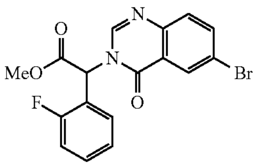 [SMILES: COC(=O)C(c1ccccc1F)n1cnc2ccc(Br)cc2c1=O] Methyl 2-(6-bromo-4-oxo-quinazolin-3(4H)-yl)-2-(2-fluoro-phenyl)acetate | 392.97 | 8.33 (s, 1H) 8.28 (d, 1H) 8.05 (dd, 1H) 7.68 (d, 1H) 7.54 (m, 1H) 7.52 (m, 1H) 7.32 (dd, 1H) 7.28 (m, 1H) 6.81 (s, 1H) 3.78 (s, 3H) | 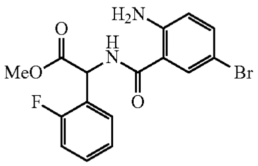 [SMILES: COC(=O)C(NC(=O)c1cc(Br)ccc1N)c1ccccc1F] |
| G | 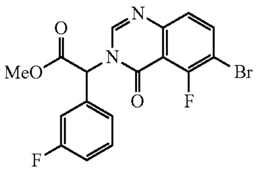 [SMILES: COC(=O)C(c1cccc(F)c1)n1cnc2ccc(Br)c(F)c2c1=O] Ethyl 2-(6-bromo-5-fluoro-4-oxo-quinazolin-3(4H)-yl)-2-(3-fluoro-phenyl)acetate | | — | 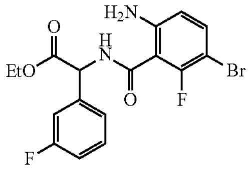 [SMILES: CCOC(=O)C(NC(=O)c1c(N)ccc(Br)c1F)c1cccc(F)c1] |
| H | 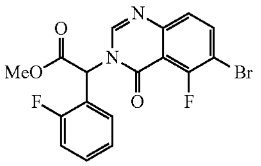 [SMILES: COC(=O)C(c1ccccc1F)n1cnc2ccc(Br)c(F)c2c1=O] Methyl 2-(6-bromo-5-fluoro-4-oxo-quinazolin-3(4H)-yl)-2-(2-fluoro-phenyl)acetate | 410.96 | $CDCl_3$ 7.97 (s, 1H) 7.90 (dd, 1H) 7.48 (m, 2H) 7.42 (dd, 1H) 7.27 (m, 1H) 7.19 (dd, 1H) 6.87 (s, 1H) 3.89 (s, 3H) | 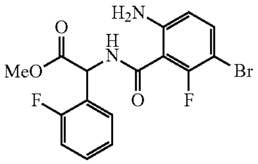 [SMILES: COC(=O)C(NC(=O)c1c(N)ccc(Br)c1F)c1ccccc1F] |
| I | 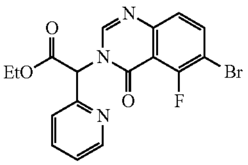 [SMILES: CCOC(=O)C(c1ccccn1)n1cnc2ccc(Br)c(F)c2c1=O] Ethyl 2-(6-bromo-5-fluoro-4-oxo-quinazolin-3(4H)-yl)-2-(pyridin-2-yl)-acetate | | | 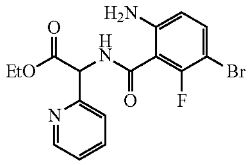 [SMILES: CCOC(=O)C(NC(=O)c1c(N)ccc(Br)c1F)c1ccccn1] |
| J | 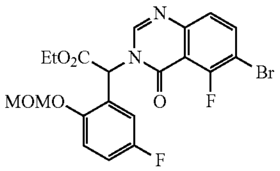 Ethyl 2-(6-bromo-5-fluoro-4-oxo-quinazolin-3(4H)-yl)-2-(5-fluoro-2-(methoxy-methoxy)phenyl)acetate | | | 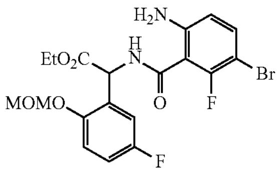 |

TABLE 10-continued

| Ester | Structure/Name | m/z [M + 1]$^+$ | $^1$H NMR (500 MHz, $d_6$-DMSO) δ | Starting materials |
|---|---|---|---|---|
| K | 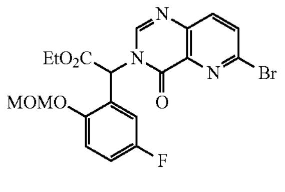 Ethyl 2-(6-bromo-4-oxo-pyrido[3,2-d]pyrimidin-3(4H)-yl)-2-(5-fluoro-2-(methoxy-methoxy)phenyl)acetate | | | 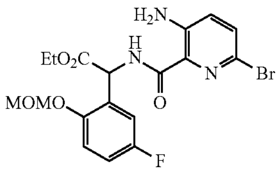 |

Amides B-G in Table 11 were prepared by a similar method to Amide A from the corresponding starting materials.

TABLE 11

| Amide | Structure/Name | m/z [M + 1]$^+$ | $^1$H NMR (500 MHz, $d_6$-DMSO) δ |
|---|---|---|---|
| B | 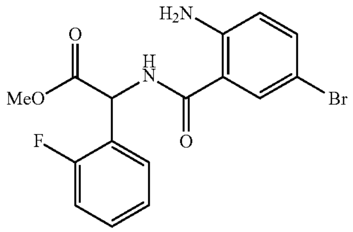 [SMILES: COC(=O)C(NC(=O)c1cc(Br)ccc1N)c1ccccc1F] Methyl 2-(2-amino-5-bromo-benzamido)-2-(2-fluorophenyl)acetate | 382.98 | 9.15 (d, 1H) 7.81 (d, 1H) 7.49 (m, 1H) 7.43 (m, 1H) 7.30 (dd, 1H) 7.25 (m, 2H) 6.69 (d, 1H) 6.59 (s, 2H) 5.91 (d, 1H) 3.68 (s, 3H) |
| C | 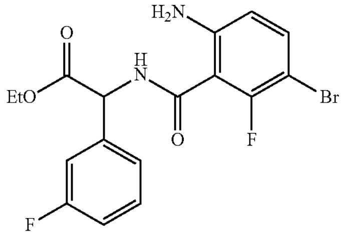 [SMILES: CCOC(=O)C(NC(=O)c1c(N)ccc(Br)c1F)c1cccc(F)c1] Ethyl 2-(6-amino-3-bromo-2-fluoro-benzamido)-2-(3-fluorophenyl)acetate | | — |
| D | 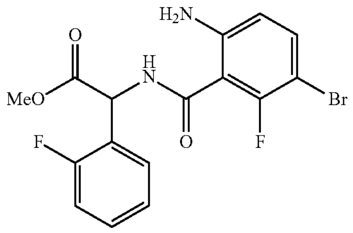 [SMILES: COC(=O)C(NC(=O)c1c(N)ccc(Br)c1F)c1ccccc1F] Methyl 2-(6-amino-3-bromo-2-fluoro-benzamido)-2-(2-fluorophenyl)acetate | 401.03 | 9.34 (d, 1H) 7.47 (m, 1H) 7.42 (m, 1H) 7.33 (dd, 1H) 7.25 (m, 2H) 6.51 (d, 1H) 5.91 (d, 1H) 3.69 (s, 3H) |

TABLE 11-continued
| Amide | Structure/Name | m/z [M + 1]+ | $^1$H NMR (500 MHz, $d_6$-DMSO) δ |
|---|---|---|---|
| E | 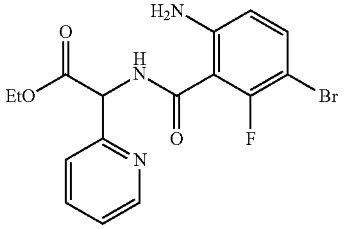 [SMILES: CCOC(=O)C(NC(=O)c1c(N)ccc(Br)c1F)c1ccccn1] Ethyl 2-(6-amino-3-bromo-2-fluoro-benzamido)-2-(pyridin-2-yl)acetate | | |
| F | 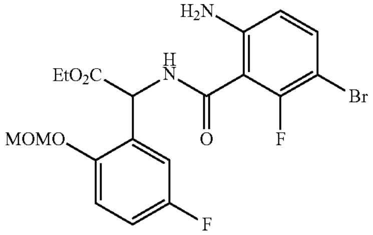 Ethyl 2-(6-amino-3-bromo-2-fluoro-benzamido)-2-(5-fluoro-2-(methoxy-methoxy)phenyl)acetate | | |
| G | 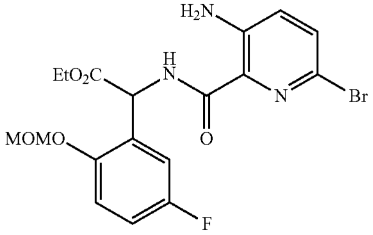 Ethyl 2-(3-amino-6-bromo-picolinamido)-2-(5-fluoro-2-(methoxymethoxy)-phenyl)acetate | 458.0 | |
Scheme 7
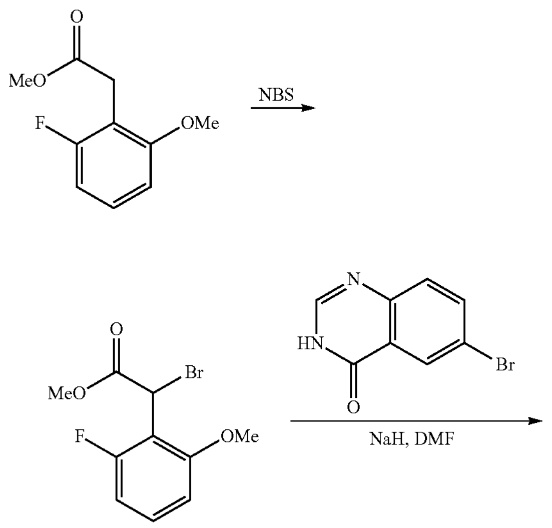
-continued
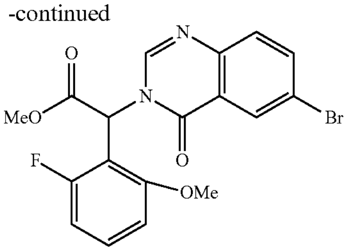
Methyl 2-bromo-2-(2-fluoro-6-methoxyphenyl)acetate
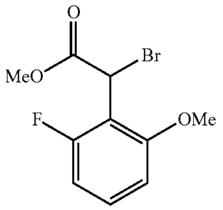 [SMILES: COC(=O)C(Br)c1c(F)cccc1OC]

N-Bromosuccinimide (4.05 g. 22.7 mmol) and benzoyl peroxide (524 mg, 2.16 mmol) were added to a solution of methyl 2-(2-fluoro-8-methoxyphenyl)acetate (4.30 g, 21.7 mmol) in $CCl_4$ (120 mL) and the reaction mixture was heated at 80° C. for 24 hours. After cooling, dichloromethane (150 mL) was added, and the organic layer was washed with saturated brine, dried ($Na_2SO_4$), and concentrated under reduced pressure. The residue was purified by silica chromatography (0-10% EtOAc in Hex) to give the title compound (3.93 g, 65%). $^1H$ NMR (500 MHz, $CDCl_3$) δ $CDCl_3$7.30 (m, 1H) 6.73 (m, 2H) 6.01 (s, 1H) 3.90 (s, 3H) 3.80 (s, 3H).

Methyl 2-(6-bromo-4-oxoquinazolin-3(4H)-yl)-2-(2-fluoro-6-methoxyphenyl)acetate

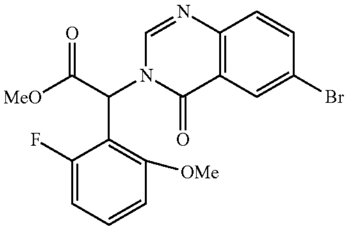 [SMILES: COC(=O)C(c1c(F)cccc1OC)n1cnc2ccc(Br)cc2c1=O]

NaH (60% in mineral oil, 356 mg) was added to a solution of 6-bromoquinazolin-4(3H)-one (1.0 g, 4.44 mmol) in DMF (20 mL) at 0° C., and the mixture was stirred at room temperature for 1 h. A solution of methyl 2-bromo-2-(2-fluoro-6-methoxyphenyl)acetate (1.5 g, 5.33 mmol) in DMF (5 mL) was added dropwise. The reaction was stirred overnight and ethyl acetate (100 mL) was added. The mixture was washed with saturated brine, dried ($Na_2SO_4$), and concentrated under reduced pressure. The residue was purified by silica chromatography (0-60% EtOAc in Hex) to give the title compound (1.42 g, 76%). $^1H$ NMR (500 MHz, $d_6$-DMSO) δ 8.30 (s, 1H) 8.05 (dd, 1H) 8.04 (s, 1H) 7.67 (d, 1H) 7.55 (m, 1H) 7.07 (d, 1H) 6.98 (m, 1H) 6.87 (s, 1H) 3.87 (s, 3H) 3.76 (s, 3H); MS (m/z): 423.09.

Preparation of Compound 061: 2-(4-Oxo-6-(pyridin-3-ylethynyl)quinazolin-3(4H)-yl)-2-phenyl-N-(thiazol-2-yl)acetamide

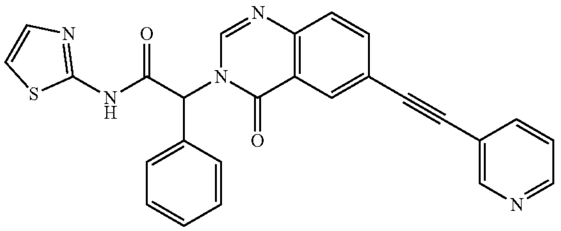 [SMILES: O=C(Nc1nccs1)C(c1ccccc1)n1cnc2ccc(C#Cc3cccnc3)cc2c1=O]

A mixture of 2-(6-iodo-4-oxoquinazolin-3(4H)-yl)-2-phenyl-N-(thiazol-2-yl)acetamide (100 mg, 0.2 mmol), triphenylphosphine (11 mg, 004 mmol), 3-ethynyl pyridine (32 mg, 0.3 mmol) and triethylamine (85 uL, 0.6 mmol) in DMF (2 mL) was degassed and re-suffused with nitrogen. $Pd(PPh_3)_2Cl_2$ (14 mg, 0.02 mmol) and Cu(I)I (4 mg, 0.02 mmol) were added and the reaction mixture was heated at 100° C. for 4 hours. After cooling, the reaction mixture was purified by reverse phase HPLC eluting with 0-80% ACN/water (TFA modifier) to give the title compound (7.6 mg, 8%). $^1H$ NMR (500 MHz, $d_6$-DMSO) δ 8.84 (m, 1H) 8.62 (dd, 1H) 8.35 (d, 1H) 8.07 (m, 1H) 8.03 (dd, 1H) 7.90 (s, 1H) 7.76 (d, 1H) 7.52 (m, 5H) 7.45 (m, 2H) 7.32 (d, 1H) 6.88 (s, 1H); MS (m/z): 463.8 $[M+1]^+$.

Preparation of 2-(5-Fluoro-2-hydroxyphenyl)-2-(6-(4-(1-methylpiperidin-4-yl)phenyl)-4-oxoquinazolin-3(4H)-yl)-N-(pyridin-2-yl)acetamide; hydrochloride (082)

Scheme 8

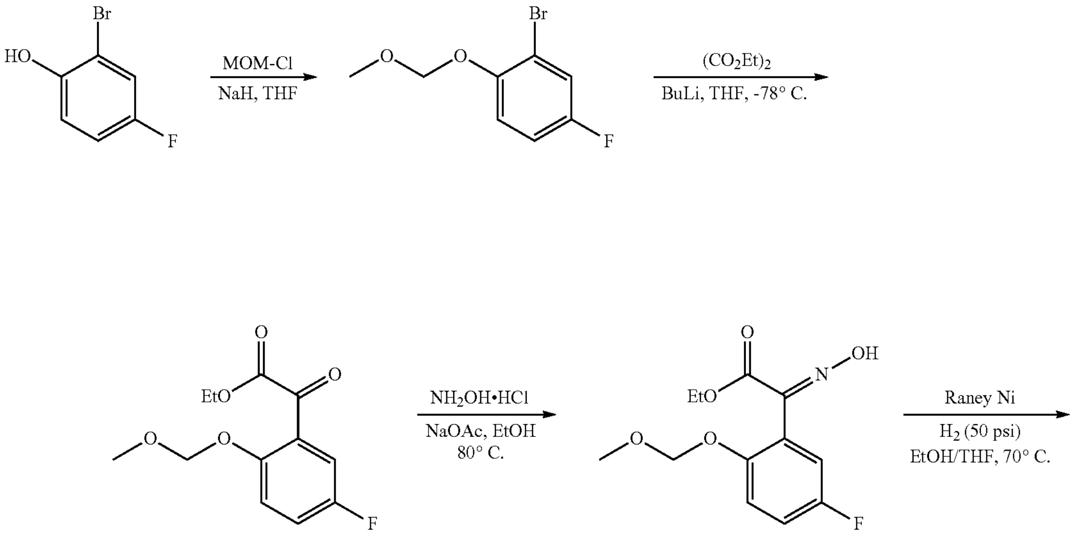

-continued
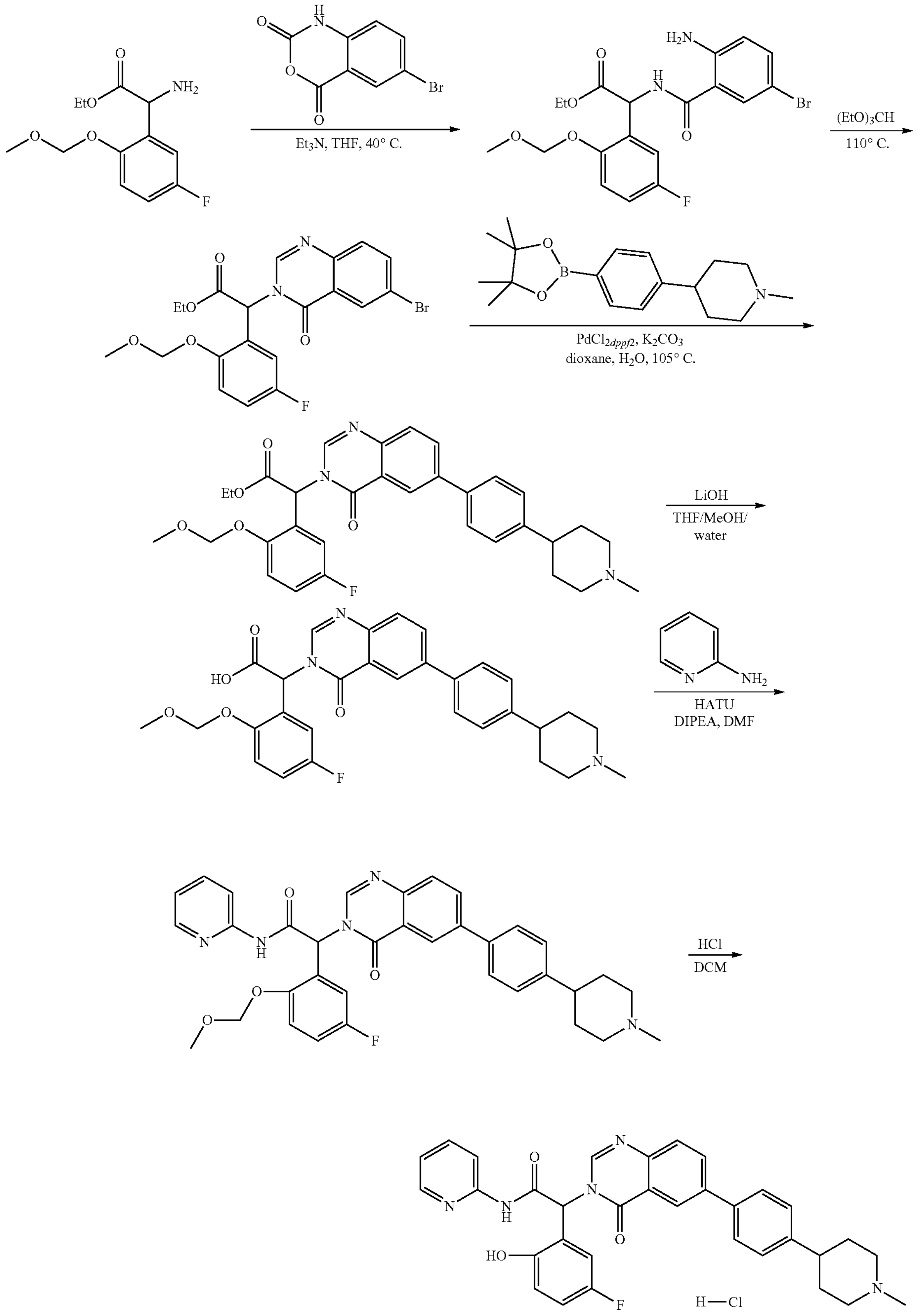

2-Bromo-4-fluoro-1-(methoxymethoxy)benzene

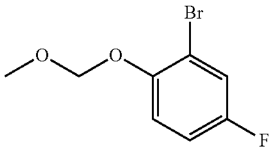

Sodium hydride (23.0 g, 575 mmol, 60% in mineral oil) was added to a solution of 2-bromo-4-fluoro-phenol (100 g, 523 mmol) in THF (1 L) at 0° C. for 4 h, followed by addition of methoxymethyl chloride (44.9, 601 mmol). After stirring at room temperature for 10 h, the reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 1-10% ethyl acetate in petroleum ether to give the title compound (80 g, 65%). $^1$H NMR (400 MHz, $CDCl_3$) δ: 7.30 (dd, 1H), 7.12 (dd, 1H), 6.97 (m, 1H), 5.07-5.24 (m, 2H), 3.46-3.62 (m, 3H).

Ethyl 2-[5-fluoro-2-(methoxymethoxy)phenyl]-2-oxo-acetate

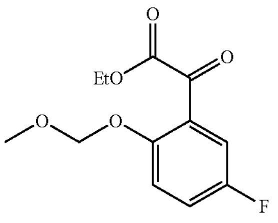 [SMILES: CCOC(=O)C(=O)c1cc(F)ccc1OCOC]

n-Butyllithium (2.5 M in hexane, 142 mL, 357 mmol) was added dropwise to a solution of 2-bromo-4-fluoro-1-(methoxymethoxy)benzene (80.0 g, 340 mmol) in THF (1 L) at −78° C. After stirring at −78° C. for 1 h, the reaction mixture was cannulated to a pre-cooled (−78° C.) solution of diethyl oxalate (74.4 g, 510 mmol) in THF (500 mL). Upon completion of addition, the reaction mixture was allowed to warm to room temperature. The reaction mixture was quenched by water and extracted with ethyl acetate three times. The combined organic extracts were washed with brine, dried over sodium sulfate, filtered and concentrated under reduced pressure. The crude product was purified by silica gel column chromatography eluting with 10% ethyl acetate in petroleum ether to give the title compound (70 g, 80%). $^1$H NMR (400 MHz, $CDCl_3$) δ: 7.57 (dd, 1H), 7.26-7.31 (m, 1H), 7.18-7.23 (m, 1H), 5.15 (s, 2H), 4.37-4.43 (m, 2H), 3.46-3.50 (m, 3H), 1.35-1.41 (m, 3H).

Ethyl-2-[5-fluoro-2-(methoxymethoxy)phenyl]-2-hydroxyimino-acetate

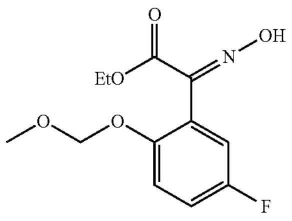 [SMILES: CCOC(=O)C(=NO)c1cc(F)ccc1OCOC]

Ethyl 2-[5-fluoro-2-(methoxymethoxy)phenyl]-2-oxo-acetate (70.0 g, 273 mmol) and sodium acetate (44.7 g, 132 mmol) were added to a solution of hydroxylamine hydrochloride (37.9 g, 546 mmol) in ethanol (500 mL). After stirring at 80° C. for 2.5 h, the solvent was removed under reduced pressure and the resulting residue was partitioned between water and dichloromethane. The aqueous phase was extracted with additional dichloromethane. The combined organic extracts were washed with brine, dried over sodium sulfate, filtered and concentrated under reduced pressure to give the title compound (68 g, 92%). $^1$H NMR (400 MHz, $CDCl_3$) δ: 9.76 (br s, 1H), 7.17-7.23 (m, 1H), 7.07-7.14 (m, 2H), 5.10 (s, 2H), 4.31-4.39 (m, 2H), 3.44-3.48 (m, 3H), 1.35-1.40 (m, 3H).

Ethyl 2-amino-2-[5-fluoro-2-(methoxymethoxy)phenyl]acetate

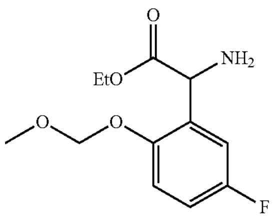 [SMILES: CCOC(=O)C(N)c1cc(F)ccc1OCOC]

Ethyl-2-[5-fluoro-2-(methoxymethoxy)phenyl]-2-hydroxyimino-acetate (34.0 g, 125 mmol) was added to a solution of Raney Ni (1.46 g, 25.0 mmol) in EtOH/THF (650 mL, 4/1). The flask was evacuated and backfilled with hydrogen and the reaction mixture was allowed to stir at 70° C. under an atmosphere of hydrogen (50 psi) for 24 h. The reaction mixture was filtered through a pad of Celite which was washed several times with ethanol. The filtrate was concentrated under reduced pressure and purified by silica gel chromatography eluting with 33% ethyl acetate in petroleum ether to give the title compound (30.6 g, 48%). $^1$H NMR (400 MHz, DMSO-$d_6$) δ: 7.23 (dd, 1H), 7.04-7.08 (m, 2H), 5.14-5.18 (m, 2H), 4.66 (s, 1H), 3.92-4.12 (m, 2H), 3.37 (s, 3H), 1.06-1.22 (m, 3H).

Ethyl 2-[(2-amino-5-bromo-benzoyl)amino]-2-[5-fluoro-2-(methoxymethoxy)phenyl]-acetate

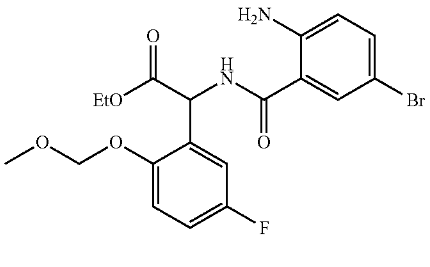 [SMILES: CCOC(=O)C(NC(=O)c1cc(Br)ccc1N)c1cc(F)ccc1OCOC]

Triethylamine (7.85 g, 77.6 mmol) was added to a solution of ethyl 2-amino-2-[5-fluoro-2-(methoxymethoxy)phenyl]acetate (10.0 g, 38.8 mmol) and 6-bromo-2,4-dihydro-1H-3,1-benzoxazine-2,4-dione (10.3 g, 42.6 mmol) in THE (80 mL). After stirring at 40° C. for 3 h, the solvent was removed under reduced pressure. The crude product was purified by silica gel column chromatography eluting with 25% ethyl acetate in petroleum ether to give the title compound (5 g, 28%). $^1$H NMR (400 MHz, DMSO-de) δ: 8.95 (d, 1H), 7.77 (d, 1H), 7.29 (dd, 1H), 7.15-7.22 (m, 3H), 6.69 (d, 1H), 6.57 (s, 2H), 5.99 (d, 1H), 5.19-5.27 (m, 2H), 4.09-4.18 (m, 2H), 3.38 (s, 3H), 1.14-1.18 (m, 3H).

Ethyl 2-(6-bromo-4-oxo-quinazolin-3-yl)-2-[5-fluoro-2-(methoxymethoxy)phenyl]acetate

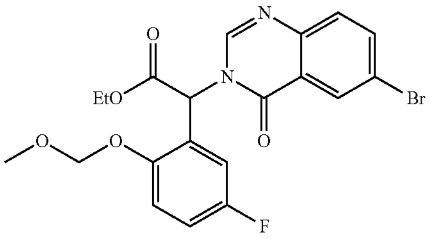 [SMILES: CCOC(=O)C(c1cc(F)ccc1OCOC)n1cnc2ccc(Br)cc2c1=O]

A solution of ethyl 2-[(2-amino-5-bromo-benzoyl) amino]-2-[5-fluor-2-(methoxymethoxy)-phenyl]acetate (5.25 g, 11.5 mmol) in triethoxy methane (20 mL) was stirred at 110° C. for 22 h. After cooling to room temperature, the solvent was removed under reduced pressure. The crude product was purified by silica gel column chromatography eluting with 10-33% ethyl acetate in petroleum ether to give the title compound (2.2 g, 41%). $^1$H NMR (400 MHz, DMSO-$d_6$) δ: 8.25-8.29 (m, 2H), 8.02 (dd, 1H), 7.66 (d, 1H), 7.26-7.37 (m, 2H), 7.14-7.21 (m, 1H), 6.68 (s, 1H), 5.17-5.25 (m, 2H), 4.22-4.30 (m, 2H), 3.26 (s, 3H) 1.15-1.25 (m, 3H).

Ethyl 2-[5-fluoro-2-(methoxymethoxy)phenyl]-2-[6-[4-(1-methyl-4-piperidyl)phenyl]-4-oxo-quinazolin-3-yl]acetate

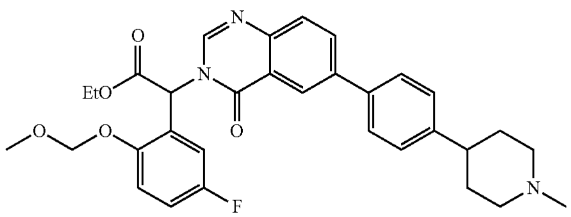

A mixture of ethyl 2-(6-bromo-4-oxo-quinazolin-3-yl)-2-[5-fluoro-2-(methoxymethoxy)-phenyl]acetate (2.2 g, 4.72 mmol), 1-methyl-4-[4-(4,4,5,5-tetramethyl-1,3,2-dioxaborolan-2-yl)phenyl]piperidine (1.98 g, 6.60 mmol), potassium carbonate (1.96 g, 14.1 mmol) and dioxane/water (20 mL, 4/1) was degassed with nitrogen gas. [1,1' Bis(diphenylphosphino)-ferrocene]dichloropalladium(II) complex with dichloromethane (0.690 g, 0.944 mmol) was added and then the reaction was degassed under nitrogen once more. The reaction mixture was heated at 105° C. for 3 h. After cooling to room temperature, the reaction mixture was poured into water and extracted with ethyl acetate three times. The combined organic extracts were washed with brine, dried over sodium sulfate, filtered and concentrated under reduced pressure. The crude product was purified by silica gel column chromatography eluting with 0-15% methanol in dichloromethane to give the title compound (1.8 g, 68%). MS m/z: 560.4 $[M+1]^+$.

2-[5-Fluoro-2-(methoxymethoxy)phenyl]-2-[6-[4-(1-methyl-4-piperidyl)phenyl]-4-oxo-quinazolin-3-yl] acetic acid

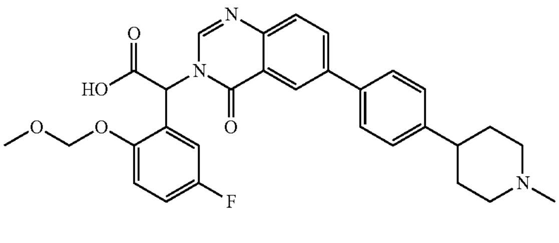

Lithium hydroxide monohydrate (0.404 g, 9.62 mmol) was added to a solution of ethyl 2-[5-fluoro-2-(methoxymethoxy)phenyl]-2-[6-[4-(1-methyl-4-piperidyl)-phenyl]-4-oxo-quinazolin-3-yl]acetate (1.80 g, 3.21 mmol) in THF/MeOH/water (30 mL, 1/1/1). After stirring at the room temperature for 3 h, the solvent was removed under reduced pressure and the resulting residue was adjusted to pH 3 by HCl (1 M). The resulting solid was collected by filtration and washed with water to give the title compound (1.5 g, 88%). MS m/z: 532.1 $[M+1]^+$.

2-[5-Fluoro-2-(methoxymethoxy)phenyl]-2-[6-[4-(1-methyl-4-piperidyl)phenyl-4]-oxo-quinazolin-3-yl]-N-(2-pyridyl)acetamide

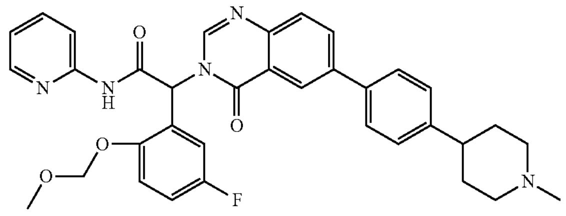 [SMILES: COCOc1ccc(F)cc1C(C(=O)Nc1ccccn1)n1cnc2ccc(-c3ccc(C4CCN(C)CC4)cc3)cc2c1=O]

DIPEA (0.434 g, 3.36 mmol) was added to a solution of 2-[5-fluoro-2-(methoxymethoxy)-phenyl]-2-[6-[4-(1-methyl-4-piperidyl)-phenyl]-4-oxo-quinazolin-3-yl]acetic acid (0.600 g, 1.12 mmol), 2-aminopyridine (0.158 g, 1.68 mmol) and HATU (0.638 g, 1.68 mmol) in DMF (10 mL). After stirring at room temperature for 10 h, the solvent was removed under reduced pressure. The crude product was purified by silica gel column chromatography eluting with 0-10% methanol in dichloromethane to give the title compound (0.20 g, 29%). MS m/z: 608.5 $[M+1]^+$.

2-(5-Fluoro-2-hydroxyphenyl)-2-(6-(4-(1-methylpiperidin-4-yl)phenyl)-4-oxoquinazolin-3(4H)-yl)-N-(pyridin-2-yl)acetamide; hydrochloride (082)

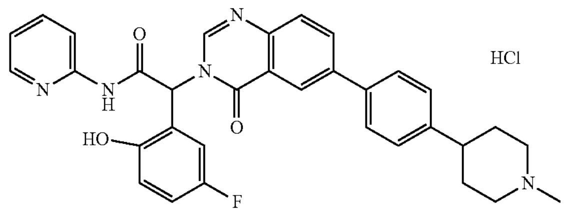 [SMILES: CN1CCC(c2ccc(-c3ccc4ncn(C(C(=O)Nc5ccccn5)c5cc(F)ccc5O)c(=O)c4c3)cc2)CC1 ; Cl]

HCl in dioxane (4 M, 0.102 mL, 0.408 mmol) was added to a solution of 2-[5-fluoro-2-(methoxymethoxy)phenyl]-2-[6-[4-(1-methyl-4-piperidyl)phenyl]-4-oxo-quinazolin-3-yl]-N-(2-pyridyl)acetamide (0.200 g, 0.329 mmol) in dichloromethane (5 mL). After stirring for 1 h at room temperature, the solvent was removed under reduced pressure. To the residue was added diethyl ether and the resulting solid was isolated via filtration to give the title compound (130 mg, 68%). $^1$H NMR (DMSO-$d_6$) δ: 8.40 (d, 1H), 8.34-8.39 (m, 1H), 8.19 (m, 1H), 8.06-8.14 (m, 1H), 7.83-7.90 (m, 2H), 7.75-7.81 (m, 3H), 7.40 (d, 2H), 7.14-7.25 (m, 2H), 6.95-7.06 (m, 3H), 3.44-3.54 (m, 2H), 3.02-3.17 (m, 2H), 2.83-2.94 (m, 1H), 2.78 (d, 3H), 1.94-2.15 (m, 4H). MS m/z: 564.3 $[M+1]^+$.

Compounds 083 and 084 were prepared following the procedure used to prepare Compound 082 from the corresponding MOM-protected intermediates.

2-(5-Fluoro-2-hydroxyphenyl)-2-(5-fluoro-6-(4-(1-methylpiperidin-4-yl)phenyl)-4-oxoquinazolin-3(4H)-yl)-N-(thiazol-2-yl)acetamide (083)

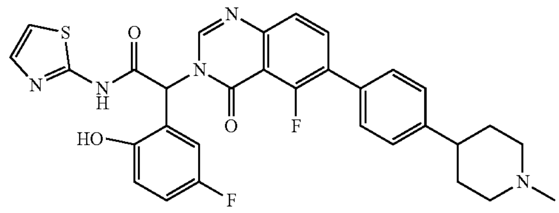 [SMILES: CN1CCC(c2ccc(-c3ccc4ncn(C(C(=O)Nc5nccs5)c5cc(F)ccc5O)c(=O)c4c3F)cc2)CC1]

$^1$H NMR (500 MHz, $d_6$-DMSO) δ 10.24 (s, 1H) 9.37 (br s, 1H) 7.97 (m, 1H) 7.90 (s, 1H) 7.60 (d, 3H) 7.52 (d, 1H) 7.39 (d, 2H) 7.32 (d, 1H) 7.21 (m, 1H) 6.96 (dd, 1H) 6.93 (dd, 1H) 6.86 (s, 1H) 3.55 (d, 2H) 3.12 (m, 2H) 2.87 (m, 1H) 2.83 (d, 3H) 2.07 (m, 2H) 1.86 (m, 2H); MS (m/z): 588.28.

2-(5-Fluoro-2-hydroxyphenyl)-2-(6-(4-(1-methylpiperidin-4-yl)phenyl)-4-oxopyrido[3,2-d]pyrimidin-3(4H)-yl)-N-(thiazol-2-yl)acetamide (084)

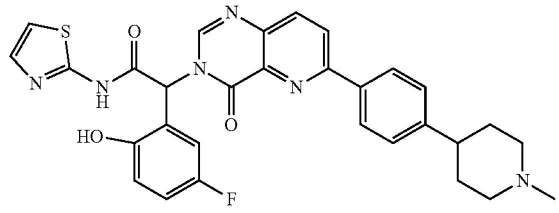 [SMILES: CN1CCC(c2ccc(-c3ccc4ncn(C(C(=O)Nc5nccs5)c5cc(F)ccc5O)c(=O)c4n3)cc2)CC1]

$^1$H NMR (500 MHz, $d_6$-DMSO) δ 10.23 (s, 1H) 9.32 (br s, 1H) 8.46 (d, 1H) 8.22 (d, 3H) 7.99 (s, 1H) 7.53 (d, 1H) 7.45 (d, 2H) 7.33 (d, 1H) 7.22 (m, 1H) 6.96 (m, 3H) 3.55 (d, 2H) 3.11 (m, 2H) 2.91 (m, 1H) 2.84 (d, 3H) 2.09 (d, 2H) 1.88 (m, 2H); MS (m/z): 571.31.

2-(2-Fluoro-6-hydroxyphenyl)-2-(6-(4-(4-methylpiperazin-1-yl)phenyl)-4-oxoquinazolin-3(4H)-yl)-N-(thiazol-2-yl)acetamide (085)

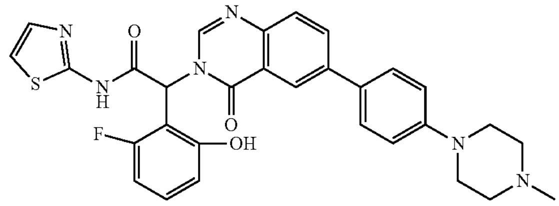 [SMILES: CN1CCN(c2ccc(-c3ccc4ncn(C(C(=O)Nc5nccs5)c5c(O)cccc5F)c(=O)c4c3)cc2)CC1]

A solution of $BBr_3$ (1M in DCM, 1.37 mL, 1.37 mmol) was added to a solution of 2-(2-fluoro-6-methoxyphenyl)-2-(6-(4-(4-methylpiperazin-1-yl)phenyl)-4-oxoquinazolin-3(4H)-yl)-N-(thiazol-2-yl)acetamide trifluoroacetoacetate (191 mg, 0.273 mmol) in dichloromethane (50 mL) at −78° C. and the reaction was stirred at room temperature overnight. It was again cooled to −78° C., a further solution of $BBr_3$ (1M in DCM, 2.73 mL, 2.73 mmol) was added and the mixture stirred overnight at room temperature. Dichloromethane (100 mL) and saturated brine (100 mL) were added, and $NaHCO_3$ was added to adjust the pH to 7. The mixture was extracted with dichloromethane (3×50 mL), and the combined organic layer was washed with saturated brine. The solvent was removed, and the residue was purified by reverse phase HPLC eluting with 1-60% ACN/$H_2O$ (0.038% TFA modifier) to give the title compound (47 mg). $^1H$ NMR (500 MHz, $d_6$-DMSO) δ 10.82 (s, 1H) 9.80 (br s, 1H) 8.36 (d, 1H) 8.18 (dd, 1H) 7.97 (s, 1H) 7.77 (d, 1H) 7.75 (d, 2H) 7.48 (d, 1H) 7.39 (m, 1H) 7.26 (d, 1H) 7.16 (d, 2H) 7.06 (s, 1H) 6.80 (d, 1H) 6.79 (m, 1H) 3.98 (d, 2H) 3.54 (m, 2H) 3.19 (m, 2H) 3.05 (m, 2H) 2.88 (s, 3H); MS (m/z): 571.28.

The following compound was prepared in a similar manner to Compound 085.

2-(2-Fluoro-6-hydroxyphenyl)-2-(6-(4-(1-methylpiperidin-4-yl)phenyl)-4-oxoquinazolin-3(4H)-yl)-N-(thiazol-2-yl)acetamide (086)

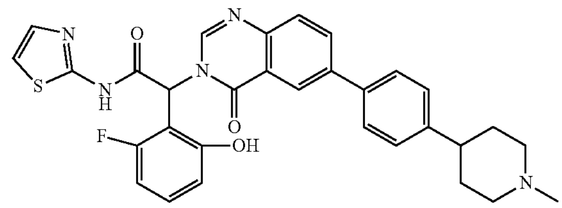 [SMILES: CN1CCC(c2ccc(-c3ccc4ncn(C(C(=O)Nc5nccs5)c5c(O)cccc5F)c(=O)c4c3)cc2)CC1]

$^1H$ NMR (500 MHz, $d_6$-DMSO) δ 10.84 (s, 1H) 9.52 (br s, 1H) 8.42 (d, 1H) 8.20 (dd, 1H) 8.00 (s, 1H) 780 (m, 3H) 7.57 (m, 1H) 7.48 (d, 1H) 7.40 (d, 2H) 7.38 (m, 1H) 7.26 (d, 1H) 7.06 (s, 1H) 6.81 (d, 1H) 6.79 (m, 1H) 3.54 (d, 2H) 3.11 (m, 2H) 2.88 (m, 1H) 2.84 (d, 3H) 2.07 (m, 2H) 1.89 (m, 2H); MS (m/z): 570.25.

Example 2: HTRF-Based EGFR Biochemical Assays

EGFR biochemical activity measurements were carried out using the homogeneous time-resolved fluorescence (HTRF) assay (Cisbio). Inhibitors and DMSO normalizations were first dispensed to empty black low-volume 384-well plates (Corning) with D300 digital liquid dispenser (HP). All reactions were carried out at room temperature and solutions were added to plates with a Multidrop Combi Reagent Dispenser (ThermoFisher). The reaction mixture (10 μL final volume) contained 1 μM tyrosine kinase peptide-biotin substrate and mutant EGFR in a reaction buffer (50 mM HEPES pH 7.0, 5 mM $MgCl_2$, 1 mM $MnCl_2$, 0.01% BSA, 2 mM TCEP, 0.1 mM $NaVO_4$). Enzyme concentrations were adjusted to accommodate varying kinase activities (L858R 0.1 nM, L858R/T790M 0.02 nM). Enzyme reaction solution (2× concentrations, 5 μL) was added to 384-well plates containing compounds and incubated for 30 mins. Enzyme reactions were initiated with the addition of 5 μL of ATP to a final concentration of 100 μM and reacted for 20 mins. Reactions were quenched with the addition of 10 μL of phospho-tyrosine antibody-Europium(III) cryptate (1-to-180 volume ratio) and Streptavidin-XL665 (46.7 nM) in EDTA-containing detection buffer, then incubated at room temperature for 1 hour, and read with a PHERAstar plate reader (excitation=337 nm, emission=620 nm and 665 nm). $IC_{50}$ values were determined by inhibition curves (11-point curves from 1.0 μM to 0.130 nM or 23-point curves from 1.0 μM to 0.130 μM) in triplicate with non-linear least squares fit in GraphPad Prism 7.0 d. The results of the HTRF-based EGFR biochemical assays are summarized in Table 12 below.

TABLE 12

| | HTRF Activity | |
|---|---|---|
| Compound No. | $IC_{50}$ (L858R/T790M) (nM) | $IC_{50}$ (L858R) (nM) |
| 001 | 62 | 1260 |
| 002 | 35 | 275 |
| 003 | 16 | 245 |
| 004 | 29 | 521 |
| 005 | 91 | >1000 |
| 006 | 36 | >1000 |
| 007 | 48 | >1000 |
| 008 | 64 | >1000 |
| 009 | 10 | >1000 |
| 010 | 54 | 1840 |
| 011 | 16 | 195 |
| 012 | 6 | 11 |
| 013 | 3 | 14 |
| 014 | 0.2 | 3 |
| 015 | 1 | 7 |
| 016 | 1 | 3 |
| 017 | 3 | 7 |
| 018 | 2 | 12 |
| 019 | 5 | 35 |
| 020 | 6 | 26 |
| 021 | 16 | 103 |
| 022 | 0.6 | 2 |
| 023 | 3 | 7 |
| 024 | 1 | 7 |
| 025 | 3 | 5 |
| 026 | 10 | 67 |
| 027 | 18 | 209 |
| 028 | 7 | 21 |
| 029 | 18 | 91 |
| 030 | 1 | 7 |
| 031 | 0.2 | 2 |
| 032 | 0.4 | 4 |
| 033 | 2 | 51 |
| 034 | 18 | >1000 |
| 035 | 11 | 101 |
| 036 | 0.3 | 4 |
| 037 | 1 | 8 |
| 038 | 2 | 9 |
| 039 | 9 | 191 |
| 040 | 1 | 9 |
| 041 | 31 | >1000 |
| 042 | 4 | 35 |
| 043 | 10 | 90 |
| 044 | 283 | >1000 |
| 045 | 297 | >1000 |
| 053 | | 1 |
| 054 | 42 | 91 |
| 055 | 79 | 264 |
| 056 | 7 | 32 |
| 057 | 7 | 50 |
| 058 | 2 | 8 |
| 059 | 8 | 48 |
| 060 | 0.6 | 4 |
| 062 | 220 | >1000 |
| 063 | 28 | 260 |
| 064 | 5 | 78 |
| 065 | 2 | 29 |
| 066 | 0.2 | 2 |
| 067 | 1 | 13 |
| 068 | 0.7 | 5 |
| 069 | 0.5 | 7 |
| 070 | 0.2 | 1 |
| 071 | 0.7 | 5 |
| 072 | 1 | 12 |
| 073 | 0.6 | 7 |

TABLE 12-continued

| HTRF Activity | | |
|---|---|---|
| Compound No. | $IC_{50}$ (L858R/T790M) (nM) | $IC_{50}$ (L858R) (nM) |
| 074 | 0.6 | 6 |
| 075 | 0.1 | 1 |
| 076 | 0.7 | 8 |
| 077 | 17 | 35 |
| 078 | 1 | 8 |
| 082 | 0.2 | 1 |
| 083 | 0.1 | 0.2 |
| 084 | 0.1 | 0.4 |
| 085 | 3 | 6. |
| 086 | 0.4 | 2 |

Example 3: Ba/F3 Cell Proliferation Models

The EGFR mutant L858R, Del E746_A750, L858R/T790M, Del E746_A750/T790M, L858R % T790M/C797S, and Del/T790M/C797S Ba/F3 cells have been previously described (Zhou, W., et al. Nature 462, 2009, 1070-1074). All cell lines were maintained in RPMI 1640 (Cellgro; Mediatech Inc., Herndon, CA) supplemented with 10% FBS, 100 units/mL penicillin, 100 units/mL streptomycin. The EGFR I941R mutation was introduced via site directed mutagenesis using the Quick Change Site-Directed Mutagenesis kit (Stratagene; La Jolla, CA) according to the manufacturer's instructions. All constructs were confirmed by DNA sequencing. The constructs were shuttled into the retroviral vector JP1540 using the Cre-recombination system (Agilent Technologies, Santa Clara, CA). Ba/F3 cells were then infected with retrovirus per standard protocols, as described previously (Zhou, et al, Nature 2009). Stable clones were obtained by selection in puromycin (2 μg/ml).

Growth and inhibition of growth was assessed by the Cell Titer Glo assay (Promega, Madison, WI) and was performed according to the manufacturer's instructions. The Cell Titer Glo assay is a luminescence-based method used to determine the number of viable cells based on quantitation of the ATP present, which is directly proportional to the amount of metabolically active cells present. Ba/F3 cells of different EGFR genotypes were exposed to compounds as a single agent or in combination with 1 μg/ml cetuximab for 72 hours and the number of cells used per experiment was determined empirically as has been previously established (Zhou, et al., Nature 2009). All experimental points were set up in triplicates in 384-well plates and all experiments were repeated at least three times. The luminescent signal was detected using a spectrometer and the data was graphically displayed using GraphPad Prism version 5.0 for Windows, (GraphPad Software; www.graphpad.com). The curves were fitted using a non-linear regression model with a sigmoidal dose response. The $IC_{50}$ values measured are shown in Table 13 below.

TABLE 13

| Inhibition of Proliferation of EGFR L858R/T790M mutant Ba/F3 Cells | | |
|---|---|---|
| Compound No. | Cell $IC_{50}$ BaF3 L858R/T790M compound + cetuximab (uM) | Cell $IC_{50}$ EGFR BaF3 L858R/T790M (uM) |
| 001 | 8.3 | >10 |
| 002 | 0.98 | >10 |
| 003 | 2.0 | >10 |
| 004 | 0.79 | >10 |

TABLE 13-continued

| Inhibition of Proliferation of EGFR L858R/T790M mutant Ba/F3 Cells | | |
|---|---|---|
| Compound No. | Cell $IC_{50}$ BaF3 L858R/T790M compound + cetuximab (uM) | Cell $IC_{50}$ EGFR BaF3 L858R/T790M (uM) |
| 005 | 4.8 | >10 |
| 006 | 1.8 | >10 |
| 007 | 1.5 | >10 |
| 008 | 2.5 | >10 |
| 009 | >10 | >10 |
| 010 | >10 | >10 |
| 011 | 0.35 | >10 |
| 012 | 0.2 | 2.15 |
| 013 | 0.38 | 2.00 |
| 014 | 0.005 | 0.51 |
| 015 | 0.02 | 2.32 |
| 016 | 0.02 | 1.19 |
| 017 | 0.062 | 1.27 |
| 018 | 0.072 | 1.52 |
| 019 | 0.044 | 1.85 |
| 020 | 0.78 | 1.42 |
| 021 | 0.97 | 2.90 |
| 022 | 0.02 | 1.26 |
| 023 | 0.11 | 2.41 |
| 024 | 0.09 | 1.77 |
| 025 | 0.02 | 0.90 |
| 026 | 0.56 | 1.22 |
| 027 | 1.7 | 3.46 |
| 028 | 0.088 | 1.58 |
| 029 | 0.56 | 3.45 |
| 030 | 0.004 | 0.80 |
| 031 | 0.01 | 1.35 |
| 032 | 0.021 | 1.58 |
| 033 | 0.044 | 1.55 |
| 034 | 1.8 | >10 |
| 035 | 0.35 | >10 |
| 036 | 0.023 | 0.92 |
| 037 | 0.022 | 2.65 |
| 038 | 0.057 | 1.86 |
| 039 | 0.076 | 1.78 |
| 040 | 0.76 | 4.07 |
| 041 | >10 | >10 |
| 042 | 0.25 | 1.46 |
| 043 | 0.38 | 2.16 |
| 044 | 0.79 | 2.46 |
| 045 | 4.1 | 4.10 |
| 053 | 0.002 | 0.35 |
| 054 | 0.41 | 2.48 |
| 055 | 1.5 | 3.94 |
| 056 | 0.41 | 3.97 |
| 057 | 0.7 | 4.73 |
| 058 | 0.012 | 0.93 |
| 059 | 0.084 | 1.37 |
| 060 | 0.009 | 0.71 |
| 061 | 0.028 | 4.52 |
| 062 | >10 | >10 |
| 063 | 4.1 | >10 |
| 064 | 0.49 | 6.15 |
| 065 | 0.38 | 7.81 |
| 066 | 0.02 | 1.88 |
| 067 | 0.041 | 3.96 |
| 068 | 0.018 | 1.56 |
| 069 | 0.028 | 2.81 |
| 070 | 0.005 | 0.55 |
| 071 | 0.020 | 2.37 |
| 072 | 0.055 | 1.60 |
| 073 | 0.015 | 1.94 |
| 074 | 0.022 | 2.35 |
| 075 | 0.007 | 1.03 |
| 076 | 0.044 | 3.36 |
| 077 | 2.1 | 6.46 |
| 078 | 0.62 | 4.20 |
| 082 | 0.002 | 0.23 |
| 083 | 0.009 | 0.04 |
| 084 | 0.048 | 0.86 |
| 085 | 0.066 | 5.77 |
| 086 | 0.033 | 3.16 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula I:

(I)

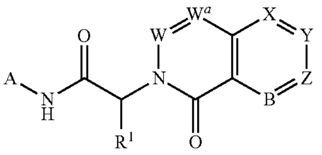

or a pharmaceutically acceptable salt thereof;

wherein:

A is a 6-10 membered aryl or a 5-10 membered heteroaryl;

W and $W^a$ are each, independently, CH, $CR^6$, or N;

X and B are each, independently, N, CH, CF, or C—($C_1$-$C_3$ alkyl);

Y and Z are each independently N, CH, or $CR^2$;

provided that at least one of X, Y, Z, or B is CH;

$R^1$ is phenyl or pyridinyl, wherein phenyl or pyridinyl is optionally substituted one or two times, independently, with $R^7$;

$R^2$ is independently, at each occurrence, selected from the group consisting of halo, 6-10 membered aryl, 5-10 membered heteroaryl, 3-6 membered cycloalkyl, 3-6 membered cycloalkenyl, 4-7 membered heterocycloalkyl, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, and $C_2$-$C_6$ alkynyl, wherein 6-10 membered aryl, 5-10 membered heteroaryl, 4-7 membered heterocycloalkyl, and 3-6 membered cycloalkyl are optionally substituted with $R^3$, and wherein $C_1$-$C_6$ alkyl, $C_2$-$C_6$ alkenyl, or $C_2$-$C_6$ alkynyl are each optionally substituted one, two, or three times with $R^4$;

$R^3$ is selected from the group consisting of halo, —OH, —SH, —CN, —$NO_2$, —$NH_2$, $OR^4$, $NR^4R^4$, $SO_2R^4$, $SO_2NHR^4$, $NHSO_2R^4$, $C(O)OR^4$, $C(O)NHR^4$, $C(O)R^4$, $C_1$-$C_6$ alkyl, $C_2$-$C_6$ alkenyl, $C_2$-$C_6$ alkynyl, 6-10 membered aryl, 5-6 membered heteroaryl, 3-6 membered cycloalkyl, 3-6 membered cycloalkenyl, and 4-7 membered heterocycloalkyl, wherein 4-7 membered heterocycloalkyl is optionally substituted with one or more substituents selected from the group consisting of $C_1$-$C_4$ alkyl, $C_1$-$C_4$ alkyl-OH, halo, and =O;

$R^4$ is independently, at each occurrence, selected from the group consisting of hydrogen, $(CH_2)_{0-3}$-(3-7 membered cycloalkyl), $(CH_2)_{0-3}$-(4-7 membered cycloalkenyl), $(CH_2)_{0-3}$-(6-10 membered aryl), $(CH_2)_{0-3}$-(5- to 6-membered heteroaryl), or $(CH_2)_{0-3}$-(4- to 7-membered heterocycloalkyl), wherein 6-10 membered aryl, 5- to 6-membered heteroaryl, or 4- to 7-membered heterocycloalkyl are each optionally substituted one, two, or three times with $R^5$;

$R^5$ is independently, at each occurrence, selected from the group consisting of $C_1$-$C_6$ alkyl, $C_1$-$C_6$ haloalkyl, $C_1$-$C_6$ alkoxy, $C_1$-$C_6$ haloalkoxy, halo, COOH, C(O)O($C_1$-$C_6$ alkyl), $O(CH_2)_{1-3}OH$, $NH_2$, OH, CN, $(CH_2)_{0-3}$(6-10 membered aryl), $(CH_2)_{0-3}$ (5- to 6-membered heteroaryl), and $(CH_2)_{0-3}$ (4- to 7-membered heterocycloalkyl), wherein 6-10 membered aryl, 5- to 6-membered heteroaryl, and 4- to 7-membered heterocycloalkyl are optionally substituted with one or more substituents independently selected from $C_1$-$C_6$ alkyl, $C_1$-$C_6$ haloalkyl, $C_1$-$C_6$ alkoxy, $C_1$-$C_6$ haloalkoxy, halo, $NH_2$, NH($C_1$-$C_6$ alkyl), N($C_1$-$C_6$ alkyl)$_2$, $SO_2NH_2$, $(CH_2)_{1-2}OH$, $C(O)(CH_2)_{1-2}OH$, and C(O)O($C_1$-$C_6$ alkyl);

$R^6$ is independently, at each occurrence, $C_1$-$C_6$ alkyl or halo; and $R^7$ is independently, at each occurrence, $C_1$-$C_3$ alkyl, $C_1$-$C_3$ haloalkyl, $C_1$-$C_3$ alkoxy, $C_1$-$C_3$ haloalkoxy, halo, OH, SH, $NO_2$, $NH_2$, $(CH_2)_{1-4}OH$, $S(O)_{0-2}H$, $S(O)_{0-2}NH_2$, or CN.

2. The compound of claim 1, wherein the compound of Formula I is a compound of Formula II:

(II)

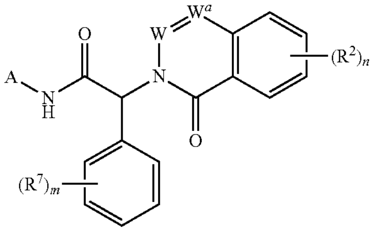

or a pharmaceutically acceptable salt thereof;

wherein:

A is a 6-10 membered aryl or a 5-10 membered heteroaryl;

W and $W^a$ are each, independently, CH, $CR^6$, or N;

$R^2$ is independently, at each occurrence, selected from the group consisting of halo, 6-10 membered aryl, 5-10 membered heteroaryl, and 3-6 membered cycloalkyl, wherein 6-10 membered aryl, 5-10 membered heteroaryl, and 3-6 membered cycloalkyl are optionally substituted with $R^3$;

$R^3$ is selected from the group consisting of halo, —OH, —SH, —CN, —$NO_2$, —$NH_2$, $C_1$-$C_6$ alkyl, $C_2$-$C_6$ alkenyl, $C_2$-$C_6$ alkynyl, 6-10 membered aryl, 5-6 membered heteroaryl, 3-6 membered cycloalkyl, 3-6 membered cycloalkenyl, and 4-7 membered heterocycloalkyl, wherein 4-7 membered heterocycloalkyl is optionally substituted with one or more substituent selected from the group consisting of $C_1$-$C_4$ alkyl, $C_1$-$C_4$ alkyl-OH, halo, and =O;

$R^7$ is selected from the group consisting of halo, —OH, —SH, —CN, —$NO_2$, and —$NH_2$;

m is 0, 1, or 2; and n is 1 or 2.

3. The compound of claim 1, wherein $R^7$ is absent or at least one $R^7$ is halo.

4. The compound of claim 3, wherein at least one $R^7$ is fluoro.

5. The compound of claim 1, wherein A is 5-6 membered heteroaryl.

6. The compound of claim 1, wherein A is thiazolyl or pyridinyl.

7. The compound of claim 1, wherein $R^2$ is selected from the group consisting of halo, 6-10 membered aryl, 5-10 membered heteroaryl, and 3-6 membered cycloalkyl, wherein 6-10 membered aryl is optionally substituted with $R^3$.

8. The compound of claim 1, wherein $R^2$ is bromo or chloro.

9. The compound of claim 1, wherein $R^2$ is phenyl further substituted with $R^3$.

10. The compound of claim 9, wherein $R^3$ is a 6-membered heterocycloalkyl optionally substituted with $C_1$-$C_4$ alkyl.

11. The compound of claim 10, wherein $R^3$ is piperidinyl or piperazinyl, each further substituted with methyl.

12. The compound of claim 1, wherein the compound of Formula I is a compound of Formula III, Formula IV, Formula V, Formula VI, Formula VII, or Formula VIII:

(III)

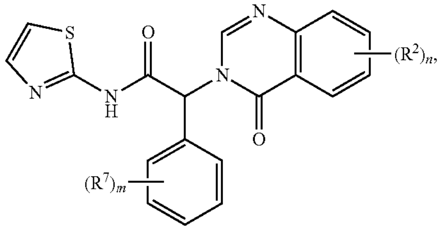

(IV)

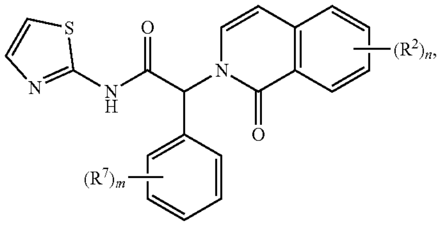

(V)

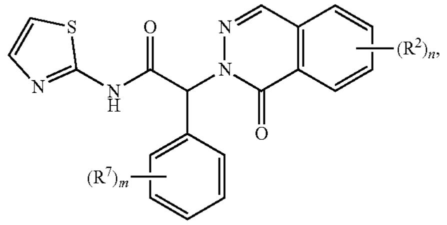

(VI)

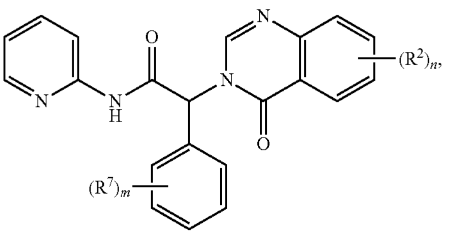

-continued (VII)

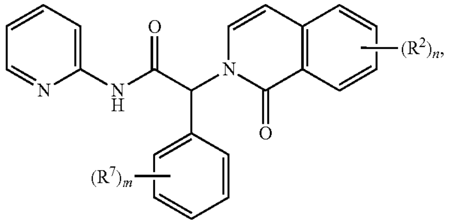

(VIII)

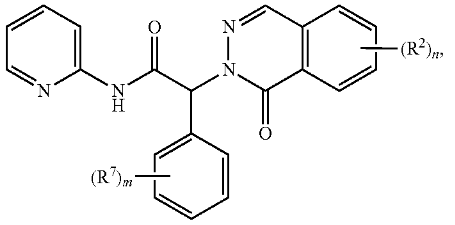

or a pharmaceutically acceptable salt thereof, wherein n=1 or 2, and m=0, 1, or 2.

13. The compound of claim 1, wherein the compound of Formula I is selected from the group consisting of:

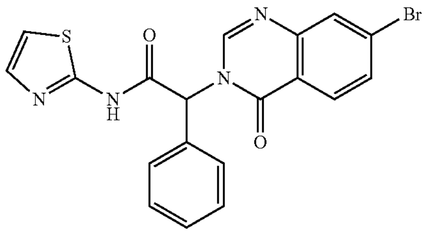

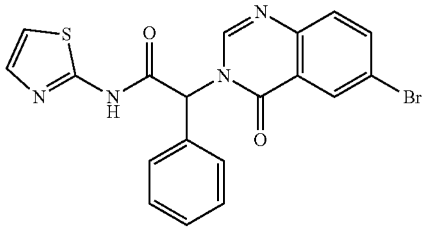

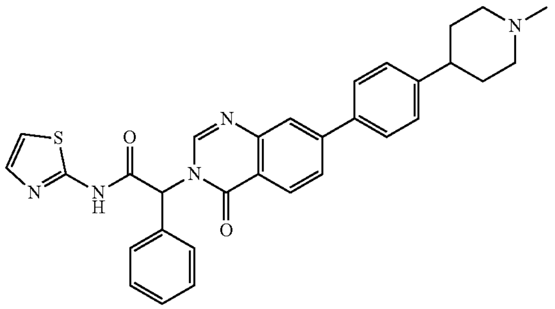

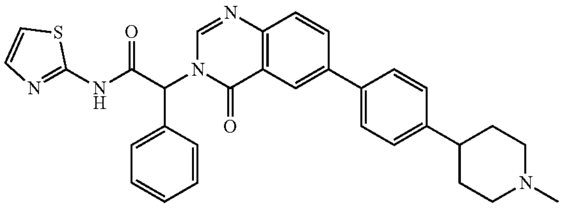

-continued
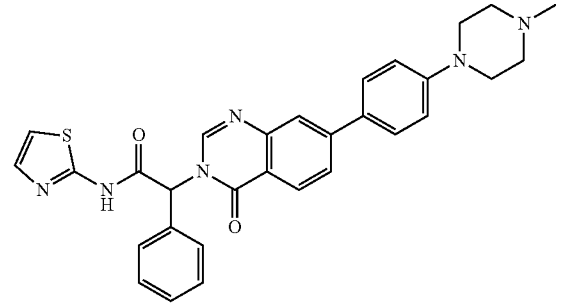
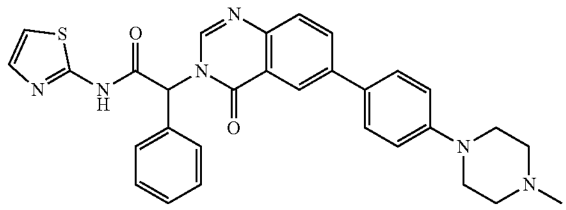
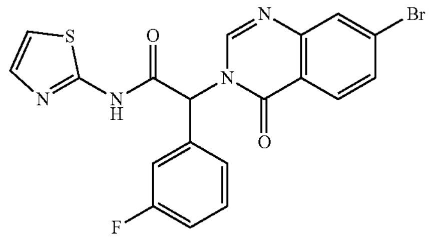
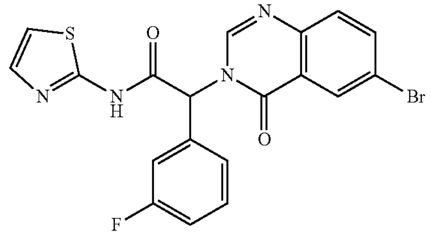
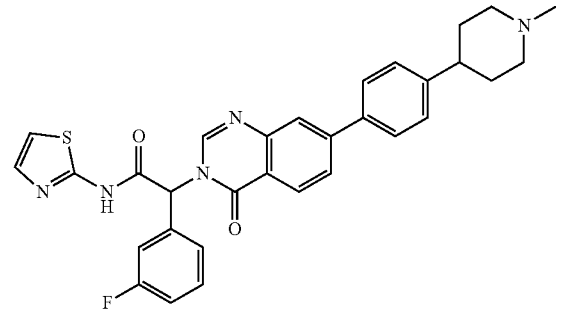
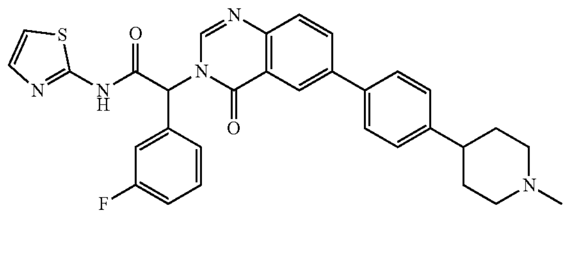
-continued
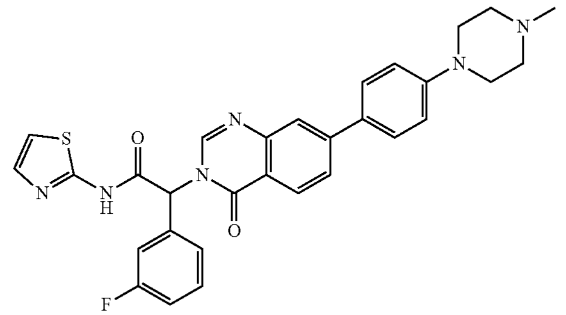
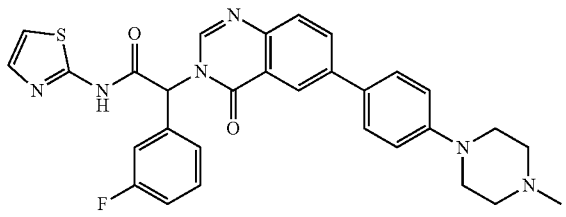
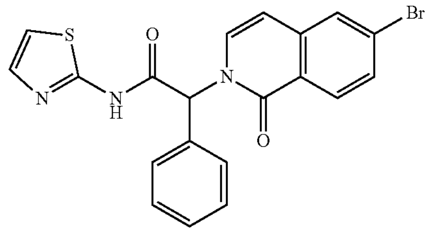
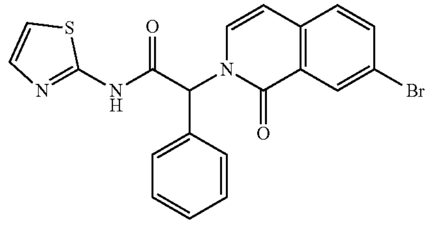
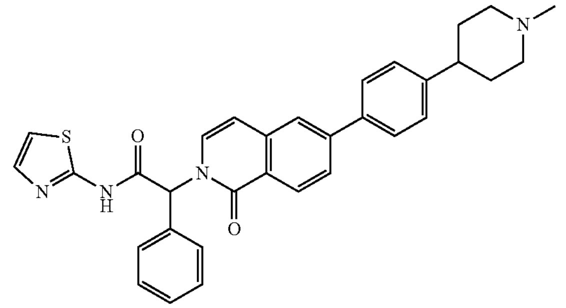
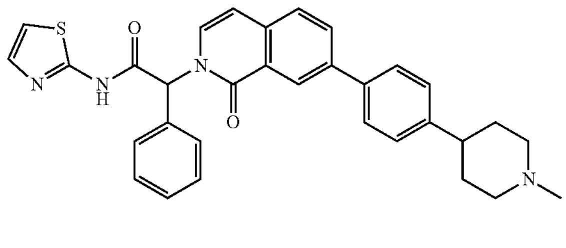

-continued
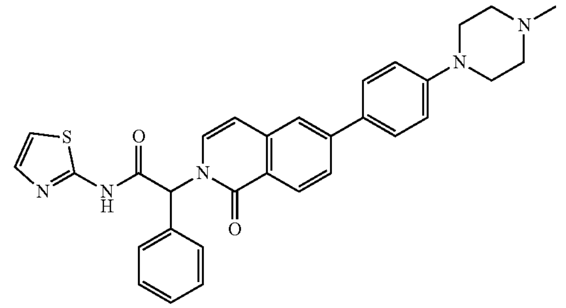
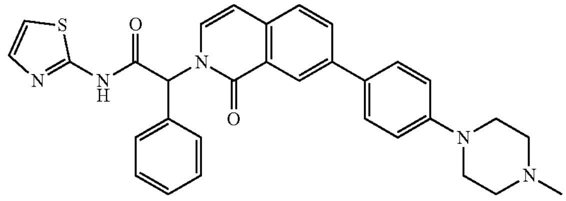
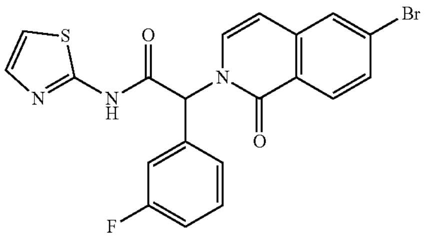
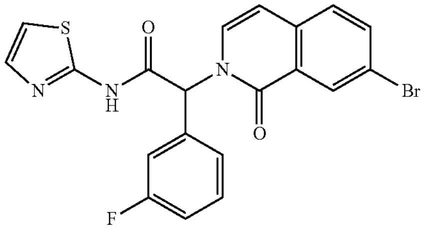
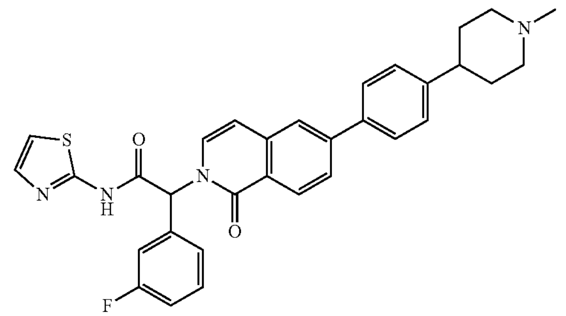
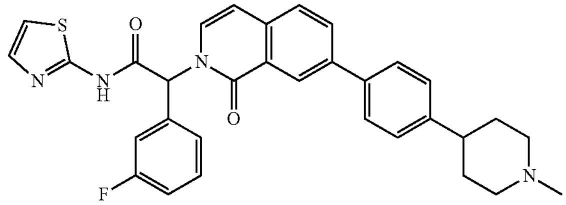
-continued
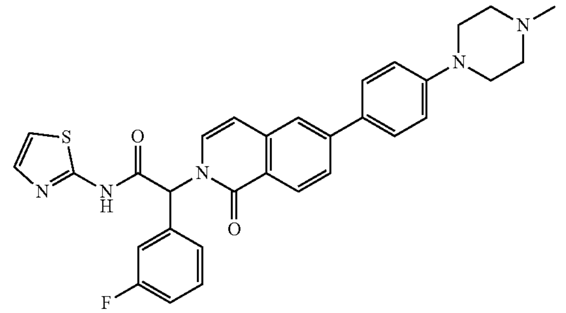
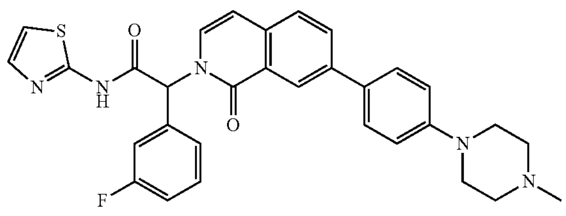
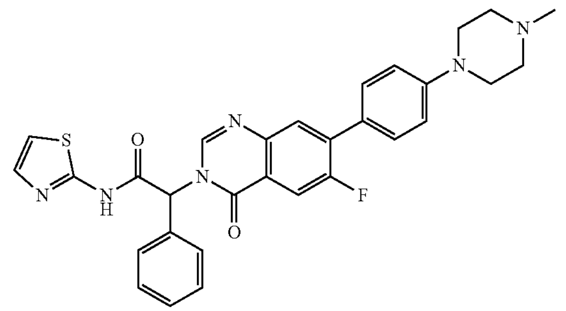
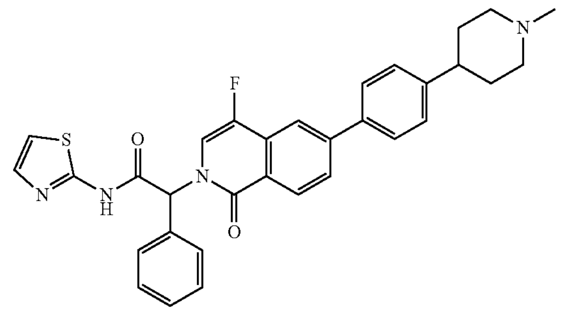
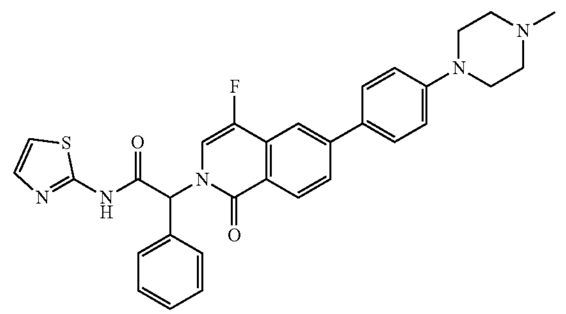

-continued
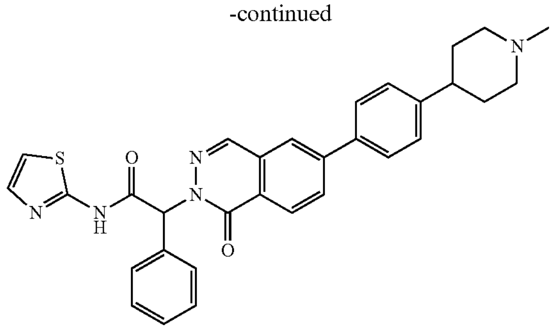
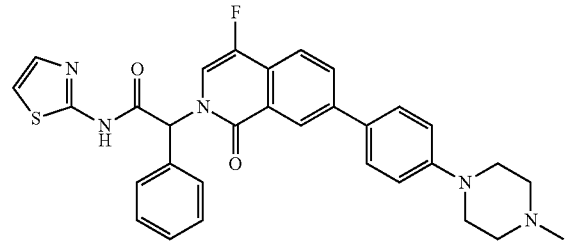
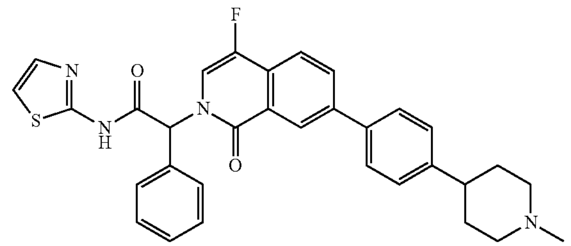
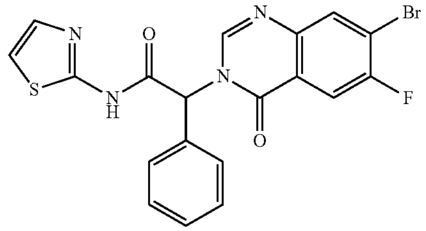
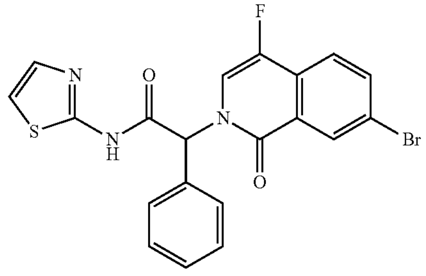
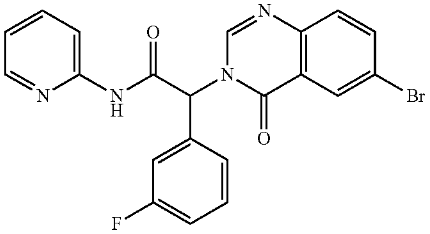
-continued
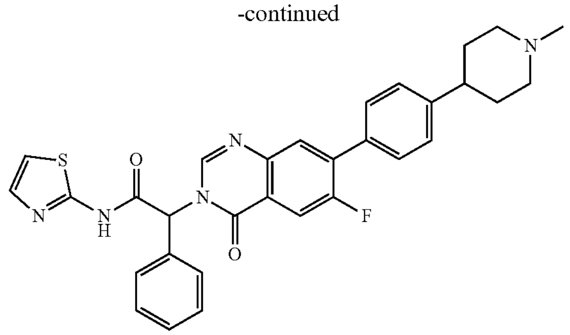
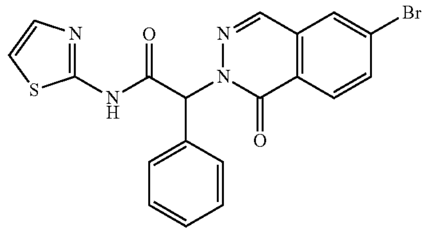
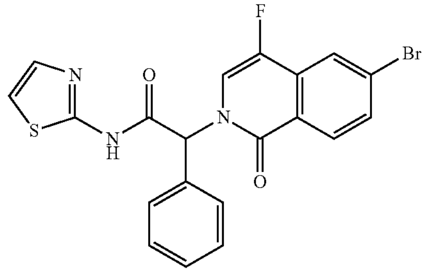
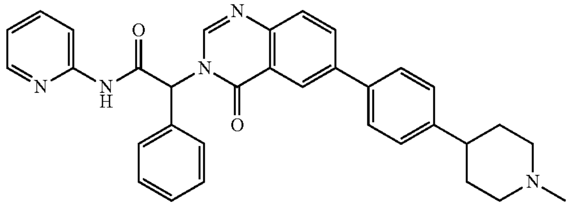
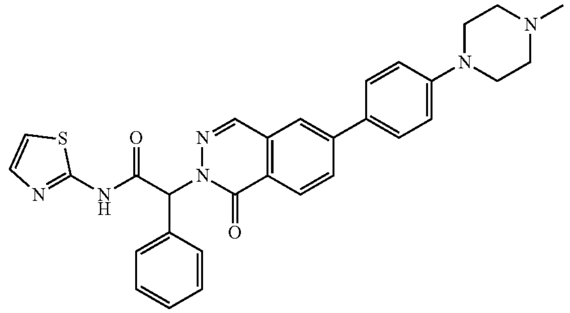
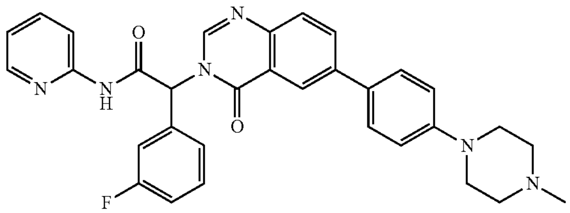

-continued
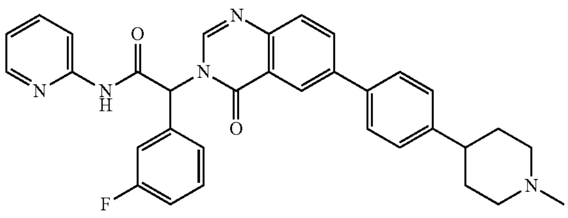
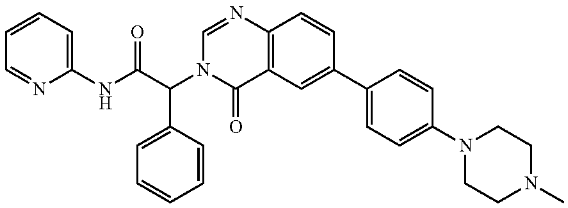
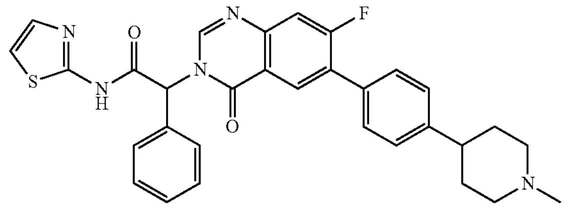
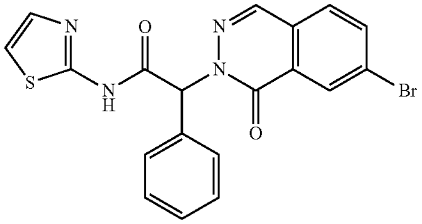
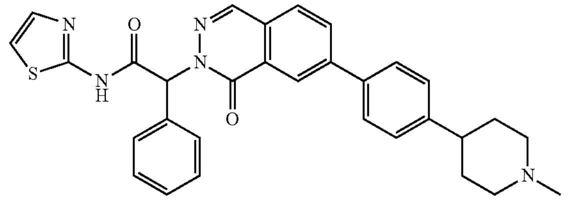
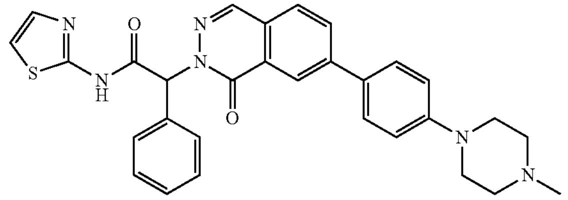
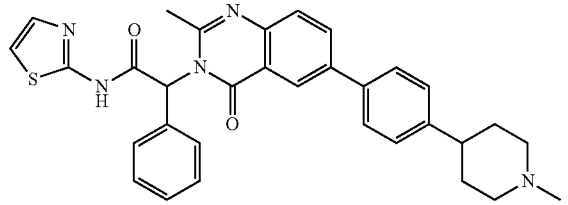
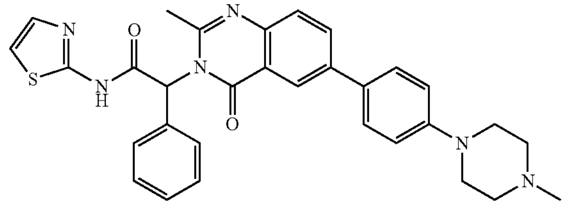
-continued
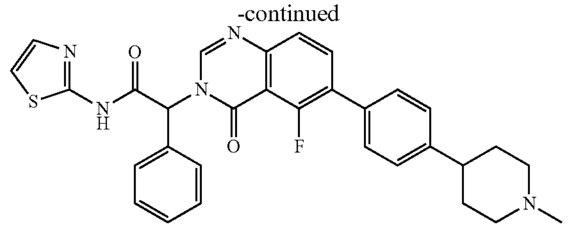
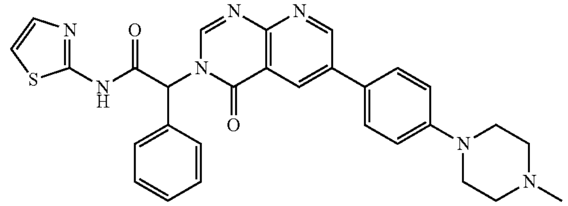
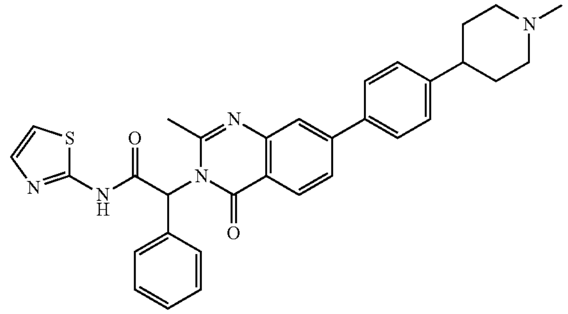
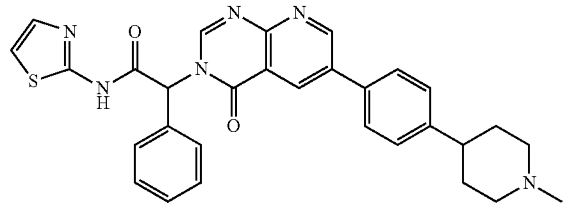
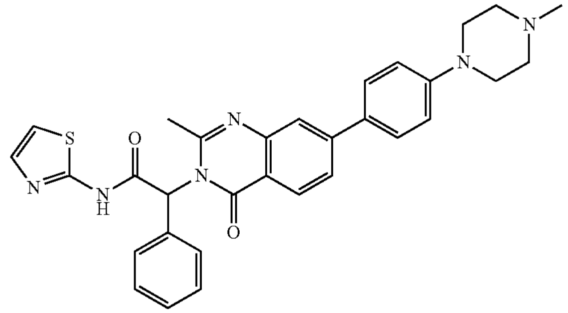
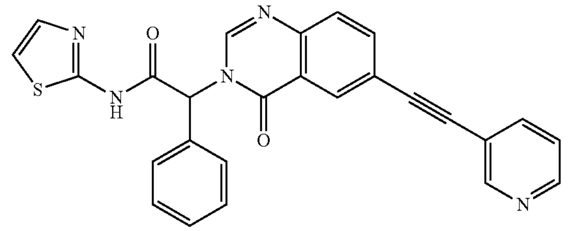
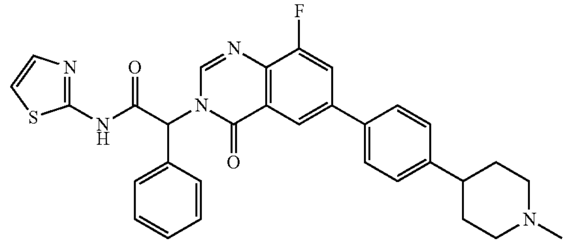

-continued
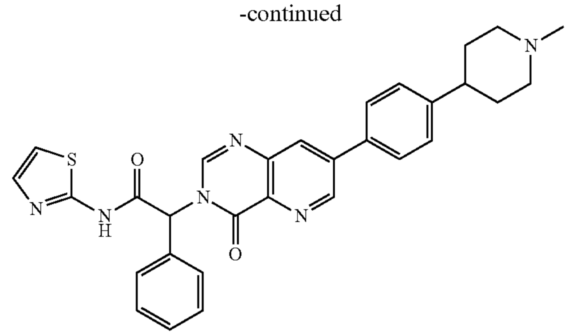
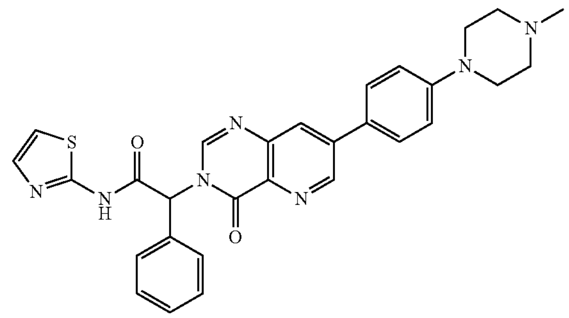
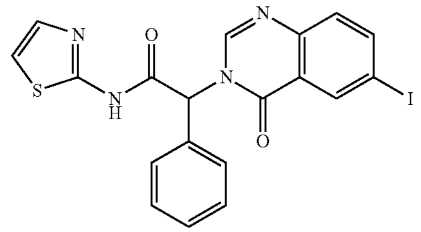
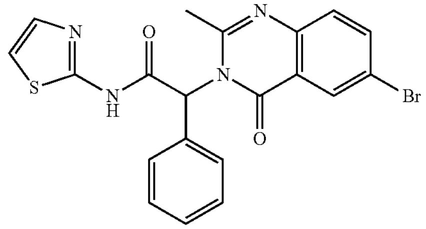
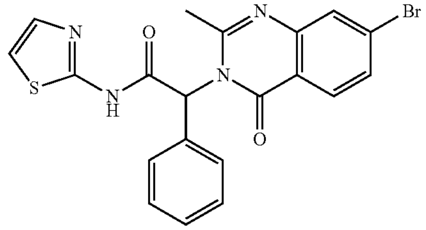
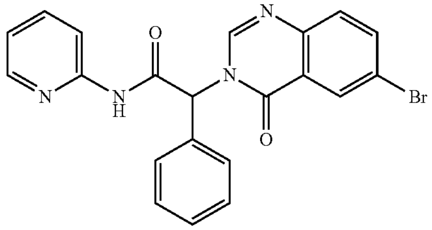
-continued
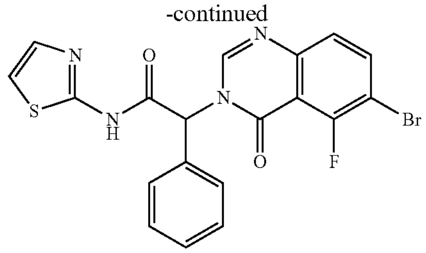
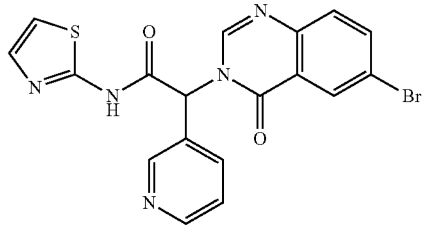
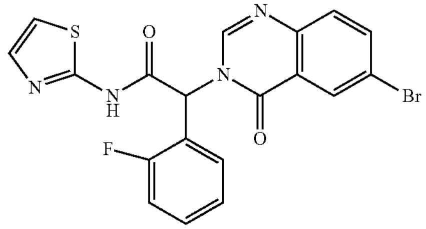
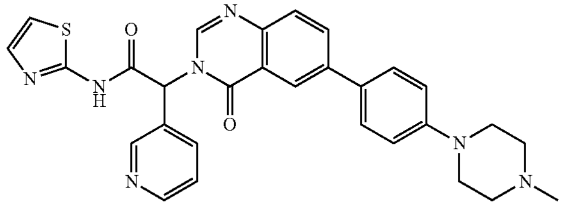
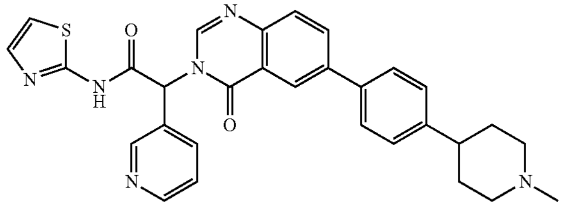
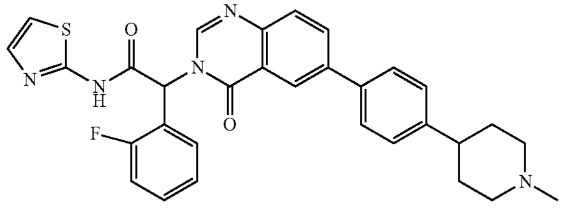
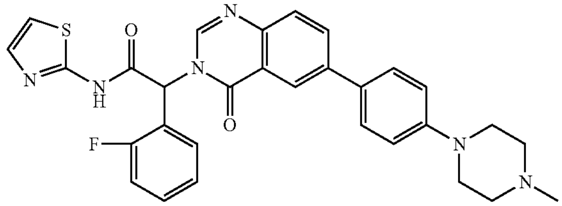
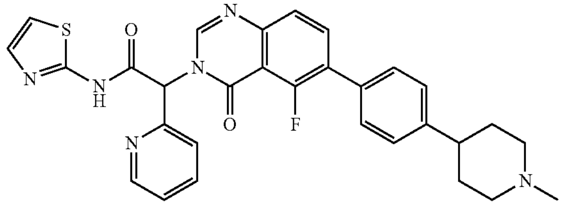

-continued
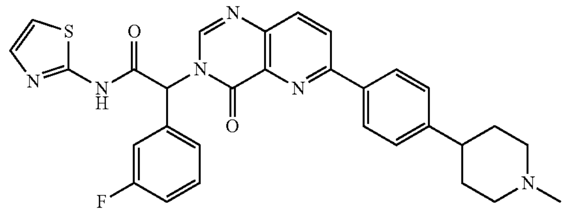
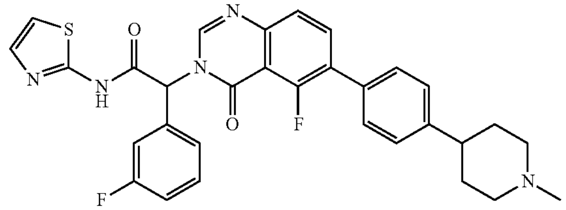
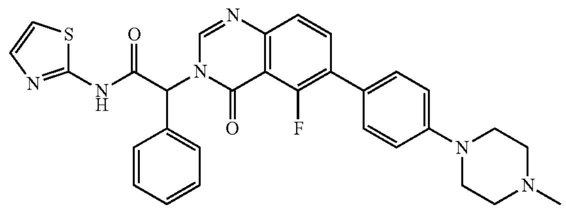
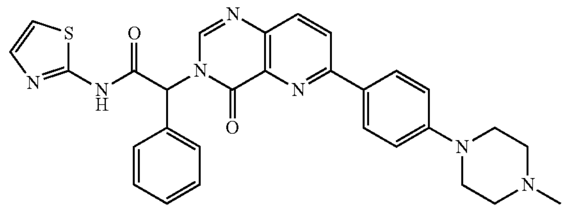
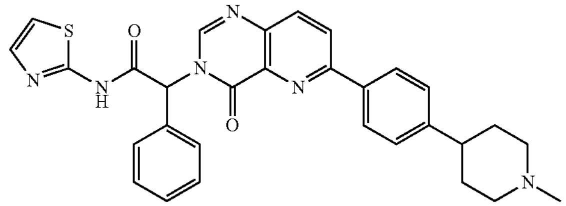
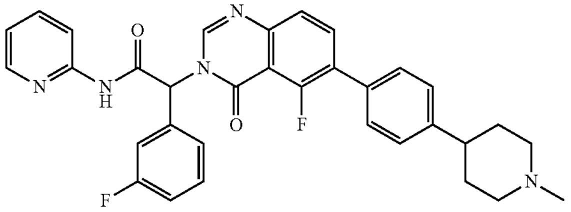
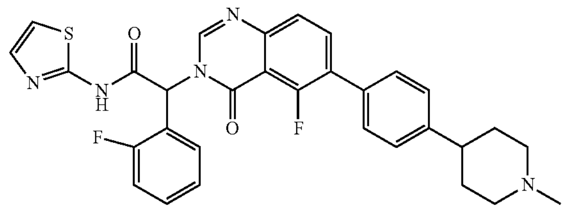
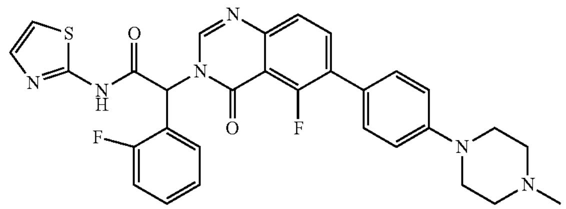
-continued
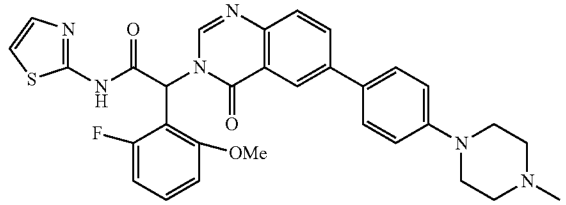
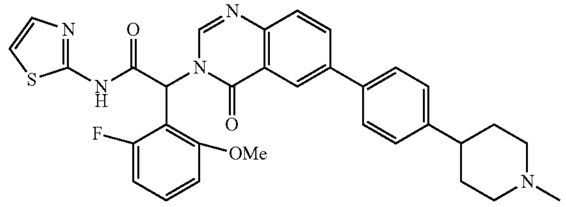
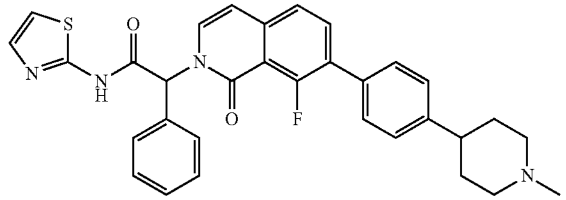
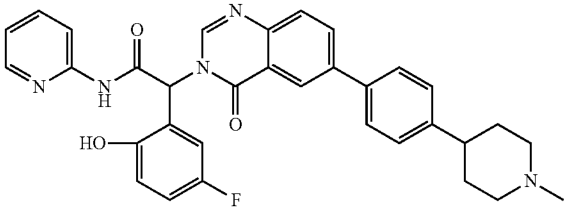
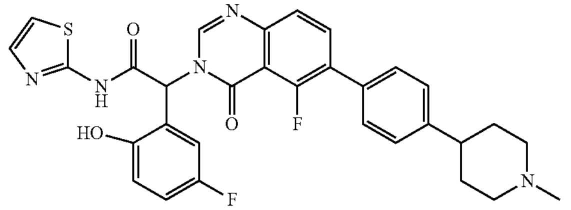
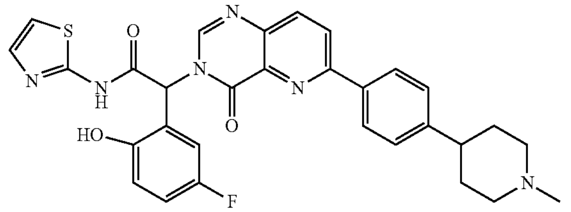
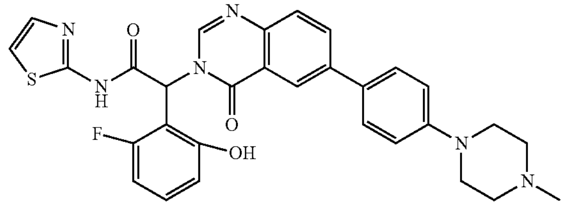
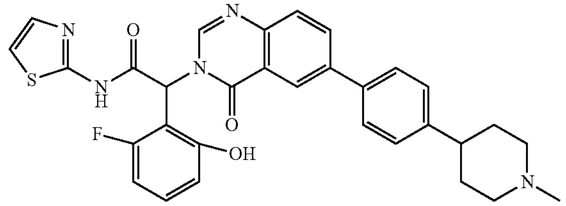
or a pharmaceutically acceptable salt thereof.

14. A pharmaceutical composition comprising a compound of claim 1, or a pharmaceutically acceptable salt thereof, and at least one pharmaceutically acceptable carrier.

15. A method of treating cancer in a subject in need thereof, comprising administering to the subject a therapeutically effective amount of a compound of claim 1, optionally in combination with a therapeutically effective amount of a second active agent.

16. The method according to claim 15, wherein the cancer is selected from the group consisting of lung cancer, colon cancer, breast cancer, endometrial cancer, thyroid cancer, glioma, squamous cell carcinoma, and prostate cancer.

17. The method according to claim 15, wherein the cancer is non-small cell lung cancer (NSCLC).

18. A method of inhibiting EGFR in a subject in need thereof, comprising administering to the subject a therapeutically effective amount of a compound of claim 1.

19. A method of treating or preventing an EGFR-mediated disorder in a subject in need thereof, comprising administering to the subject a therapeutically effective amount of a compound of claim 1.

20. The method according to claim 19, wherein the EGFR-mediated disorder is resistant to an EGFR-targeted therapy.

* * * * *